US008143293B2

(12) United States Patent
Flynn et al.

(10) Patent No.: US 8,143,293 B2
(45) Date of Patent: Mar. 27, 2012

(54) KINASE INHIBITORS USEFUL FOR THE TREATMENT OF MYLEOPROLIFIC DISEASES AND OTHER PROLIFERATIVE DISEASES

(75) Inventors: Daniel L. Flynn, Lawrence, KS (US); Peter A. Petillo, Lawrence, KS (US); Michael D. Kaufman, Lawrence, KS (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 0 days.

(21) Appl. No.: 12/105,408

(22) Filed: Apr. 18, 2008

(65) Prior Publication Data
US 2008/0261965 A1 Oct. 23, 2008

Related U.S. Application Data

(60) Provisional application No. 60/913,216, filed on Apr. 20, 2007.

(51) Int. Cl.
*A61K 31/44* (2006.01)
*C07D 417/00* (2006.01)
*C07D 401/00* (2006.01)

(52) U.S. Cl. ............... 514/341; 546/271.1; 546/256; 546/278.4; 546/278.7

(58) Field of Classification Search ............ 546/275.4, 546/271.1, 256, 278.7, 278.4; 514/406, 341
See application file for complete search history.

(56) References Cited

U.S. PATENT DOCUMENTS

| 3,528,980 | A | 9/1970 | Islip |
| 3,818,024 | A | 6/1974 | Krenzer |
| 3,939,122 | A | 2/1976 | Merten et al. |
| 3,949,002 | A | 4/1976 | Feasey et al. |
| 4,093,624 | A | 6/1978 | Revankar et al. |
| 4,296,237 | A | 10/1981 | Cragoe, Jr. et al. |
| 4,366,189 | A | 12/1982 | Burdeska et al. |
| 4,432,992 | A | 2/1984 | Cragoe, Jr. et al. |
| 4,525,450 | A | 6/1985 | Itoh et al. |
| 4,816,454 | A | 3/1989 | Zoller et al. |
| 5,103,014 | A | 4/1992 | Musser et al. |
| 5,162,360 | A | 11/1992 | Creswell et al. |
| 5,319,099 | A | 6/1994 | Kamata et al. |
| 5,494,925 | A | 2/1996 | Court et al. |
| 5,621,010 | A | 4/1997 | Sueda et al. |
| 5,721,231 | A | 2/1998 | Moriwaki et al. |
| 5,811,456 | A | 9/1998 | Seman et al. |
| 6,020,357 | A | 2/2000 | Pinto et al. |
| 6,080,763 | A | 6/2000 | Regan et al. |
| 6,197,599 | B1 | 3/2001 | Chin et al. |
| 6,235,786 | B1 | 5/2001 | Dai et al. |
| 6,294,573 | B1 | 9/2001 | Curtin et al. |
| 6,319,921 | B1 | 11/2001 | Cirillo et al. |
| 6,410,254 | B1 | 6/2002 | Finer et al. |
| 6,500,628 | B1 | 12/2002 | Robison |
| 6,525,046 | B1 | 2/2003 | Cirillo et al. |
| 6,645,990 | B2 | 11/2003 | Askew et al. |
| 6,916,924 | B2 | 7/2005 | Tan et al. |
| 7,135,550 | B2 | 11/2006 | Come et al. |
| 7,144,911 | B2 | 12/2006 | Flynn et al. |
| 7,202,257 | B2 | 4/2007 | Flynn et al. |
| 7,211,575 | B2 | 5/2007 | Moss et al |
| 7,342,037 | B2 | 3/2008 | Flynn et al. |
| 7,531,566 | B2 | 5/2009 | Flynn et al. |
| 2002/0058678 | A1 | 5/2002 | Cirillo et al. |
| 2003/0060455 | A1 | 3/2003 | Moss et al. |
| 2003/0232865 | A1 | 12/2003 | Cirillo et al. |
| 2004/0043388 | A1 | 3/2004 | Come et al. |
| 2004/0171075 | A1 | 9/2004 | Flynn et al. |
| 2004/0180906 | A1 | 9/2004 | Flynn et al. |
| 2005/0288286 | A1 | 12/2005 | Flynn et al. |
| 2007/0078121 | A1 | 4/2007 | Flynn et al. |
| 2007/0191336 | A1 | 8/2007 | Flynn et al. |
| 2008/0045531 | A1 | 2/2008 | Flynn et al. |
| 2008/0045706 | A1 | 2/2008 | Flynn et al. |
| 2008/0090856 | A1 | 4/2008 | Flynn et al. |
| 2008/0113967 | A1 | 5/2008 | Flynn et al. |
| 2008/0132506 | A1 | 6/2008 | Flynn et al. |
| 2008/0187978 | A1 | 8/2008 | Flynn et al. |
| 2008/0220497 | A1 | 9/2008 | Flynn et al. |
| 2008/0248487 | A1 | 10/2008 | Flynn et al. |
| 2008/0248548 | A1 | 10/2008 | Flynn et al. |

(Continued)

FOREIGN PATENT DOCUMENTS

DE 1115350 10/1961

(Continued)

OTHER PUBLICATIONS

"Additions and Corrections", Journal of Medicinal Chemistry, 32(12):2583 (1989).
"NHLBI LBC Computational Biophysics Scetion", CHARMM Documentation Index, http://www.lobos.nih.gov/Charmm/chmdoc. html, printed Mar. 4, 2005 (1 page).
"Trilateral Project WM4 - Comparative Studies in New Technologies: Report on Comparative Study on Protein 3-Dimensional Structure Related Claims—ANNEX 3: Comments of the USPTO", Vienna, Austria, Nov. 4-8, pp. 58-79 (2002).

(Continued)

*Primary Examiner* — Janet L Andres
*Assistant Examiner* — Binta M Robinson
(74) *Attorney, Agent, or Firm* — Cooley LLP

(57) ABSTRACT

Compounds of the present invention find utility in the treatment of mammalian cancers and especially human cancers including but not limited to malignant, melanomas, glioblastomas, ovarian cancer, pancreatic cancer, prostate cancer, lung cancers, breast cancers, kidney cancers, cervical carcinomas, metastasis of primary tumor sites, myeloproliferative diseases, leukemias, papillary thyroid carcinoma, non small cell lung cancer, mesothelioma, hypereosinophilic syndrome, gastrointestinal stromal tumors, colonic cancers, ocular diseases characterized by hyperproliferation leading to blindness including various retinopathies, rheumatoid arthritis, asthma, chronic obstructive pulmonary disease, mastocyclosis, mast cell leukemia, a disease caused by c-Abl kinase, oncogenic forms thereof, aberrant fusion proteins thereof and polymorphs thereof, or a disease caused by c-Kit kinase, oncogenic forms thereof, aberrant fusion proteins thereof and polymorphs thereof.

22 Claims, No Drawings

U.S. PATENT DOCUMENTS

| | | | |
|---|---|---|---|
| 2008/0261961 A1* | 10/2008 | Flynn et al. | 514/227.8 |
| 2009/0069310 A1 | 3/2009 | Flynn et al. | |
| 2009/0075986 A1 | 3/2009 | Flynn et al. | |
| 2009/0105230 A1 | 4/2009 | Flynn et al. | |
| 2009/0137021 A1 | 5/2009 | Flynn et al. | |
| 2009/0312349 A1 | 12/2009 | Flynn et al. | |

FOREIGN PATENT DOCUMENTS

| | | |
|---|---|---|
| DE | 4343831 | 6/1995 |
| EP | 0021228 | 1/1981 |
| EP | 0025232 | 3/1981 |
| EP | 0154190 A1 | 9/1985 |
| EP | 0661276 A1 | 7/1995 |
| EP | 0692483 | 1/1996 |
| EP | 0739884 A2 | 10/1996 |
| EP | 0867435 | 9/1998 |
| EP | 0927555 | 7/1999 |
| EP | 0956855 | 11/1999 |
| EP | 1281399 | 2/2003 |
| FR | 2337554 | 8/1977 |
| FR | 2396549 | 2/1979 |
| GB | 971307 | 9/1964 |
| GB | 1410279 A | 10/1975 |
| GB | 2220206 | 1/1990 |
| JP | 59-15247 | 1/1984 |
| JP | 9221476 A | 8/1997 |
| JP | 107804 | 1/1998 |
| JP | 2000275886 | 10/2000 |
| JP | 20012687 A | 7/2002 |
| WO | WO-91/19708 | 12/1991 |
| WO | WO-92/08693 | 5/1992 |
| WO | WO-94/18176 A1 | 8/1994 |
| WO | WO-94/21617 A1 | 9/1994 |
| WO | WO-94/24095 | 10/1994 |
| WO | WO-95/15954 | 6/1995 |
| WO | WO-95/29902 A1 | 11/1995 |
| WO | WO-95/34540 | 12/1995 |
| WO | WO-96/16046 | 5/1996 |
| WO | WO-96/19477 | 6/1996 |
| WO | WO-97/34900 | 9/1997 |
| WO | WO-98/22103 | 5/1998 |
| WO | WO-98/52558 | 11/1998 |
| WO | WO-99/15164 | 4/1999 |
| WO | WO-99/23091 | 5/1999 |
| WO | WO-99/23093 | 5/1999 |
| WO | WO-99/32106 | 7/1999 |
| WO | WO-99/32110 | 7/1999 |
| WO | WO-99/32111 | 7/1999 |
| WO | WO-99/32455 | 7/1999 |
| WO | WO-99/37622 A1 | 7/1999 |
| WO | WO-99/59959 | 11/1999 |
| WO | WO-00/06550 | 2/2000 |
| WO | WO-00/07980 | 2/2000 |
| WO | WO-00/18738 | 4/2000 |
| WO | WO-00/21927 A2 | 4/2000 |
| WO | WO-00/41698 A1 | 7/2000 |
| WO | WO-00/42012 A1 | 7/2000 |
| WO | WO-00/43384 | 7/2000 |
| WO | WO-00/55139 | 9/2000 |
| WO | WO-00/59506 A1 | 10/2000 |
| WO | WO-01/12621 | 2/2001 |
| WO | WO-01/14372 | 3/2001 |
| WO | WO-01/74771 | 10/2001 |
| WO | WO-01/96298 | 12/2001 |
| WO | WO-02/14291 | 2/2002 |
| WO | WO-02/14311 A2 | 2/2002 |
| WO | WO-02/28835 | 4/2002 |
| WO | WO-02/34727 | 5/2002 |
| WO | WO-02/060869 | 8/2002 |
| WO | WO-02/060876 | 8/2002 |
| WO | WO-02/062763 A2 | 8/2002 |
| WO | WO-02/070662 | 9/2002 |
| WO | WO-03/005999 | 1/2003 |
| WO | WO-03/053368 | 7/2003 |
| WO | WO-03/059373 | 7/2003 |
| WO | WO-03/068223 | 8/2003 |
| WO | WO-03/072577 | 9/2003 |
| WO | WO-03/084539 | 10/2003 |
| WO | WO 03/099771 A2 | 12/2003 |
| WO | WO-2004/004720 A1 | 1/2004 |
| WO | WO-2004/056783 | 7/2004 |
| WO | WO-2004/060306 | 7/2004 |
| WO | WO-2004/061084 | 7/2004 |
| WO | WO-2004/078128 A2 | 9/2004 |
| WO | WO-2004/113352 | 12/2004 |
| WO | WO-2005/002673 A1 | 1/2005 |
| WO | WO-2005/110994 | 11/2005 |
| WO | WO-2006/014290 | 2/2006 |
| WO | WO-2006071940 A2 | 7/2006 |
| WO | WO-2006/081034 | 8/2006 |
| WO | WO-2007/008917 | 1/2007 |
| WO | WO-2007/076473 A2 | 7/2007 |
| WO | WO-2008046003 A2 | 4/2008 |
| WO | WO-2008/131276 A1 | 10/2008 |

OTHER PUBLICATIONS

Aklilu, et al., "Increased PTHRP Production by a Tyrosine Kinase Oncogene, Tpr-Met: Rose of the Ras Signaling Pathway", The American Physiological Society, pp. E277-E283 (1996).

Albericio, et al., "Synthesis of a Sulfaydantion Library", J. Comb. Chem., 3:290-300 (2001).

Almerico, et al., "On the Preparation of 1-aryl-2-heteroaryl- and 2-aryl-1-heteroaryl-pyrroles as Useful Building Blocks for Biologically Interesting Heterocycles", ARKIVOC, Rudy Abramovitch Issue, pp. 129-142 (2001).

Anzai, et al., "Alkyl- and Arylthiation of Uracil and Indole", J. Heterocyclic Chem., 16:567-569 (1979).

Askew, et al., "Molecular Recognition with Convergent Functional Groups: 6. Synthetic and Structural Studies with a Model Receptor for Nucleic Acid Components", J. Am. Chem., 111:1082-1090 (1989).

Bais, et al., "Inhibition of Endogenous Wxalate Production: Biochemical Consideration of the Roles of Glycollate Oxidase and Lactate Dehydrogenase", Clinical Science, 76:303-309 (1989).

Baker, et al., "Irreversible Enzyme Inhibitors. 188. Inhibition of Mammalian Thymidine Phosphorylase", Journal of Medicinal Chemistry, 14:612-616 (1971).

Barker, et al., "Characterization of pp60c-src Tyrosine Kinase Activities Using a Continuous Assay: Autoactivation of the Enzyme is an Intermolecular Autophosphorylation Process", Biochemistry, 35:14843-14851 (1995).

Bausch, et al., "Proton-Transfer Chemistry of Urazoles and Related Imides, and Diacyl Hydrazides", J. Org. Chem., 56:5643-5651 (1991).

Benvenuti, et al., "Crystallization of Soluble Proteins in Vapor Diffusion for X-Ray Crystallography", Nature Protocols, 2(7):1633-1651 (2007).

Bosca, et al., "Circular Dichroism Analysis of Ligand-Induced Conformational Changes in Protein Kinase C", Biochem J., 290:827-832 (1993).

Boschelli, et al., "4-Anilino-3-quinolinecarbonitriles: An Emerging Class of Kinase Inhibitors", Current Topics in Medicinal Chemistry, 2:1051-1063 (2002).

Bourdonnec, et al., "Synthesis and Pharmacological Evaluation of New Pyrazolidine-3,5- diones as $AT_1$ Angiotensin II Receptor Antagonists", J. Med. Chem., 43:2685-2697 (2000).

Boyer, "Small Molecule Inhibitors of KDR (VEGFR-2) Kinase: An Overview of Structure Activity Relationships", Current Topics in Medicinal Chemisty, 2:973-1000 (2002).

Brady, et al., "Fast Prediction and Visualization of Protein Binding Pockets with PASS". Journal of Computer-Aided Molecular Design, 14:383-401 (2000).

Brasher, et al., "C-Abul has High Intrinsic Tyrosine Kinase Activity that is Stimulated by Mutation of the Src Homology 3 Domain and by Autophosphorylation at Two Distinct Regulatory Tyrosines", Journal of Biological Chemistry, 275:35631-35637 (2000).

Bullock, et al., "Prospects for Kinase Activity Modulators in the Treatment of Diabetes and Diabetic Complications", Current Topics in Medicinal Chemistry, 2:915-938 (2002).

Byron, et al., "The Synthesis of some Substituted Biphenyl-4-carboxylic Acids, 4-Biphenylylacetic Acids, and 4-Aminobiphenyls", J. Chem. Soc. (C), Organic, pp. 840-845 (1966).

Cardillo, et al., "Sulle 1,2-difenil-3.5-dichetopirazolidine", Gazz. Chim., Ital., 9:973-985 (1966)—Italian Language.

Chen, et al., "Biochemical Evidence for the Autophosphorylation and Transphosphorylation of Transforming Growth Factor β Receptor Kinases", Proc. Natl. Acad. Sci. USA, 92:1565-1569 (1995).

Cheng, et al., "Novel Solution Phase Strategy for the Synthesis of Chemical Libraries Containing Small Organic Molecules", J. Am. Chem. Soc., 118:2567-2573 (1996).

Cheng, et al., "Synthesis and SAR of Heteroaryl-phenyl-substituted Pyrazole Derivatives as Highly Selective and Potent Canine COX-2 Inhibitors", Bioorganic & Medicinal Chemistry Letters, 16:2076-2080 (2006).

Chu, et al., "Using Affinity Capillary Electrophoresis to Determine Binding Stoichiometries of Protein-Ligand Interactions", Biochemistry, 33:10616-10621 (1994).

Cirillo, et al. "The Non-Diaryl Heterocycle Classes of p38 MAP Kinase Inhibitors", Current Topics in Medicinal Chemistry, 2:1021-1035 (2002).

Closier, et al., "Nitrofuryl Heterocyclics. 1", Journal of Medicinal Chemistry, 13(4):638-640 (1970).

Cockerill, et al., "Small Molecule Inhibitors of the Class 1 Receptor Tyrosine Kinase Family", Current Topics in Medicinal Chemistry, 2:1001-1010 (2002).

Colton, et al., "Affinity Capillary Electrophoresis: A Physical-Organic Tool for Studying Interactions in Biomolecular Recognition", Electrophoresis, 19:367-382 (1998).

Cortes, et al., "Results of Imatinib Mesylate Therapy in Patients with Refractory or Recurrent Acute Myeloid Leukemia, High-Risk Myelodysplastic Syndrime, and Myeloproliferative Disorders", Cancer, 97(11):2760-2766 (2003).

Cross, et al., "Inhibition of Glycogen Synthase Kinase-3 by Insulin Mediated by Protein Kinase B", Nature, 378:785-789 (1995).

Cudney, "Preface: Protein Crystallization and Dumb Luck", The Rigaku Journal, 16(1):1-7 (1999).

Dajani, et al., "Crystal Structur of Glycogen Synthase Kinas 3β: Structural Basis for Phosphate-Primed Substrate Specificity and Autoinhibition", Cell, 105:721-732 (2001).

Dajani, et al., "Structural Basis for Recruitment of Glycogen Synthase Kinase 3β to the Axin-APC Scaffold Complex", EMBO, 22(3):494-501 (2003).

Daley, et al., "Induction of Chronic Myelogenous Leukemia in Mice by the P210$^{bcr/abl}$ Gene of the Philadelphia Chromosome", Science, 247:824-830 (1990) (8 pgs).

Davis, et al., "Iterative Size-Exclusion Chromatography Coupled with Liquid Chromatographic Mass Spectrometry to Enrich and Identify Tight-Binding Ligands from Complex Mixtures", Tetrahedron, 55:11653-11667 (1999).

de Boer, et al., "Synthesis and Characterization of Conjugated Mono- and Dithiol Oligomers and Characterization of Their Self-Assembled Monolayers", Langmuir, 19:4272-4284 (2003).

de Silva, et al., "Gastrointestinal Stromal Tumors (GIST): C-kin Mutations, CD117 Expression, Differential Diagnosis and Targeted Cancer Therapy with Imatinib", Pathology Oncology Research, 9(1):13-19 (2003).

Deng, et al., "Expression, Characterization, and Crystallization of the Pyrophosphate-Dependent Phosphofructo-1-Kinase of Borrelia Burgdorferi", Archives of Biochemistry and Biophysics, 371(2):326-331 (1999).

Dess, et al., "A Useful 12-I-5 Triacetoxyperiodiane (the Dess-Martin Periodiane) for Selective Oxidation of Primary or Secondary Alcohols and a Variety of Related 12-I-5 Species", J. Am. Chem., Soc., 113:7277-7287 (1991).

Dumas, "Preface", *Current Topics in Medicinal Chemisty* (2002) (1 Page).

Dumas, "Protein Kinase Inhibitors: Emerging Pharmacophores", Exp. Opin. Ther. Patent, 11:405-429 (2001).

Dumas, et al., "Discovery of a New Class of p38 Kinase Inhibitors", Bioorganic & Medicinal Chemistry Letters, 10:2047-2050 (2000).

Dumas, et al., "Recent Developments in the Discovery of Protein Kinase Inhibitors from the Urea Class", Current Opinion in Drug Discovery & Development, 7(5):600-616 (2004).

Ettmayer, et al., "Lessons Learned from Marketed and Investigational Prodrugs", Journal of Medicinal Chemistry, 47(10):2393-2404 (2004).

Ewing, "Critical Evaluation of Search Algorithms for Automated Molecular Docking and Database Screening", Journal of Computational Chemistry, 18(9):1175-1189 (1997).

Farooqui, et al., "Interactions Between Neural Membrane Glycerophospholipid and Sphingolipid Mediators: A Recipe for Neural Cell Survival or Suicide", Journal of Neuroscience Research, 85:1834-1850 (2007).

Fathalla, "Synthesis of New Pyrazolo[1,5-a]pyrimidine Derivative Using 5-Aminouracil and Ketene Dithiacetal", Arch Pharm Res, 22(6):571-574 (1999).

Fathalla, et al., "Synthesis of New Uracil-5-Sulfonamide Derivatives and Immuno-Stimulatory Effect of a Chemically Modified Hemolymph of Biomphalaria Alexandrina on Schistosoma Manosi Infected Mice", Arch Pharm Res., 26(5):358-366 (2003).

Fathalla, et al., "Synthesis of New Uracil-5-Sulphonamide-p-Phenyl Derivatives and Their Effect on *Biomphalaria alexandrina* Snail's Nucleoproteins", Arch. Pharm. Res., 23(2):128-138 (2000).

Flatt, et al., "Synthesis of Thiol Substituted Oligoanilines for Molecular Device Candidates", Tetrahedron Letters, 44:6699-6702 (2003).

Fletcher, et al., "Diagnosis of Gastrointestinal Stromal Tumors: A Consensus Approach", 33(5):459-465 (2002).

Frame, et al., "A Common Phosphate Binding Site Explains the Unique Substrate Specificity of GSK3 and Its Inactivation by Phosphorylation", Molecular Cell, 7:1321-1327 (2001).

Furyua, et al., "Addition of 4-Ethoxyimidazoles to Dimethyl Acetylenedicarboxylate and Transformation of the Adducts to Pyrimidian-5-yl Acetates", Chem. Pharm. Bull., 36(5):1669-1675 (1988).

Garcia-Tellado, et al., "Molecular Recognition in the Solid Waste State: Controlled Assembly of Hydrogen-Bonded Molecular Sheets", J. Am. Chem. Soc., 113:9265-9269 (1991).

Gishizky, et al., "Efficient Transplantation of BCR-ABL-Induced Chronic Myelogenous Leukemia-Like Syndrome in Mice", Proceedings of the National Academy of Sciences of the United States of America, 90(8):3755-3759 (1993) (6 pages).

Greene, et al., "Chapter 7: Protection for the Amino Group", in Protective Groups in Organic Synthesis, Third Edition, pp. 494-653 (1999).

Griffith, et al., "TPAP: Tetra-n-propylammonium Perruthenate, A Mild and Convenient Oxidant for Alcohols", Aldrichimica Acta, 23(1):13-19 (1990).

Guzel, "Investigation of the Relationship Between the Inhibitory Activity of Glycolic Acid Oxidase (GAO) and its Chemical Structure: Electron-Topological Approach", Journal of Molecular Structure, 366:131-137 (1996).

Haar, et al., "Structure of GSK3β Reveals a Primed Phosphorylation Mechanism", Nature Structural Biology, 8(7):593-596 (2001).

Haesslein, et al., "Recent Advances in Cyclin-Dependent Kinase Inhibition. Purine-Based Derivatives as Anti-Cancer Agents. Roles and Perspectives for the Future", Current Topics in Medicinal Chemistry, 2:1037-1050 (2002).

Heegaard, et al., "Affinity Capillary Electrophoresis: Important Application Areas and Some Recent Developments", Journal of Chromatography B, 715:29-54 (1998).

Honda, et al., "Determination of the Association Constant of Monovalent Mode Protein-Sugar Interaction by Capillary Zone Electrophoresis", Journal of Chromatography, 597:377-382 (1992).

Hu, et al., "Capillary Electrophoresis for the Analysis of Biopolymers", Anal., Chem., 74:2833-2850 (2002).

Huang, et al., "Inhibition of Nucleoside Transport by Protein Kinase Inhibitors", The Journal of Pharmacology and Experimental Therapeutics, 304(2):753-760 (2003).

Hubbard, "Crystal Structure of the Activated Insulin Receptor Tyrosine Kinase in Complex with Peptide Substrate and ATP Analog", EMBO, 16(18):5573-5581 (1997).

Hubbard, et al., "Crystal Structure of the Tyrosine Kinase Domain of the Human Insulin Receptor", Nature, 374:746-754 (1994).
Hughes, et al., "Modulation of the Glycogen Synthase Kinase-3 Family by Tyrosine Phosphorylation", EMBO, 12(2):803-808 (1993).
Huse, et al., "Crystal Structure of the Cytoplasmic Domain of the Type I TGFβ Receptor in Complex with FKBP12", Cell, 96:425-436 (1999).
Huse, et al., "The Confomational Plasticity of Protein Kinases", Cell, 109:275-282 (2002).
Huse, et al., "The TGFβ Receptor Activation Process: An Inhibitor- to Substrate-Binding Switch", Molecular Cell, 8:671-682 (2001).
Igarashi, et al., "Antimicrobial Activities of 2-arylthio-N-alkylmaleimides", Journal of Industrial Microbiology, 9:91-96 (1992).
International Human Genome Sequencing Consortium, "Initial Sequencing and Analysis of the Human Genome", Nature, 409:860-921 (2001).
International Search Report issued for PCT/US2008/060867, mailed Sep. 29, 2008 (5 pages).
International Search Report issued for PCT/US2008/060896, mailed Sep. 29, 2008 (5 pages).
Ishida, et al., "Molecular Arrangement and Electrical Conduction of Self-Assembled Monolayers Made from Terphenyl Thiols", Surface Sciences, 514:187-193 (2002).
Islip, et al., "Nitrofuryl Heterocyclics 3", Journal of Medicinal Chemistry, 16(11):1309-1310 (1973).
Jackson, et al., "N-Terminal Mutations Activate the Leukemogenic Potential of the Myristoylated form of c-abl", EMBO, 8(2):449-456 (1989).
Jackson, et al., "Pyridinylimidazole Based p38 MAP Kinase Inhibitors", Current Topics in Medicinal Chemistry, 2:1011-1020 (2002).
Jiang, et al., ""Soft Docking": Matching of Molecular Surface Cubes", J. Mol. Biol., 219:79-102 (1991).
Jiang, et al., "Synthesis and SAR Investigations for Novel Melanin-Concentrating Hormone 1 Receptor (MCH[1]) Antagonists Part 1. The Discovery of Arylacetamides as Viable Replacements for the Dihydropyrimidione Moiety of an HTS Hit", J. Med. Chem., 50:3870-3882 (2007).
Johnson, "Circular Dichroism Spectroscopy and The Vacuum Ultraviolet Region", Ann. Rev. Phys. Chem., 29:93-114 (1978).
Johnson, "Protein Secondary Structure and Circular Dichroism: A Practical Guide", Proteins: Structure, Function, and Genetics, 7:205-214 (1990).
Johnson, et al., "An Evaluation of the Effect of Light Stabilisers on the Exterior Durability of Polyester Powder Coatings for the Architectural Market", Surface Coatings International, 3:134-141 (1999).
Johnson, et al., "The Stereochemistry of Oxidation at Sulfur Oxidation of 2-Thiabicyclo[2.2.1]Hpetane", Tetrahedron, 25:5649-5653 (1969).
Katritzky, et al., "Novel Chromophoric Heterocycles Based on Maleimide and Naphthoquinone", J. Heterocyclic Chem., 26:885-892 (1989).
Kern, et al., "Synthese von Makromolekeln einheitlicher Broβe. II Mitt: Syntheses neuer Diol-oligo-urethane nach dem Duplikationsverfahren", Makromolekulara Chemie, 16:89-107 (1955)—English Summary (20 pages).
Kim, et al., "Solid Phase Synthesis of Benzamidine and Butylamine-Derived Hydantoin Libraries", Molecular Diversity, 3:129-132 (1998).
Klayman, et al., "The Reaction of S-Methiodide Derivatives of Activated Thioureas with Hydroxylic Compounds. A Novel Synthesis of Mercaptans", J. Org. Chem., 37(10):1532-1537 (1972).
Kleywegt, et al., "Detection, Delineation, Measurement and Display of Cavities in Macromolecular Structures", Acta Cryst, D50:178-185 (1994).
Koch, et al., "QSAR and Molecular Modelling for a Series of Isomeric X-Sulfanilamido-1-phenylpyrazoles", Quant. Struct. Act. Relat., 12:373-382 (1993).
Krasovitskii, et al., "Synthesis and Spectral-Luminescence Properties of Hetarylethylene Derivatives of 2,5-Diphenyloxazole and 2,5-Diphenyl-1,3,4-Oxadiazole", Khimiya Geterotsiklicheskikh Soedinenii, 5:617-621 (1982)—English Translation (10 pages).

Kuhn, et al., "The Genesis of High-Throughput Structure-Based Drug Discovery using Protein Crystallography", Analytical Techniques, Current Opinion in Chemical Biology, 6:704-710 (2002).
Kumar, et al., "P38 Map Kinases: Key Signalling Molecules as Therapeutic Targets for Inflammatory Diseases", Nature Reviews Drug Discovery, 2:717-726 (2003).
Kundrot, "Which Strategy for a Protein Crystallization Project", CMLS, Cell. Mol. Life Sci., 61:525-536 (2004).
Kundu, et al., "Depropargylation Under Palladium-Copper Catatlysis: Synthesis of Diaryl Sulfides", Tetrahedron, 57:5885-5895 (2001).
Kurogi, et al., "Discovery of Novel Mesangial Cell Proliferation Inhibitors Using a Three-Dimensional Database Searching Method", J. Med. Chem., 44:2304-2307 (2001).
Kwong, et al., "A General, Efficient, and Inexpensive Catalyst System for the Coupling Aryl Iodides and Thiols", Organic Letters, 4(20):3517-3520 (2002).
Laskowski, "SURFNET: A Program for Visualizing Molecular Surfaces, Cavities, and Intermolecular Interactions", Journal of Molecular Graphics, 13:323-330 (1995).
Leca, et al., "A New Practical One-Pot Access to Sulfonimidates", Organic Letters, 4(23):4093-4095 (2002).
Lefevre, et al., "Roles of Stem Cell Factor/c-Kit and Effects of Glivec®/STI571 in Human Uveal Melanoma Cell Turmorigenesis", Journal of Biological Chemistry, 279(30):31769-31779 (2004).
Lesort, et al., "Insulin Transiently Increases Tau Phosphorylation: Involvement of Glycogen Synthase Kinase-3β and Fyn Tyrosine Kinase", Journal of Neurochemistry, 72(2):576-584 (1999).
Leung, et al., "The Difluoromethylensulfonic Acid Groups as a Monoanionic Phosphate Surrogate for Obtaining PTP1B Inhibitors", Bioorganic & Medicinal Chemistry, 10:2309-2323 (2002).
Li, et al., "Targeting Serine/Threonine Protein Kinase B/Akt and Cell-cycle Checkpoint Kinases for Treating Cancer", Current Topics in Medicinal Chemistry, 2:939-971 (2002).
Li, et al., "The P190, {210, and P230 Forms of the BCR/ABL Oncogene Induce a Similar Chronic Myeloid Leukemia-like Syndrome in Mice but Have Different Lymphoid Leukemogenic Activity", J. Exp. Med., 189(9):1399-1412 (1999).
Link, et al., "Synthesis of 8-Substituted 5-Deazaflavins", J. Heterocyclic Chem, 22:841-848 (1985).
Lipinski, et al., "Experimental and Computational Approaches to Estimate Solubility and Permeability in Drug Discovery and Development Settings", Advanced Drug Delivery Reviews, 23:3-25 (1997).
Loren, et al., "NH-1,2,3-Triazoles from Azidomethyl Pivalate and Carbamates: Base-Labile N-Protecting Groups", SYNLETT, 18:2847-2850 (2005).
Lorenzi, et al., "Amino Acid Ester Prodrugs of 2-Bromo-5,6-dichloro-1-(β-D-ribofuranosyl)benzimidazole Enhance Metabolic Stability in Vitro and in Vivo", Journal of Pharmacology and Experimental Therapeutics, 314(2):883-890 (2005).
Lowinger, et al., "Design and Discovery of Small Molecules Targeting Raf-1 Kinase", Current Pharmaceutical Design, 8:2269-2278 (2002) (11 pages).
Ma, et al., "c-MET Mutational Analysis in Small Cell Lung Cancer: Novel Juxtamembrane Domain Mutations Regulating Cytoskeletal Functions", Cancer Research, 63:6272-6281 (2003).
Ma, et al., "c-MET: Structure, Functions and Potential for Therapeutic Inhibition", Cancer and Metastasis Reviews, 22:309-325 (2003).
Mallakpour, et al., "Uncatalyzed Polymerization of Bistriazolinediones with Electron-Rich Aromatic Compounds via Electrophilic Aromatic Substitution", Journal of Polymer Science: Part A: Polymer Chemistry, 27:217-235 (1989).
Mamaev, et al., "Synthesis of 2,5'-Bipyrimidines from Substituted 5-Cyanopyrimidines", Khimiya Geterotsiklicheskikh Soedinenni, 24(3):371-375- (1988)—English Translation.
*March's Advanced Organic Chemistry: Reactions, Mechanisms, and Structure, Fifth Edition*, Smith and March Editors, Wiley-Interscience Publication (2001) (4 pages).
March, et al., "Tautomerism", from *March's Advanced Organic Chemistry, 4th Edition*, Wiley-Interscience, pp. 69-74.
Martinez, et al., "First Non-ATP Competitive Glycogen Synthase Kinase 3β (GSK-3β) Inhibitors: Thiadizolidinones (TDZD) as Potential Drugs for the Treatment of Alzheimers Disease", J. Med. Chem., 45(2002)1292-1299 (2002).

Mattsson, et al., "Six X-Linked Agammaglobulinemia-Causing Missense Mutations in the Src Homology 2 Domain of Bruton's Tyrosine Kinase: Phosphotyrosine-Binding and Circular Dichroism Analysis", Journal of Immunology, pp. 4170-4177 (2000).

McPherson, "Current Approaches to Macromolecular Crystallization", Eur. J. Biochem, 189:1-23 (1990).

Medebielle, et al., "A Convenient Synthesis of Perfluoroalkylated and Fluorinated-Aryl Nitrogen Bases by Electrochemically Induced SRN1 Substitution", J. Org. Chem., 61:1331-1340 (1996).

Medebielle, et al., "A New Convenient Synthesis of 5-Aryl Uracils Using SRN1 Aromatic Nucleophilic Substitution", Tetrahedron Letters, 34(21):3409-3412 (1993).

Mikhaleva, et al., "Relative Reactivities of the Chlorine Atoms of 2,2',4-Trichloro-4',5-Dipyrimidinyl in its Reaction with Piperidine", Khimiya Geterotsiklicheskikh Soedinenii, 6:821-826 (1979)—English Translation (12 pages).

Morris, et al., "Automated Docking of Flexible Ligands to Macromolecules", AutoDock Website, www.scripps.edu/mb/olson/doc/autodock/, printed Mar. 3, 2005 (3 pages).

Morris, et al., "Automated Docking Using a Lamarckian Genetic Algorithm and an Empirical Binding Free Energy Function", Journal of Computational Chemistry, 19(14):1639-1662 (1998).

Morstyn, et al., "Stem Cell Factor Is a Potent Synergistic Factor in Hematopoiesis", Oncology, 51:205-214 (1994).

Moss, et al., "Basic Terminology of Stereochemistry", Pure & Appl. Chem., 6812):2193-2222 (1996).

Muller, "Glossary of Terms Used in Physical Organic Chemistry", Pure & Appl. Chem., 66(5):1077-1184 (1994).

Muller, et al., "A General Synthesis of 4-Substituted 1,1-Dioxo-1,2,5-thiadiazolidin-3-ones Derived from α-Amino Acids", J. Org. Chem., 54:4471-473 (1989).

Murayama, et al., "JNK (c-Jun $NH_2$ Terminal Kinase) and p38 During Ischemia Reperfusion Injury in the Small Intestine" Transplantation, 81(9):1325-1330 (2006).

Mutlib, et al., "Disposition of 1-[3-(Aminomethyl)phenyl]-N-[-fluoro-2'-(methylsulfonyl)-[1,1'-biphenyl]-4-yl]-3(trifluoromethyl)-1H-pyrazole-5-carboxamide (DPC 423) by Novel Metabolic Pathways. Characterization of Unusual Metabolites by Liquid Chromatography/Mass Spectrometry and NMR", Chem. Res. Toxicol., 15:48-62 (2002).

Mutlib, et al., "P450-Mediated Metabolism of 1-[3-(Aminomethyl)phenyl]-N-[3-fluoro-2'-(methylsulfonyl)-[1,1'-biphenyl]-4-yl]-3(trifluoromethyl)-1H-pyrazole-5-carboxamide (DCP 423) and Its Analogues to Aldoximes. Characterization of Glutathione Conjugates of Postulated Intermediates Derived from Aloximes", Chem. Res. Toxicol., 15:63-75 (2002).

Nagar, et al., "Crystal Structures of the Kinase Domain of c-Abl in Complex with the Small Molecule Inhibitors PD173955 and Imatinib (STI-571)", Cancer Research, 62:4236-4243 (2002).

Nagar, et al., "Structural Basis for the Autoinhibition of c-Abl Tyrosine Kinase", Cell, 112:859-871 (2003).

Nakopoulou, et al., "c-Met Tyrosine Kinase Receptor Expression is Associated with Abnormal (β-catenin Expression and Favourable Prognostic Factors in Invasive Breast Carcinoma", Histopathology, 36:313-325 (2000).

Nantaka-Namirski, et al., "Condensation Reaction of Ethyl (4-Uracil)-Acetate with Ethyl Orthoformate", ACTA Polon. Pharm XXVII, 28(5):455-463 (1971).

National Academy of Sciences, "Abstracts of Papers Presented at the Autumn Meeting, Nov. 14-16, 1960", Science, 132:1488-1501 (1960) (15 pages).

Nicolaou, et al., "Molecular Design and Chemical Synthesis of a Highly Potent Epothilone", ChemMedChem, 1:41-44 (2006).

Nikolaev, et al., "Solubility Polytherm in the System $HNO_3$-$H_2O$-$(C_4H_9O)PO(C_4H_9)2$", Doklady Akademii Nauk SSSR, 160(4):841-844 (1965)—English Translation.

Nofal, et al., "Synthesis of Novel Uracil-5-Sulphonamide Derivatives of Possible Biological Activity", Egypt J. Chem., 33(4):375-380 (1990).

O'Dell, et al., "Treatment of Rheumatoid Arthritis with Methotrexate Alone, Sulfasalazine and Hydroxychloroquine, or a Combination of All Three Medications", New England J. Med., 334(20):1287-1291(1996).

O'Neill, "Targeting Signal Transduction as a Strategy to Treat Inflammatory Diseases", Nature Review Drug Discovery, Published Online Jun. 9, 2006, www.nature.com/reviews/drugdisc (15 pages).

Okano, et al., "o-Bromophenylzinc Compound: A Readily Available and Efficient Synthetic Equivalent of o-Phenylene 1-Anion 2-Cation", Tetrahedron Letters 39:3001-3004 (1998).

Okishio, et al., "Differential Ligand Recognition by the Src and Phosphatidylinositol 3-Kinase Src Homology 3 Domains: Circular Dichroism and Ultraviolet Resonance Raman Studies", Biochemistry, 42:208-216 (2003).

Okishio, et al., "Identification of Tyrosine Residues Involved in Ligand Recognition by the Phosphatidylinositol 3-Kinase Src Homology 3 Domain: Circular Dichroism and UV Resonance Raman Studies", Biochemistry, 40:15797-15804 (2001).

Okishio, et al., "Role of the Conserved Acidic Residue Asp21 in the Structure of Phosphatidylinositol 3-Kinase Src Homolgy 3 Domain: Circular Dichroism and Nuclear Magnetic Resonance Studies", Biochemistry 40:119-129 (2001).

Parang, et al., "Mechanism-based Design of a Protein Kinase Inhibitor", Nature Structural Biology, 8(1):37-41 (2001).

Pargellis, et al., "Inhibition of p38 MAP Kinase by Utilizing a Novel Allosteric Binding Site", Nature Structural Biology, 9(4):268-272 (2002).

Park, et al., "Mechanism of *met* Oncogene Activation", Cell, 45:895-904 (1986).

Pearlman, et al., "Assisted Model Building with Energy Refinement", Amber Home Page, amber.scripts.edu (9 pages).

Pedersen, "The Preparation of Some N-Methyl-1,2,3-Triazoles", Acta Chimica Scandinavica, 13(5):888-892 (1959).

Peng, et al., "Identification of Novel Inhibitors of BCR-ABL Tyrosine Kinase via Virtual Screening", Bioorganic & Medicinal Chemistry Letters, 13:3693-3699 (2003).

Pereira, et al., "The Role of c-kit and Imatinib Mesylate in Uveal Melonoma", Journal of Carcinogenesis, 4:19 (2005), downloaded from www.carcinogenesis.com/content/4/1/19, Sep. 3, 2008 (8 pages).

Picard, et al., "Inhibitors of Acyl-CoA: Cholesterol O-Acyltrasferase. 17. Structure-Activity Relationships of Several Series of Compounds Derived from N-Chlorosulfonyl Isocyanate", J. Med. Chem., 39:1243-1252 (1996).

Pluk, et al., "Autoinhibition of c-Abl", Cell, 108:247-259 (2002).

Ponzetto, et al., "A Novel Recognition Motif for Phosphatidylinositol 3-Kinase Binding Mediates Its Association with the Hepatocyte Growth Factor/Scatter Factor Receptor", Molecular and Cellular Biology, 13(8):4600-4608 (1993).

Raimbault, et al., "Effects of pH and KCI on the Conformations of Creatine Kinase from Rabbit Muscle", Eur. J. Biochem., 234:570-578 (1995).

Rebek, et al. "Convergent Functional Groups: Synthetic and Structural Studies", J. Am. Chem. Soc., 107:7476-7481 (1985).

Rebek, et al., "Convergent Functional Groups. 2. Structure and Selectivity in Olefin Epoxidation with Peracids", J. Org. Chem., 51:1649-1653 (1986).

Reed, et al., "Circular Dichroic Evidence for an Ordered Sequence Ligand/Binding Site Interactions in the Catalytic Reaction of the cAMP-Dependent Protein Kinase", Biochemistry, 24:2967-2973 (1985).

Regan, et al., "Pyrazole Urea-Based Inhibitors of p38 MAP Kinase: From Lead Compound to Clinical Candidate", J. Med. Chem., 45:2994-3008 (2002).

Regan, et al., "Structure-Activity Relationships of the p38α MAP Kinase Inhibitor 1-(5-*tert*-Butyl-2-*p*-tolyl-2*H*-pyrazol-3-yl)-3-[4-(2-morpholin-4-yl-ethoxy)naph-thalen-1-yl]urea (BIRB 796)", J. Med. Chem., 46:4676-4686 (2003).

Rooney, et al., "Inhibitors of Gylcolic Acid Oxidase. 4-Substituted 3-Hydroxy-1H-pyrrole-2,5-dione Derivatives", J. Med. Chem., 26(5):700-714 (1983).

Roux, et al., "ERK and p38 MAPK-Activated Protein Kinases: a Family of Protein Kinases with Diverse Biological Functions", Microbiology and Molecular Biology Reviews, 68(2):320-344 (2004).

Rowley, "A New Consistent Chromosomal Abnormality in Chronic Myelogenous Leukaemia Identified by Quinacrine Fluorescence and Giemsa Staining", Nature, 243:290-293 (1973).

Russell, et al., "3-[3-(Piperdin-1-yl)propyl]indoles as Highly Selective h5-HT$_{1D}$ Receptor", J. Med. Chem., 42:4981-5001 (1999).

Saiga, et al., "Consecutive Cross-Coupling of o-Phenylenedizinc Compound with Acyl and/or Aryl Halides in the Presence of Pd(0)-tris(2,4,6-trimethoxyphenyl)phosphine", Tetrahedron Letters, 41:4629-4632 (2000).

Sakamoto, et al., "Condensed Heteroaromatic Ring Systems. XIX. Synthesis and Reactions of 5-(Tributylstannyl)Isoxazoles", Tetrahedron, 47(28):5111-5118 (1991).

Sakuma, et al., "c-kit Gene Mutations in Intracranial Germinomas", Cancer Sci, 95(9):716-720 (2004).

Satsangi, et al., "1-(4-Substituted-thiazol-2-yl)hydatoins as Anti-inflammatory and CNS-Active Agents", Pharmazie, 38:341-342 (1983).

Schindler, et al., "Structural Mechanism for STI-571 Inhibition of Abelson Tyrosine Kinase", Science, 289:1938-1942 (2000).

Schmidt, et al., "Germline and Somatic Mutations in the Tyrosine Kinase Domain of the MET proto-oncogene in Papillary Renal Carcinomas", Nature Genetics, 16:68-73 (1997).

Schmidt, et al., "Novel Mutations of the MET Proto-oncogene in Papillary Renal Carcinomas", Oncogene, 18:2343-2350 (1999).

Seimiya, et al., "Telomere Shortening and Growth Inhibition of Human Cancer Cells by Novel Synthetic Telomerase Inhibitors MST-312, MST-295, and MST-199", Molecular Cancer Therapeutics, 1:657-665 (2002).

Seminario, et al., "Theoretical Study of a Molecular Resonant Tunneling Diode", J. Am. Chem. Soc., 122:3015-3020 (2000).

Shah, et al., "Circular Dichroic Studies of Protein Kinase C and its Interactions with Calcium and Lipid Vesicles", Biochimica et Biophysica Acta, 1119:19-26 (1992).

Shi, et al., "Abnormal Diels-Alder Reaction of 5-Alkoxythiazoles with Highly Reactive Dienophiles; 4-Phenyl-3H-1,2,4-triazole-3,5(4H)-dione, Diethyl Azodicarboxylate, and Diethyl Oxomalonate", Bull. Chem. Soc. Jpn., 65:3315-3321 (1992).

Shinkai, et al., "Coenzyme Models, Part 45. Synthesis of Atropisomeric Flavins and their Novel Redox-induced Racemisation", J. Chem. Soc. Perkin Trans., pp. 313-319 (1988).

Shiozaki, et al., "Impaired Differentiation of Endocrine and Exocrine Cells of the Pancreas in Transgenic Mouse Expressing the Truncated Type II Activin Receptor", Biochimica et Biophysica Acta, 1450:1-11 (1999).

Stout, et al., "High-Throughput Structural Biology in Drug Discovery: Protein Kinases", Current Pharmaceutical Design, 10:1069-1082 (2004).

Sugden, et al., ""Stress-Responsive" Mitogen-Activated Protein Kinases (c-Jun N-Terminal Kinases and p38 Mitogen-Activated Protein Kinases) in the Myocardium", Circulation Research—Journal of the American Heart Association, 83:345-352 (1998).

Tanis, et al., "Two Distinct Phosphorylation Pathways Have Additive Effects on Abl Family Kinase Activation", Molecular and Cellular Biology, 23(11):3884-3896 (2003).

Teague, "Implications of Protein Flexibility for Drug Discovery", Nature Reviews, 2:527-541 (2003).

Tominaga, et al., "General model for Estimation of the Inhibition of Protein Kinases Using Monte Carlo Simulations", J. Med. Chem., 47:2534-2549 (2004).

Tremblay, et al., "Efficient Solid-Phase Synthesis of Sulfahydantoins", J. Comb. Chem., 4:429-435 (2002).

Tsuzuki, et al., "Synthesis and Structure-Activity Relationships of Novel 7-Substituted 1,4-Dihydro-4-oxo-1-(2-thiazolyl)-1,8-napthyridine-3-carboxylic Acids as Antitumor Agents. Part 2", J. Med. Chem., 47:2097-2109 (2004).

Van Etten, "Cycling, Stressed-Out and Nervous: Cellular Functions of c-Abl", Trends in Cell Biology, 9:179-186 (1999).

Venter, et al., "The Sequence of the Human Genome", Science, 291:1304-1351, Feb. 16, 2001; Erratum, Jun. 8, 2001 (49 pages).

Waetzig, et al., "Review Article: Mitogen-Activated Protein Kinases in Chronic Intestinal Inflammation—Targeting Ancient Pathways to Treat Modern Diseases", Aliment Pharmacol Ther, 18:17-32 (2003).

Wan, et al., "Mechanism of Activation of the RAF-ERK Signaling Pathway by Oncogenic Mutations of B-RAF", Cell, 116:855-867 (2004).

Welker, et al., "Glucocorticoid-Induced Modulation of Cytokine Secretion from Normal and Leukemic Human Myelomonocytic Cells", Int. Arch. Allergy Immunol, 109:110-115 (1996).

Wentland, et al., "3-Quinolinecarboxamides. A Series of Novel Orally-Active Antiherpetic Agents", J. Med. Chem., 36:1580-1596 (1993).

Wilson, et al., "The Structural Basis for the Specificity of Pyridinylimidazole Inhibitors of p38 MAP Kinase", Chemistry & Biology, 4(6):423-431 (1997).

Wilson, et el., "Laser-Jet Delayed Trapping: Electron-Transfer Trapping of the Photoenol from 2-Methylbenzophenone", J. Am. Chem. Soc., 109:4743-4745 (1987).

Wolter, et al., "Copper-Catalyzed Coupling of Aryl Iodides with Aliphatic Alcohols", Organic Letters, 4(6):973-976 (2002).

Wrana, et al., "Mechanism of Activation of the TGF-β Receptor", Nature, 370:341-347 (1994).

Wu, et al., "Discovery of a Novel Family of CDK Inhibitors with the Program LIDAEUS: Structual Basis for Ligand-Induced Disordering of the Acivation Loop", Structure, 11:399-410 (2003).

Yang, et al., "Molecular Mechanism for the Regulation of Protein Kinase B/Akt by Hydrophobic Motif Phosphorylation", Molecular Cell, 9:1227-1240 (2002).

Yang, et al., "Palladium-Catalyzed Amination of Arly Halides and Sulfonates", Journal of Organometallic Chemistry, 576:125-146 (1999).

Yarden, et al., "Human Proto-oncogene c-kit: a New Cell Surface Receptor Tyrosine Kinase for an Unidentified Ligand", The EMBO Journal, 6(11):3341-3351 (1987).

Yoneda, et al., "A New Synthesis of Purines", J.C.S. Chem. Comm., p. 551 (1974).

Yonezawa, et al., "Synthesis of Sequentially Controlled Isomeric, Wholly aromatic Polyketones Composed of 2-trifluoromethylbiphenylene and 2,2'-dimethoxybiphenylene Units", Reactive & Functional Polymers, 52:19-30 (2002).

Yoshimoto, et al., "Correlation Analysis of Baker's Studies on Enzyme Inhibition. 2. Chymotrypsin, Trypsin, Thymidine Phosphorylase, Uridine Phosphorylase, Thimidylate Synthetase, Cytosine Nucleoside Deaminase, Dihodrofolate Reductase, Malate Dehydrogenase, Glutamate Dehydrogenase, Lactate Dehydrogenase, and Glyceraldehyde-phosphate Dehydrogenase", Journal of Medicinal Chemistry, 19(1):71-98 (1976).

Yoshino, et al., "Organic Phosphorous Compounds. 2. Synthesis and Coronary Vasodilator Activity of (Benzothiazolybenzyl) Phosphonate Derivatives", J. Med. Chem., 32:1528-1532 (1989).

Yu, et al., "Frequency of TPR-MET Rearrangement in Patients with Gastric Carcinoma and in First-Degree Relatives", Cancer, 88(8):1801-1806 (2000).

Zaidi, et al., "New Anti-Mycobacterial Hydantoins", Pharmazie, 35:755-756 (1980).

Zhen, et al., "Structural and Functional Domains Critical for Constitutive Activation of the HGF-Receptor (Met)", Oncogene, 9(6):1691-1697 (1994).

Zinner, et al., "Zur Weiteren Kenntnis Bicyclischer 3.5-Dioxopyrazolidine", Die Pharmazie, 25(5):309-312 (1970).

Zvilichovsky, et al., "Aminolysis and Polymerization of 3-(p-Toluenesulfonoxy) Hydantoin", Israel Journal of Chemistry, 7:547-554 (1969).

International Search Report issued for PCT/US2008/060896, mailed Sep. 28, 2008 (4 pages).

Supplemental European Search Report issued for EP 08 74 6333, completed Jul. 6, 2010 (9 pages).

Supplementary European Search Report for EP Application No. 08746279.2 dated Jul. 30, 2010, 4 pages.

International Search Report for PCT/US2008/060833 dated Sep. 30, 2008, 3 pages.

* cited by examiner

KINASE INHIBITORS USEFUL FOR THE TREATMENT OF MYLEOPROLIFIC DISEASES AND OTHER PROLIFERATIVE DISEASES

CROSS-REFERENCE TO RELATED APPLICATIONS

This application claims the benefit of Provisional Application 60/913,216 filed Apr. 20, 2007. This provisional application is incorporated by reference herein in its entirety.

SEQUENCE LISTING

This application contains a Sequence Listing in both paper and computer readable format in accordance with 37 C.F.R. 1.821 (c) and (e), the contents of which are hereby incorporated by reference in their entirety.

FIELD OF THE INVENTION

The present invention relates to novel kinase inhibitors and modulator compounds useful for the treatment of various diseases. More particularly, the invention is concerned with such compounds, kinase/compound adducts, methods of treating diseases, and methods of synthesis of the compounds. Preferably, the compounds are useful for the modulation of kinase activity of C-Abl, c-Kit, VEGFR; PDGFR kinases, Flt-3, c-Met, FGFR, the HER family and disease causing polymorphs thereof.

BACKGROUND OF THE INVENTION

Several members of the protein kinase family have been clearly implicated in the pathogenesis of various proliferative and myeloproliferative diseases and thus represent important targets for treatment of these diseases. Some of the proliferative diseases relevant to this invention include cancer, rheumatoid arthritis, atherosclerosis and retinopathies. Important examples of kinases which have been shown to cause or contribute to the pathogensis of these diseases include C-Abl kinase and the oncogenic fusion protein bcr-Abl kinase; c-Kit kinase, PDGF receptor kinase; VEGF receptor kinases; and Flt-3 kinase.

C-Abl kinase is an important non-receptor tyrosine kinase involved in cell signal transduction. This ubiquitously expressed kinase—upon activation by upstream signaling factors including growth factors, oxidative stress, integrin stimulation, and ionizing radiation—localizes to the cell plasma membrane, the cell nucleus, and other cellular compartments including the actin cytoskeleton (Van Etten, *Trends Cell Biol.* (1999) 9: 179). There are two normal isoforms of Abl kinase: Abl-1A and Abl-1B. The N-terminal half of c-Abl kinase is important for autoinhibition of the kinase domain catalytic activity (Pluk et al., *Cell* (2002) 108: 247). Details of the mechanistic aspects of this autoinhibition have recently been disclosed (Nagar et al, *Cell* (2003) 112: 859). The N-terminal myristolyl amino acid residue of Abl-1B has been shown to intramolecularly occupy a hydrophobic pocket formed from alpha-helices in the C-lobe of the kinase domain. Such intramolecular binding induces a novel binding area for intramolecular docking of the SH2 domain and the SH13 domain onto the kinase domain, thereby distorting and inhibiting the catalytic activity of the kinase. Thus, an intricate intramolecular negative regulation of the kinase activity is brought about by these N-terminal regions of c-Abl kinase. An aberrant dysregulated form of c-Abl is formed from a chromosomal translocation event, referred to as the Philadelphia chromosome (P. C. Nowell et al, *Science* (1960) 132: 1497; J. D. Rowley, *Nature* (1973) 243: 290). This abnormal chromosomal translocation leads aberrant gene fusion between the Abl kinase gene and the breakpoint cluster region (BCR) gene, thus encoding an aberrant protein called bcr-Abl (G. Q. Daley et al, *Science* (1990) 247: 824; M. L. Gishizky et al, *Proc. Natl. Acad. Sci. USA* (1993) 90: 3755; S. Li et al, *J Exp. Med.* (1999) 189: 1399). The bcr-Abl fusion protein does not include the regulatory myristolylation site (B. Nagar et al, *Cell* (2003) 112: 859) and as a result functions as an oncoprotein which causes chronic myeloid leukemia (CML). CML is a malignancy of pluripotent hematopoietic stem cells. The p210 form of bcr-Abl is seen in 95% of patients with CML, and in 20% of patients with acute lymphocytic leukemia and is exemplified by sequences such as e14a2 and e13a2. The corresponding p190 form, exemplified by the sequence e1a2 has also been identified. A p185 form has also been disclosed and has been linked to being causative of up to 10% of patients with acute lymphocytic leukemia. It will be appreciated by one skilled in the art that "p210 form", "p190 form" and "p185 form" each describe a closely related group of fusion proteins, and that Sequence ID's used herein are merely representative of each form and are not meant to restrict the scope solely to those sequences.

C-KIT (Kit, CD117, stem cell factor receptor) is a 145 IDa transmembrane tyrosine kinase protein that acts as a type-III receptor (Pereira et al *J Carcin.* (2005), 4: 19). The c-KIT proto-oncogene, located on chromosome 4q11-21, encodes the c-KIT receptor, whose ligand is the stem cell factor (SCF, steel factor, kit ligand, mast cell growth factor, Morstyn G, et al. *Oncology* (1994) 51(2):205. Yarden Y, et al. *Embo J* (1987) 6(11):3341). The receptor has tyrosine-protein kinase activity and binding of the ligands leads to the autophosphorylation of KIT and its association with substrates such as phosphatidylinositol 3-kinase (P13K). Tyrosine phosphorylation by protein tyrosine kinases is of particular importance in cellular signalling and can mediate signals for major cellular processes, such as proliferation, differentiation, apoptosis, attachment, and migration. Defects in KIT are a cause of piebaldism, an autosomal dominant genetic developmental abnormality of pigmentation characterized by congenital patches of white skin and hair that lack melanocytes. Gain-of-function mutations of the c-KIT gene and the expression of phosphorylated KIT are found in most gastrointestinal stromal tumors and mastocytosis. Further, almost all gonadal seminomas/dysgerminomas exhibit KIT membranous staining, and several reports have clarified that some (10-95%) have a c-KIT gene mutation (Sakuma, Y. et al. *Cancer Sci* (2004) 95:9, 716). KIT defects have also been associated with testicular tumors including germ cell tumors (OCT) and testicular germ cell tumors (TGCT).

The role of c-kit expression has been studied in hematologic and solid tumours, such as acute leukemias (Cortes J. et al *Cancer* (2003) 97(11):2760) and Gastrointestinal stromal tumors (GIST, Fletcher C. D. et al. *Hum Pathol* (2002) 33(5): 459). The clinical importance of c-kit expression in malignant tumors relies on studies with Gleevec® (imatinib mesylate, STI571, Novartis Pharma AG Basel, Switzerland) that specifically inhibits tyrosine kinase receptors (Lefevre G. et al. *J Biol Chem* 7 (2004) 279(30):31769). Moreover, a clinically relevant breakthrough has been the finding of anti-tumor effects of this compound in GIST, a group of tumors regarded as being generally resistant to conventional chemotherapy (de Silva C M, Reid R: *Pathol Oncol Res* (2003) 9(1):13-19).

GIST most often become Gleevec resistant and molecularly targeted small therapies that target c-KIT mutations remain elusive.

c-MET is a unique receptor tyrosine kinase (RTK) located on chromosome 7p and activated via its natural ligand hepatocyte growth factor. c-MET is found mutated in a variety of solid tumors (Ma P. C. et al. *Cancer Metastasis* (2003) 22:309). Mutations in the tyrosine kinase domain are associated with hereditary papillary renal cell carcinomas (Schmidt L et al. *Nat. Genet.* (1997) 16:68; Schmidt L, et al. *Oncogene* (1999) 18:2343), whereas mutations in the sema and juxtamembrane domains are often found in small cell lung cancers (SCLC; Ma P. C. et al. *Cancer Res* (2003) 63:6272). Many activating mutations are also found in breast cancers (Nakopoulou et al. *Histopath* (2000) 36(4): 313). The panoply of tumor types for which c-Met mediated growth has been implicated suggests this is a target ideally suited for modulation by specific c-MET small molecule inhibitors.

The TPR-MET oncogene is a transforming variant of the c-MET RTK and was initially identified after treatment of a human osteogenic sarcoma cell line transformed by the chemical carcinogen N-methyl-N'-nitro-N-nitrosoguanidine (Park M. et al. *Cell* (1986) 45:895). The TPR-MET fusion oncoprotein is the result of a chromosomal translocation, placing the TPRS locus on chromosome 1 upstream of a portion of the c-MET gene on chromosome 7 encoding only for the cytoplasmic region. Studies suggest that TPR-MET is detectable in experimental cancers (e.g. Yu J. et al. *Cancer* (2000) 88:1801). Dimerization of the M, 65,000 TPR-MET oncoprotein through a leucine zipper motif encoded by TPR leads to constitutive activation of the c-MET kinase (Zhen Z. et at *Oncogene* (1994) 9:1691). TPR-MET acts to activated wild-type c-MET RTK and can activate crucial cellular growth pathways, including the Ras pathway (Aklilu F. et al. *Am J Physiol* (1996) 271:E277) and the phosphatidylinositol 3-kinase (P13K)/AKT pathway (Ponzetto C. et al. *Mol Cell Biol* (1993) 13:4600). Conversely, in contrast to c-MET RTK, TPR-MET is ligand independent, lacks the CBL binding site in the juxtamembrane region in c-MET, and is mainly cytoplasmic. c-Met immunohistochemical expression seems to be associated with abnormal β-catenin expression, and provides good prognostic and predictive factors in breast cancer patients.

The majority of small molecule kinase inhibitors that have been reported have been shown to bind in one of three ways. Most of the reported inhibitors interact with the ATP binding domain of the active site and exert their effects by competing with ATP for occupancy. Other inhibitors have been shown to bind to a separate hydrophobic region of the protein known as the "DFG-in-conformation" pocket wherein such a binding mode by the inhibitor causes the kinase to adopt the "DFG-out" conformation, and still others have been shown to bind to both the ATP domain and the "DFG-in-conformation" pocket again causing the kinase to adopt the "DGF-out" conformation. Examples specific to inhibitors of Raf kinases can be found in Lowinger et al, *Current Pharmaceutical Design* (2002) 8: 2269; Dumas, J. et al., *Current Opinion in Drug Discovery & Development* (2004) 7: 600; Dumas, J. et al, WO 2003068223 A1 (2003); Dumas, J. et al, WO 9932455 A1 (1999), and Wan, P. T. C., et al, *Cell* (2004) 116: 855.

Physiologically, kinases are regulated by a common activation/deactivation mechanism wherein a specific activation loop sequence of the kinase protein binds into a specific pocket on the same protein which is referred to as the switch control pocket. Such binding occurs when specific amino acid residues of the activation loop are modified for example by phosphorylation, oxidation, or nitrosylation. The binding of the activation loop into the switch pocket results in a conformational change of the protein into its active form (Huse, M. and Kuriyan, J. *Cell* (109) 275)

SUMMARY OF THE INVENTION

Compounds of the present invention find utility in the treatment of mammalian cancers and especially human cancers including but not limited to malignant, melanomas, glioblastomas, ovarian cancer, pancreatic cancer, prostate cancer, lung cancers, breast cancers, kidney cancers, cervical carcinomas, metastasis of primary tumor sites, mycloproliferative diseases, leukemias, papillary thyroid carcinoma, non small cell lung cancer, mesotnelioma, hypereosinophilic syndrome, gastrointestinal stromal tumors, colonic cancers, ocular diseases characterized by hyperproliferation leading to blindness including various retinopathies, rheumatoid arthritis, asthma, chronic obstructive pulmonary disorder, a disease caused by c-Abl kinase, oncogenic forms thereof, aberrant fusion proteins thereof and polymorphs thereof, or a disease caused by c-Kit, oncogenic forms thereof; aberrant fusion proteins thereof and polymorphs thereof.

SECTION 1—DESCRIPTION OF THE PREFERRED EMBODIMENTS

The following descriptions refer to various compounds, stereo-, regioisomers and tautomers of such compounds and individual moieties of the compounds thereof.

Cycloalkyl refers to monocyclic saturated carbon rings taken from cyclopropyl, cyclobutyl, cyclopentyl, cyclohexyl, cycloheptanyl and cyclooctanyl;

Aryl refers to monocyclic or fused bicyclic ring systems characterized by delocalized 7E electrons (aromaticity) shared among the ring carbon atoms of at least one carbocyclic ring; preferred aryl rings are taken from phenyl, naphthyl, tetrahydronaphthyl, indenyl, and indanyl;

Heteroaryl refers to monocyclic or fused bicyclic ring systems characterized by delocalized π electrons (aromaticity) shared among the ring carbon or heteroatoms including nitrogen, oxygen, or sulfur of at least one carbocyclic or heterocyclic ring; heteroaryl rings are taken from, but not limited to, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, triazinyl, indolyl, indolinyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, pyrazolopyridinyl, imidazolonopyridinyl, thiazolopyridinyl, thiazolonopyridinyl, oxazolopyridinyl, oxazolonopyridinyl, isoxazolopyridinyl, isothiazolopyridinyl, triazolopyridinyl, imidazopyrimidinyl, pyrazolopyrimidinyl, imidazolonopyrimidinyl, thiazolopyridiminyl, thiazolonopyrimidinyl, oxazolopyridiminyl, oxazolonopyrimidinyl, isoxazolopyrimidinyl, isothiazolopyrimidinyl, triazolopyrimidinyl, dihydropurinonyl, pyrrolopyrimidinyl, purinyl, pyrazolopyrimidinyl, phthalimidyl, phthalimidinyl, pyrazinylpyridinyl, pyridinopyrimidinyl, pyrimidinopyrimidinyl, ciumolinyl, quinoxalinyl, quinazolinyl, quinolinyl, isoquinolinyl, phthalazinyl, benzodioxyl, benzisothiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, and benzoxazepinyl;

Heterocyclyl refers to monocyclic rings containing carbon and heteroatoms taken from oxygen, nitrogen, or sulfur and wherein there is not delocalized X electrons (aromaticity) shared among the ring carbon or heteroatoms; heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpliolinyl, thiomorpholinyl S-oxide, thiomorpholinyl S-dioxide, piperazinyl, azepinyl, oxepinyl, diazepinyl, tropanyl, and homotropanyl;

Poly-aryl refers to two or more monocyclic or fused aryl bicyclic ring systems characterized by delocalized a electrons (aromaticity) shared among the ring carbon atoms of at least one carbocyclic ring wherein the rings contained therein are optionally linked together;

Poly-heteroaryl refers to two or more monocyclic or fused bicyclic systems characterized by delocalized π electrons (aromaticity) shared among the ring carbon or heteroatoms including nitrogen, oxygen, or sulfur of at least one carbocyclic or heterocyclic ring wherein the rings contained therein are optionally linked together, wherein at least one of the monocyclic or fused bicyclic rings of the poly-heteroaryl system is taken from heteroaryl as defined broadly above and the other rings are taken from either aryl, heteroaryl, or heterocyclyl as defined broadly above;

Poly-heterocyclyl refers to two or more monocyclic or fused bicyclic ring systems containing carbon and heteroatoms taken from oxygen, nitrogen, or sulfur and wherein there is not delocalized π electrons (aromaticity) shared among the ring carbon or heteroatoms wherein the rings contained therein are optionally linked, wherein at least one of the monocyclic or fused bicyclic rings of the poly-heteroaryl system is taken from heterocyclyl as defined broadly above and the other rings are taken from either aryl, heteroaryl, or heterocyclyl as defined broadly above;

Alkyl refers to straight or branched chain C1-C6alkyls;

Halogen refers to fluorine, chlorine, bromine, and iodine;

Alkoxy refers to —O-(alkyl) wherein alkyl is defined as above;

Alkoxylalkyl refers to -(alkyl)-O-(alkyl) wherein alkyl is defined as above;

Alkoxylcarbonyl refers to —C(O)O-(alkyl) wherein alkyl is defined as above;

CarboxylC1-C6alkyl refers to —(C1-C6)alkyl wherein alkyl is defined as above;

Substituted in connection with a moiety refers to the fact that a further substituent may be attached to the moiety to any acceptable location on the moiety.

The term salts embraces pharmaceutically acceptable salts commonly used to form alkali metal salts of free acids and to form addition salts of free bases. The nature of the salt is not critical, provided that it is pharmaceutically-acceptable. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, and heterocyclyl containing carboxylic acids and sulfonic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid. Suitable pharmaceutically-acceptable salts of free acid-containing compounds of Formula I include metallic salts and organic salts. More preferred metallic salts include, but are not limited to appropriate alkali metal (group Ia) salts, alkaline earth metal (croup Ia) salts and other physiological acceptable metals. Such salts can be made from aluminum, calcium, lithium, magnesium, potassium, sodium and zinc. Preferred organic salts can be made from primary amines, secondary amines, tertiary amines and quaternary ammonium salts, including in part tromethamine, diethylamine, tetra-N-methylammonium, N,N'-dibenzylethylenediamine, chloroprocaine, choline, diethanolamine, ethylenediamine, meglumine (N-methylglucamine) and procaine.

The term prodrug refers to derivatives of active compounds which revert in vivo into the active form. For example, a carboxylic acid form of an active drug may be esterified to create a prodrug, and the ester is subsequently converted in vivo to revert to the carboxylic acid form. See Ettmayer et. al, *J. Med. Chem* (2004) 47; 2393 and Lorenzi et. al, *J Pharm. carp. Therapeutics* (2005) 883 for reviews.

Structural, chemical and stereochemical definitions are broadly taken from IUPAC recommendations, and more specifically from Glossary of Terms used in Physical Organic Chemistry (IUPAC Recommendations 1994) as summarized by P. Müller, Pure Appl. Chem., 66, 1077-1184 (1994) and Basic Terminology of Stereochemistry (IUPAC Recommendations 1996) as summarized by G. P. Moss Pure and Applied Chemistry, 68, 2193-2222 (1996). Specific definitions are as follows:

Atropisomers are defined as a subclass of conformers which can be isolated as separate chemical species and which arise from restricted rotation about a single bond.

Regioisomers or structural isomers are defined as isomers involving the same atoms in different arrangements.

Enantiomers are defined as one of a pair of molecular entities which are mirror images of each other and non-superimposable.

Diastereomers or diastereoisomers are defined as stereoisomers other than enantiomers. Diastereomers or diastereoisomers are stereoisomers not related as mirror images. Diastereoisomers are characterized by differences in physical properties, and by some differences in chemical behavior towards achiral as well as chiral reagents.

Tautomerism is defined as isomerism of the general form

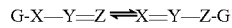

where the isomers (called tautomers) are readily interconvertible; the atoms connecting the groups X, Y, Z are typically any of C, H, O, or S, and G is a group which becomes an electrofuge or nucleofuge during isomerization. The commonest case, when the electrofuge is H⁺, is also known as "prototropy".

Tautomers are defined as isomers that arise from tautomerism, independent of whether the isomers are isolable.

1. First Aspect of the Invention—Compounds, Methods, Preparations and Adducts

The invention includes compounds of the formula Ia:

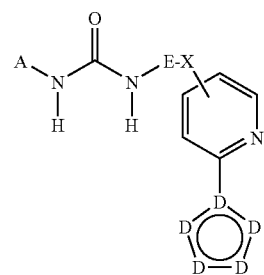

and wherein the pyridine ring may be optionally substituted with one or more R20 moieties;

each D is individually taken from the group consisting of C, CH, C—R20, N—Z3, and N, such that the resultant ring is a pyrazole;

wherein E is selected from the group consisting of phenyl, pyridyl, and pyrimidinyl;

E may be optionally substituted with one or two R16 moieties;

wherein A is a ring system selected from the group consisting of phenyl, naphthyl, cyclopentyl, cyclohexyl, G1. G2, and G3;

G1 is a heteroaryl taken from the group consisting of pyrrolyl, furyl, thienyl, oxazolyl, thiazolyl, isoxazol-4-yl, isoxazol-5-yl, isothiazolyl, imidazolyl, pyrazolyl, oxadiazolyl, thiadiazolyl, triazolyl, tetrazolyl, pyrazinyl, pyridazinyl, triazinyl, pyridinyl, and pyrimidinyl;

G2 is a fused bicyclic heteroaryl taken from the group consisting of indolyl, indolinyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, pyrazolopyridinyl, imidazolonopyridinyl, thiazolopyridinyl thiazolonopyridinyl, oxazolopyridinyl, oxazolonopyridinyl, isoxazolopyridinyl, isothiazolopyridinyl, triazolopyridinyl, imidazopyrimidinyl, pyrazolopyrimidinyl, imidazolonopyrimidinyl, thiazolopyridiminyl, thiazolonopyrimidinyl, oxazolopyridimilnyl, oxazolonopyrimidinyl, isoxazolopyrimidinyl, isothiazolopyrimidinyl, triazolopyrimidinyl, dihydropurinonyl, pyrrolopyrimidinyl, purinyl, pyrazolopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, benzisothiazolone-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, and benzoxazepinyl;

G3 is a heterocyclyl taken from the group consisting of oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl thiomorpliolinyl S-oxide, thiomorpholinyl S-dioxide, piperazinyl, azepinyl, oxepinyl, diazepinyl, tropanyl, and homotropanyl;

the A ring may be optionally substituted with one or two R2 moieties;

X is selected from the group consisting of —O—, —S(CH$_2$)$_n$—, —N(R3)(CH$_2$)$_n$—, —(CH$_2$)$_p$—, and wherein the carbon atoms of —(CH$_2$)$_n$—, —(CH$_2$)$_p$—, of X may be further substituted by oxo or one or more C1-C6alkyl moieties;

when A, G1, G2 or G3 has one or more substitutable sp2-hybridized carbon atoms, each respective sp2 hybridized carbon atom may be optionally substituted with a Z1 substituent;

when A, G1, G2 or G3 has one or more substitutable sp3-hybridized carbon atoms, each respective sp3 hybridized carbon atom may be optionally substituted with a Z2 substituent;

when A, G1, G2 or G3 has one or more substitutable nitrogen atoms, each respective nitrogen atom may be optionally substituted with a Z4 substituent;

each Z1 is independently and individually selected from the group consisting of C1-6alkyl, branched C3-C7alkyl, C3-C8cycloalkyl, halogen, fluoroC1-C6alkyl wherein the alkyl moiety can be partially or fully fluorinated, cyano, C1-C6alkoxy, fluoroC1-C6alkoxy wherein the alkyl moiety can be partially or fully fluorinated, —(CH$_2$)$_n$OH, oxo, C1-C6alkoxyC1-C6alkyl, (R4)$_2$N(CH$_2$)$_n$—, (R3)$_2$N(CH$_2$)$_n$—, (R4)$_2$N(CH$_2$)$_q$N(R4)(CH$_2$)$_n$—, (R4)$_2$N(CH$_2$)$_q$—O—(CH$_{12}$)$_n$—, (R3)$_2$NC(O)—, (R4)$_2$NC(O)—, (R4)$_2$NC(O)C1-C6alkyl-, —(R4)NC(O)R8, C1-C6alkoxycarbonyl-, -carboxyC1-C6alkyl, C1-C6alkoxycarbonylC1-C6alkyl-, (R3)$_2$NSO$_2$—, —SOR3, (R4)$_2$NSO$_2$—, —N(R4)SO$_2$R8, —O(CH$_2$)$_q$OC1-C6alkyl, —SO$_2$R3, —SOR4, —C(O)R8, —C(O)R6, —C(=NOH)R6, —C(=NOR3)R6, —(CH$_2$)$_n$N(R4)C(O)R8, —N(R3)(CH$_2$)$_q$O-alkyl, —N(R3)(CH$_2$)$_q$N(R4)$_2$, nitro, —CH(OH)CH(OH)R4, —C(=NH)N(R4)$_2$, —C(=NOR3)N(R4)$_2$, and —NHC(=NH)R8, R17 substituted G3, R17 substituted pyrazolyl and R17 substituted imidazolyl;

in the event that Z1 contains an alkyl or alkylene moiety, such moieties may be further substituted with one or more C1-C6alkyls;

each Z2 is independently and individually selected from the group consisting of aryl, C1-C6alkyl, C3-C8cycloalkyl, branched C3-C7alkyl, hydroxyl, hydroxyC1-C6alkyl-, cyano, (R3)$_2$N—, (R4)$_2$N—, (R4)$_2$NC1-C6alkyl-, (R4)$_2$NC2-C6alkylN(R4)(CH$_2$)$_n$—, (R4)$_2$NC2-C6alkylO(CH$_2$)$_n$—, (R3)$_2$NC(O)—, (R4)$_2$NC(O)—, (R4)$_2$NC(O)—C1-C6alkyl-, carboxyl, -carboxyC1-C6alkyl, C1-C6alkoxycarbonyl-, C1-C6alkoxycarbonylC1-C6alkyl-, (R3)$_2$NSO—, (R4)$_2$NSO$_2$—, —SO$_2$R8, —(CH$_2$)$_n$N(R4)C(O)R8, —C(O)R8, =O, =NOH, and =N(OR6);

in the event that Z2 contains an alkyl or alkylene moiety, such moieties may be further substituted with one or more C1-C6alkyls;

each Z3 is independently and individually selected from the group consisting of H, C1-C6alkyl, branched C3-C7alkyl, C3-C8cycloalkyl, fluoroC1-C6alkyl wherein the alkyl moiety can be partially or fully fluorinated, hydroxyC2-C6alkyl-, C1-C6alkoxycarbonyl-, —C(O)R8, R5C(O)(CH$_2$)$_n$—, (R4)$_2$NC(O)—, (R4)$_2$NC(O)C1-C6alkyl-, R8C(O)N(R4)(CH$_2$)$_q$—, (R3)$_2$NSO$_2$—, (R4)$_2$NSO$_2$—, —(CH$_2$)$_q$N(R3)$_2$, and —(CH$_2$)$_q$N(R4)$_2$;

each Z4 is independently and individually selected from the group consisting of C1-C6alkyl, branched C3-7alkyl, hydroxyC2-C6alkyl-, C1-C6alkoxyC2-C6alkyl-, (R4)$_2$N—C2-C6alkyl-, (R4)$_2$N—C2-C6alkylN(R4)-C2-C6alkyl-, (R4)$_2$N—C2-C6alkyl-O—C2-C6alkyl-, (R4)$_2$NC(O)C1-C6alkyl-, carboxyC1-C6alkyl, C1-C6alkoxycarbonylC1-C6alkyl-, —C2-C6alkylN(R4)C(O)R8, R8-C(=NR3)-, —SO$_2$R8, and —COR8;

in the event that Z4 contains an alkyl or alkylene moiety, such moieties may be further substituted with one or more C1-C6alkyls;

each R2 is selected from the group consisting of H, C1-C6alkyl, branched C3-C8alkyl, R19 substituted C3-C8cycloalkyl-, fluoroC1-C6alkyl- wherein the alkyl is fully or partially fluorinated, halogen, cyano, C1-C6alkoxy-, and fluoroC1-C6alkoxy- wherein the alkyl group is fully or partially fluorinated, hydroxyl substituted C1-C6alkyl-, hydroxyl substituted branched C3-C8alkyl-, cyano substituted C1-C6alkyl-, cyano substituted branched C3-C8alkyl-, (R3)$_2$NC(O)C1-C6alkyl-, (R3)$_2$NC(O)C3-C8 branched alkyl-;

wherein each R3 is independently and individually selected from the group consisting of H, C1-C6alkyl, branched C3-C7alkyl, and C3-C8cycloalkyl;

each R4 is independently and individually selected from the group consisting of H, C1-C6alkyl, hydroxyC1-C6alkyl-, dihydroxyC1-C6alkyl-, C1-C6alkoxyC1-C6alkyl-, branched C3-C7alkyl, branched hydroxyC1-C6alkyl-, branched C1-C6alkoxyC1-C6alkyl-, branched dihydroxyC1-C6alkyl-, —(CH$_2$)$_p$N(R7)$_2$, —(CH$_2$)$_p$C(O)N(R7)$_2$, —(CH$_2$)$_n$C(O)OR3, R19 substituted C3-C8cycloalkyl-;

each R5 is independently and individually selected from the group consisting of

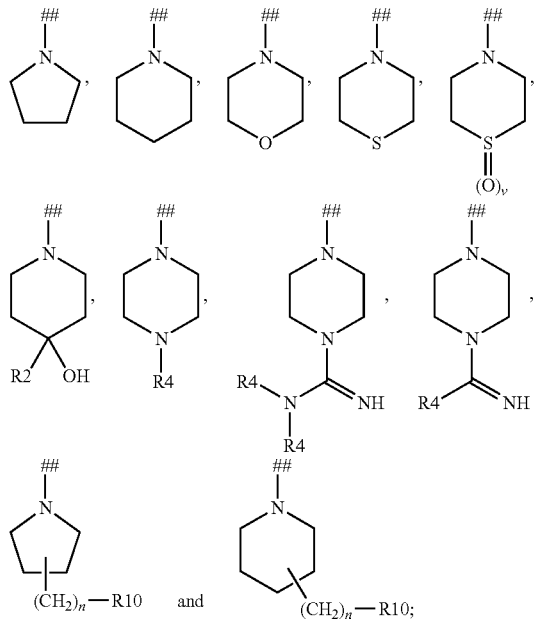

and wherein the symbol (##) is the point of attachment to Z3;
each R6 is independently and individually selected from the group consisting of C1-C6alkyl, branched C3-C7alkyl, and R19 substituted C3-C8cycloalkyl-;
each R7 is independently and individually selected from the group consisting of H, C1-C6alkyl, hydroxyC2-C6alkyl-, dihydroxyC2-C6alkyl-, C1-C6alkoxyC2-C6alkyl-, branched C3-C7alkyl, branched hydroxyC2-C6alkyl-, branched C1-C6alkoxyC2-C6alkyl-, branched dihydroxyC2-C6alkyl-, —(CH$_2$)$_n$C(O)OR3, R19 substituted C3-C8cycloalkyl- and —(CH$_2$)$_n$R17;
each R8 is independently and individually selected from the group consisting of C1-C6alkyl, branched C3-C7alkyl, fluoroC1-C6alkyl- wherein the alkyl moiety is partially or fully fluorinated, R19 substituted C3-C8cycloalkyl-, —OH, C1-C6alkoxy, —N(R3)$_2$, and —N(R4)$_2$;
each R10 is independently and individually selected from the group consisting of —CO$_2$H, —CO$_2$C1-C6alkyl, —C(O)N(R4)$_2$, OH, C1-C6alkoxy, and —N(R4)$_2$;
each R16 is independently and individually selected from the group consisting of H, C1-C6alkyl, branched C3-C7alkyl, R19 substituted C3-C8cycloalkyl-, halogen, fluoroC1-C6alkyl- wherein the alkyl moiety can be partially or fully fluorinated, cyano, hydroxyl, C1-C6alkoxy, fluoroC1-C6alkoxy- wherein the alkyl moiety can be partially or fully fluorinated, —N(R3)$_2$, —N(R4)$_2$, R3 substituted C2-C3alkynyl- and nitro;
each R17 is independently and individually selected from the group consisting of H, C1-C6alkyl, branched C3-C7alkyl, R19 substituted C3-C8cycloalkyl-, halogen, fluoroC1-C6alkyl- wherein the alkyl moiety can be partially or fully fluorinated, cyano, hydroxyl, C1-C6alkoxy, fluoroC1-C6alkoxy- wherein the alkyl moiety can be partially or fully fluorinated, —N(R3)$_2$, —N(R4)$_2$, and nitro;
each R19 is independently and individually selected from the group consisting of H, OH and C1-C6alkyl;
each R20 is independently and individually selected from the group consisting of C1-C6alkyl, branched C3-C7alkyl, R19 substituted C3-C8cycloalkyl-, halogen, fluoroC1-C6alkyl- wherein the alkyl moiety can be partially or fully fluorinated, cyano, hydroxyl, C1-C6alkoxy, fluoroC1-C6alkoxy- wherein the alkyl moiety can be partially or fully fluorinated, —N(R3)$_2$, —N(R4)$_2$, —N(R3)C(O)R3, —C(O)N(R3)$_2$ and nitro and wherein two R4 moieties independently and individually taken from the group consisting of C1-C6alkyl, branched C3-C6alkyl, hydroxyalkyl-, and alkoxyalkyl and attached to the same nitrogen heteroatom may cyclize to form a C3-C7 heterocyclyl ring;

and k is 0 or 1; n is 0-6; p is 1-4; q is 2-6; r is 0 or 1; t is 1-3; v is 1 or 2; m is 0-2;

and stereo-, regioisomers and tautomers of such compounds.

1.1 Compounds of Formula Ia which Exemplify Preferred D Moieties

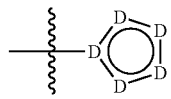

In a preferred embodiment of compounds of formula Ia, said compounds have preferred

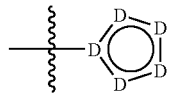

moieties of the formula:

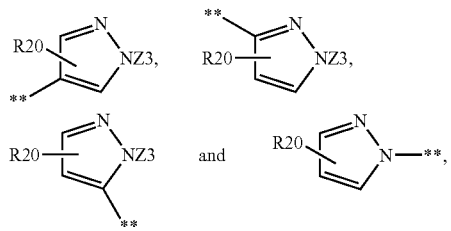

wherein the symbol (**) indicates the point of attachment to the pyridine ring.

1.1.1 Compounds of Formula Ia which Exemplify Preferred A Moieties

In a preferred embodiment of compounds of formula Ia, said compounds have structures of formula Ib

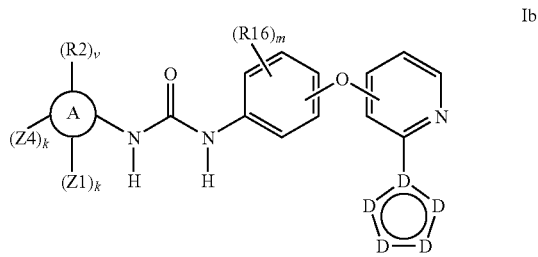

Ib wherein A is any possible isomer of pyrazole.

1.1.2 Compounds of Formula Ia which Exemplify Preferred A and R16 Moieties

In a more preferred embodiment of compounds of formula Ib, said compounds have structures of formula Ic

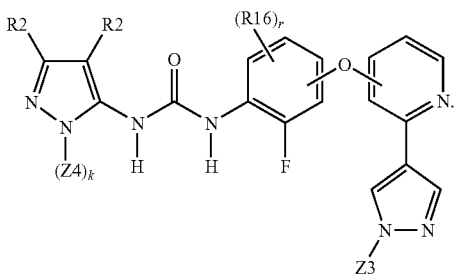

Ic

1.1.3 Compounds of Formula Ia which Exemplify Preferred A and R16 Moieties

In a more preferred embodiment of compounds of formula Ib, said compounds have structures of formula Id

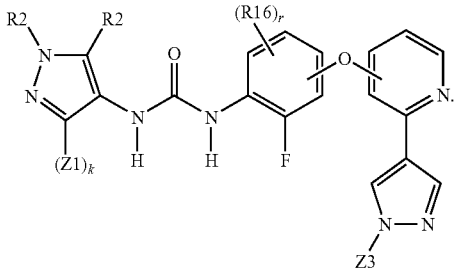

Id

1.14 Compounds of Formula which Exemplify Preferred A and R16 Moieties

In a more preferred embodiment of compounds of formula Ib, said compounds have structures of formula Ie

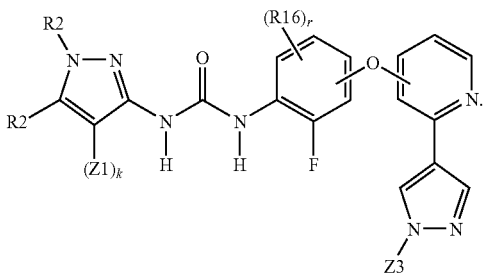

Ie

1.1.5 Compounds of Formula Ia which Exemplify Preferred A and R16 to Moieties In a more preferred embodiment of compounds of formula Ia, said compounds have structures of formula If

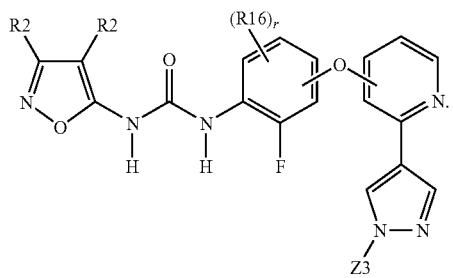

If

1.1.6 Compounds of Formula a which Exemplify Preferred A Moieties

In a preferred embodiment of compounds of formula Ia, said compounds have structures of formula Ig

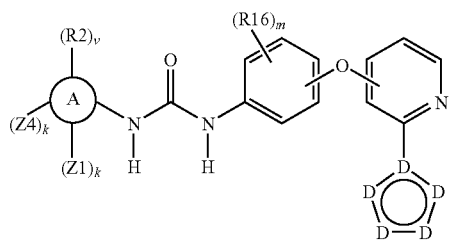

Ig wherein A is selected from the group consisting of any isomer of phenyl and pyridine.

1.1.7 Compounds of Formula Ia which Exemplify Preferred A and R16 Moieties

In a more preferred embodiment of compounds of formula Ig, said compounds have structures of formula Ih

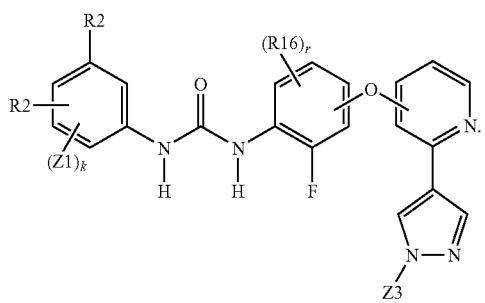

Ih

1.1.8 Compounds of Formula Ia which Exemplify Preferred A and R16 Moieties

In a more preferred embodiment of compounds of formula Ig, said compounds have structures of formula Ii

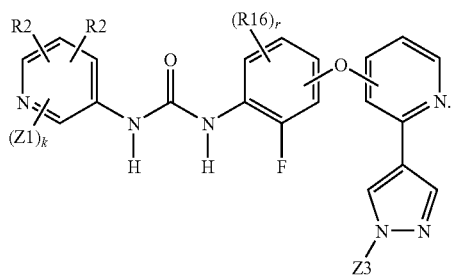

Ii

1.1.9 Compounds of Formula Ia Which Exemplify Preferred A Moieties

In a preferred embodiment of compounds of formula Ia, said compounds have structures of formula Ij

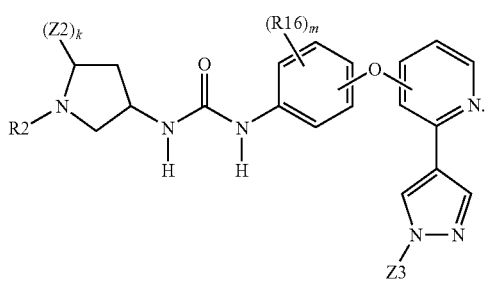

Ij

1.1.10 Compounds of Formula Ia which Exemplify Preferred A and R16 Moieties

In a more preferred embodiment of compounds of formula Ia, said compounds have structures of formula Ik

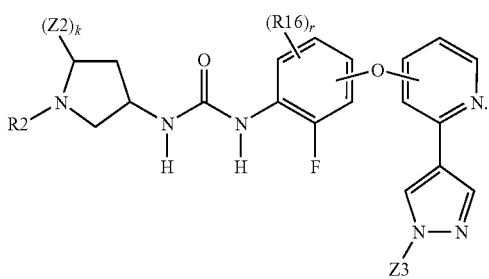

Ik

1.1.11 Most Preferred Compounds of Formula Ia 1-(3-tert-butylisoxazol-5-yl)-3-(2-fluoro-4-(2-(1-methyl-1H-pyrazol-4-yl)pyridin-4-yloxy)phenyl)urea, 1-(3-tert-butyl-1-methyl-1H-pyrazol-5-yl)-3-(2-fluoro-4-(2-(1-methyl-1H-pyrazol-4-yl)pyridin-4-yloxy)phenyl)urea, 1-(3-tert-butylisoxazol-5-yl)-3-(3-methyl-4-(2-(1-methyl-1H-pyrazol-4-yl)pyridin-4-yloxy)phenyl)urea, 1-(3-tert-butyl-1-methyl-1H-pyrazol-5-yl)-3-(3-methyl-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(3-(trifluoromethyl)phenyl)urea, 1-(4-(2-(1-methyl-1H-pyrazol-4-yl)pyridin-4-yloxy)phenyl)-3-(3-(trifluoromethyl)phenyl)urea, 1-(5-tert-butylisoxazol-3-yl)-3-(2-fluoro-4-(2-(1-methyl-1H-pyrazol-4-yl)pyridin-4-yloxy)phenyl)urea, 1-(5-tert-butylisoxazol-3-yl)-3-(4-(2-(1-methyl-1H-pyrazol-4-yl)pyridin-4-yloxy)phenyl)urea, 1-(1-tert-butyl-1H-pyrazol-4-yl)-3-(2-fluoro-4-(2-(1-methyl-1H-pyrazol-4-yl)pyridin-4-yloxy)phenyl)urea, 1-(4-(2-(1-methyl-1H-pyrazol-4-yl)pyridin-4-yloxy)phenyl)-3-(5-(trifluoromethyl)pyridin-3-yl)urea, 1-(4-chloro-3-(trifluoromethyl)phenyl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy phenyl)-3-(5-isopropylisoxazol-3-yl)urea, 1-(2-difluorophenyl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(3-(trifluoromethyl)isoxazol-5-yl)urea, 1-(1-tert-butyl-1H-pyrazol-4-yl)-3-(2,3-difluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(3-isopropylisoxazol-5-yl)urea, 1-(1-tert-butyl-5-(trifluoromethyl)-1H-pyrazol-4-yl)-3-(2-fluoro-4-(1-methyl-1H-pyrazol-4-yl)pyridin-4-yloxy)phenyl)urea, 1-(1-tert-butyl-5-methyl-1H-pyrazol-4-yl)-3-(2-fluoro-4-(2-(1-methyl-1H-pyrazol-4-yl)pyridin-4-yloxy)phenyl)urea, 1-(5-tert-butyl-1,3,4-thiadiazol-2-yl)-3-(2-fluoro-4-(2-(1-methyl-1H-pyrazol-4-yl)pyridin-4-yloxy)phenyl)urea, 1-(3,5-dichlorophenyl)-3-(2-fluoro-4-(2-(1-methyl-1H-pyrazol-4-yl)pyridin-4-yloxy)phenyl)urea, 1-cyclohexyl-3-(2-fluoro-4-(2-(1-methyl-1H-pyrazol-4-yl)pyridin-4-yloxy)phenyl)urea, 1-(3-tert-butyl-1-(2-(dimethylamino)ethyl)-1H-pyrazol-5-yl)-3-(2-fluoro-4-(2-(1-methyl-1H-pyrazol-4-yl)pyridin-4-yloxy)phenyl)urea, 1-cyclopentyl-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(1-isopropyl-1H-pyrazol-4-yl)urea, 1-(2-fluoro-4-(2-(1-methyl-1H-pyrazol-4-yl)pyridin-4-yloxy)phenyl)-3-(3-(1-methylcyclopentyl)isoxazol-5-yl)urea, 1-(4-chlorophenyl)-3-(2-fluoro-4-(2-(1-methyl-1H-pyrazol-4-yl)pyridin-4-yloxy)phenyl)urea, 1-(3-cyclopentylisoxazol-5-yl)-3'-(2-fluoro-4-(2-(1-methyl-1H-pyrazol-4-yl)pyridin-4-yloxy)phenyl)urea, 1-(1-cyclopentyl-1H-pyrazol-4-yl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(1-methyl-3-(1-methylcyclopentyl)-1H-pyrazol-5-yl)urea, 1-(2-fluoro-4-(2-(1-methyl-1H-pyrazol-4-yl)pyridin-4-yloxy)phenyl)-3-(1-methyl-3-(trifluoromethyl)-1H-pyrazol-5-yl)urea, 1-(2-fluoro-4-(2-(1-methyl-1H-pyrazol-4-yl)pyridin-4-yloxy)phenyl)-3-(2-fluoro-5-(trifluoromethyl)phenyl)urea, 1-(3-tert-butyl)phenyl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(2-fluoro-5-methyl)phenyl)urea, 1-(1-tert-butyl-1H-pyrazol-4-yl)-3-(2-fluoro-3-methyl-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(3-isopropyl)phenyl)urea, 1-(1-tert-butyl-1H-pyrazol-4-yl)-3-(3-fluoro-4-(1-(1-methyl-1H-pyrazol-4-yl)pyridin-4-yloxy)phenyl)urea, 1-(5-fluoro-2-methyl)phenyl)-3-(2-fluoro-4-(2-(1-methyl-1H-pyrazol-4-yl)pyridin-4-yloxy)phenyl)urea, 1-(3-cyclopentyl-1-methyl-1H-pyrazol-5-yl)-3-(2-fluoro-4-(2-(1-methyl-1H-pyrazol-4-yl)pyridin-4-yloxy)phenyl)urea, 1-(1-tert-butyl-1H-pyrazol-4-yl)-3-(2-fluoro-4-(2-(1-propyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(3-fluorophenyl)urea, 1-(2-fluoro-4-(2-(1-methyl-1H-pyrazol-4-yl)pyridin-4-yloxy)phenyl)-3-(1-isopropyl-3-(trifluoromethyl)-1H-pyrazol-4-yl)urea, 1-(2-fluoro-3- methyl-4-(2-(1-methyl-1H-pyrazol-4-yl)pyridin-4-yloxy)phenyl)-3-(1-isopropyl-1H-pyrazol-4-yl)urea, 1-(2-fluoro-4-(2-(1-methyl-1H-pyrazol-4-yl)pyridin-4-yloxy)phenyl)-3-(1-isopropyl-5-methyl-1H-pyrazol-4-yl)urea, 1-(2-fluoro-4-(2-(1-methyl-1H-pyrazol-4-yl)pyridin-4-yloxy)phenyl)-3-(1-isopropyl-3-methyl-1H-pyrazol-4-yl)urea, 1-(2-fluoro-4-(2-(1-methyl-1H-pyrazol-4-yl)pyridin-4-yloxy)phenyl)-3-(5-(trifluoromethyl)pyridin-3-yl)urea, 1-cyclohexyl-3-(2,3-difluoro-4-(2-(1-methyl-1H-pyrazol-4-yl)pyridin-4-yloxy)phenyl)urea, 1-cyclohexyl-3-(2-fluoro-3-meth-yl-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(5-isopropylpyridin-3-yl)urea, 1-(1-cyclopentyl-5-methyl-1H-pyrazol-4-yl)-3-(2-fluoro-4-(2-(1-methyl-1H-pyrazol-4-yl)pyridin-4-yloxy)phenyl)urea, 1-(1-cyclopentyl-5-methyl-1H-pyrazol-4-yl)-3-(2,3-difluoro-4-(2-(1-methyl-1H-pyrazol-4-yl)pyridin-4-yloxy)phenyl)urea, 1-(benzo[d]isoxazol-3-yl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(5-fluoropyridin-3-yl)urea, 1-(3-cyanophenyl)-3-(2-fluoro-4-(2-(1-methyl-1H-pyrazol-4-yl)pyridin-4-yloxy)phenyl)urea, 1-(3-tert-butylisoxazol-5-yl)-3-(2,3-difluoro-4-(2-(1-me-thyl-1H-pyrazol-4-yl)pyridin-4-yloxy)phenyl)urea, 1-(3-tert-butylisoxazol-5-yl)-3-(2-fluoro-3-methyl-4-(2-(1-me-thyl-1H-pyrazol-4-yl)pyridin-4-yloxy)phenyl)urea, 1-(3-tert-butylisoxazol-5-yl)-3-(3-fluoro-4-(2-(1-methyl-1H-pyrazol-4-yl)pyridin-4-yloxy)phenyl)urea, 1-(2-tert-butyloxazol-5-yl)-3-(2-fluoro-4-(2-(1-methyl-1H-pyrazol-4-yl)pyridin-4-yloxy)phenyl)urea, 1-(3-tert-butyl-1-methyl-1H-pyrazol-5-yl)-3-(2,3-difluoro-4-(2-(1-methyl-1H-pyrazol-4-yl)pyridin-4-yloxy)phenyl)urea, 1-(3-tert-butyl-1-methyl-1H-pyrazol-5-yl)-3-(2-fluoro-3-methyl-4-(2-(1-methyl-1H-pyrazol-4-yl)pyridin-4-yloxy)phenyl)urea, 1-(1-cyclopentyl-1H-pyrazol-4-yl)-3-(2,3-difluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(2-oxo-5-(trifluoromethyl)-1,2-dihydropyridin-3-yl)urea, 1-(5-tert-butyl-2-methylfuran-3-yl)-3-(2-fluoro-4-(2-(1-methyl-1H-pyrazol-4-yl)pyridin-4-yloxy)phenyl)urea, 1-(2,3-difluoro-4-(2-(1-methyl-1H-pyrazol-4-yl)pyridin-4-yloxy)phenyl)-3-(3-isopropylisoxazol-5-yl)urea, 1-(2-fluoro-3-methyl-4-(2-(1-methyl-1H-pyrazol-4-yl)pyridin-4-yloxy)phenyl)-3-(3-isopropylisoxazol-5-yl)urea, 1-(2-fluoro-4-(2-(1-methyl-1H-pyrazol-4-yl)pyridin-4-yloxy)phenyl)-3-(6-fluorobenzo[d]thiazol-2-yl)urea, 1-(2-fluoro-3-methyl-4-(2-(1-methyl-1H-pyrazol-4-yl)pyridin-4-yloxy)phenyl)-3-(6-fluorobenzo[d]thiazol-2-yl)urea, 1-(1-tert-butyl-1H-pyrrol-3-yl)-3-(2-fluoro-4-(2-(1-methyl-1H-pyrazol-4-yl)pyridin-4-yloxy)phenyl)urea, 1-(3-tert-butyl-4-methylisoxazol-5-yl)-3-(2-fluoro-4-(2-(1-methyl-1H-pyrazol-4-yl)pyridin-4-yloxy)phenyl)urea, 1-(2-fluoro-3-methyl-4-(2-(1-methyl-1H-pyrazol-4-yl)pyridin-4-yloxy)phenyl)-3-(5-isopropylpyridin-3-yl)urea, 1-(2,3-difluoro-4-(2-(1-methyl-1H-pyrazol-4-yl)pyridin-4-yloxy)phenyl)-3-(5-isopropylpyridin-3-yl)urea, 1-(2-fluoro-4-(2-(1-methyl-1H-pyrazol-4-yl)pyridin-4-yloxy)phenyl)-3-(5-methylpyridin-3-yl)urea, 1-(2-fluoro-3-methyl-4-(2-(1-methyl-1H-pyrazol-4-yl)pyridin-4-yloxy)phenyl)-3-(5-(trifluoromethyl)pyridin-3-yl)urea, 1-(2,3-difluoro-4-(2-(1-methyl-1H-pyrazol-4-yl)pyridin-4-yloxy)phenyl)-3-(5-(trifluoromethyl)pyridin-3-yl)urea, 1-(5-ethylpyridin-3-yl)-3-(2-fluoro-4-(2-(1-methyl-1H-pyrazol-4-yl)pyridin-4-yloxy)phenyl)urea, 1-(5-chloropyridin-3-yl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(3-isopropyl-1-methyl-1H-pyrazol-5-yl)urea, 1-(3-cyclopropyl-1-methyl-1H-pyrazol-5-yl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(1-isopropyl-1H-imidazol-4-yl)urea, 1-(1-tert-butyl-5-oxopyrrolidin-3-yl)-3-(2-fluoro-4-(2-(1-methyl-1H-pyrazol-4-yl)pyridin-4-yloxy)phenyl)urea, 1-(1-tert-butylpyrrolidin-3-yl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(2-methyl-5-(trifluoromethyl)pyridin-3-yl)urea, 1-(2-tert-butyl-4-(piperazin-1-yl)pyrimidin-5-yl)-3-(2-fluoro-4-(2-(1-methyl-1H-pyrazol-4-yl)pyridin-4-yloxy)phenyl)urea, 1-(2-tert-butyl-4-morpholinopyrimidin-5-yl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(2-(1-methyl-1H-pyrazol-4-yl)-5-(trifluoromethyl)pyridin-3-yl)urea, and 1-(1-tert-butyl-5-methyl-1H-pyrazol-3-yl)-3-(2-fluoro-4-(2-(1-methyl-1H-pyrazol-4-yl)pyridin-4-yloxy)phenyl)urea, 1.2 Methods 1.2a Methods of Protein Modulation The invention includes methods of modulating kinase activity of a variety of kinases, e.g. C-Abl kinase, bcr-Abl kinase, Flt-3, VEGFR-2 kinase mutants, c-Met, c-Kit, PDGFR and the HER family of kinases. The kinases may be wildtype kinases, oncogenic forms thereof, aberrant fusion proteins thereof or polymorphs of any of the foregoing. The method comprises the step of contacting the kinase species with compounds of the invention and especially those set forth in sections section 1. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, inhibition of phosphorylation, oxidation or nitrosylation of said kinase by another enzyme, enhancement of dephosphorylation, reduction or denitrosylation of said kinase by another enzyme, kinase cellular localization, and recruitment of other proteins into signaling complexes through modulation of kinase conformation.

1.2b Treatment Methods

The methods of the invention also include treating individuals suffering from a condition selected from the group consisting of cancer and hyperproliferative diseases. These methods comprise administering to such individuals compounds of the invention, and especially those of section 1, said diseases including, but not limited to, malignant melanomas, glioblastomas, ovarian cancer, pancreatic cancer, prostate cancer, lung cancers, breast cancers, kidney cancers, cervical carcinomas, metastasis of primary tumor secondary sites, myeloproliferative diseases, leukemias, papillary thyroid carcinoma, non small cell lung cancer, mesothelioma, hypereosinophilic syndrome, gastrointestinal stromal tumors, colonic cancers, ocular diseases characterized by hyperproliferation leading to blindness including various retinopathies including diabetic retinopathy and age-related macular degeneration, rheumatoid arthritis, asthma, chronic obstructive pulmonary disorder, mastocytosis, mast cell leukemia, a disease caused by c-Abl kinase, oncogenic forms thereof, aberrant fusion proteins thereof and polymorphs thereof, or a disease caused by a c-Kit kinase, oncogenic forms thereof, aberrant fusion proteins thereof and polymorphs thereof. The administration method is not critical, and may be from the group consisting of oral, parenteral, inhalation, and subcutaneous.

1.3 Pharmaceutical Preparations

The compounds of the invention, especially those of section 1 may form a part of a pharmaceutical composition by combining one or more such compounds with a pharmaceutically acceptable carrier. Additionally, the compositions may include an additive selected from the group consisting of adjuvants, excipients, diluents, and stabilizers.

SECTION 2. SYNTHESIS OF COMPOUNDS OF THE PRESENT INVENTION

The compounds of the invention are available by the procedures and teachings of WO 2006/071940, incorporated by reference, and by the general synthetic methods illustrated in the Schemes below and the accompanying examples.

As indicated in Scheme 1, ureas of general formula 1 can be readily prepared by the union of amines of general formula 2 with isocyanates 3 or isocyanate surrogates, for example trichloroethyl carbamates (4) or isopropenyl carbamates (5). Preferred conditions for the preparation of compounds of general formula 1 involve heating a solution of 4 or 5 with 2 in the presence of a tertiary base such as diisopropylethylamine, triethylamine or N-methylpyrrolidine in a solvent such as dimethylformamide, dimethylsulfoxide, tetrahydrofuran or 1,4-dioxane at a temperature between 50 and 100° C. for a period of time ranging from 1 hour to 2 days.

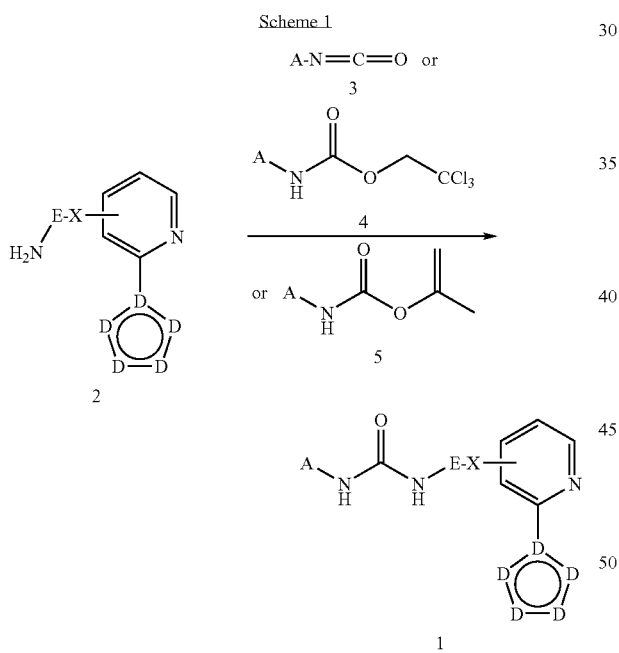

As shown in Scheme 2, isocyanates 3 can be prepared from amines A-NH, 6 with phosgene, or a phosgene equivalent such as diphosgene, triphosgene, or N,N-dicarbonylimidazole. Trichloroethyl carbamates 4 and isopropenyl carbamates 5 are readily prepared from amines A-NH, (6) by acylation with trichloroethyl chloroformate or isopropenyl chloroformate by standard conditions familiar to those skilled in the art. Preferred conditions for the preparation of 4 and 5 include treatment of compound 6 with the appropriate chloroformate in the presence of pyridine in an aprotic solvent such as dichloromethane or in the presence of aqueous hydroxide or carbonate in a biphasic aqueous/ethyl acetate solvent system.

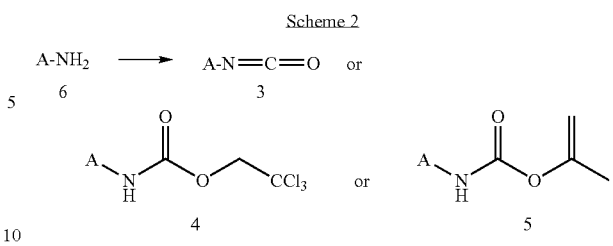

Additionally, compounds of formula 1 can also be prepared from carboxylic acids 7 by the intermediacy of in-situ generated acyl azides (Curtius rearrangement) as indicated in Scheme 3. Preferred conditions for Scheme 3 include the mixing of acid 7 with amine 2 and diphenylphosphoryl azide in a solvent such as 1,4-dioxane or dimethylformamide in the presence of base, such as triethylamine, and raising the temperature of the reaction to about 80-120° C. to affect the Curtius rearrangement.

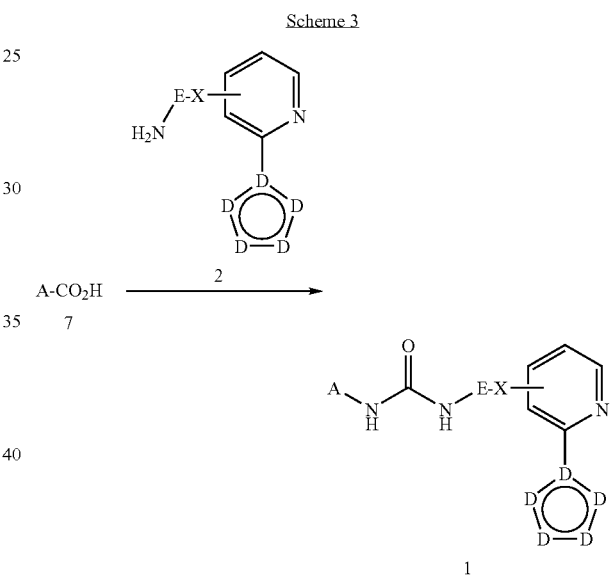

By analogy to Schemes 1 and 3 above, it will be recognized by those skilled in the art that the compounds of formula 1 can also be prepared by the union of amines A-NH$_2$ 6 with isocyanates 8 (Scheme 4). Isocyanates 8 can be prepared from general amines 2 by standard synthetic methods. Suitable methods for example, include reaction of 2 with phosgene, or a phosgene equivalent such as diphosgene, triphosgene, or N,N-dicarbonylimidazole. In addition to the methods above for converting amines 2 into isocyanates 8, the isocyanates 8 can also be prepared in situ by the Curtius rearrangement and variants thereof. Those skilled in the art will further recognize that isocycanates 8 need not be isolated, but may be simply generated in situ. Accordingly, acid 2 can be converted to compounds of formula 1 either with or without isolation of 8. Preferred conditions for the direct conversion of acid 9 to compounds of formula 1 involve the mixing of acid 97 amine A-NH$_2$ 6 diphenylphosphoryl azide and a suitable base, for example triethylamine, in an aprotic solvent, for example dioxane. Heating said mixture to a temperature of between 80 and 120° C. provides the compounds of formula 1.

Scheme 4

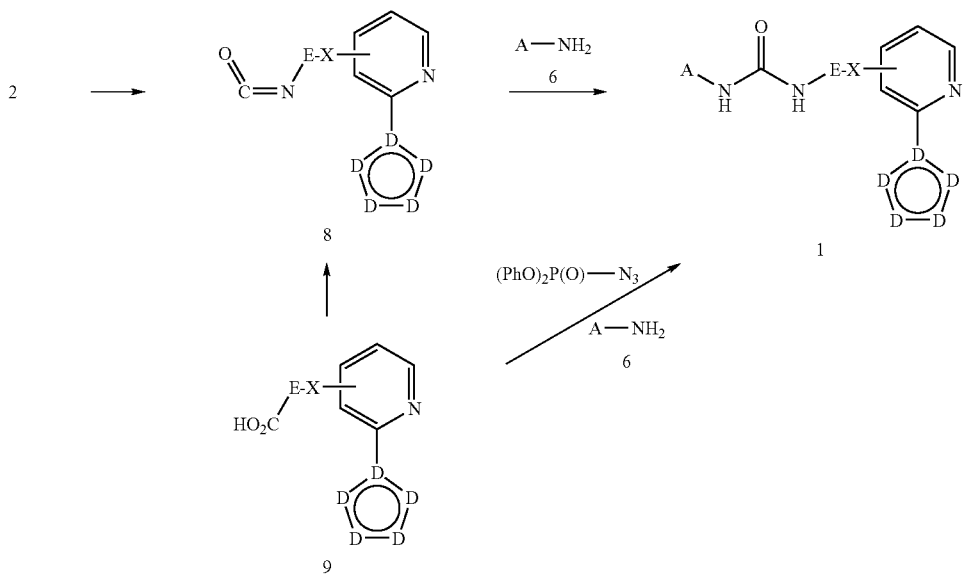

Additionally, compounds of formula 1 can also be prepared from amines 2 by first preparing stable isocyanate equivalents, such as carbamates (Scheme 5). Especially preferred carbamates include trichloroethyl carbamates (10) and isopropenyl carbamates (11) which are readily prepared from recognize that certain carbamates can also be prepared from acid 9 by Curtius rearrangement and trapping with an alcoholic co-solvent. For example, treatment of acid 9 (Scheme 5) with diphenylphosphoryl azide and trichloroethanol at elevated temperature provides trichloroethyl carbamate 10.

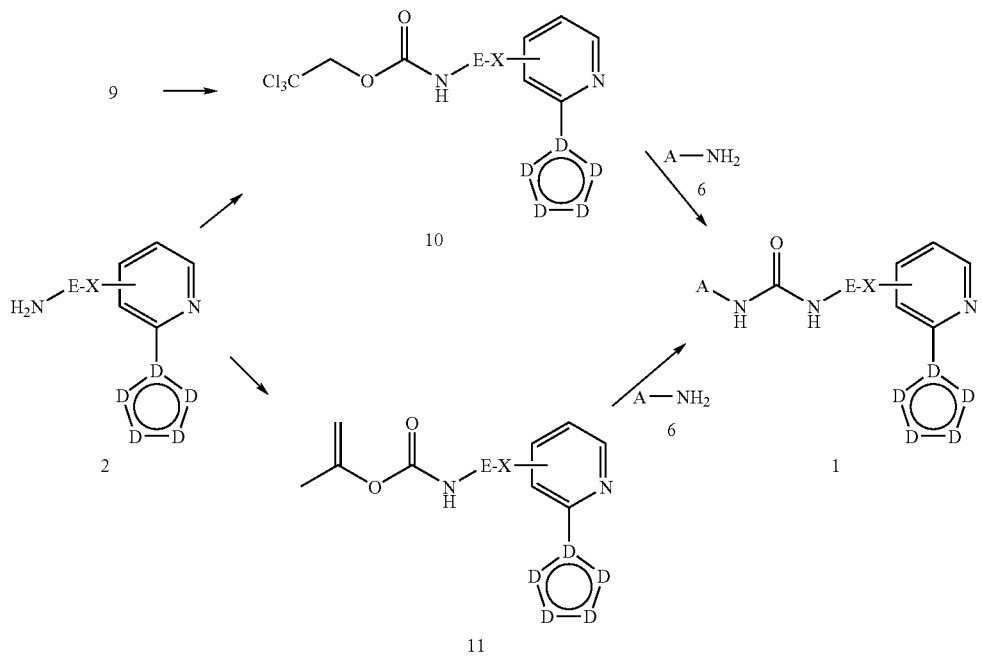

amine 2 by reaction with trichloroethyl chloroformate or isopropenyl chloroformate respectively using standard conditions familiar to those skilled in the art. Further reaction of carbamates 10 or 11 with amine A-NH$_2$ 6 provides compounds of formula 1. Those skilled in the art will further Many methods exist for the preparation of amines A-NH, 6 and acids A-CO$_2$H 7, depending on the nature of the A-moiety. Indeed, many such amines (6) and acids (7) useful for the preparation of compounds of formula 1 are available from commercial vendors. Some non-limiting preferred synthetic methods for the preparation of amines 6 and acids 7 are outlined in the following schemes and accompanying examples.

As illustrated in Scheme 6. Z4-substituted pyrazol-5-yl amines 14 (a preferred aspect of A-NH$_2$ 6, Scheme 2) are available by the condensation of hydrazines 12 and beta-keto nitrites 13 in the presence of a strong acid. Preferred conditions for this transformation are by heating in ethanolic HCl. Many such hydrazines 12 are commercially available. Others can be prepared by conditions familiar to those skilled in the art, for example by the diazotization of amines followed by reduction or, alternately from the reduction of hydrazones prepared from carbonyl precursors.

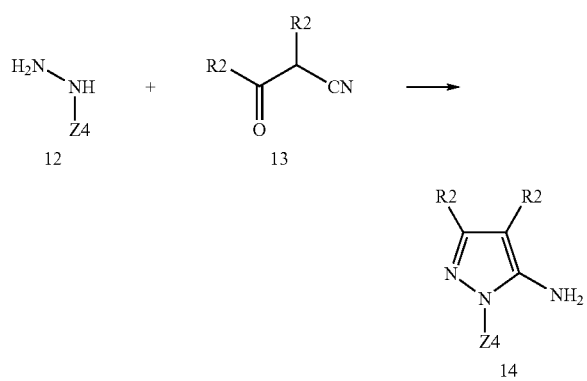

Another preferred method for constructing Z4-substituted pyrazoles is illustrated by the general preparation of pyrazole acids 19 and 20. (Scheme 7), aspects of general acid A-CO$_2$H 7 (Scheme 3). As indicated in Scheme 7, pyrazole 5-carboxylic esters 17 and 18 can be prepared by the alkylation of pyrazole ester 16 with Z4-X 15, wherein X represents a leaving group on a Z4 moiety such as a halide, triflate, or other sulfonate. Preferred conditions for the alkylation of pyrazole 16 include the use of strong bases such as sodium hydride, potassium tert-butoxide and the like in polar aprotic solvents such as dimethylsulfoxide, dimethylformamide or tetrahydrofuran. Z4-substituted pyrazoles 17 and 18 are isomers of one another and can both be prepared in the same reactions vessel and separated by purification methods familiar to those skilled in the art. The esters 17 and 18 in turn can be converted to acids 19 and 20 using conditions familiar to those skilled in the art, for example saponification in the case of ethyl esters, hydrogenation in the case of benzyl esters or acidic hydrolysis in the case of tert-butyl esters.

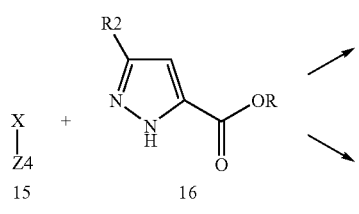

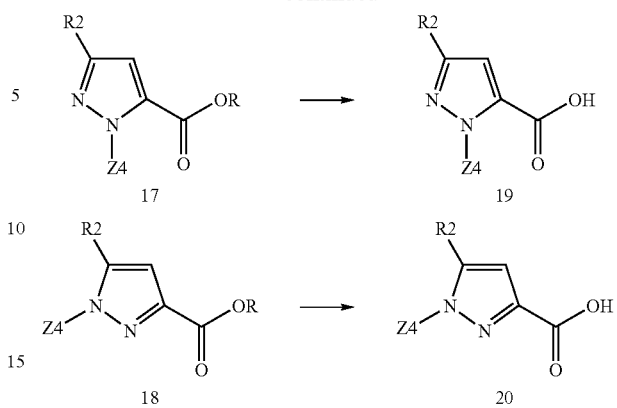

Scheme 8 illustrates the preparation of pyrazole amine 95, a further example of general amine A-NH-6. Acid-catalyzed condensation of EC-substituted hydrazine 21 with 1,1,3,3-tetramethoxypropane 22 provides R2-substituted pyrazole 23. Those skilled in the art will further recognize that R2-substituted pyrazole 23 can also be prepared by direct alkylation of pyrazole. Pyrazole 23 can be regioselectively nitrated to provide nitro-pyrazole 24 by standard conditions familiar to those skilled in the art. Finally, hydrogenation of nitro-pyrazole 24 employing a hydrogenation catalyst, such as palladium or nickel provides pyrazole amine 25, an example of general amine A-NH$_2$ 6.

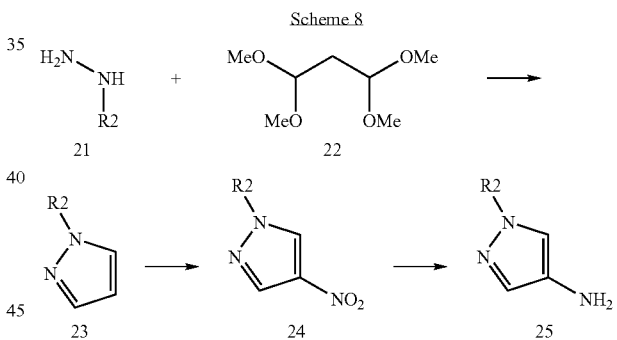

Additional pyrazoles useful for the synthesis of compounds of formula 1 can be prepared as described in Scheme 9. Thus, keto-ester 26 can be reacted with N,N-dimethylformamide dimethyl acetal to provide 27. Reaction of 27 with either 21 or 28 (wherein P is an acid-labile protecting group) in the presence of acid provides 29 or 30. In practice, both 29 and 30 can be obtained from the same reaction and can be separated by standard chromatographic conditions. In turn, esters 29 and 30 can be converted to acids 31 and 32 respectively as described in Scheme 7.

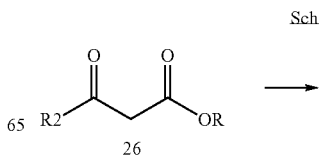

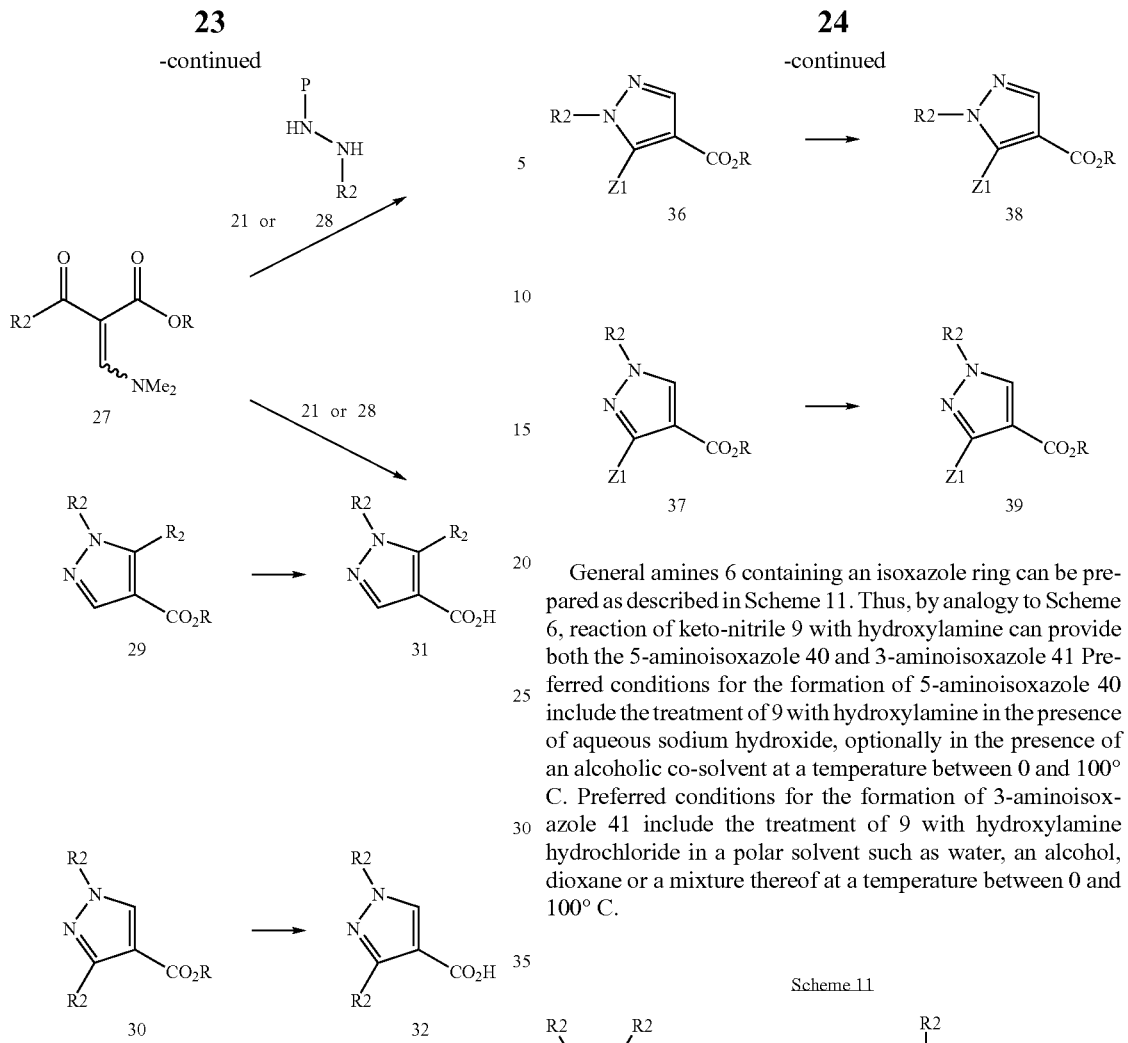

In a manner similar to Scheme 9, NH-pyrazole 34 can be prepared by reaction of acrylate D with hydrazine (Scheme 10). Alkylation of 34 with R2-X 35 as described above for Scheme 7 provides mixtures of pyrazole esters 36 and 37 which are separable by standard chromatographic techniques. Further conversion of esters 36 and 37 to acids 38 and 39 can be accomplished as described in Scheme 7.

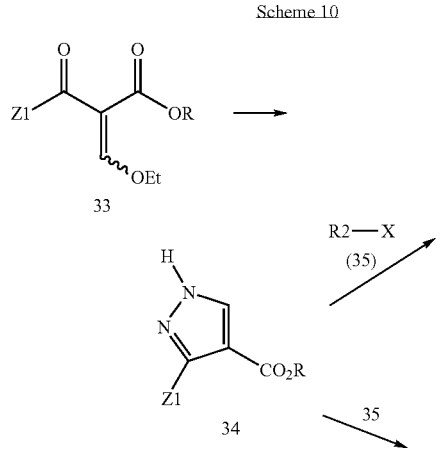

General amines 6 containing an isoxazole ring can be prepared as described in Scheme 11. Thus, by analogy to Scheme 6, reaction of keto-nitrile 9 with hydroxylamine can provide both the 5-aminoisoxazole 40 and 3-aminoisoxazole 41 Preferred conditions for the formation of 5-aminoisoxazole 40 include the treatment of 9 with hydroxylamine in the presence of aqueous sodium hydroxide, optionally in the presence of an alcoholic co-solvent at a temperature between 0 and 100° C. Preferred conditions for the formation of 3-aminoisoxazole 41 include the treatment of 9 with hydroxylamine hydrochloride in a polar solvent such as water, an alcohol, dioxane or a mixture thereof at a temperature between 0 and 100° C.

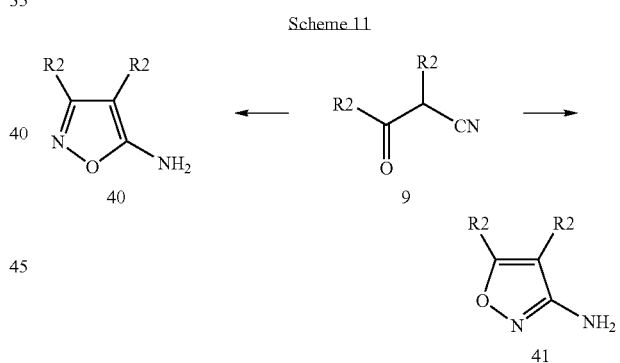

Amines 2 useful for the invention can be synthesized according to methods commonly known to those skilled in the art. Amines of general formula 2 contain three rings and can be prepared by the stepwise union of three monocyclic subunits as illustrated in the following non-limiting Schemes. Scheme 12 illustrates one mode of assembly in which an E-containing subunit 42 is combined with the central pyridine ring 43 to provide the bicyclic intermediate 44. In one aspect this general Scheme, the "M" moiety of 42 represents a hydrogen atom of a heteroatom on the X linker that participates in a nucleophilic aromatic substitution reaction with monocycle 43. Such reactions may be facilitated by the presence of bases (for example, potassium tert-butoxide), thus M may also represent a suitable counterion (for example potassium, sodium, lithium, or cesium) within an alkoxide, sulfide or amide moiety. Alternately, the "M" group can represent a metallic species (for example, copper, boron, tin, zirconium, aluminum, magnesium, lithium, silicon, etc.) on a carbon atom of the X moiety that can undergo a transition-metal-mediated coupling with monocycle 43.

The "Y" group of monocyclic species 42 is an amine or an amine surrogate, such as an amine masked by a protecting group ("P" in formula 4), a nitro group, or a carboxy acid or ester that can be used to prepare an amine via known rearrangement. Examples of suitable protecting groups "P" include but are not limited to tert-butoxycarbonyl (Boc), benzyloxycarbonyl (Cbz), and acetamide. In the instances wherein the "Y"-group of intermediate 42 is not an amine, the products of Scheme 11 will be amine surrogates such as 45 or 46 that can be converted to amine 2 by a deprotection, reduction or rearrangement (for example, Curtius rearrangement) familiar to those skilled in the art.

In these instances, the "LG" of monocycle 43 represents a moiety that can either be directly displaced in a nucleophilic substitution reaction (with or without additional activation) or can participate in a transition-mediated union with fragment 42. The W group of monocycle 43 or bicycle 44 represents a moiety that allows the attachment of the pyrazole. In one aspect, the "W" group represents a halogen atom that will participate in a transition-metal-mediated coupling with a preformed heterocyclic reagent (for example a boronic acid or ester, or heteroaryl stannane) to give rise to amine 2. In another aspect, the "W" group of 43 and 44 represents a functional group that can be converted to a five-membered heterocycle by an annulation reaction. Non-limiting examples of such processes would include the conversion of a cyano, formyl, carboxy, acetyl, or alkynyl moiety into a pyrazole moiety. It will be understood by those skilled in the art that such annulations may in fact be reaction sequences and that the reaction arrows in Scheme 11 may represent either a single reaction or a reaction sequence. Additionally, the "W" group of 44 may represent a leaving group (halogen or triflate) that can be displaced by a nucleophilic nitrogen atom of a pyrazole ring.

Scheme 12

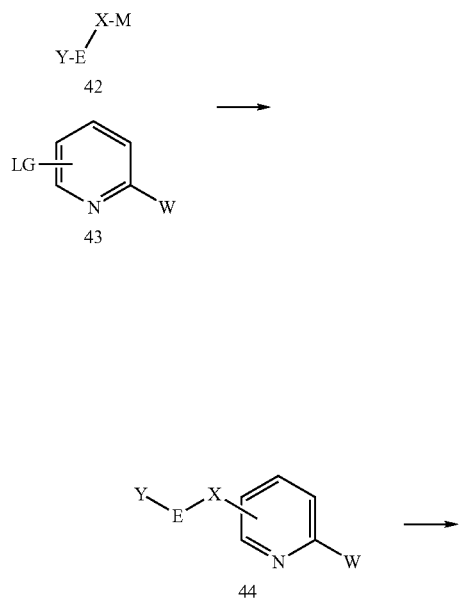

-continued

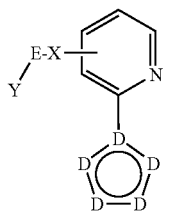

2 Y = NH$_2$
45 Y = NH—P or NO$_2$
46 Y = CO$_2$R

Some non-limiting examples of general Scheme 12 are illustrated in the Schemes below. Scheme 13 illustrates the preparation of pyrazole 51 an example of general amine 2. In Scheme 13, commercially available 3-fluoro-4-aminophenol (47) is reacted with potassium tert-butoxide and 2,4-dichloropyridine 48 to provide chloropyridine 49. The preferred solvent for this transformation is dimethylacetamide at a temperature between 80 and 100° C. Subsequent union of chloropyridine 49 with the commercially available pyrazole-4-boronic acid pinacol ester 50 in the presence of a palladium catalyst, preferably palladium tetrakis(triphenylphosphine), provides amine 51.

Scheme 13

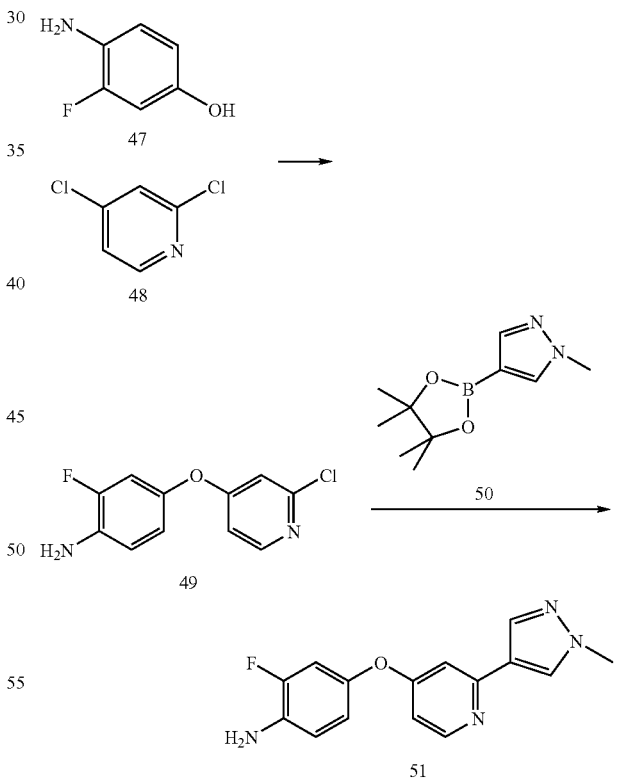

Scheme 14 illustrates a non-limiting examples of Scheme 12 wherein the "W" group is a leaving group for nucleophilic aromatic substitution. Thus, amine 53 an example of general amine 2, can be prepared from general intermediate 49 by reaction with pyrazole (52). Preferred conditions include the use of polar aprotic solvents such as 1-methyl-2-pyrrolidinone, dimethylacetamide, or dimethylsulfoxide in the presence of non-nucleophilic bases such as potassium carbonate, sodium hydride, 1,8-diaza-bicyclo[5.4.0]undec-7-ene (DBU)7 and the like. Preferred temperatures are from ambient temperature up to about 250° C. and may optionally include the use of microwave irradiation or sonication.

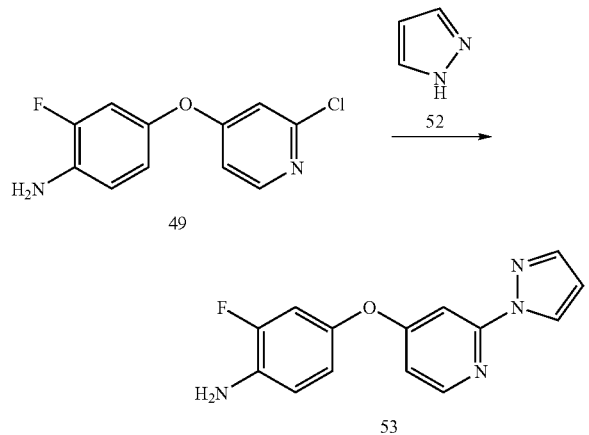

Scheme 15 illustrates the preparation of amine 54, a non-limiting example of a general amine of formula 2 by way of an annulation sequence according to general Scheme 12. Conversion of chloropyridine 49 into alkyne 53 can be accomplished by Sonogashira cross-coupling with trimethylsilylacetylene, followed by aqueous hydrolysis of the trimethylsilyl group, conditions familiar to those skilled in the art. Further reaction of alkyne 53 with trimethylsilyl diazomethane at elevated temperature affords the pyrazole amine 54 (see for example, Tsuzuki, et. al, *J. Med. Chem* 2004, (47), 2097).

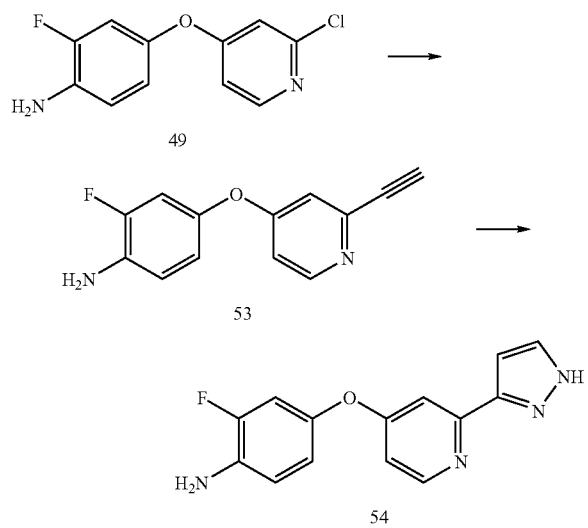

Additional preferred synthetic methods for the preparation of compounds of formula 1 are found in the following examples.

SECTION 4. EXAMPLES

General Method A: To a solution of the starting pyrazole amine (1 eq) in EtOAc were added 2,2,2-trichloroethylchloroformate (1.1 eq) and saturated NaHCO, (2-3 eq) at 0° C. After stirring for 3 h at RT, the layers were separated and the aqueous layer extracted with EtOAc. The combined organic extracts were washed with brine, dried $Na_2SO_4$) and concentrated under vacuum to yield the crude TROC carbamate of The pyrazole amine.

To the TROC carbamate (1 eq) in DMSO were added diisopropylethylamine (2 eq), the appropriate amine (2 eq) and the mixture was stirred at 60° C. for 16 h or until all the starting carbamate was consumed. Water was added to the mixture and the product was extracted with EtOAc (2×25 mL). The combined organic extracts were washed with brine solution, dried ($Na_2SO_4$) and concentrated to yield crude product, which was purified by column chromatography to yield the target compound.

General Method B: To a suspension of the amine (usually 0.67 mmol) in EtOAc (2 mL) was added aqueous 1N NaOH. The reaction mixture was cooled to 0° C. and treated with isopropenyl chloroformate (0.1 mL, 0.94 mmol) over 30 sec. The reaction mixture was stirred for 15 min at 0° C. and 1 h at RT. The reaction was poured into THF-EtOAc (1:1; 40 mL) and washed with $H_2O$ (2×10 mL) and brine (2×10 mL). The organics were dried ($Na_2SO_4$), concentrated and the residue purified via column chromatography or recrystallization to provide the target (prop-1-en-2-yl)carbamate. To the carbamate (usually 0.26 mmol) was added the appropriate amine (usually 0.26 mmol) in THF (2 n-L) and 1-methylpyrrolidine (catalytic amounts and the reaction mixture was stirred at 60° C. for 18 h. The mixture was diluted with $CH_2Cl_2$ (2 mL) and hexane (0.5 mL) solution, and stirred for 10 min. The resultant solid was filtered and dried.

General Method C: To a stirring solution of the carboxylic acid (0.24 mmol) and TEA (1.2 mmol) in 1,4-dioxane (4.5 mL) at RT was added DPPA (0.29 nmol). After stirring for 0.5 h at RT, the appropriate amine (0.71 mmol) was added and the reaction was stirred with heating at 100° C. for 2 h. The reaction was cooled to RT, diluted with brine (15 mL) and extracted with EtOAc (3×30 mL). The combined organic layers were dried ($MgSO_4$) and concentrated. The residue was purified by chromatography to afford the target compound.

General Method D: To a stirring suspension of amine (3.2 mmol, 1.0 eq) in THF (6 ml) at −78° C. was added 1.0M LiHMDS/THF (6.4 mmol, 2.00 eq). After 30 min at −78° C., the resulting solution was treated with isopropenyl chloroformate (3.2 mmol, 1.0 eq). After another 30 min at −78° C., the completed reaction was diluted with 3M HCl, warmed to RT and extracted with EtOAc (2×). The combined organics were washed with $H_2O$ (1×), satd. $NaHCO_3$ (1×), and brine (1×), dried ($MgSO_4$), filtered and concentrated in vacuo to afford the target prop-1-en-2-yl carbamate which was used as is, purified by silica gel chromatography or recrystallized.

To the carbamate (usually 0.26 mmol) was added the appropriate amine (usually 0.26 mmol) in THF (2 mL) and 1-methylpyrrolidine (catalytic amount) and the reaction was stirred at 60° C. for 18 h. The mixture was diluted with $CH_2Cl_2$ (2 mL) and hexane (0.5 mL) solution, and stirred for 10 min. The resultant solid was filtered and dried and the resulting solid converted to the amine hydrochloride salt by treatment with 0.1 N HCl solution and lyophilization or purified via column chromatography.

General Method E: To a stirring solution of amine (2 mmol, 1.00 eq) and pyridine (4mmol, 2.00 eq) in $CH_2Cl_2$ (18 ml) at RT was added isopropenyl chloroformate (1.87 mmol, 1.05 eq). After 4 hours the reaction was washed with 3M HCl (1×), satd. NaHCO$_3$ (1×), dried (Na$_2$SO$_4$), filtered and evaporated to afford the target prop-1-en-2-yl carbamate. The material was used as is in the next reaction.

To the carbamate (usually 0.26 mmol) was added the appropriate amine (usually 0.26 mmol) in THF (2 mL) and 1-methylpyrrolidine (catalytic amount) and the reaction was stirred at 60° C. for 18 h. The mixture was diluted with CH$_2$Cl$_2$ (2 mL) and hexane (0.5 mL) solution, and stirred for 10 nm. The resultant solid was filtered and dried.

General Method F: To a solution of amine (6.53 mmol) in ethyl acetate (20 mL) at RT was added a solution of sodium bicarbonate (11.90 mmol) in water (20 mL) and isopropenyl chloroformate (9.79 mmol). The resultant mixture was stirred for 3 h at RT. The organic layer was separated. The aqueous layer was extracted once with ethyl acetate. The combined organic extracts were washed with brine, dried (MgSO$_4$) and concentrated in vacuo. The residue was used without further purification or purified via recrystallization or chromatography to provide the corresponding prop-1-en-2-yl carbamate.

Example A1

A suspension of 3-fluoro-4-aminophenol (8.0 g, 63.0 mmol) in dimethylacetamide (80 mL) was de-gassed in vacuo and treated with potassium tert-butoxide (7.3 g, 65 mmol). The resultant mixture was stirred at RT for 30 min. 2,4-Dichloropyridine (8 g, 54 mmol) was added and the mixture was heated to 80° C. for 12 h. The solvent was removed under reduced pressure to give a residue which was partitioned between water and EtOAc (3×100 mL). The organic layers were washed with saturated brine, dried (MgSO$_4$), concentrated in vacuo and purified by silica gel column chromatography to give 4-(2-chloro-pyridin-4-yloxy)-2-fluoro-phenylamine (11 g, 86% yield). $^1$H NMR (300 MHz, DMSO-d6), δ 8.24 (d, J=5.7 Hz, 1 H), 7.00 (dd, J=9.0, 2.7 Hz, 1 H), 6.89-6.73 (m, 4 H), 5.21 (br s, 2 H); MS (ESI) m/z: 239.2 (M+H+).

A solution of 4-(2-chloropyridin-4-yloxy)-2-fluorobenzenamine (3 g, 12.6 mmol), 1-methyl-3-(4,4,5,5-tetramethyl-[1,3,2]dioxaborolan-2-yl)-1H-pyrazole (5.2 g, 25.2 mmol), and Na$_2$CO$_3$ (2.7 g, 25.2 mmol) in DME (18 mL) and water (6 mL) was sparged with nitrogen for 20 min. Pd(PPh$_3$)$_4$ (729 mg, 0.63 mmol) was added and the resulting mixture was heated to 100° C. for 16 h. The solvent was removed under reduced pressure and the crude product was suspended in water and extracted with EtOAc. The organic layer was washed with brine, dried (NaSO$_4$), filtered, concentrated in vacuo and purified via silica gel chromatography to give 2-fluoro-4-(2-(1-methyl-1H-pyrazol-4-yl)pyridin-4-yloxy) benzenamine (2 g, 56% yield). $^1$H NMR (300 MHz, DMSO-d$_6$): δ 8.31 (d, J=5.7 Hz, 1 H), 8.21 (s, 1 H), 7.92 (s, 1 H), 7.12 (d, J=2.4 Hz, 1 H), 6.96 (m, 1 H), 6.85-6.72 (m, 2 H), 6.56 (m, 1 H), 5.15 (s, 2 H), 3.84 (s, 3H); MS (ESI) m/z: 285.0 (M+H+).

Example A2

4-amino-phenol (8.9 g, 81.6 mmol) and potassium tert-butoxide (10.7 g, 95.2 mmol) were suspended in DMF (100 mL) and stirred at RT for 30 min. 2,4-Dichloro-pyridine (10 g, 68 mmol) was added and the resulting mixture was heated to 90° C. for 3 h. The solvent was removed under vacuum and the residue was extracted with DCM (2×100 mL). The combined organics were dried (MgSO$_4$), concentrated in vacuo and purified by silica gel chromatography to afford 4-(2-chloro-pyridin-4-yloxy)-phenylamine (9.0 g, 60% yield). $^1$H NMR (DMSO-d$_6$): δ 8.21 (d, J=5.6 Hz, 1 H), 6.85-6.82 (m, 4 H), 6.61 (d, J=6.6 Hz, 2 H), 5.17 (s, 2 H); MS (ESI) m/z: 221 (M+H+).

4-(2-Chloro-pyridin-4-yloxy)-phenylamine (0.7 g, 3.2 mmol), 1-methyl-4-(4,4,5,5-tetramethyl-[1,3,2]dioxaborolan-2-yl)-4H-pyrazole (1.0 g, 4.8 mmol), Cs$_2$CO$_3$ (4.0 g, 12.3 mmol) and Pd(PPh$_3$)$_4$ (0.45 g, 0.4 mmol) were combined in a mixture of DMF and water (3:1, 20 mL). The reaction mixture was degassed, blanketed with argon and heated to 90° C. overnight. The reaction mixture was diluted with water and extracted with EtOAc (3×50 mL). The combined organics were washed with saturated brine, dried (MgSO$_4$), concentrated in vacuo and purified by silica gel chromatography to provide 4-(2-(1-methyl-1H-pyrazol-4-yl)pyridin-4-yloxy) benzenamine (0.7 g, 74% yield). $^1$H NMR (300 MHz, DMSO-d$_6$), δ 8.29 (d, J=5.7 Hz, 1 H), 8.19 (s, 1 H), 7.90 (s, 1 H), 7.10 (d, J=2.4 Hz, 1 H), 6.83 (d, J=8.7 Hz, 2 H), 6.62 (d, J=8.7 Hz 2 H), 6.52 (dd, J=2.4, 5.7 Hz, 1 H), 5.10 (s, 2 H), 3.84 (s, 3 H); MS (ESI) m/z: 267.3 (M+H+)

Example A3

1,2,3-Trifluoro-4-nitro-benzene (30 g, 0.17 mol), benzyl alcohol (18.4 g, 0.17 mol) and K$_2$CO$_3$ (35 g, 0.25 mol) were combined in DMF (300 mL) and were stirred at RT for 8 h. Water (300 mL) was added, and the mixture was extracted with EtOAc (3×500 mL). The combined organic layers were washed with brine, dried (MgSO$_4$), concentrated in vacuo and purified by column chromatography on silica gel to give 1-benzyloxy-2,3-difluoro-4-nitro-benzene (16 g, 36% yield). $^1$H NMR (400 MHz, DMSO-d$_6$): δ 8.06 (m, 1 H), 7.49-7.30 (m, 6 H), 5.37 (s, 2 H).

A solution of 1-benzyloxy-2,3-difluoro-4-nitro-benzene (14 g, 52.8 mmol) in MeOH (200 mL) was stirred with Pd/C (10%, 1.4 of 1.3 mmol) under a hydrogen atmosphere (30 psi) for 2 h. The catalyst was removed by filtration, and the filtrate was concentrated in vacuo to afford 4-amino-2,3-difluorophenol (7 g, 92.1% yield). $^1$H NMR (400 MHz, DMSO-d$_6$): δ 9.05 (s, 1 H), 6.45 (t, J=8.8 Hz, 1 H), 6.34 (t, J=9.2 Hz, 1 H), 4.67 (s, 2 H); MS (ESI) m/z: 146.1[M+H]+.

4-amino-2,3-difluorophenol (6 g, 41.4 mmol) and potassium tert-butoxide (4.9 g, 43.5 mmol) were suspended in DMAc (200 mL) and stirred at RT for 30 min under Ar atmosphere. 2,4-Dichloropyridine (6.1 g, 41.4 mmol) was added, and the resulting mixture was heated at 70° C. for 8 h. The reaction mixture was filtered, concentrated in vacuo and purified by silica gel chromatography to afford 4-(2-chloro-pyridin-4-yloxy)-2,3-difluoro-phenylamine (7 g, 66% yield). $^1$H NMR (400 MHz, DMSO-d$_6$): δ 8.27 (d, J=6.0 Hz, 1 H), 7.05 (s, 1 H), 6.95 (m, 1 H), 6.92 (m, 1 H), 6.62 (m, 1 H), 5.60 (s, 2 H); MS (ESI) m/z: 257.1[M+H]+.

Nitrogen was bubbled though a solution of 4-(2-chloro-pyridin-4-yloxy)-2,3-difluoro-phenylamine (2 g, 7.8 mmol), 1-methyl-4-(4,4,5,5-tetramethyl-[1,3,2]dioxaborolan-2-yl)-1H-pyrazole (1.6 g, 7.8 mmol) and Na$_2$CO$_3$ (1.65 g, 15.6 mmol) in DME (12 mL) and H$_2$O (4 mL) for 20 min. Pd(PPh$_3$)$_4$ (450 mg, 0.4 mmol), was added and then resulting mixture was degassed in vacuo, blanketed with nitrogen and heated to 70° C. for 16 h. The reaction was concentrated to dryness under reduced pressure. The crude product was suspended in water and extracted with EtOAc (3×10 mL). The organic layer was washed with brine, dried (Na$_2$SO$_4$), concentrated in vacuo and purified by silica gel chromatography to give 2,3-difluoro-4-[2-(1-methyl-1H-pyrazol-4-yl)-pyridin-4-yloxy]-phenylamine (1.3 g, 55% yield). $^1$H NMR (400 MHz, DMSO-d$_6$), δ 8.40 (d, J=6.0 Hz, 1 H), 8.32 (s, 1 H), 8.02

(s, 1 H), 7.26 (s, 1 H), 6.96 (t, J=8.8 Hz, 1 H), 6.71-6.68 (m, 2 H), 5.62 (s, 2 H), 3.92 (s, 3 H); MS (ESI) m/z: 303.2[M+H]$^+$.

Example A4

A solution of 1,3-difluoro-2-methyl-benzene (15 g, 0.12 mol) in conc. H$_2$SO$_4$ (100 mL) was treated drop wise with 65% HNO$_3$ (11.4 g, 0.12 mol) at −10° C. and the resultant mixture was stirred for about 30 min. The mixture was poured into ice-water and extracted with ethyl acetate (3×200 mL). The combined organic layers were washed with brine, dried (Na$_2$SO$_4$) and concentrated in vacuo to give 1,3-difluoro-2-methyl-4-nitro-benzene (16 g, 78% yield) $^1$H NMR (400 MHz, CDCl$_3$): δ 7.80 (m, 1 H), 6.95 (m, 1H), 2.30 (s, 3 H).

1,3-Difluoro-2-methyl-4-nitro-benzene (16 g, 0.092 mol), benzyl alcohol (10 g, 0.092 mol) and K$_2$CO$_3$ (25.3 g, 0.18 mol), were combined in DMF (300 mL) and heated to 100° C. overnight. The mixture was poured into water and extracted with ethyl acetate (3×200 mL). The combined organic layers were washed with brine, dried (Na$_2$SO$_4$), concentrated in Vacuo and purified by silica gel chromatography to give 1-benzyloxy-3-fluoro-2-methyl-4-nitro-benzene (8 g, 33% yield). $^1$H NMR (400 MHz, DMSO-d$_6$): δ 8.04 (t, J=8.8 Hz, 1 H), 7.30-7.46 (m, 5 H), 7.08 (d, J=9.2 Hz, 1 H), 5.28 (s, 2 H), 2.13 (s, 3H).

Using a procedure analogous to Example A3, 1-benzyloxy-3-fluoro-2-methyl-4-nitro-benzene (8 g, 0.031 mol) was hydrogenated to give 4-amino-3-fluoro-2-methyl-phenol (4.2 g, 96% yield). $^1$H NMR (300 MHz, DMSO-d$_6$): δ 8.61 (s, 1 H), 6.36 (m, 2 H), 4.28 (s, 2 H), 1.96 (s, 3 H); MS (ESI) m/z: 142.1 [M+H]$^+$.

Potassium tert-butoxide (3.5 g, 31 mmol) was added to a solution of 4-amino-3-fluoro-2-methyl-phenol (4.2 g, 30 mmol) in dimethylacetamide. The mixture was stirred at RT for 30 min. A solution of 2,4-dichloropyridine (4.38 g, 30 mmol) in dimethylacetamide was added and the mixture was heated at 100° C. overnight. The reaction mixture was concentrated in vacuo and the residue was dissolved in ethyl acetate (200 mL) and filtered through silica gel. The filter cake was washed with ethyl acetate and the combined filtrates were concentrated in vacuo and purified by silica gel chromatography to give 4-(2-chloro-pyridin-4-yloxy)-2-fluoro-3-methyl-phenylamine (3.2 g, 42% yield). $^1$H NMR (400 MHz, DMSO-d$_6$): δ 8.21 (d, J=6.4 Hz, 1 H), 6.84 (d, J=2.0 Hz, 1 H), 6.81 (dd, J=5.6, 2.4 Hz, 1 H), 6.67-6.65 (m, 2 H), 5.13 (s, 2H), 1.91 (s, 3 H); MS (ESI): m/z 253.2 [M+H]$^+$.

Using a procedure analogous to Example A3, 4-(2-chloro-pyridin-4-yloxy)-2-fluoro-3-methyl-phenylamine (1.0 g, 3.3 mmol), 1-methyl-4-(4,4,5,5-tetramethyl-[1,3,2]dioxaborolan-2-yl)-1H-pyrazole (1 g, 4.8 mmol), Na$_2$CO$_3$ (0.84 g, 6.6 mmol) and Pd(PPh$_3$)$_4$ (0.25 g, 0.2 mmol) were combined to give 2-fluoro-3-methyl-4-[2-(1-methyl-1H-pyrazol-4-yl)-pyridin-4-yloxy]-phenylamine (0.74 g, 75% yield). $^1$H NMR (400 MHz, DMSO-d$_6$): δ 8.27 (d, J=6.4 Hz, 1 H), 8.18 (s, 1 H), 7.90 (s, 1 H), 7.07 (s, 1 H), 6.68-6.61 (m, 2 H), 6.45 (dd, J=5.6, 2.4 Hz, 1 H), 5.06 (s, 2 H), 3.89 (s, 3 H), 1.95 (s, 3H); MS (ESI) m/z: 299.2 [M+H]$^+$.

Example B1

To an aqueous solution of sodium hydroxide solution (40.00 g, 1 mol, in 200 ml of water) was added hydroxylamine hydrochloride (24.00 g, 346 mmol) and pivaloylacetonitrile (40.00 g, 320 mmol). The resulting solution was stirred at 50° C. for 3 hrs. The reaction mixture cooled and the resultant white crystalline solid filtered, washed with water and dried to provide 3-t-butylisoxazol-5-amine as a white crystalline solid (34 g, yield 76% yield). $^1$H NMR (DMSO-d$_6$) δ 6.41 (brs, 2H), 4.85 (s, 1H), 1.18 (s, 9H): LC-MS (ES, m/z, M+H) 141.3.

Example B2

Methyl hydrazine and 4,4-dimethyl-3-oxopentanenitrile were combined according to literature procedures to yield 3-t-butyl-1-methyl-1H-pyrazol-5-amine. See WO 2006/071940.

Example B3 t-Butylhydrazine and 1,1,3,3-tetramethoxypropane were combined according to literature procedures to yield 1-t-butyl-1H-pyrazol-4-amine. See Ger. Offen., DE3332270, 21 Mar. 1985.

Example B4

To a suspension of KCN (1.90 g, 29.1 mmol) in MeOH (35 mL) was added dropwise 3-bromo-1,1,1-trifluoropropan-2-one oxime (5.00 g, 24.3 mmol) in MeOH (72 mL) at RT. The reaction mixture was stirred at RT for 3 hours. The solution was concentrated in vacuo, the residue was dissolved in EtOAc and stirred at RT. The solid was filtered and the filtrate was evaporated to obtain the crude product. The crude product was purified by silica gel column chromatography EtOAc/hexanes) to obtain 3-(trifluoromethyl)isoxazol-5-amine (1.38 g, 37% yield). MS (ESI) m/z: 153.0 (M+H$^+$).

Example B5

Using a procedure analogous to Example B6, ethyl 1-tert-butyl-5-(trifluoromethyl)-1H-pyrazole-4-carboxylate (750 mg, 2.84 mmol) was converted to 1-tert-butyl-5-(trifluoromethyl)-1H-pyrazole-4-carboxylic acid (646 mg, 94% yield) using lithium hydroxide hydrate (357 mg, 8.51 mmol). $^1$H NMR (300 MHz, DMSO-d$_6$), δ 1.63 (s, 9 H), 7.92 (s, 1 H); MS (ESI) m/z: 259.0 (M+Na$^+$).

Example B6

In ethanol (10 mL) was placed the tert-butylhydrazine hydrochloride (1.35 g, 10.8 mmol) and ethyl 2-((dimethylamino)methylene)-3-oxobutanoate (2.00 g, 10.8 mmol). The mixture warmed to reflux and stirred for 2 hrs, then cooled to RT and stirred overnight. The mixture was evaporated at reduced pressure to give an oil which was dissolved in ether (25 mL) and washed successively with water (25 mL), saturated sodium bicarbonate (25 mL) and brine (25 mL), dried (Na$_2$SO$_4$), evaporated at reduced pressure and purified by chromatography (S1-25 column, ethyl acetate/hexanes) to give ethyl 1-tert-butyl-5-methyl-1H-pyrazole-4-carboxylate (1.48 g, 65% yield) as an oil. MS (ESI) m/z: 211.0 (M+H$^+$).

In a mixture of ethanol:water:dioxane (1:1:1, 21 mL) was placed ethyl 1-tert-butyl-5-methyl-1H-pyrazole-4-carboxylate (1.48 g, 7.04 mmol) and lithium hydroxide hydrate (886 mg, 21.12 mmol). The reaction was stirred at 40° C. for 3 hrs and then at RT overnight. The reaction was diluted with water (25 mL) and ether (25 mL). The ether layer was discarded and the aqueous phase made acidic (pH~=4) with 1N HCl. The acidic phase was then extracted with ethyl acetate (2×25 mL) and the combined ethyl acetate layers were washed with brine, dried (Na$_2$SO$_4$), and evaporated at reduced pressure to give 1-tert-butyl-5-methyl-1H-pyrazole-4-carboxylic acid as a white solid (1.12 g, 87% yield). $^1$H NMR (300 MHz, DMSO-d$_6$): δ 1.56 (s, 9 H), 2.67 (s, 3 H), 7.65 (s, 1 H), 12.13 (s, 1 H); MS (ESI) m/z: 183.0 (M+$^+$).

Example B7

A solution of nBuLi in hexanes (242 mL, 387 mmol) was added to a −78° C. solution of diisopropylamine (39.1 g, 387 mmol) in anhydrous THF (300 mL) and the resultant mixture was stirred for 30 min at −78° C. A solution of ethyl cyclopentanecarboxylate (50 g, 352 mmol) in anhydrous THF (150 mL) was added dropwise into the mixture and the reaction mixture was stirred at −78° C. for 1 h. Iodomethane (79.2 g, 558 mmol) was added dropwise and the resulting mixture was warmed to RT and stirred overnight. The mixture was poured into water and extracted with ethyl ether. The combined extracts were washed with brine, dried (MgSO$_4$) and concentrated in vacuo to give ethyl 1-methylcyclopentanecarboxylate (47 g, 85%). $^1$H NMR (300 MHz, DMSO-d$_6$): δ 4.03 (q, J=7.2 Hz, 2 H), 1.37-2.03 (m, 8 H), 1.15-1.12 (m, 6 H).

Ethyl 1-methylcyclopentanecarboxylate (47 g, 301 mmol), acetonitrile (14.5 g, 363 mmol), NaH (18 g, 450 mmol), NaOH (6.8 g, 170 mmol) and hydroxylamine hydrochloride (4 g, 57 mmol) were sequentially combined by a procedure analogous to Example B10 to provide 3-(1-methylcyclopentyl)isoxazol-5-amine (7 g, 70% yield over 2 steps). $^1$H NMR (400 MHz, DMSO-d$_6$): δ 6.41 (s, 2 H), 4.81 (s, 1 H), 1.91-1.86 (m, 2H), 1.67-1.48 (m, 6 H), 1.19 (s, 3 H); MS (ESI) m/z: 167.1 (M+H$^+$).

Example B8

Sodium metal (13.8 g, 0.5 mol) was added portionwise to ice-cold anhydrous EtOH (700 mL). After complete dissolution of the Na, a mixture of 3,3-dimethylbutan-2-one (50 g, 0.5 mol) and oxalic acid diethyl ester (77 ml, 0.5 mol) was added drop-wise. The reaction mixture was stirred in ice-salt bath until TLC indicated completion of the reaction. Acetic acid (38.1 ml, 0.5 mol) was added and the mixture was stirred at RT for 30 min. The reaction mixture was cooled in an ice-salt bath and treated with hydrazine hydrate (29.4 g, 0.5 mol). After complete addition, the mixture was warmed to RT and stirred until judged complete by TLC. The reaction mixture was concentrated under reduced pressure and re-dissolved in EtOAc. The EtOAc solution was washed with NaHCO$_3$, brine and water, dried (MgSO$_4$) and concentrated in vacuo. The resultant solid was washed with cold petroleum ether to give ethyl 3-tert-butyl-1H-pyrazole-5-carboxylate (49 g, 50% yield over two steps) as a white solid. $^1$H NMR (400 MHz, CDCl$_3$): δ 6.65 (s, 1 H), 4.38 (q, J=6.8 Hz, 2 H), 11.39 (t, J=6.8 Hz, 3 H), 1.35 (s, 1 H); MS (ESI) m/z 197.2 (M+H$^+$).

Potassium t-butoxide (2.6 g, 23 mmol) was dissolved in DMSO (10 mL) and to this solution was added ethyl 3-tert-butyl-1H-pyrazole-5-carboxylate (4.5 g, 23 mmol) in small portions and stirred under Ar for 15 min. To this solution was added t-butyl-bromoacetate (5.4 g, 28 mmol) slowly at 0° C. with stirring for 45 min at RT. Sat. NH$_4$Cl solution was added and product was extracted with ethyl acetate (3×50 mL). The combined organic layers were washed with brine, dried (Na$_2$SO$_4$) and concentrated to afford (7.0 g) coupled product as a pasty mass. The above pasty mass was dissolved in TFA (10 mL) and stirred for 3 h at RT. Solvents were removed, water (100 mL) was added and product was extracted with DCM (3×50 ml). The combined organic extracts were washed with brine solution, dried (Na$_2$SO$_4$) and concentrated to yield 2-(3-tert-butyl-5-(ethoxycarbonyl)-1H-pyrazol-1-yl)acetic acid (5.8 gm, 100%) as a pasty mass. $^1$H NMR (400 MHz, Acetone-d$_6$): δ 6.78 (s, 1H), 5.25 (s, 2H), 4.30 (q, J=7.2 Hz, 2H), 1.35-1.30 (m, 12H); MS (ESI) m/z: 255.2 (M+H$^+$).

To a solution of acid (0.41 g, 1.6 mmol) in DMF (5 mL) was added PyBop (0.84 g, 1.6 mmol), DIPEA (0.42 g, 3.2 mmol) and dimethylamine hydrochloride (0.26 g, 3.2 mmol). After stirring the mixture for 1 h at RT, water (50 mL) was added, and the product was extracted with ethyl acetate (2×30 ml). The combined organic layers were washed with 3M HCl solution (1×30 mL), dried (Na$_2$SO$_4$) and concentrated to afford crude product which was purified by chromatography (EtOAc/DCM) to afford ethyl 3-tert-butyl-1-(2-(dimethylamino)-2-oxoethyl)-1H-pyrazole-5-carboxylate (0.25 g, 55%) as a thick paste. $^1$H NMR (400 MHz, Acetone-d$_6$): δ 6.73 (s, 1H), 5.35 (s, 2H), 4.27 (q, J=7.2 Hz, 2H), 3.15 (s, 3H), 2.90 (s, 3H), 1.33-1.28 (m, 12H); MS (ESI) m/z: 282.3 (M+H$^+$).

To a solution of ethyl 3-tert-butyl-1-(2-(dimethylamino)-2-oxoethyl)-1H-pyrazole-5-carboxylate (1.16 g, 4 mmol) in THF (10 mL) was added 1M borane/THF (12 ml, 12 mmol) at 0° C. under Ar and stirring continued for 12 h at 60° C. The mixture was cooled to 0° C., quenched with 3M HCl solution and heated to 60° C. for 30 min. The mixture was basified with solid NaHCO$_3$ to pH around 8 and the product was extracted with CHCl$_3$ (2×30 ml). The combined organics were washed with brine, dried (Na$_2$SO$_4$), concentrated in vacuo and purified by silica gel chromatography to provide ethyl 3-ten-butyl-1-(2-(dimethylamino)ethyl)-1H-pyrazole-5-carboxylate as a pasty mass (0.47 g, 43% yield). $^1$H NMR (400 MHz, MeOH-d$_4$): δ 6.73 (s, 1H), 4.66 (t, J=6.8 Hz, 2H), 4.35 (q, J=7.2 Hz, 2H), 2.80 (t, J=7.2 Hz, 2H), 2.34 (s, 6H), 1.38 (t, J=7.2 Hz, 3H), 1.31 (s, 9H); MS (ESI) m/z: 268.2 (M+H$^+$).

To a solution of ethyl 3-tert-butyl-1-(2-(dimethylamino) ethyl)-1H-pyrazole-5-carboxylate (0.47 g, 1.8 mmol) in THF (10 mL) was added aqueous LiOH (0.22 g, 5.3 mmol, 5 mL) and the mixture was stirred for 16 h at RT. Solvents were removed, the thick liquid was diluted with water (5 mL) and acidified with 50% aq. acetic acid solution to pH 5-6. The product was extracted with EtOAc (2×50 ml) and the combined organics were washed with brine, dried (Na$_2$SO$_4$) and concentrated in vacuo to afford 3tert-butyl-1-(2-(dimethylamino)ethyl)-1H-pyrazole-5-carboxylic acid as a pasty mass (0.12 g, 29% yield). $^1$H NMR (400 MHz, DMSO-d$_6$): δ 6.56 (s, 1H), 4.66 (t, J=6.0 Hz, 2H), 3.17 (t, J=6.0 Hz, 2H), 2.53 (s, 6H), 1.17 (s, 9H); MS (ESI) m/z: 240.3 (M+H$^+$).

Example B9

NaH (6.8 g, 0.17 mol) was added portionwise to a 0° C. solution of 1H-pyrazole (10 g, 0.15 mol) in DMF (150 mL) and the resulting mixture was stirred at RT for 30 min. 2-Iodopropane (30 mL, 0.3 mol) was added dropwise to the above mixture at 0° C., then the reaction mixture was stirred at RT for 10 h. H$_2$O was added and the mixture was extracted with ethyl ether (3×100 mL). The combined organic layers were washed with brine, (Na$_2$SO$_4$), concentrated in vacuo and the residue distilled under reduced pressure to afford 1-isopropyl-1H-pyrazole (6.6 g, 40% yield). $^1$H NMR (400 MHz, DMSO-d$_6$): δ 7.68 (d, J=1.6 Hz, 1 H), 7.38 (d, J=1.2 Hz, 1 H), 6.17 (t, J=2.0 Hz, 1 H), 4.46 (m, 1 H), 1.37 (d, J=6.8 Hz, 6 H).

To a solution of 1-isopropyl-1H-pyrazole (5 g, 45.5 mmol) in conc. H$_2$SO$_4$ (50 mL) was added KNO$_3$ (5.0 go, 50 mmol) portionwise at 0° C. After the addition, the resulting mixture was heated to 50° C. for 8 h. The reaction mixture was cooled to RT, poured into ice water, and the mixture was extracted with EtOAc. The combined organics were washed with saturated Na$_2$CO$_3$ solution, brine, dried (Na$_2$SO$_4$), concentrated in vacuo and purified via column chromatography to provide 1-isopropyl-4-nitro-1H-pyrazole (3.2 g, 46% yield). $^1$H NMR (400 MHz, DMSO-$d_6$): δ 8.99 (s, 1 H), 8.32 (s, 1H), 4.65 (m, 1 H), 1.51 (d, J=6.8 Hz, 6 H).

A solution of 1-isopropyl-4-nitro-1H-pyrazole (3 g, 19 mmol) in EtOH (30 mL) was stirred under a hydrogen atmosphere for 2 h in the presence of 10% Pd/C (300 mg). The catalyst was removed by filtration and the filtrate was concentrated under reduced pressure to afford 1-isopropyl-1H-pyrazol-4-ylamine (1.8 g, 75% yield). $^1$H NMR (400 MHz, DMSO-$d_6$): δ 6.99 (s, 1 H), 6.84 (s, 1 H), 4.23 (m, 1 H), 3.70 (s, 2 H), 1.28 (d, J=6.8 Hz, 6 H); MS (ESI) m/z: 126.2 [M+H]$^+$.

Example B10

A solution of ethyl cyclopentanecarboxylate (prepared by esterification of commercially available cyclopentanetecarboxylic acid, 30 g, 0.21 mol) and acetonitrile (10.1 g, 0.25 mol) in dry THF (80 mL) was added dropwise to a suspension of NaH (12.5 g, 0.31 mol) in dry THF (80 mL) and the resulting mixture was refluxed overnight. The reaction mixture was concentrated under reduced pressure and partitioned between water and EtOAc. The aqueous layer was separated, adjusted to pH 8 and extracted with EtOAc. The combined extracts were washed with brine, dried (MgSO$_4$), and concentrated to give 3-cyclopentyl-3-oxopropanenitrile (26 g, 90% yield), which was used in the next step without further purification. $^1$H NMR (400 MHz, DMSO-$d_6$): δ 4.06 (s, 2 H), 2.92 (m, 1 H), 1.41-1.77 (m, 8 H).

Hydroxylamine hydrochloride (6 g, 86 mmol) and 3-cyclopentyl-3-oxopropanenitrile (10 g, 73 mmol) were added to a solution of NaOH (9 g, 225 mmol) in water (100 mL) and the resulting mixture was heated at 50° C. overnight. The precipitate was collected by filtration, washed with water, and dried to give 3-cyclopentylisoxazol-5-amine (6.7 g, 61% yield). $^1$H NMR (400 MHz, DMSO-$d_6$): δ 6.43 (s, 2 H), 4.77 (s, 1 H), 2.84 (m, 1 H), 1.87-1.51 (m, 8 H); MS (ESI) m/z: 153.1 (M+H$^+$).

Example B11

A mixture of 1,1,3,3-tetramethoxy-propane (13.6 g, 83 mmol) and 1-cyclopentylhydrazine-2-carboxylic acid tert-butyl ester from Ex B18 (16.6 g, 83 mmol) in water (150 mL) was treated with conc HCl (21 mL, 252 mmol) and the resulting mixture was heated at reflux overnight. The reaction mixture was allowed to cool to RT and was extracted with ether. The extracts were washed with brine, dried over anhydrous MgSO$_4$ and filtered. The filtrate was concentrated in vacuo to give 1-cyclopentyl-1H-pyrazole (8.0 g, 71% yield). $^1$H NMR (400 MHz, CDCl$_3$): δ 7.52 (s, 1 H), 7.43 (s, 1 H), 6.24 (s, 1 H), 4.68 (m, 1 H), 2.20-1.71 (m, 8 H); MS (ESI) m/z: 137.1 [M+H$^+$]

To a suspension of Na$_2$CO$_3$ (13 g, 124 mmol) in DCM (100 mL) was added 1-cyclopentyl-1H-pyrazole (8.35 g, 62 mmol) and Br$_2$ (3.2 mL, 62.3 mmol). The resulting mixture was stirred at RT overnight. The solids were removed by filtration and the filter cake was washed with DCM. The filtrate was washed with water and brine, was dried over anhydrous MgSO$_4$, and was concentrated in vacuo to give 4-bromo-1-cyclopentyl-1H-pyrazole (14 g, 93% yield). $^1$H NMR (300 MHz, CDCl$_3$): δ 7.46 (s, 1 H), 7.44 (s, 1H), 4.64 (m, 1 H), 2.18-1.67 (m, 8 H); MS (ESI) m/z: 215.0 [M+H]$^+$.

To a solution of 4-bromo-1-cyclopentyl-1H-pyrazole (9.0 g, 42 mmol) in THF (100 mL) at −78° C. under nitrogen was added a solution of n-BuLi in hexanes (2.5 M, 18.5 mL, 46.2 mmol). The resulting mixture was stirred at −78° C. for 30 min. Dry-ice (solid CO$_2$) was added at −78° C. and the reaction mixture was allowed to slowly warm to RT overnight. The solvent was removed under reduced pressure. Water was added, and the mixture was acidified (pH 3) by the addition of aq. HCl. The aqueous layer was extracted with EtOAc, and the extracts were washed with brine, dried over MgSO$_4$, and concentrated in vacuo. The residue was recrystallized (EtOAc-petroleum ether) to provide 1-cyclopentyl-1H-pyrazole-4-carboxylic acid (3.5 g, 47% yield). $^1$H NMR (400 MHz, DMSO-$d_6$): δ 12.50 (br s, 1 H), 8.31 (s, 1 H), 7.85 (s, 1 H), 4.78 (m, 1 H), 2.16-1.68 (m, 8 H); MS (ESI) m/z: 181.0 [M+H]$^+$.

Example B12

A solution of ethyl trifluoroacetate (14.2 g, 0.1 mol) and anhydrous acetonitrile (5.0 g, 0.12 mol) in THF (100 mL) was added dropwise to a suspension of NaH (60%, 6.0 g, 0.15 mol) in THF (100 mL) at 80° C. The resulting mixture was heated to reflux overnight, and then cooled to RT. The reaction mixture was concentrated in vacuo and the residue was diluted with EtOAc and 10% aq HCl. The organic layer was washed with water and brine, dried (MgSO$_4$) and concentrated in vacuo to yield crude 4,4,4-trifluoro-3-oxo-butyronitrile (15 g), which was used without further purification.

A solution of methylhydrazine (5.0 g, 60 mmol) and 4,4,4-trifluoro-3-oxo-butyronitrile (9.8 g, 71 mmol) in EtOH (50 mL) was treated with conc. HCl (5 mL) and the resultant mixture was heated to reflux overnight. The solvent was removed in vacuo and the crude product was dissolved in EtOAc washed with saturated aq. Na$_2$CO$_3$ solution until the washings were pH 8. The organics were concentrated and purified by prep-HPLC to provide 2-methyl-5-trifluoromethyl-2H-pyrazol-3-ylamine (2.07 g, 21% yield). $^1$H NMR (300 MHz, DMSO-$d_6$), δ 5.57 (s, 1 H), 5.54 (br s, 2 H), 3.55 (s, 3 H); MS (ESI) m/z: 166.1 (M+H$^+$).

Example B13

A solution of hydrazine hydrate (459 mg, 9.16 mol) in ethanol (5 mL) was added to a solution of ethyl 3-ethoxy-2-(trifluoroacetyl)acrylate (2.00 g, 8.33 mmol) in ethanol (15 mL) at 0° C. The reaction was allowed to warm to RT and stirred for 24 hrs. The reaction was concentrated in vacuo, dissolved in ethyl acetate (30 mL), washed with 5% citric acid (25 mL), saturated sodium bicarbonate (25 mL) and brine (25 mL), dried (Na$_2$SO$_4$) and concentrated in vacuo to afford ethyl 3-(trifluoromethyl)-1H-pyrazole-4-carboxylate (1.365 g, 79% yield). $^1$H NMR (300 MHz, DMSO-$d_6$): δ 1.24 (t, 3 H), 4.22 (q, 2 H), 8.56 (s, 1 H); MS (ESI) m/z: 209.0 (M+H$^+$).

Isopropyl iodide (1.225 g, 7.21 mmol) was added to a solution of ethyl 3-(trifluoromethyl)-1H-pyrazole-4-carboxylate (500 mg, 2.402 mmol) and DIEA (652 mg, 5.04 mmol) in DMF (5 mL) and the reaction stirred at RT for 3 h and 60° C. for 3 h. The reaction was diluted with ethyl acetate (30 mL), washed with 5% citric acid (30 mL), saturated sodium bicarbonate (30 mL) and brine (30 mL), dried (Na$_2$SO$_4$) and concentrated in vacuo to give an oil. LC and LCMS showed starting material still present (~40%). The oil was dissolved in DMF (4 mL), treated with DIEA (652 mg, 5.04 mmol), isopropyliodide (1.22 g, 7.21 mmol) and catalytic 4-dimethylaminopyridine (~5 mg) and stirred at RT overnight. The reaction was diluted with ethyl acetate (30 mL), washed with 5% citric acid (30 mL) saturated sodium bicarbonate (30 mL) and brine (30 mL), dried Na$_2$SO$_4$), concentrated in vacuo and purified by column chromatography (ethyl acetate/hexane) to afford ethyl 1-isopropyl-3-(trifluoromethyl)-1H-pyrazole-4-carboxylate (266 mg, 44% yield).

$^1$H NMR (300 MHz, DMSO-d$_6$): δ 1.26 (s, 9 H), 1.43 (d, 6 H), 4.23 (q, 2 H), 4.64 (hp, 1 H), 8.62 (s, 1 H); MS (ESI) m/z: 251.0 (M+H$^+$).

A solution of ethyl 1-isopropyl-3-(trifluoromethyl)-1H-pyrazole-4-carboxylate (266 mg, 1.06 mmol) and lithium hydroxide (102 mg, 4.25 mmol) in ethanol:water:dioxane (1:1:1, 6 mL) was warmed to 40° C. and stirred overnight. The mix cooled to RT, diluted with water (25 mL) and washed with ether (20 mL). The aqueous phase made acidic with 3N HCl (pH~2) and extracted with ethyl acetate (2×15 mL). The combined ethyl acetate layers were washed with brine (20 mL), dried (Na$_2$SO$_4$) and concentrated in vacuo to give 1-isopropyl-3-(trifluoromethyl)-1H-pyrazole-4-carboxylic acid (199 mg, 84% yield) as a white solid. MS (ESI) m/z: 223.0.

Example B14

In a procedure analogous to Example B6, isopropylhydrazine hydrochloride (896 mg, 8.10 mmol) and ethyl 2-acetyl-3-(dimethylaminomethylene)acrylate (1.50 g, 8.10 mmol) were combined and purified by chromatography (ethyl acetate/hexane) to afford ethyl 1-isopropyl-5-methyl-1H-pyrazole-4-carboxylate (faster elution, 537 mg), $^1$H NMR (300 MHz, DMSO-d$_6$): δ 1.30 (t, 3 H), 1.39 (d, 6 H), 4.23 (q, 2 H), 4.61 (hp, 1 H), 7.82 (s, 1 H); MS (ESI) m/z: 197.0 (M+H$^+$) and ethyl 1-isopropyl-3-methyl-1H-pyrazole-4-carboxylate (slower elution, 91 mg), $^1$H NMR (300 MHz, DMSO-d$_6$), δ 1.29 (t, 3 H), 1.42 (d, 6 H), 2.36 (s, 3 H), 4.21 (q, 2 H), 4.49 (hp, 1 H), 8.24 (s, 1 H); MS (ESI) m/z: 197.0 (M+H$^+$).

In a procedure analogous to Example B6, ethyl 1-isopropyl-5-methyl-1H-pyrazole-4-carboxylate (537 mg, 2.74 mmol) and lithium hydroxide (459 mg, 10.95 mmol) were combined to give 1-isopropyl-5-methyl-1H-pyrazole-4-carboxylic acid (32 mg, 70% yield) as an off white solid. MS (ESI) m/z: 169.0 (M+H$^+$).

Example B15

In a procedure analogous to Example B6, ethyl 1-isopropyl-3-methyl-1H-pyrazole-4-carboxylate from Example B14 (91 mg, 0.464 mmol) and lithium hydroxide (78 mg, 1.855 mmol) were combined to afford 1-isopropyl-3-methyl-1H-pyrazole-4-carboxylic acid (62 mg, 79% yield). MS (ESI) m/z: 169.0 (M+H$^+$).

Example B16

3-nitro-5-(trifluoromethyl)pyridin-2-ol (6.80 g, 32.7 mmol) and quinoline (2.72 g, 21.06 mmol) were combined in a 200 mL round-bottom flask with an oversized magnetic stir bar. The assembly was cooled with an RT water bath. Phosphorus oxychloride (4.07 ml, 43.7 mmol) was cautiously added with vigorous stirring. After 5 mm, the resulting gel would no longer stir. The apparatus was equipped with a reflux condenser and was transferred to a 120° C. oil bath. The gel quickly melted and stirring resumed with gentle refluxing. After 3 h, the mixture was cooled to RT and added portion wise to ice water with vigorous stirring. Sodium hydroxide was added to adjust the alkalinity to pH 8-9 and the mixture was extracted with EtOAc (2×100 mL) and CH$_2$Cl$_2$ (2×100 mL). The combined organics were dried (MgSO$_4$), concentrated in vacuo and chromatographed (EtOAc/CH$_2$Cl$_2$) provided 2-chloro-3-nitro-5-(trifluoromethyl)pyridine (6.65 g, 90% yield) as a yellow liquid. $^1$H NMR (400 MHz, DMSO-d$_6$): δ 9.21 (m, 1 H), 9.09 (m, 1 H).

A Parr hydrogenation flask was charged with 10% Palladium on carbon, 50% wet (0.050 g, 0.023 mmol) and ethanol (10 mL). Triethylamine (1.0 ml, 3.09 mmol), 2-chloro-3-nitro-5-(trifluoromethyl)pyridine (0.70 g, 3.09 mmol) and an additional 10 mL of ethanol were added. The flask was purged of air, charged with 48 psi of hydrogen, and shaken for 6 h. The reaction mixture was purged of hydrogen in vacuo and filtered through Celite®, washing with EtOAc (20 mL) and EtOH (20 mL). The filtrate was concentrated in vacuo and the product partitioned between EtOAc (40 mL) and water (20 mL). The organics were washed with sat aq NaHCO3 (20 mL) and brine (20 mL), dried (MgSO$_4$) and concentrated in vacuo to provide 5-(trifluoromethyl)pyridin-3-amine (498 mg, 99% yield). $^1$H NMR (400 MHz, DMSO-d$_6$): δ 8.14 (m, 1 H), 8.00 (s, 1 H), 7.13 (m, 1 H), 5.84 (s, 2 H); MS (ESI) m/z 163.0 (M+H$^+$).

Example B17

5-Bromopyridin-3-amine (0.433 g, 2.5 mmol), 4,4,5,5-tetramethyl-2-(prop-1-en-2-yl)-1,3,2-dioxaborolane (0.630 g, 3.75 mmol), Cs$_2$CO$_3$ (3.10 g, 9.5 mmol) and Pd(PPh$_3$)$_4$ (0.289 g, 0.25 mmol) were suspended in DMF/H$_2$O (3:1, 20 mL). The reaction mixture was degassed with N$_2$ and heated at 90° C. for 16 h. Solvent was removed under reduced pressure. The residue was diluted with H$_2$O (20 mL) and extracted with EtOAc (3×50 mL). The combined organic layers were washed with brine (20 mL), dried, concentrated in vacuo and purified by chromatography to afford 5-(prop-1-en-2-yl)pyridin-3-amine (0.773 g, 230%) as a dark yellow oil. MS (ESI) m/z: 135.0 (M+H$^+$).

To a solution of 5-(prop-1-en-2-yl)pyridin-3-amine (0.773 g, 2.48 mmol) in ethanol (8 mL) was added 10% Pd/C (0.132 g, 0.124 mmol) and the resulting suspension was stirred under a hydrogen atmosphere (1 atm) for 18 h. The reaction was filtered through Celite® and washed forward with EtOH. The filtrate was concentrated, diluted with EtOAc (30 mL) and washed with H$_2$O (1×15 ml) and brine (1×15 ml). The aqueous phase was back-extracted with EtOAc (1×20 ml). The combined organic layers were dried (MgSO$_4$) and concentrated to afford 5-isopropylpyridin-3-amine (0.453 g, 134%) as a light yellow oil. MS (ESI) m/z: 137.1 (M+H$^+$).

Example B18

A mixture of cyclopentanone (20 g, 238 mmol) and hydrazinecarboxylic acid tert-butyl ester (31.4 g, 0.238 mol) in MeOH (300 mL) was stirred at RT for 2 h. The reaction mixture was concentrated in vacuo and the resulting solid was dried under vacuum to give 1-cyclopentylidenehydrazine-2-carboxylic acid tert-butyl ester (47.1 g, 100% yield).

Sodium cyanoborohydride (6.4 g, 0.101 mol) was added portion-wise to a suspension of 1-cyclopentylidenehydrazine-2-carboxylic acid tert-butyl ester (20 g, 0.101 mol) in a mixture of acetic acid and methanol (288 mL, 1:1). The resulting solution was stirred at RT for 2 h. The reaction mixture was neutralized with 1 N aq NaOH and extracted with CH$_2$Cl$_2$. The organic layer was washed with saturated NaHCO$_3$, dried (Na$_2$SO$_4$) and concentrated under reduced pressure to give 1-cyclopentylhydrazine-2-carboxylic acid tert-butyl ester (18.4 g) as an oil.

To a solution of 1-cyclopentylhydrazine-2-carboxylic acid tert-butyl ester (18.4 g, 92 mmol) in a mixture of ethanol (300 mL) and conc. HCl (7.7 mL, 92 mmol) was added ethyl 2-acetyl-3-(dimethylamino)acrylate (25.5 g, 0.138 mol). The resulting mixture was refluxed for 2 h. The reaction was concentrated in vacuo, dissolved in CH$_2$Cl$_2$ (300 mL), washed with satd NaHCO$_3$, and brine, dried (Na$_2$SO$_4$), concentrated in vacuo and purified by chromatography on silica gel to give ethyl 1-cyclopentyl-5-methyl-1H-pyrazole-4-carboxylate (15.6 g, 76% yield). $^1$H NMR (400 MHz, DMSO-d$_6$): δ 8.15 (s, 1 H), 4.61 (m, 1 H), 4.15 (q, J=8 Hz, 2 H), 2.29 (s, 3 H), 2.04-1.97 (m, 2 H), 1.89-1.85 (m, 2 H), 1.78-1.71 (m, 2 H), 1.62-1.59 (m, 2 H), 1.23 (t, J=8 Hz, 3 H).

A solution of ethyl 1-cyclopentyl-5-methyl-1H-pyrazole-4-carboxylate (15.5 g, 70 mmol) in EtOH (200 mL) was treated with a solution of LiOH (6 g, 250 mmol) in water (100 mL) and the resultant mixture was stirred at 60° C. overnight. The reaction was concentrated in vacuo and the residue was partitioned between EtOAc and water. The aqueous layer was acidified with aq HCl (2 M) to pH 3 and was extracted with EtOAc. The extract was concentrated under reduced pressure to give 1-cyclopentyl-5-methyl-1H-pyrazole-4-carboxylic acid (8.7 g, 64% yield). $^1$H NMR (300 MHz, DMSO-d$_6$): δ 12.05 (br s, 1 H), 8.10 (s, 1 H), 4.60 (m, 1 H), 2.28 (s, 3 H, 2.04-1.97 (m, 2 H), 1.89-1.85 (m, 2H), 1.78-1.71 (m, 2 H), 1.62-1.59 (m, 2 H); MS (ESI) m/z: 194.99 [M+H]$^+$.

Example B19

A solution of 2,4-dinitrobenzenesulfonic acid (16.5 g, 62.0 mmol) in minimum quantity of CH$_3$CN was added at once to a translucent solution of iodobenzene diacetate (10 g, 31.0 mmol) in CH$_3$CN (100 mL). The reaction mixture was stirred for 1 hour at RT. The solution was chilled in ice and then the solution was kept in freezer. The solid was filtered and washed with Et$_2$O to obtain [hydroxy(2,4-dinitrobenzenesulfonyloxy)iodo]benzene (HDNIB) (13.9 g, 96% yield). $^1$H NMR (400 MHz, DMSO-d$_6$): δ 9.91 (brs, 1H), 8.71 (d, J=2.4 Hz, 1H), 8.56 (dd, J=2.0, and 8.4 Hz, 1H), 8.38 (m, 2H), 8.24 (d, J=8.4 Hz, 1H), 7.88 (m, 1H), 7.77 (m, 2H).

A solution of ethyl pyruvate (2.0 g, 17.2 mmol) and HDNIB (9.7 g, 20.7 mmol) in trimethylacetonitrile (15 mL) was heated to reflux for 3 hours. After the reaction mixture was cooled to RT, 2,6-lutidine (0.2 mL, 1.7 mmol) was added. The reaction mixture was refluxed for an additional 8 hours. The reaction was checked by LC-MS and the solvent was removed. The residue was dissolved in CH$_2$Cl$_2$C washed with water and brine, dried (Na$_2$SO$_4$), concentrated in vacuo and purified via silica gel column chromatography (EtOAc/hexane) to obtain ethyl 2-tert-butyloxazole-5-carboxylate (1.0 g, 29% yield). $^1$H NMR (400 MHz, DMSO-d$_6$): δ 8.89 (s, 1H), 4.42 (d, J=7.2 Hz, 2H), 1.49 (s, 9H), 1.43 (d, J=7.2 Hz, 3H); MS (ESI) m/z: 198.1 (M+H$^+$).

To a stirring suspension of ethyl 2-tert-butyloxazole-5-carboxylate (1.0 g, 5.07 mmol) in 1:1:1 THF/EtOH/H$_2$O (15 ml) at RT was added LiOH.H$_2$O (486 mg) and the mixture was stirred at RT for 3 hours. The reaction mixture was checked by LC-MS and the completed reaction was concentrated to an aqueous residue, acidified (pH 3-4) with 3M HCl and extracted with EtOAc (3×). The combined organics were washed with brine (1×), dried (MgSO$_4$) and evaporated to afford desired product, 2-tert-butyloxazole-5-carboxylic acid (0.67 g, 78% yield). $^1$H NMR (400 MHz, DMSO-d$_6$): δ 12.9 (brs, 1H), 8.62 (s, 1H), 1.30 (s, 9H); (ESI) m/z: 170.0 (M+H$^+$).

Example B20

To a solution of 1-tert-butyl-1H-pyrrole-3-carbaldehyde (0.339 g, 2.24 mmol) in acetone (40 mL) was added, over a 2 h period, a solution of KMnO$_4$ (0.708 g, 4.48 mmol) in Acetone/H$_2$O (1:1, 60 mL). After 3 h, the reaction was poured into a solution of 10% NaHSO$_3$/1N HCl (120 mL) and the solution was extracted with DCM (3×60 mL). The combined extracts were washed with H$_2$O (2×60 mL) and 5% NaHCO$_3$ (3×60 mL). The bicarbonate washes were carefully acidified to pH 3 and extracted with DCM (3×60 mL). The combined organic layers were washed with brine (1×), dried (MgSO$_4$) and concentrated afford 1-tert-butyl-1H-pyrrole-3-carboxylic acid (0.270 g, 72% yield) as a white solid. MS (ESI) m/z: 168.1 (M+H$^+$).

Example B21

A 60% Sodium hydride (5.16 g, 129 mmol) slurry in benzene (20 mL) was warmed to 80° C. for 15 min and then treated sequentially and dropwise (over 15 min.), first with a solution of propionitrile (7.11 g, 129 mmol) and second with a solution of methyl trimethylacetate (7.50 g, 64.6 mmol). The mixture was stirred at 80° C. overnight. The reaction was cooled to RT, quenched with i-propanol (25 mL) and water (25 mL) and diluted with ethyl acetate (50 mL). The mixture was acidified (6N HCl, pH~=1) and the organic phase separated. The organic phase was washed with brine (25 nm), dried (Na$_2$SO$_4$) and concentrated in vacuo to give 2-methyl pivaloylacetonitrile as an oil.

Hydroxylamine hydrochloride (5.61 g, 81 mmol) was added portionwise to a solution of sodium hydroxide (11.62 g, 291 mmol) at 0° C. in water (40 mL). The mixture was stirred until a complete salvation occurred. To this was then added crude 2-methyl pivaloylacetonitrile, the solution was warmed to 50° C. for 4 hrs, cooled to RT and allowed to stand overnight. The white solid was collected by filtration, washed with water (4×10 mL) and air dried for 1 hr to afford 3-tert-butyl-4-methylisoxazol-5-amine (4.25 g, 42% yield). $^1$H NMR (400 MHz, DMSO-d$_6$): δ 1.19 (s, 9 H), 1.79 (s, 3 H), 6.09 (br. s, 2 H); MS (ESI) m/z: 155.1 (M+H$^+$).

Example B22

5-Bromopyridin-3-amine (0.94 g, 5.43 mmol), PdCl$_2$(PPh$_3$)$_2$ (0.076 g, 0.109 mmol) and ethynyltrimethylsilane (0.64 g, 6.52 mmol) were combined in TEA (12.0 mL). After stirring for 5 min, CuI (0.010 g, 0.054 mmol) was added. The reaction mixture was flushed with N$_2$ and stirred at RT overnight, followed by at 55° C. overnight. The reaction was filtered and the solid was washed with EtOAc (30 mL). The combined organics were concentrated in vacuo and purified by chromatography to afford 5-(2-(trimethylsilyl)ethynyl)pyridin-3-amine (0.279 g, 27% yield) as a white solid. MS (ESI) m/z: 191.1 (M+H$^+$).

To a solution of 5-(2-(trimethylsilyl)ethynyl)pyridin-3-amine (0.279 g, 1.466 mmol) in MeOH (2.0 mL) was added K$_2$CO$_3$ (0.304 g, 2.20 mmol). The reaction was stirred at RT overnight. Solvent was removed under reduced pressure and the residue was extracted with EtOAc (2×). The combined organic layers were washed with H$_2$O (1×) and brine (1×), dried (MgSO$_4$) and concentrated to afford 5-ethynylpyridin-3-amine (0.168 g, 97%) as a light yellow solid.

5-Ethynylpyridin-3-amine (0.122 g, 1.03 mmol) and 10% Pd/C (0.11 g, 0.102 mmol) were suspended in MeOH (15 mL). This was hydrogenated (42 psi) in a Parr hydrogenation apparatus overnight. The reaction was filtered through Celite® and washed forward with MeOH. The filtrate was concentrated to afford 5-ethylpyridin-3-amine (0.070 g, 56% yield) as a light yellow oil. $^1$H NMR (400 MHz, DMSO-d$_6$): δ 7.72 (d, J=2.4 Hz, 1H), 7.58 (d, J=1.6 Hz, 1H), 6.71 (t, J=2.0 Hz, 1H), 5.16 (s, 2H), 2.43 (q, J=7.2 Hz, 2H), 1.11 (t, J=7.6 Hz, 3H).

Example B23

In ethanol (5 mL) was placed the t-butylhydrazine hydrochloride (0.79 g, 6.3 mmol) and ethyl 2-acetyl-3-(dimethylaminomethylene)acrylate (1.0 g, 6.3 mmol). The mixture was refluxed for 8 hours. The mix was evaporated at reduced pressure to give an oil. The oil was dissolved in ether (25 mL) and washed successively with water (25 mL), saturated sodium bicarbonate (25 mL) and brine (25 mL) was dried ($Na_2SO_4$), concentrated in vacuo and purified by silica gel column chromatography (EtOAc/hexanes) to obtain ethyl 1-tert-butyl-5-methyl-1H-pyrazole-3-carboxylate (0.60 g, 45% yield). $^1$H NMR (400 MHz, DMSO-$d_6$): δ 6.54 (s, 1H), 4.22 (q, J=7.2 Hz, 2H), 2.44 (s, 3H), 2.42 (s, 3H), 1.57 (s, 9H), 1.25 (t, J=7.2 Hz, 3H); MS (ESI) m/z: 211.1 (M+H$^+$).

To a solution of ethyl 1-tert-butyl-5-methyl-1H-pyrazole-3-carboxylate (0.60 g, 2.85 mmol) in a mix of ethanol:water:dioxane (1:1:1, 9 mL) was added lithium hydroxide (0.48 mg, 11.4 mmol). The mixture was stirred at 40° C. for 5 hours. The solution was checked by LC-MS and diluted with water (10 mL) and the pH adjusted to 2 with 1N HCl. The solution was extracted with EtOAc (2×10 mL) and the combined organic phases washed with brine (20 mL), dried (NaSO$_4$), and concentrated in vacuo to obtain 1-tert-butyl-5-methyl-1H-pyrazole-3-carboxylic acid (0.50 g, 96% yield). $^1$H NMR (400 MHz, DMSO-$d_6$): δ 12.4 (s, 1H), 5.47 (s, 1H), 2.42 (s, 3H), 1.56 (s, 9H); MS (ESI) m/z: 183.1 (M+H$^+$).

Example B24

4-nitroimidazole (0.500 g, 4.42 mmol), 2-iodopropane (0.553 ml, 5.53 mmol) and powdered $K_2CO_3$ (0.917 g, 6.63 mmol) were combined and stirred in DMF (25 ml) at 50° C. After 5 h, the reaction was cooled to RT. The reaction was diluted with EtOAc and filtered to remove inorganic salts, rinsing forward with EtOAc. The filtrate was evaporated to near dryness. The residue was diluted in EtOAc, washed with $H_2O$ (2×) and brine (1×), dried (MgSO$_4$) and evaporated to afford 1-isopropyl-4-nitro-1H-imidazole (0.66 g, 96% yield) as a pale yellow oil. $^1$H NMR (400 MHz, DMSO-$d_6$): δ 8.51 (s, 1H) 7.98 (s, 1H), 4.52-4.49 (m, 1H), 1.44 (d, 6H); MS (ESI) m/z: 156.0 (M+H$^+$), 178.0 (M+Na$^+$).

1-isopropyl-4-nitro-1H-imidazole (0.66 g, 4.25 mmol) was hydrogenated (1 atm) over 10% Pd/C (50% w/w $H_2O$) (0.905 g, 0.425 mmol) in EtOAc (43 ml) overnight. The completed reaction was filtered through Celite®, rinsing forward with EtOAc (30-35 ml). The combined filtrates containing 1-isopropyl-1H-imidazol-4-amine were used directly in the next reaction. MS (ESI) m/z: 126.1 (M+H$^{30}$).

To a stirring solution of 1-isopropyl-1H-imidazol-4-amine (0.532 g, 4.25 mmol) in EtOAc (70 ml) was added Troc-Cl (0.614 ml, 4.46 mmol) followed by satd. NaHCO$_3$ (17.23 ml 12.75 mmol). The biphasic mixture was stirred briskly at RT. After 6 h, the layers were separated and the aqueous was extracted with EtOAc (1×). The combined organics were washed with satd. NaHCO$_3$ (1×) and brine (1×), dried, evaporated and triturated (EtOAc/hexanes). The solids were collected by filtration, rinsed with hexanes and dried on the filter to afford 2,2,2-trichloroethyl 1-isopropyl-1H-imidazol-4-ylcarbamate (0.392 g, 31% yield) as a pink-orange solid. $^1$H NMR (400 MHz, DMSO-$d_6$): δ 10.2 (s, 1H), 7.49 (s, 1H), 7.02 (s, 1H), 4.80 (s, 2H), 4.3-4.25 (m, 1H), 1.35 (d, 6H); MS (ESI) m/z: 300.0 (M+H$^+$), 302.0 (M+2+H$^+$).

Example B25

A solution of 2-chloro-3-nitro-5-(trifluoromethyl)pyridine from Example B16 (400 mg, 1.766 mmol) in THF (5 mL) was treated sequentially with dimethyl malonate (250 μl, 2.187 mmol) and sodium hydride (60%, 85 mg, 2.119 mmol). The resultant mixture was stirred at RT overnight. The mixture was diluted with EtOAc and washed with 0.1 M aq HCl, water, and brine, dried (MgSO$_4$), concentrated in vacuo and purified by silica gel chromatography to provide dimethyl 2-(3-nitro-5-(trifluoromethyl)pyridin-2-yl)malonate (320 mg, 56% yield) of sufficient purity for the next step. MS (ESI) m/z: 323.0 (M+H$^+$).

Dimethyl 2-(3-nitro-5-(trifluoromethyl)pyridin-2-yl)malonate (320 mg, 0.993 mmol) was combined with aq HCl (3 M, 5 mL, 15.00 mmol) and the mixture was heated to reflux overnight. The reaction mixture was cooled to RT and poured into EtOAc. Aqueous NaOH (2 M, 10 mL, 20 mmol) was added and the organic layer was separated and washed with water and brine, dried (MgSO$_4$) and concentrated in vacuo to provide 2-methyl-3-nitro-5-(trifluoromethyl)pyridine (53 mg, 9% yield). $^1$H NMR (400 MHz, DMSO-$d_6$): δ 9.19 (s, 1 H), 8.80 (s, 1 H), 2.82 (s, 3 H).

2-Methyl-3-nitro-5-(trifluoromethyl)pyridine (51 mg, 0.247 mmol) and 10% Pd/C, (50% wet, 10 mg, 4.70 μmol) in EtOH (10 mL) were combined in a Parr hydrogenation flask. The reaction mixture was purged of air under vacuum and pressurized with hydrogen (33 psi). The flask was shaken for 18 h. An additional portion of 10% Pd/C, (50% wet, 20 mg, 9.40 μmol) was added and the mixture was hydrogenated (40 psi) overnight. The reaction mixture was filtered through Celite® and the filter cake was washed with EtOH. The combined filtrate and washings were concentrated in vacuo and purified by silica gel chromatography to provide 2-methyl-5-(trifluoromethyl)pyridin-3-amine (17 mg, 399% yield). $^1$H NMR (400 MHz, DMSO-$d_6$): δ 7.93 (s, 1 H), 7.13 (s, 1H), 5.56 (s, 2 H), 2.31 (s, 3 H); MS (ESI) m/z; 177.0 (M+H$^+$).

Example B26

Using a procedure analogous to Example B27, 2-tert-butyl-4-chloropyrimidine-5-carboxylate from Example B27 (0.30 g, 1.24 mmol) and tert-butyl piperazine-1-carboxylate (1.15 g, 6.18 mmol) in presence of NMP (catalytic amount) were combined to afford 4-(4-(tert-butoxycarbonyl)piperazin-1-yl)-2-tert-butylpyrimidine-5-carboxylic acid (0.36 g, 80% yield). MS (ESI) m/z: 365.0 (M+H$^+$).

Example B27

In ethanol (40 mL) was placed t-butylcarbamidine hydrochloride (3.71 g, 27.2 mmol). This was treated with 21% sodium ethoxide in ethanol (8.80 g, 27.2 mmol) and stirred at RT for 15 min. To this was added the diethyl ethoxymethylenemalonate (5.87 g, 27.2 mmol) and the reaction mixture was stirred overnight at RT. The reaction mixture was refluxed for 1 hour and then cooled to RT. The solution was evaporated, the residue dissolved in water (100 mL) and the pH adjusted to 3-4 (wet litmus) with acetic acid. The mixture formed a precipitate. The solid collected by filtration, washed with water (50 mL) and dried in vacuo to obtain ethyl 2-tert-butyl-4-hydroxypyrimidine-5-carboxylate (2.18 g, 36% yield). $^1$H NMR (400 MHz, DMSO-$d_6$): δ 12.6 (brs, 1H), 8.44 (s, 1H), 4.20 (q, J=7.2 Hz, 2H), 1.25 (s, 9H), 1.23 (t, J=7.2 Hz, 3H); MS (ESI) m/z: 225.0 (M+H$^+$).

In cold (~0° C.) POCl$_3$ (20 mL) was dropped triethylamine (0.55 mL) with stirring. To this was added in parts ethyl 2-tert-butyl-4-hydroxypyrimidine-5-carboxylate (2.18 g, 9.72 mmol). The mixture then warmed to 40° C. and stirred under Argon for 1 hour. The mixture was evaporated until free of POCl₃, diluted with CHCl₃ (100 mL) and poured carefully into ice (300 mL). The solution was stirred until it reached RT. The organic phase was separated, washed with sodium bicarbonate (100 mL), water (100 mL), dried (Na₂SO₄) and concentrated in vacuo to give ethyl 2-tert-butyl-4-chloropyrimidine-5-carboxylate (2.0 g, 85% yield). ¹H NMR (400 MHz, DMSO-d₆): δ 9.12 (s, 1H), 4.34 (q, J=6.8 Hz, 2H), 1.33 (s, 9H), 1.27 (t, J=6.8 Hz, 3H); MS (ESI) m/z: 243.0 (M+H⁺).

To a solution of ethyl 2-tert-butyl-4-chloropyrimidine-5-carboxylate (0.30 g, 1.24 mmol) in NMP (3 mL) was added morpholine (0.54 g, 6.16 mmol) and it was heated at 80° C. for 1.5 hour. The reaction was checked by LC-MS, water was added and the solution was extracted with ethyl acetate (3×). The organic layer was washed with brine, dried Na₂SO₄) and solvent was removed to obtain tert-butyl 4-(5-(3-tert-butyl-5-(ethoxycarbonyl)-1H-pyrazol-1-yl)pyridin-2-yl)piperazine-1-carboxylate. MS (ESI) m/z: 294.0 (M+H⁺).

To a stirring suspension of ethyl 2-tert-butyl-4-morpholinopyrimidine-5-carboxylate (0.36 g, 1.24 mmol) in 1:1:1 THF/EtOH/H₂O (9 ml) at RT was added LiOH.H₂O (130 mg, 4.95 mmol) and the mixture was stirred overnight at RT. The reaction mixture was checked by LC-MS and the completed reaction was concentrated to an aqueous residue, acidified (pH 3-4) with 3M HCl and the solution was extracted with EtOAc (3×). The combined organics were washed with brine (1×), dried (MgSO₄), filtered and concentrated in vacuo. The crude was dissolved in isopropanol and the solids (LiCl and NaCl) were filtered and washed with isopropanol. The filtrate was concentrated to obtain the desired product, 2-tert-butyl-4-morpholinopyrimidine-5-carboxylic acid (0.15 g, 46% yield). MS (ESI) m/z: 266.0 (M+H⁺).

Example B28

3-Nitro-5-(trifluoromethyl)pyridin-2-ol (6.80 g, 32.7 mmol) and quinoline (2.72 g, 21.06 mmol) were combined in a 200 mL round-bottom flask with an oversized magnetic stir bar. The assembly was cooled with an RT water bath. Phosphorus oxychloride (4.07 ml, 43.7 mmol) was cautiously added with vigorous stirring. After 5 min, the resulting gel would no longer stir. The apparatus was equipped with a reflux condenser and was transferred to a 120° C. oil bath. The gel quickly melted and stirring resumed with gentle refluxing. After 3 h, the mixture was cooled to RT and added portionwise to ice water with vigorous stirring. Sodium hydroxide was added to adjust the alkalinity to pH 8-9 and the mixture was extracted with EtOAc (2×100 mL) and CH₂Cl₂ (2×100 mL). The combined organics were dried (MgSO₄), concentrated in vacuo and purified via chromatography on silica gel (EtOAc- CH₂Cl₂) to provide 2-chloro-3-nitro-5-(trifluoromethyl)pyridine (6.65 g, 90% yield) as a yellow liquid. ¹H NMR (400 MHz, DMSO-d₆): δ 9.21 (m, 1 H), 9.09 (m, 1 H).

2-Chloro-3-nitro-5-(trifluoromethyl)pyridine (406 mg, 1.79 mmol), 1-methyl-4-(4,4,5,5-tetramethyl-1,3,2-dioxaborolan-2-yl)-1H-pyrazole (559 mg, 2.69 mmol), cesium carbonate (1752 mg, 5.38 mmol) and palladium tetrakis (207 mg, 0.179 mmol) were combined in DMF (3 mL) and water (1 mL). The headspace was evacuated and back-filled with nitrogen (4×). The mixture was heated to 90° C. overnight. The mixture was poured into EtOAc (40 mL) and washed with water (3×20 mL) and satd brine (3×20 mL). The organics were concentrated in vacuo and purified by silica gel chromatography to provide 2-(1-methyl-1H-pyrazol-4-yl)-5-(trifluoromethyl)pyridin-3-amine (21 mg, 5% yield). ¹H NMR (400 MHz, DMSO-d₆): δ 8.29 (s, 1 H), 8.13 (br s, 1 H), 7.98 (s, 1 H), 7.40 (d, J=2.0 Hz, 1 H) 5.55 (s, 2 H), 3.91 (s, 3 H); MS (ESI): m/z 473.0 (M+H⁺).

Example 1

Using General Method A, Example B1 (0.072 g, 0.23 mmol) and Example A1 (0.062 g, 0.22 mmol) were combined and the resultant product purified via column chromatography to yield 1-(3-t-butylisoxazol-5-yl)-3-(2-fluoro-4-(2-(1-methyl-1H-pyrazol-4-yl)pyridin-4-yloxy)phenyl)urea, which was converted to corresponding mesylate salt (0.0685 g, 57% yield) by reacting with methanesulfonic acid (1.0 eq). ¹H NMR (DMSO-d₆): δ 10.4 (s, 1H), 8.89 (s, 1H), 8.59-8.57 (m, 2H), 8.24-8.20 (m, 2H), 7.65 (s, 1H) 7.45 (dd, J=11.6, 2.4 Hz, 1H), 7.17 (dd, J=8.8, 1.2 Hz, 1H), 7.12 (d, J=4.8 Hz, 1H), 6.09 (s, 1H), 3.93 (s, 3H), 2.33 (s, 3H), 1.26 (s, 9H); MS (ESI) m/z: 451.2 (M+H⁺).

Example 2

Using general method C, Example B2 (0.0712 g, 0.30 mmol) and Example A1 (0.0853 g, 0.30 mmol) were combined and the resultant product purified via column chromatography to yield 1-(3-t-butyl-1-methyl-1H-pyrazol-5-yl)-3-(2-fluoro-4-(2-(1-methyl-1H-pyrazol-4-yl)pyridin-4-yloxy)phenyl)urea (0.139 g, 100% yield) as a white foam. ¹H NMR (DMSO-d₆): δ 8.99-8.95 (m, 2H), 8.58-8.56 (m, 2H), 8.28-8.23 (m, 2H), 7.65 (s, 1H), 7.42 (dd, J=11.6, 2.4 Hz, 1H), 7.14-7.11 (m, 2H), 3.91 (s, 3H), 3.61 (s, 3H), 2.32 (s, 3H), 1.20 (s, 9H); MS (ESI) m/z: 464.2 (M+H⁺).

Example 3

In THF (10 mL) was placed Example A1 (87 mg, 0.31 mmol) and 3-trifluoromethyl)phenylisocyanate (60 mg, 0.32 mmol). The mixture was stirred overnight at RT. Hexane was added and then the solution was stirred for 1 h. The solid was filtered and dried under vacuum to obtain 1-(2-fluoro-4-(2-(1-methyl-1H-pyrazol-4-yl)pyridin-4-yloxy)phenyl)-3-(3-(trifluoromethyl)phenyl)urea (126 mg, 88% yield). ¹H NMR (400 MHz, DMSO-d₆): δ 9.39 (s, 1H), 8.68 (d, J=2.0 Hz, 1H), 8.36 (d, J=5.6 Hz, 1H), 8.25 (s, 1H), 8.15 (t, J=8.8 Hz, 1H), 8.08 (s, 1H), 7.96 (s, 1H), 7.51 (m, 2H), 7.32 (m, 1H), 7.26 (dd, J=2.8, and 12.0 Hz, 1H), 7.23 (d, J=2.4 Hz, 1H), 7.01 (dt, J=1.2, and 8.8 Hz, 1H), 6.67 (dd, J=2.4, and 5.6 Hz, 1H), 3.84 (s, 3H); LC-MS (EI) m/z: 472.0 (M+H⁺).

Example 4

Using general method B, 5-t-butylisoxazol-3-amine (60 mg, 0.27 mmol) and Example A1 (76 mg, 0.27 mmol) were combined and the resultant product purified via column chromatography to yield 1-(5-t-butylisoxazol-3-yl)-3-(2-fluoro-4-(2-(1-methyl-1H-pyrazol-4-yl)pyridin-4-yloxy)phenyl) urea (40 mg, 38% yield). ¹H NMR (400 MHz, DMSO-d₆): δ 9.83 (s, 1H), 8.83 (br s, 1H), 8.36 (d, J=5.6 Hz, 1H), 8.25 (s, 1H), 8.15 (t, J=9.2 Hz, 1H), 7.96 (s, 1H), 7.27 (dd, J=2.8, and 11.6 Hz, 1H), 7.22 (d, J=2.4 Hz, 1H), 7.01 (m, 1H), 6.67 (dd, J=2.8, and 6.0 Hz, 1H) 6.47 (s, 1H), 3.84 (s, 3H), 1.28 (s, 9H); LC-MS (EI) in/Z: 451.2 (M+H⁺).

Example 5

Using General Method B, Example B3 (0.061 g, 0.27 mmol), and Example A1 (0.078, 0.27 mmol) were combined and the resultant product purified via column chromatography to yield 1-(1-t-butyl-1H-pyrazol-4-yl)-3-(2-fluoro-4-(2-(1-methyl-1H-pyrazol-4-yl)pyridin-4-yloxy)phenyl)urea (42 mg, 34% yield) as a white solid. $^1$H NMR (400 MHz, DMSO-$d_6$): δ 8.71 (s, 1H), 8.62 (s, 1H), 8.54-8.52 (m, 2H), 8.26 (t, J=9.2 Hz, 1H), 8.20 (s, 1H), 7.81 (s, 1H), 7.58 (brs, 1H), 7.42 (s, 1H), 7.37-7.34 (m, 1H), 7.09-7.06 (m, 2H), 3.90 (s, 3H), 2.28 (s, 3H), 1.47 (s, 9H); MS (ESI) m/z: 450.2 (M+H$^+$).

Example 6

Using General Method A and purification via chromatography (ethyl acetate/hexane), 3-trifluoromethyl-5-aminopyridine (250 mg, 1.54 mmol) was converted to 2,2,2-trichloroethyl 5-(trifluoromethyl)pyridin-3-ylcarbamate (215 mg, 41% yield) and isolated as a thick oil. MS (ESI) m/z: 339.0 (M+H$^+$).

Using General Method A, 2,2,2-trichloroethyl 5-(trifluoromethyl)pyridin-3-ylcarbamate (215 mg, 0.637 mmol) and Example A2 (170 mg, 0.637 mmol) were combined and purified by reverse phase chromatography (C18-25 column, acetonitrile/water/0.1% TEA) to give a foam. The residue was treated with 10% potassium carbonate (2 mL) and the mix extracted with ethyl acetate (2×25 mL). The combined organic phases were washed with brine, dried (Na$_2$SO$_4$) and concentrated in vacuo to afford 1-(4-(2-(1-methyl-1H-pyrazol-4-yl)pyridin-4-yloxy)phenyl)-3-(5-(trifluoromethyl)pyridin-3-yl)urea (121 mg, 41% yield). $^1$H NMR (300 MHz, DMSO-$d_6$) δ 3.84 (s, 3 H), 6.58-6.60 (m, 1 H), 7.13 (d, 2 H), 7.20 (s, 1 H), 7.57 (d, 2 H), 7.94 (s, 1 H), 8.23 (s, 1 H), 8.33 (d, 1 H), 8.42 (s, 1 H), 8.54 (s, 1 H), 8.78 (s, 1 H), 9.13 (s, 1 H), 9.29 (s, 1 H); MS (ESI) m/z: 455.3 (M+H$^+$).

Example 7

Using General Method B, the prop-1-en-2-yl carbamate of Example B4 (60 mg, 0.25 mmol) and Example A1 (72 mg, 0.25 mmol) in presence of N-methyl pyrrolidine (catalytic amount) were combined and the resultant product purified via trituration with methylene chloride and filtration to afford 1-(2-fluoro-4-(2-(1-methyl-1H-pyrazol-4-yl)pyridin-4-yloxy)phenyl)-3-(3-(trifluoromethyl)isoxazol-5-yl)urea (80 mg, 68% yield). $^1$H NMR (400 MHz, DMSO-$d_6$): δ 11.0 (s, 1H), 8.90 (brs, 1H), 8.36 (d, J=6.0 Hz, 1H), 8.24 (s, 1H), 8.04 (t, J=9.2 Hz, 1H), 7.94 (s, 1H) 7.28 (dd, J=2.8, and 11.6 Hz, 1H), 7.23 (d, J=2.4 Hz, 1H), 7.03 (m, 1H), 6.67 (dd, J=2.4, and 5.6 Hz, 1H), 6.49 (s, 1H), 3.83 (s, 3H); MS (ESI) m/z: 463.0 (M+H$^+$).

Example 8

Prop-1-en-2-yl 1-tert-butyl-1H-pyrazol-4-ylcarbamate (0.074 g, 0.331 mmol), synthesized from Example B3 using General Method E, was reacted with Example A9 (0.100 g, 0.331 mol) in presence of N-methylpyrrolidine (0.005 g, 0.06 mmol) in dioxane (2 ml) at 80° C. for 15 hours. The completed reaction was concentrated in vacuo and purified via recrystallization (hexanes/ethyl acetate) to provide 1-(1-tert-butyl-1H-pyrazol-4-yl)-3-(2,3-difluoro-4-(2-(1-methyl-1H-pyrazol-4-yl)pyridin-4-yloxy)phenyl)urea (0.102 g, 66% yield). $^1$H NMR (400 MHz, DMSO-$d_6$): δ 8.71 (brs, 1H), 8.69 (s, 1H), 8.34 (d, J=6 Hz, 1H), 8.24 (s, 1H), 7.97 (m, 1H), 7.95 (s, 1H), 7.79 (s, 1H), 7.40 (s, 1H), 7.23 (d, J=2.21 Hz, 1H), 7.12 (m, 1H), 6.69 (dd, J=5.5, 2.5 Hz, 1H), 3.82 (s, 3H), 1.45 (s, 9H); MS (ESI) m/z: 468.0 (M+H$^+$).

Example 9

Using general method C, Example B5 (60 mg, 0.25 mmol) and Example A1 (72 mg, 0.25 mmol) in presence of DPPA (60 μL, 0.25 mmol) and (39 μL, 0.25 mmol) were combined and the resultant product purified via column chromatography (CH$_2$Cl$_2$/MeOH) to afford 1-(1-tert-butyl-5-(trifluoromethyl)-1H-pyrazol-4-yl)-3-(2-fluoro-4-(2-(1-methyl-1H-pyrazol-4-yl)pyridin-4-yloxy)phenyl)urea (75 mg, 57% yield). $^1$H NMR (400 MHz, DMSO-$d_6$): δ 9.10 (brs, 1H), 8.53 (s, 1H), 8.35 (d, J=6.0 Hz, 1H), 8.24 (s, 1H), 8.18 (t, J=8.8 Hz, 1H), 7.94 (m, 2H), 7.24 (dd, J=2.4, and 1.6 Hz, 1H), 7.20 (d, J=2.4 Hz, 1H), 6.98 (m, 1H), 6.66 (dd, J=2.4, and 5.6 Hz, 1H), 3.83 (s, 3H), 1.57 (s, 9H); MS (ESI) m/z: 518.0 (M+H$^+$).

Example 10

Using General Method C, Example B6 (50 mg, 0.27 mmol) and Example A1 (78 mg, 0.27 mmol) in presence of DPPA (65 μL, 0.27 mmol) and (42 μL, 0.27 mmol) were combined and the resultant product purified via column chromatography (CH$_2$Cl$_2$/MeOH) to afford 1-(1-tert-butyl-5-methyl-1H-pyrazol-4-yl)-3-(2-fluoro-4-(2-(1-methyl-1H-pyrazol-4-yl)pyridin-4-yloxy)phenyl)urea (55 mg, 43% yield). $^1$H NMR (400 MHz, DMSO-$d_6$): δ 8.57 (brs, 1H), 8.35 (d, J=5.6 Hz, 1H), 8.25 (s, 1H), 8.20 (t, J=9.2 Hz, 1H), 8.15 (s, 1H), 7.96 (s, 1H), 7.44 (s, 1H), 7.22 (m, 2H), 6.97 (m, 1H), 6.66 (dd, J=2.4, and 5.6 Hz, 1H), 3.84 (s, 3H), 2.31 (s, 3H), 1.54 (s, 9H); MS (ESI) m/z: 464.2 (M+H$^+$).

Example 11

Using general method D, 2-amino-5-t-butyl-1,3,4-thiadiazole (0.5000 g, 3.2 mmol) was converted to prop-1-en-2-yl 5-tert-butyl-1,3,4-thiadiazol-2-ylcarbamate (0.73 g, 95% yield) as a beige solid which was used as is in the next reaction. $^1$H NMR (400 MHz, acetone-$d_6$): δ 4.77-4.66 (m, 2H), 1.95 (s, 3H), 1.38 (s, 9H); MS (ESI) m/z: 242.3 (M+H$^+$).

Prop-1-en-2-yl 5-tert-butyl-1,3,4-thiadiazol-2-ylcarbamate (60 mg, 0.249 mmol), Example A1 (70.7 mg, 0.249 mmol), and 1-methylpyrrolidine (1.293 μl, 0.012 mmol) were combined in THF (2.5 ml) and stirred with heating at 70° C. overnight in a sealed screw-cap vial. The completed reaction was cooled to RT and purified directly by reverse phase chromatography to afford 1-(5-tert-butyl-1,3,4-thiadiazol-2-yl)-3-(2-fluoro-4-(2-(1-methyl-1H-pyrazol-4-yl)pyridin-4-yloxy)phenyl)urea (84 mg, 72% yield) as an off-white solid following lyophilization. $^1$H NMR (400 MHz, DMSO-$d_6$): δ 9.04 (brs, 1H), 8.54-8.52 (m, 1H), 8.48 (brs, 1H), 8.2-8.16 (m, 2H), 7.54 (brs, 1H), 7.44-7.40 (m, 1H), 7.15-7.13 (m, 1H), 7.01-7.00 (m, 1H), 3.91 (s, 3H), 1.39 (s, 9H); MS (ESI) m/z: 438.0 (M+H$^+$).

Example 12

Using General Method C, Example B8 (0.15 g, 0.63 mmol), Example A1 (0.15 g, 0.53 mmol) in presence of triethylamine (0.16, 1.58 mmol) and DPPA (0.29 g, 1.05 mmol) were combined to afford 1-(3-tert-butyl-1-(2-(dimethylamino)ethyl)-11H-pyrazol-5-yl)-3-(2-fluoro-4-(2-(1-methyl-1H-pyrazol-4-yl)pyridin-4-yloxy)phenyl)urea (0.085 g, 31% yield) as a white solid. $^1$H NMR (400 MHz, DMSO-$d_6$): δ 9.23 (s, 1H), 9.07 (s, 1H), 8.41 (d, J=5.6 Hz, 1H), 8.29 (s, 1H), 8.15 (t, J=9.2 Hz, 1H), 8.00 (s, 1H), 7.31-7.27 (m, 2H), 7.04 (dt, J=9.2 Hz, 1.2 Hz, 1H), 6.71 (dd, J=5.6 Hz, 2.0 Hz, 1H), 6.11 (s, 1H), 4.0 (t, J=6.8 Hz, 2H), 3.89 (s, 3H), 2.61 (t, J=6.8 Hz, 2H), 2.60 (s, 6H), 1.24 (s, 9H); MS (ESI) m/z: 521.3)(M+H$^+$).

Example 13

Using General Method B, the prop-1-en-2-yl carbamate of Example B7 (60 mg, 0.24 mmol) and Example A1 (68 mg, 0.24 mmol) in presence of N-methyl pyrrolidine (catalytic amount) were combined and the resultant product purified via tituration with $CH_2Cl_2$ and filtration to afford 1-(3-cyclopentylisoxazol-5-yl)-3-(2-fluoro-4-(2-(1-methyl-1H-pyrazol-4-yl)pyridin-4-yloxy)phenyl)urea (71 mg, 62% yield). $^1$H NMR (400 MHz, DMSO-$d_6$): δ 10.3 (s, 1H), 8.77 (brs, 1H), 8.37 (d, J=6.0 Hz, 1H), 8.26 (s, 1H), 8.11 (t, J=8.8 Hz, 1H), 7.96 (s, 1H), 7.28 (dd, J=2.4, and 11.6 Hz, 1H), 7.24 (d, J=2.4 Hz, 1H), 7.03 (m, 1H), 6.68 (dd, J=2.4, and 5.6 Hz, 1H), 6.02 (s, 1H), 3.85 (s, 3H), 1.95 (m, 2H), 1.62 (m, 6H), 1.26 (s, 3H); MS (ESI) m/z: 477.0 (M+H$^+$).

Example 14

Using general method B, the prop-1-en-2-yl carbamate of Example B10 (60 mg, 0.25 mmol) and Example A1 (72 mg, 0.25 mmol) in presence of N-methyl pyrrolidine (catalytic amount) were combined and the resultant product purified via tituration with $CH_2Cl_2$ and filtration to afford 1-(2-fluoro-4-(2-(1-methyl-1H-pyrazol-4-yl)pyridin-4-yloxy)phenyl)-3-(3-(1-methylcyclopentyl)isoxazol-5-yl)urea (68 mg, 58% yield). $^1$H NMR (400 MHz, DMSO-$d_6$): δ 10.3 (s, 1H), 8.78 (brs, 1H), 8.37 (d, J=5.6 Hz, 1H), 8.26 (s, 1H), 8.11 (t, J=9.2 Hz, 1H), 7.96 (s, 1H), 7.28 (dd, J=2.8, and 12.0 Hz, 1H), 7.24 (d, J=2.4 Hz, 1H), 7.03 (m, 1H), 6.68 (dd, J=2.8, and 6.0 Hz, 1H), 5.98 (s, 1H), 3.85 (s, 1H), 3.02 (m, 1H), 1.95 (m, 2H), 1.62 (m, 6H); MS (ESI) m/z: 463.0 (M+H$^+$).

Example 15

Using General Method C, Example B11 (60 mg, 0.33 mmol) and Example A1 (95 mg, 0.33 mmol) in presence of DPPA (79 μL, 0.33 mmol) and (51 μL, 0.33 mmol) were combined and the resultant product purified via column chromatography ($CH_2Cl_2$/MeOH) to afford 1-(1-cyclopentyl-1H-pyrazol-4-yl)-3-(2-fluoro-4-(2-(1-methyl-1H-pyrazol-4-yl)pyridin-4-yloxy)phenyl)urea (53 mg, 34% yield). $^1$H NMR (400 MHz, DMSO-$d_6$): δ 8.70 (s, 1H), 8.51 (d, J=2.0 Hz, 1H), 8.37 (d, J=5.6 Hz, 1H), 8.26 (s, 1H), 8.18 (t, J=8.8 Hz, 1H), 7.96 (s, 1H), 7.78 (s, 1H) 7.22 (m, 2H), 6.99 (m, 1H), 6.67 (dd, J=2.4, and 5.6 Hz, 1H), 4.62 (m, 1H), 3.86 (s, 3H), 2.03 (m, 2H), 1.87 (m, 2H), 1.76 (m, 2H), 1.61 (m, 2H); MS (ESI) m/z: 462.3 (M+H$^+$).

Example 16

Using General Method D. Example B12 (0.20 g, 1.2 mmol) and isopropenyl chloroformate (0.15 mL) in presence of LiHMDS (1.0M, 2.5 mL) were combined to afford prop-1-en-2-yl 1-methyl-3-(trifluoromethyl)-1H-pyrazol-5-ylcarbamate (0.2 g, 67% yield). MS (ESI) m/z: 250.0 (M+H$^+$).

Using General Method D, prop-1-en-2-yl 1-methyl-3-(trifluoromethyl)-1H-pyrazol-5-ylcarbamate (60 mg, 0.24 mmol) and Example A1 (68 mg, 0.24 mmol) in presence of N-methylpyrrolidine (catalytic amount) were combined and the resultant product purified via tituration with $CH_2Cl_2$ and filtration to afford 1-(2-fluoro-4-(2-(1-methyl-1H-pyrazol-4-yl)pyridin-4-yloxy)phenyl)-3-(1-methyl-3-(trifluoromethyl)-1H-pyrazol-5-yl)urea (51 mg, 45% yield). $^1$H NMR (400 MHz, DMSO-$d_6$): δ 9.30 (s, 1H), 8.99 (d, J=2.4 Hz, 1H), 8.38 (d, J=5.6 Hz, 1H), 8.27 (s, 1H), 8.16 (t, J=9.2 Hz, 1H), 7.97 (s, 1H), 7.29 (dd, J=2.4, and 11.6 Hz, 1H), 7.24 (d, J=2.4 Hz, 1H), 7.04 (m, 1H), 6.69 (dd, J=2.4, and 5.6 Hz, 1H), 6.63 (s, 1H), 3.86 (s, 3H), 3.79 (s, 3H); MS (ESI) m/z: 476.0 (M+H$^+$).

Example 17

The prop-1-en-2-yl carbamate of Example B3 (0.075 g, 0.335 mmol), prepared using General Method U, was reacted with Example A4 (0.1 g, 0.335 mmol) in presence of N-methylpyrrolidine (0.006 g, 0.06 mmol) in dioxane (2 ml) at 80° C. for 15 hours. The completed reaction was concentrated in vacuo and the residue purified by flash chromatography (hexane/ethyl acetate) to provide 1-(1-tert-butyl-1H-pyrazol-4-yl)-3-(2-fluoro-3-methyl-4-(2-(1-methyl-1H-pyrazol-4-yl)pyridin-4-yloxy)phenyl)urea (0.115 g, 74% yield). $^1$H NMR (400 MHz, DMSO-$d_6$): δ 8.74 (s, 1H), 8.52 (brs, 1H), 8.39 (d, J=6 Hz, 1H), 8.29 (s, 1H), 8.07 (t, J=9 Hz, 1H), 7.98 (s, 1H), 7.84 (s, 1H), 7.45 (s, 1H), 7.20 (d, J=2.3 Hz, 1H), 6.96 (m, 1H), 6.58 (dd, J=5.5, 2.5 Hz, 1H), 3.88 (s, 3H), 2.08 (brs, 3H), 1.52 (s, 9H); MS (ESI) m/z: 464.2 (M+H$^+$).

Example 18

Using General Method C, Example B13 (100 mg, 0.450 mmol), triethylamine (52 mg, 0.518 n-mol), Example A1 (128 mg, 0.450 mmol) and DPPA (142 mg, 0.518 mmol) were combined, purified by reverse phase chromatography (C18-25 column, acetonitrile/water), treated with saturated sodium bicarbonate (10 mL) and extracted with ethyl acetate (2×20 mL). The combined organic phases washed with brine (20 mL), dried ($Na_2SO_4$), concentrated in vacuo, dissolved in acetonitrile/water and lyophilized to give 1-(2-fluoro-4-(2-(1-methyl-1H-pyrazol-4-yl)pyridin-4-yloxy)phenyl)-3-(1-isopropyl-3-(trifluoromethyl)-1H-pyrazol-4-yl)urea (112 mg, 49% yield). $^1$H NMR (300 MHz, DMSO-$d_6$): δ 1.48 (d, 6 H), 3.92 (s, 3 H), 4.63 (hp, 1 H), 6.73-6.75 (m, 1 H), 7.06-7.08 (m, 1 H), 7.29 (s, 1 H), 7.29-7.34 (m, 1 H), 8.03 (s, 1 H), 8.27-8.32 (m, 3H), 8.40-8.44 (m, 1 H), 8.73 (s, 1 H), 9.15 (s, 1 H); MS (ESI) m/z: 504.0 (M+H$^+$).

Example 19

Using General Method C, Example 1314 (150 mg, 0.892 mmol), triethylamine (104 mg, 1.026 mmol), Example A1 (254 mg, 0.892 mmol) and DPPA (282 mg, 1.026 mmol) were combined and purified by chromatography (methanol/dichloromethane) to afford 1-(2-fluoro-4-(2-(1-methyl-1H-pyrazol-4-yl)pyridin-4-yloxy)phenyl)-3-(1-isopropyl-5-methyl-1H-pyrazol-4-yl)urea (98 mg, 24% yield) as a foam. $^1$H NMR (300 MHz, DMSO-$d_6$): δ 1.44 (d, 6 H), 2.29 (s, 3 H), 4.00 (s, 3 H), 4.56 (hp, 1 H), 7.10 (br s, 1 H), 7.15-7.18 (m, 1 H), 7.43-7.46 (m, 1 H), 7.62 (s, 2H), 8.30 (br s, 1 H), 8.38 (t, 1 H), 8.44 (s, 1 H), 8.58-8.62 (m, 2 H), 8.78 (br s, 1 H); MS (ESI) m/z: 450.2 (M+H$^+$).

Example 20

Using General Method C, Example B115 (62 mg, 0.369 mmol), triethylamine (43 mg, 0.424 mmol), Example A1 (105 mg, 0.369 mmol) and DPPA (117 mg, 0.424 mmol) were combined and purified by column chromatography (methanol/dichloromethane) to afford 1-(2-fluoro-4-(2-(1-methyl-1H-pyrazol-4-yl)pyridin-4-yloxy)phenyl)-3-(1-isopropyl-3-methyl-1H-pyrazol-4-yl)urea (88 mg, 53% yield) as a foam. $^1$H NMR (300 MHz, DMSO-$d_6$): δ 1.46 (d, 6 H), 2.22 (s, 3 H), 3.98 (s, 3 H), 4.45 (hp, 1 H), 6.89 (br s, 1 H), 7.11-7.14 (m, 1 H), 7.37-7.41 (m, 1 H), 7.44 (br s, 1 H), 7.88 (s, 1 H), 8.15 (br s, 1 H), 8.37 (t, 1 H), 8.44-8.53 (m, 3 H), 8.77 (s, 1 H); MS (ESI) m/z: 450.2 (M+H$^+$).

Example 21

A mixture of Example A1 (2.0 g, 7.04 mmol) and saturated aq $NaHCO_3$ (100 mL) in EtOAc (100 mL) was cooled in an ice bath and treated with isopropenyl chloroformate (1.6 mL, 14.64 mmol). The reaction mixture was allowed to slowly warm to RT overnight. The organic layer was separated and washed with sat aq NaHCO$_3$ (25 mL) and brine (25 mL), dried (MgSO$_4$), concentrated in vacuo and was re-crystallized (diethylether) to provide prop-1-en-2-yl 2-fluoro-4-(2-(1-methyl-1H-pyrazol-4-yl)pyridin-4-yloxy)phenylcarbamate (2.32 g, 90% yield). $^1$H NMR (400 MHz, DMSO-d$_6$): δ 9.69 (br s, 1 H), 8.38 (d, J=5.6 Hz, 1 H), 8.26 (s, 1 H), 7.96 (d, J=0.8 Hz, 1 H), 7.67 (br t, J=8.4 Hz, 1 H), 7.27 (d, J=2.4 Hz, 1 H), 7.22 (dd, J=11.2, 2.4 Hz, 1 H), 7.00 (m, 1 H), 6.69 (dd, J=5.6, 2.4 Hz, 1 H), 4.74 (m, 1 H), 4.72 (s, 1 H), 3.84 (s, 3 H), 1.92 (s, 3H); MS (ESI) m/z: 369.1(M+H$^+$).

Example B16 (81 mg, 0.500 mmol), prop-1-en-2-yl 2-fluoro-4-(2-(1-methyl-1H-pyrazol-4-yl)pyridin-4-yloxy) phenylcarbamate (180 mg, 0.489 mmol) and N-methylpyrrolidine (4.25 mg, 0.050 mmol) were combined in THF (1 mL) and heated to 55° C. for 48 h. The reaction mixture was concentrated in vacuo and purified by silica gel chromatography to provide 1-(2-fluoro-4-(2-(1-methyl-1H-pyrazol-4-yl)pyridin-4-yloxy)phenyl)-3-(5-(trifluoromethyl)pyridin-3-yl)urea (168 mg, 72% yield). $^1$H NMR (400 MHz, DMSO-d$_6$) δ 9.60 (s, 1 H), 8.89 (d, J=1.7 Hz, 1 H), 8.77 (d, J=2.4 Hz, 1 H), 8.59 (d, J=1.0 Hz, 1 H), 8.46 (t, J=2.0 Hz, 1 H), 8.39 (d, J=5.8 Hz, 1 H), 8.27 (s, 1 H), 8.13 (t, J=9.0 Hz, 1 H), 7.98 (s, 1 H), 7.29 (dd, J=11.8, 2.6 Hz, 1 H), 7.26 (d, J=2.5 Hz, 1 H), 7.05 (m, 1 H), 6.70 (dd, J=5.6, 2.2 Hz, 1 H), 3.86 (s, 3 H); MS (ESI) m/z 473.0 (M+H$^+$).

Example 22

Using General Method F, Example B17 (0.453 g, 2.48 mmol) was converted to prop-1-en-2-yl 5-isopropylpyridin-3-ylcarbamate (0.185 g, 34%) as a white solid. $^1$H NMR (400 MHz, DMSO-d$_6$): δ 10.10 (s, 1H), 8.44 (d, J=2.4 Hz, 1H), 8.16 (d, J=2.0 Hz, 1H) 7.84 (s, 1H), 4.77 (t, J=1.2 Hz, 1H), 4.74 (s, 1H), 2.91 (m, 1H), 1.94 (d, J=0.8 Hz, 3H), 1.21 (d, J=6.8 Hz, 6H); MS (ESI) m/z: 221.1 (M+H$^+$).

Prop-1-en-2-yl 5-isopropylpyridin-3-ylcarbamate (0.053 g, 0.24 mmol), Example A1 (0.068 g, 0.238 mmol) and N-methylpyrrolidine (0.0020 g, 0.024 mmol) were combined in THF (1.0 mL). The mixture was heated at 55° C. for 12 h. Solvent was removed and the residue was purified by chromatography to afford 1-(2-fluoro-4-(2-(1-methyl-1H-pyrazol-4-yl)pyridin-4-yloxy)phenyl)-3-(5-isopropylpyridin-3-yl)urea (0.0648 g, 61% yield) as a white solid. $^1$H NMR (400 MHz, DMSO-d$_6$); δ 9.23 (s, 1H), 8.75 (d, J=2.0 Hz, 1H), 8.45 (d, J=2.0 Hz, 1H), 8.42 (d, J=4.8 Hz, 1H), 8.31 (s, 1H), 8.22 (t, J=8.8 Hz, 1H), 8.18 (d, J=1.6 Hz, 1H), 8.02 (s, 1H), 7.90 (t, J=1.8 Hz, 1H), 7.32 (dd, J=12.0, 2.8 Hz, 1H), 7.29 (d, J=2.0 Hz, 1H), 7.06 (m, 1H), 6.73 (dd, J=5.6, 2.4 Hz, 1H), 3.90 (s, 3H), 2.97 (m, 1H), 1.27 (d, J=6.8 Hz, 6H); MS (ESI) m/z: 447.3 (M+H$^+$).

Example 23

Using General Method C, Example B18 0.133 g, 0.686 mmol), triethylamine (0.139 g, 1.372 mmol), DPPA (0.189 g, 0.686 mmol) and Example A1 (0.130 g, 0.457 mmol) were combined and the residue purified via recrystallization (acetonitrile) to afford 1-(1-cyclopentyl-5-methyl-1H-pyrazol-4-yl)-3-(2-fluoro-4-(2-(1-methyl-1H-pyrazol-4-yl)pyridin-4-yloxy)phenyl)urea (0.11 g, 50.6% yield) as a white solid. $^1$H NMR (400 MHz, DMSO-d$_6$): δ 8.72 (s, 1H), 8.45 (m, 2H), 8.33 (m, 2H), 8.05 (s, 1H), 7.86 (s, 1H), 7.32 (m, 2H), 7.07 (m, 1H), 6.75 (dd, J=2.5 Hz, 1H), 4.56 (m, 1H), 3.94 (s, 3H), 2.19 (s, 3H), 2.09-1.59 (m, 8H); MS (ESI) m/z: 476.2 (M+H$^+$).

Example 24

Using General Method A, benzo[d]isoxazol-3-amine (500 mg, 3.37 mmol) and Troc-Cl (1.185 g, 5.59 mmol) were combined, purified by column chromatography (ethyl acetate/hexanes), triturated with hexanes (30 mL), filtered and dried to afford 2,2,2-trichloroethyl benzo[d]isoxazol-3-ylcarbamate. $^1$H NMR (300 MHz, DMSO-d$_6$): δ 5.15 (s, 2 H), 7.50 (t, 1 H), 7.77-7.83 (m, 2 H), 8.16 (d, 1 H), 11.51 (s, 1 H); MS (ESI) m/z: 310.9 (M+H$^+$).

Using General Method A, 2,2,2-trichloroethyl benzo[d] isoxazol-3-ylcarbamate (109 mg, 0.352 mmol) and Example A1 (100 mg, 0.352 mmol) were combined and purified by normal phase chromatography (methanol/dichloromethane) and reverse phase chromatography (acetonitrile/water) to give a white solid. The solid was slurried in saturated sodium bicarbonate (4 mL)/ethyl acetate (15 mL), filtered, washed with water (5 mL) and ethyl acetate (5 mL) and dried to afford 1-(benzo[d]isoxazol-3-yl)-3-(2-fluoro-4-(2-(1-methyl-1H-pyrazol-4-yl)pyridin-4-yloxy)phenyl)urea (17 mg, 10% yield). $^1$H NMR (300 MHz, DMSO-d$_6$): δ 3.96 (s, 3 H), 6.85 (br s, 1 H), 7.21-7.25 (m, 1 H), 7.37-7.54 (m, 3 H), 7.80 (br s, 2 H), 8.11 (br s, 1 H), 8.29-8.41 (m, 3 H), 8.52 (br s, 1 H), 9.56 (br s, 1 H), 10.64 (br s, 1 H); MS (ESI) m/z: 445.1 (M+H$^+$).

Example 25

2,2,2-trichloroethyl 3-tert-butylisoxazol-5-ylcarbamate (0.125 g, 0.397 mmol), synthesized according to General Method A from Example B1, was reacted with Example A3 (0.100 g, 0.331 mmol) in dioxane (2 ml) in presence of N-methylpyrrolidine (0.028 g, 0.331 mmol) at 80° C. for 13 hours. The reaction mixture was concentrated in vacuo and the residue purified via recrystallization (methanol) to provide 1-(3-tert-butylisoxazol-5-yl)-3-(2,3-difluoro-4-(2-(1-methyl-1H-pyrazol-4-yl)pyridin-4-yloxy)phenyl)urea (0.043 g, 28% yield) as a white solid. $^1$H NMR (400 MHz, DMSO-d$_6$): δ 10.54 (s, 1H), 9.10 (s, 1H), 8.52 (d, J=6 Hz, 1H), 8.42 (s, 1H), 8.12 (s, 1H), 8.06 (m, 1H), 7.41 (brs, 1H), 7.35 (m, 1H), 6.87 (dd, J=6, 2.5 Hz, 1H), 6.20 (s, 1H), 3.98 (s, 3H), 1.38 (s, 9H); MS (ESI) m/z: 469.1 (M+H$^+$).

Example 26

Using General Method C, Example B19 (50 mg, 0.30 mmol) and Example A1 (84 mg, 0.30 mmol) in presence of DPPA (70 μL, 0.30 mmol) and (45 μL, 0.30 mmol) were combined and the resultant product purified via column chromatography (CH$_2$Cl$_2$/MeCOH) to afford 1-(2-tert-butyloxazol-5-yl)-3-(2-fluoro-4-(2-(1-methyl-1H-pyrazol-4-yl)pyridin-4-yloxy)phenyl)urea (22 mg, 17% yield). $^1$H NMR (400 MHz, DMSO-d$_6$): δ 9.33 (s, 1H), 8.65 (brs, 1H), 8.36 (brd, J=5.6 Hz, 1H), 8.25 (s, 1H), 8.18 (brt, J=9.2 Hz, 1H), 7.95 (s, 1H), 7.75 (s, 2H), 7.24 (m, 1H) 7.21 (s, 1H), 6.99 (m, 1H), 6.67 (m, 1H), 3.84 (s, 3H), 1.30 (s, 9H); MS (ESI) m/z: 451.2 (M+H$^+$).

Example 27

3-Amino-5-(trifluoromethyl)pyridin-2(1H)-one (44 mg, 0.247 mmol), prop-1-en-2-yl 2-fluoro-4-(2-(1-methyl-1H-pyrazol-4-yl)pyridin-4-yloxy)phenylcarbamate from Example 21 (85 mg, 0.231 mmol) and N-methylpyrrolidine (7.5 mg, 0.088 mmol) were combined in 1,4-dioxane (0.8 mL). The resultant mixture was heated to 80° C. After 13 h, the mixture was cooled to RT and diluted with ethyl acetate (3 mL). The resultant precipitate was collected by filtration, washed with ethyl acetate and dried in vacuo to provide 1-(2-fluoro-4-(2-(1-methyl-1H-pyrazol-4-yl)pyridin-4-yloxy)phenyl)-3-(2-oxo-5-(trifluoromethyl)-1,2-dihydropyridin-3-yl)urea as an off-white solid (65 mg, 58% yield). $^1$H NMR (400 MHz, DMSO-$d_6$): δ 12.47 (s, 1 H), 9.56 (s, 1 H), 9.35 (s, 1 H), 8.36 (d, J=5.3 Hz, 1 H), 8.25 (br s, 2 H), 8.17 (t, J=9.4 Hz, 1 H), 7.96 (s, 1 H), 7.59 (s, 1 H), 7.25-7.22 (m, 2 H), 7.00 (d, J=8.5 Hz, 1 H), 6.68 (m, 1 H), 3.84 (s 3 H); MS (ESI) m/z: 489.1 (M+H$^+$).

Example 28

To a solution of 5-tert-butyl-2-methylfuran-3-carbonyl chloride (0.341 g, 1.699 mmol) in THF (2 ml) added lithium hydroxide (0.107 g, 2.55 mmol) in water (1 mL) and the mixture was stirred for 2 h at RT. Solvent was removed in vacuo and the residue was acidified with 2N HCl to afford solid which was filtered and air dried to afford 5-tert-butyl-2-methylfuran-3-carboxylic acid (0.29 g, 94% yield) as a white solid. MS (ESI) m/z: 183.1 (M+H$^+$).

Using General Method C 5-tert-butyl-2-methylfuran-3-carboxylic acid (0.07 g, 0.37 mmol), Example A1 (0.07 g, 0.25 mmol), triethylamine (0.07 g, 0.75 mmol) and DPPA (0.13 g, 0.5 mmol) were combined to afford 1-(5-tert-butyl-2-methylfuran-3-yl)-3-(2-fluoro-4-(2-(1-methyl-1H-pyrazol-4-yl)pyridin-4-yloxy)phenyl)urea (0.065 g, 56% yield) as a white solid. $^1$H NMR (400 MHz, DMSO-$d_6$): δ 8.60 (s, 1H), 8.36-8.34 (m, 2H), 8.24 (s, 1H), 8.17 (t, J=9.2 Hz, 1H), 7.95 (s, 1H), 7.23-7.20 (m, 2H), 6.96 (dd, J=8.8 Hz, 2.4 Hz, 1H), 6.65 (dd, J=5.6 Hz, 2.4 Hz, 1H), 6.26 (s, 1H), 3.84 (s, 3H), 2.16 (s, 3H), 1.19 (s, 9H); MS (ESI) m/z: 464.2 (M+H$^+$).

Example 29

Using General Method B, 6-fluorobenzo[d]thiazol-2-amine (2.00 g, 11.89 mmol) was converted to prop-1-en-2-yl 6-fluorobenzo[d]thiazol-2-ylcarbamate (2.00 g, 67% yield) as a white solid. $^1$H NMR (400 MHz, DMSO-$d_6$): δ 12.33 (s, 1H), 7.86 (dd, J=9, 3 Hz, 1H), 7.69 (dd, J=9, 5 Hz, 1H), 7.24 (dt, J=9, 2.5 Hz, 1H), 4.84 (s, 1H), 4.80 (s, 3H), 1.94 (s, 3H); MS (ESI) m/z: 253.1 (M+H$^+$).

Prop-1-en-2-yl 6-fluorobenzo[d]thiazol-2-ylcarbamate (0.060 g, 0.238 mmol) was reacted with Example A1 (0.068 g, 0.238 mmol) in the presence of a catalytic amount of N-methylpyrrolidine in dioxane (5 ml) at 70° C. for 3 hours. The reaction mixture was cooled and the product filtered, washed and dried to provide 1-(2-fluoro-4-(2-(1-methyl-1H-pyrazol-4-yl)pyridin-4-yloxy)phenyl)-3-(6-fluorobenzo[d]thiazol-2-yl)urea (0.08 g, 70% yield) as a white solid. $^1$H NMR (400 MHz, DMSO-$d_6$): δ 11.03 (s, 1H), 9.15 (s, 1H), 8.38 (d, J=6 Hz, 1H), 8.26 (s, 1H), 8.15 (t, J=9 Hz, 1H), 7.96 (s, 1H), 7.85 (dd, J=9, 2.5 Hz, 1H), 7.68 (m, 1H), 7.31 (dd, J=12, 2.5 Hz, 1H), 7.24 (m, 2H), 7.04 (m, 1H), 6.69 (dd, J=6, 7.5 Hz, 1H), 3.84 (s, 3H); MS (ESI) m/z: 479.1 (M+H$^+$).

Example 30

Using General Method C, Example B20 (0.070 g, 0.419 mmol), TEA (0.088 mL, 0.628 mmol), DPPA (0.135 mL, 0.628 mmol) and Example A1 (0.119 g, 0.419 mmol) were combined to afford 1-(1-tert-butyl-1H-pyrrol-3-yl)-3-(2-fluoro-4-(2-(1-methyl-1H-pyrazol-4-yl)pyridin-4-yloxy) phenyl)urea (0.011 g, 6% yield) as a white solid. $^1$H NMR (400 MHz, DMSO-$d_6$): δ 8.51 (s, 1H), 8.36-8.34 (m, 2H), 8.25-8.19 (m, 2H), 7.95 (s, 1H), 7.22-7.18 (m, 2H), 6.99 (t, J=2.0 Hz, 1H), 6.95 (m, 1H), 6.72 (t, J=2.8 Hz, 1H), 6.65 (dd, J=5.6, 2.4 Hz, 1H), 5.86 (t, J=2.0 Hz, 1H), 3.84 (s, 3H), 1.43 (s, 9H); MS (ESI) m/z, 449.2 (M+H$^+$).

Example 31

Using General Method A, 2,2,2-trichloroethyl 3-tert-butyl-4-methylisoxazol-5-ylcarbamate (100 mg, 0.30 mmol), prepared via General Method A from Example B21 and Example A1 (86 mg, 0.30 mmol) in presence of DIEA (0.12 mL) were combined and the resultant product purified via column chromatography (EtOAc/hexanes) to afford 1-(3-tert-butyl-4-methylisoxazol-5-yl)-3-(2-fluoro-4-(2-(1-methyl-1H-pyrazol-4-yl)pyridin-4-yloxy)phenyl)urea (65 mg, 46% yield). $^1$H NMR (400 MHz, DMSO-$d_6$): δ9.15 (s, 1H), 8.83 (brs, 1H), 8.36 (d, J=5.6 Hz, 1H), 8.25 (s, 1H), 8.05 (t, J=9.2 Hz, 1H), 7.96 (s, 1H), 7.26 (dd, J=2.8, and 12.0 Hz, 1H), 7.23 (d, J=2.0 Hz, 1H), 7.00 (m, 1H), 6.67 (dd, J=2.4, and 5.6 Hz, 1H), 3.84 (s, 3H), 1.96 (s, 3H), 1.29 (s, 9H); MS (ESI) m/z: 465.2 (M+H$^+$).

Example 32

A mixture of prop-1-en-2-yl 2-fluoro-4-(2-(1-methyl-1H-pyrazol-4-yl)pyridin-4-yloxy)phenylcarbamate from Example 21 (0.096 g, 0.262 mmol), Example B22 (0.032 g, 0.262 mmol) and N-methylpyrrolidine (2.23 mg, 0.026 mmol) in dioxane (1.0 mL) was heat at 70° C. overnight. Solvent was removed under reduced pressure. The residue was purified by chromatography to afford 1-(5-ethylpyridin-3-yl)-3-(2-fluoro-4-(2-(1-methyl-1H-pyrazol-4-yl)pyridin-4-yloxy)phenyl)urea (0.054 g, 47% yield) as a white solid. $^1$H NMR (400 MHz, DMSO-$d_6$): δ 9.39 (s, 1H), 8.82 (d, J=2.0 Hz, 1H), 8.50 (d, J=2.4 Hz, 1H), 8.41 (d, J=5.6 Hz, 1H), 8.31 (s, 1H), 8.20-8.14 (m, 2H), 8.01 (s, 1H), 7.88 (d, J=2.0 Hz, 1H), 7.31-7.27 (m, 2H), 7.04 (d, J=9.2 Hz, 1H), 6.74 (dd, J=5.6, 2.6 Hz, 1H), 3.87 (s, 3H), 2.64 (q, J=7.6 Hz, 2H), 1.21 (t, J=7.6 Hz, 3H); MS (ESI) m/z: 433.1 (M+H$^+$).

Example 33

To a solution of 3-cyclopropyl-1-methyl-1H-pyrazol-5-amine (60 mg, 0.434 mmol) in dioxane (1 mL) was added prop-1-en-2-yl 2-fluoro-4-(2-(1-methyl-1H-pyrazol-4-yl)pyridin-4-yloxy)phenylcarbamate from Example 21 (0.16 g, 0.434 mmol), and DBU (6.61 mg, 0.043 mmol) and the mixture was stirred overnight at 70° C. The reaction was checked by LC-MS, solvent was removed and the residue was purified by silica gel column chromatography (EtOAc/hexane→CH2Cl2/MeOH). Pure fractions were combined and concentrated. The residue was dissolved in CH$_3$CN:H$_2$O (1:1, 2 mL) and lyophilized to obtain 1-(3-cyclopropyl-1-methyl-1H-pyrazol-5-yl)-3-(2-fluoro-4-(2-(1-methyl-1H-pyrazol-4-yl)pyridin-4-yloxy)phenyl)urea (26 mg, 13% yield). $^1$H NMR (400 MHz, DMSO-$d_6$): δ 8.92 (s, 1H), 8.82 (d, J=2.0 Hz, 1H), 8.39 (d, J=6.0 Hz, 1H), 8.28 (s, 1H), 8.18 (t, J=9.6 Hz, 1H), 7.99 (s, 1H), 7.26 (m, 2H), 7.02 (m, 1H), 6.70 (dd, J=2.4, and 6.0 Hz, 1H), 3.87 (s, 3H), 3.59 (s, 3H), 1.76 (m, 1H), 0.80 (m, 2H), 0.59 (m, 2H); MS (ESI) m/z; 448.1 (M+H$^+$).

Example 34

Example B24 (100 mg, 0.333 mmol), Example A1 (95 mg, 0.333 mmol) and iPr$_2$NEt (0.127 ml, 0.732 mmol) were combined in DMSO (4 ml) and stirred with heating at 80° C. After 72 h, the crude reaction mixture was purified directly without aqueous workup by reverse phase chromatography to afford 1-(2-fluoro-4-(2-(1-methyl-1H-pyrazol-4-yl)pyridin-4-yloxy)phenyl)-3-(1-isopropyl-1H-imidazol-4-yl)urea (110 mg, 60% yield) as the TFA salt. $^1$H NMR (400 MHz, DMSO-d$_6$): δ 9.49 (s, 1H), 9.11 (brs, 1H), 8.50 (brs, 1H), 8.49 (d, 1H), 8.41 (s, 1H), 8.16-8.13 (m, 1H), 8.05 (s, 1H), 7.47-7.38 (brm, 2H), 7.37-7.31 (m, 1H), 7.09-7.05 (m, 1H), 6.92-6.87 (m, 1H), 4.55-4.46 (m, 1H), 3.88 (s, 3H), 1.44 (d, 6H); MS (ESI) m/z: 436.1 (M+H$^+$).

Example 35

Using General Method C, 1-tert-butyl-5-oxopyrrolidine-3-carboxylic acid (0.1 g, 0.54 mmol), Example A1 0.15 g, 0.54 mmol), Et$_3$N (0.23 mL, 1.62 mmol) and DPPA (0.18 mL, 0.81 mmol) were combined and purified by silica gel column chromatography (EtOAc→CH2Cl2/MeOH) to obtain 1-(1-tert-butyl-5-oxopyrrolidin-3-yl)-3-(2-fluoro-4-(2-(1-methyl-1H-pyrazol-4-yl)pyridin-4-yloxy)phenyl)urea (0.13 g, 50% yield). $^1$H NMR (400 MHz, DMSO-d$_6$): δ 8.35 (d, J=5.6 Hz, 1H), 8.29 (brs, 1H), 8.24 (s, 1H), 8.15 (t, J=9.2 Hz, 1H), 7.94 (s, 1H), 7.19 (m, 2H), 7.01 (d, J=6.8 Hz, 1H), 6.95 (m, 1H), 6.64 (m, 1H), 4.14 (m, 1H), 3.84 (s, 3H), 3.71 (m, 1H), 3.22 (dd, J=3.6, and 10.4 Hz, 1H), 2.60 (m, 1H), 2.07 (m, 1H), 1.32 (s, 9H); MS (ESI) m/z: 467.2 (M+H$^+$).

Example 36

To a stirring solution of 1-(1-tert-butyl-5-oxopyrrolidin-3-yl)-3-(2-fluoro-4-(2-(1-methyl-1H-pyrazol-4-yl)pyridin-4-yloxy)phenyl)urea from Example 35 (95 mg, 0.20 mmol) in dry THF (3 ml) at RT was added 1.0 M LAH/THF (0.81 ml, 0.82 mmol). The resulting mixture was stirred overnight at RT. It was carefully quenched by the sequential addition of H$_2$O (0.1 ml), 3M NaOH (0.1 ml) and H$_2$O (0.3 ml) and then EtOAc was added. The mixture was stirred at RT for 4 hours. The solution was filtered through a pad of Celite® and washing forward with EtOAc. The organic layer was dried (Na$_2$SO$_4$), concentrated in vacuo and purified via silica gel column chromatography (CH$_2$Cl$_2$/MeOH), dissolved in CH$_3$CN:H$_2$O (1:1 2 mL) and lyophilized to obtain 1-(1-tert-butylpyrrolidin-3-yl)-3-(2-fluoro-4-(2-(1-methyl-1H-pyrazol-4-yl)pyridin-4-yloxy)phenyl)urea (45 mg, 49% yield). $^1$H NMR (400 MHz, DMSO-d$_6$): δ 8.42 (brs, 1H), 8.34 (d, J=6.0 Hz, 1H), 8.24 (s, 1H), 8.16 (t, J=8.8 Hz, 1H), 7.94 (s, 1H), 7.16 (m, 2H), 6.93 (m, 2H), 6.63 (dd, J=2.4, and 5.6 Hz, 1H), 4.05 (m, 1H), 3.84 (s, 3H), 2.3-2.8 (m, 4H), 2.03 (m, 1H), 1.48 (m, 1H), 1.01 (s, 9H); MS (ESI) m/z: 453.1 (M+H$^+$).

Example 37

Using a procedure analogous to Example 21, Example B25 (16 mg, 0.091 mmol), prop-1-en-2-yl 2-fluoro-4-(2-(1-methyl-1H-pyrazol-4-yl)pyridin-4-yloxy)phenylcarbamate from Example 21 (35 mg, 0.095 mmol) and N-methylpyrrolidine (1 mg, 0.012 mmol) were combined in 1,4-dioxane (0.8 mL) at 60° C. to afford 1-(2-fluoro-4-(2-(1-methyl-1H-pyrazol-4-yl)pyridin-4-yloxy)phenyl)-3-(2-methyl-5-(trifluoromethyl)pyridin-3-yl)urea (28 mg, 63% yield). $^1$H NMR (400 MHz, DMSO-d$_6$): δ 9.30 (s, 1 H), 8.79 (s, 1 H), 8.68 (s, 1 H), 8.47 (s, 1 H), 8.37 (d, J=5.6 Hz, 1 H), 8.25 (s, 1 H), 8.22 (t, J=9.4 Hz, 1 H), 7.96 (s, 1 H), 7.28 (dd, J=12.3, 1.9 Hz, 1 H), 7.23 (s, 1 H), 7.02 (m, 1 H), 6.67 (m, 1 H), 3.84 (s, 3 H), 2.57 (s, 3 H); MS ESI m/z: 487.2 (M+H$^+$).

Example 38

Using General Method C, Example B23 (64 mg, 0.35 mmol), Example A1 (0.1 g, 0.35 mmol), Et$_3$N (54 μL, 0.38 mmol) DPPA (83 μL, 0.38 mmol) were combined and purified by reverse-phase column chromatography (CH$_3$CN/H$_2$O (0.1% TFA)) provide the TFA salt of 1-(1-tert-butyl-5-methyl-1H-pyrazol-3-yl)-3-(2-fluoro-4-(2-(1-methyl-1H-pyrazol-4-yl)pyridin-4-yloxy)phenyl)urea, The salt was treated with EtOAc and NaHCO$_3$ and then the solution was stirred at RT for 1 hour. The organic was separated, dried (Na$_2$SO$_4$), and titurated (Et2O) to obtain 1-(1-tert-butyl-5-methyl-1H-pyrazol-3-yl)-3-(2-fluoro-4-(2-(1-methyl-1H-pyrazol-4-yl)pyridin-4-yloxy)phenyl)urea (55 mg, 35% yield). $^1$H NMR (400 MHz, DMSO-d$_6$): δ 9.38 (brs, 1H), 8.35 (m, 1H), 8.30 (m, 1H), 8.25 (s, 1H), 7.95 (m, 1H), 7.25 (dd, J=2.4, and 12.0 Hz, 1H), 7.20 (d, J=2.0 Hz, 1H), 7.00 (m, 1H), 6.67 (dd, J=2.4, and 5.6 Hz, 1H), 5.82 (brs, 1H), 3.84 (s, 3H), 2.36 (s, 3H), 1.54 (s, 9H); MS (ESI) m/z: 464.2 (M+H$^+$).

Example 40

Using General Method C, Example B26 (70 mg 0.19 mmol) and Example A1 (55 mg, 0.19 mmol) in presence of DPPA (55 μL, 0.21 mmol) and (30 μL, 0.21 mmol) were combined and the resultant product purified via column chromatography (methanol/methylene chloride) to afford tert-butyl 4-(2-tert-butyl-5-(3-(2-fluoro-4-(2-(1-methyl-1H-pyrazol-4-yl)pyridin-4-yloxy)phenyl)ureido)pyrimidin-4-yl piperazine-1-carboxylate. MS (ESI) m/z: 646.3 (M+H$^+$). This was then treated with HCl (4.0 M, in dioxane) to afford tert-butyl 4-(2-tert-butyl-5-(3-(2-fluoro-4-(2-(1-methyl-1H-pyrazol-4-yl)pyridin-4-yloxy)phenyl)ureido)pyrimidin-4-yl)piperazine-1-carboxylate HCl salt (67 mg, 56% yield). $^1$H NMR (400 MHz, DMSO-d$_6$): δ 9.51 (brs, 1H), 9.31 (brs, 2H), 8.68 (brs, 1H), 8.51 (m, 2H), 8.36 (brs, 1H), 8.20 (t, J=9.2 Hz, 1H), 7.65 (brs, 1H), 7.41 (brd, J=11.6 Hz, 1H), 7.12 (brd, J=9.6 Hz, 1H), 7.06 (brs, 1H), 3.95 (m, 4H), 3.90 (s, 3H), 3.26 (m, 4H), 1.35 (s, 9H); MS (ESI) m/z: 646.3 (M+H$^+$).

Example 41

Using General Method C, Example B27 (60 mg, 0.23 mmol) and Example A1 (64 mg, 0.23 mmol) in presence of DPPA (57 μL, 0.23 mmol) and (36 μL, 0.23 mmol) were combined and the resultant product purified via column chromatography (CH$_2$Cl$_2$/MeOH) to afford 1-(2-tert-butyl-4-morpholinopyrimidin-5-yl)-3-(2-fluoro-4-(2-(1-methyl-1H-pyrazol-4-yl)pyridin-4-yloxy)phenyl)urea (94 mg, 76% yield). $^1$H NMR (400 MHz, DMSO-d$_6$): δ 8.95 (brs, 1H), 8.39 (s, 1H), 8.36 (d, J=5.6 Hz, 1H), 8.24 (m, 2H), 8.16 (t, J=9.6 Hz, 1H), 7.95 (s, 1H), 7.24 (dd, J=2.8, and 11.6 Hz, 1H), 7.21 (d, J=2.4 Hz, 1H), 7.00 (m, 1H), 6.66 (dd. J=2.4, and 6.0 Hz, 1H), 3.84 (s, 3H), 3.71 (m, 4H), 3.49 (m, 4H), 1.29 (s, 9H); MS (ESI) m/z: 547.3 (M+H$^+$).

Example 42

A mixture of Example A1 (2.0 g, 7.04 mmol) and saturated aq NaHCO$_3$ (100 mL) in EtOAc (100 mL) was cooled in an ice bath and treated with isopropenyl chloroformate (1.6 mL, 14.64 mmol). The reaction mixture was allowed to slowly warm to RT overnight. The organic layer was separated and washed with sat aq NaHCO$_3$ (25 mL) and brine (25 mL), dried (MgSO$_4$), concentrated in vacuo and re-crystallized (diethylether) to provide prop-1-en-2-yl 2-fluoro-4-(2-(1-methyl-1H-pyrazol-4-yl)pyridin-4-yloxy)phenylcarbamate (2.32 g, 90% yield). $^1$H NMR (400 MHz, DMSO-d$_6$): δ 9.69 (br s, 1 H), 8.38 (d, J=5.6 Hz, 1 H), 8.26 (s, 1 H), 7.96 (d, J=0.8 Hz, 1 H), 7.67 (br t, J=8.4 Hz, 1 H), 7.27 (d, J=2.4 Hz, 1 H), 7.22 (dd, J=11.2, 2.4 Hz, 1 H), 7.00 (m, 1 H), 6.69 (dd, J=5.6, 2.4 Hz, 1 H), 4.74 (m, 1 H), 4.72 (s, 1 H), 3.84 (s, 3 H), 1.92 (s, 3 H); MS (ESI) m/z: 369.1 (M+H$^+$).

Example B28 (20 mg, 0.083 mmol), prop-1-en-2-yl 2-fluoro-4-(2-(1-methyl-1H-pyrazol-4-yl)pyridin-4-yloxy) phenylcarbamate (30 mg, 0.083 mmol) and N-methylpyrrolidine (1 mg, 0.012 mmol) were combined in THF (1.5 mL) and heated to 55° C. in capped vial for 6 days. 1,8-Diazabicyclo[5.4.0]undece-7-ene (1 drop) was added and the mixture was heated for an additional 3 h at 55° C. The solvent was removed in vacuo and the residue was purified by silica gel chromatography. A second reverse-phase chromatography provided 1-(2-fluoro-4-(2-(1-methyl-1H-pyrazol-4-yl)pyridin-4-yloxy)phenyl)-3-(2-(1-methyl-1H-pyrazol-4-yl)-5-(trifluoromethyl)pyridin-3-yl)urea (16 mg, 35% yield). $^1$H NMR (400 MHz, Acetone-d$_6$): δ 9.15 (s, 1 H), 8.81 (s, 1 H), 8.61 (s, 1 H), 8.59 (s, 1 H), 8.40-8.31 (m, 3 H), 8.13 (s, 1 H), 8.04 (s, 1 H), 7.94 (s, 1 H), 7.19 (d, J=2.4 Hz, 1 H), 7.09 (dd, J=11.6, 2.6 Hz, 1 H), 7.02 (m, 1 H), 6.71 (dd, J=5.6, 2.6 Hz, 1 H), 3.97 (s, 3 H), 3.91 (s, 3 H); MS (ESI); m/z 553.2 (M+H$^+$).

Using the synthetic procedures and methods described herein and methods known to those skilled in the art, the following compounds were made: 1-(3-tert-butylisoxazol-5-yl)-3-(3-methyl-4-(2-(1-methyl-1H-pyrazol-4-yl)pyridin-4-yloxy) phenyl)urea 1-(3-tert-butyl-1-methyl-1H-pyrazol-5-yl)-3-(3-methyl-4-(2-(1-methyl-1H-pyrazol-4-yl)pyridin-4-yloxy)phenyl)urea, 1-(4-(2-(1-methyl-1H-pyrazol-4-yl)pyridin-4-yloxy)phenyl)-3-(3-(trifluoromethyl)phenyl)urea, 1-(5-tert-butylisoxazol-3-yl)-3-(4-(2-(1-methyl-1H-pyrazol-4-yl)pyridin-4-yloxy)phenyl)urea, 1-(4-chloro-3-(trifluoromethyl)phenyl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(5-isopropylisoxazol-3-yl)urea, 1-(2,3-difluorophenyl)-3-(2-fluoro-4-(2-(1-methyl-1H-pyrazol-4-yl)pyridin-4-yloxy) phenyl)urea, 1-(2-fluoro-4-(2-(1-methyl-1H-pyrazol-4-yl) pyridin-4-yloxy)phenyl)-3-(3-isopropylisoxazol-5-yl)urea, 1-(3,5-dichlorophenyl)-3'-(2-fluoro-4-(2-(1-methyl-1H-pyrazol-4-yl)pyridin-4-yloxy)phenyl)urea, 1-cyclohexyl-3-(2-fluoro-4-(2-(1-methyl-1H-pyrazol-4-yl)pyridin-4-yloxy) phenyl)urea 1-cyclopentyl-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(1-isopropyl-1H-pyrazol-4-yl)urea, 1-(4-chlorophenyl)-3-(2-fluoro-4-(2-(1-methyl-1H-pyrazol-4-yl)pyridin-4-yloxy) phenyl)urea, 1-(2-fluoro-4-(2-(1-methyl-1H-pyrazol-4-yl) pyridin-4-yloxy)phenyl)-3-(1-methyl-3-(1-methylcyclopentyl)-1H-pyrazol-5-yl)urea, 1-(2-fluoro-4-(2-(1-methyl-1H-pyrazol-4-yl)pyridin-4-yloxy)phenyl), 1-(2-fluoro-5-(trifluoromethyl)phenyl)urea, 1-(3-tert-butyl phenyl)-3-(2-fluoro-4-(2-(1-methyl-1H-pyrazol-4-yl) pyridin-4-yloxy)phenyl)urea, 1-(2-fluoro-4-(2-(1-methyl-1H-pyrazol-4-yl)pyridin-4-yloxy)phenyl)-3-(2-fluoro-5-methyl)phenyl)urea, 1-(2-fluoro-4-(2-(1-methyl-1H-pyrazol-4-yl)pyridin-4-yloxy)phenyl)-3-(3-isopropyl) phenyl)urea, 1-(1-tert-butyl-1H-pyrazol-4-yl)-3-(3-fluoro-4-(2-(1-methyl-1H-pyrazol-4-yl)pyridin-4-yloxy)phenyl)urea, 1-(5-fluoro-2-methyl)phenyl)-3-(2-fluoro-4-(2-(1-methyl-1H-pyrazol-4-yl)pyridin-4-yloxy)phenyl)urea, 1-(3-cyclopentyl-1-methyl-1H-pyrazol-5-yl)-3-(2-fluoro-4-(2-(1-methyl-1H-pyrazol-4-yl)pyridin-4-yloxy)phenyl)urea, 1-(1-tert-butyl-1H-pyrazol-4-yl)-3-(2-fluoro-4-(2-(1-propyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(3-fluorophenyl)urea, 1-(2-fluoro-3-methyl-4-(2-(1-methyl-1H-pyrazol-4-yl)pyridin-4-yloxy)phenyl)-3-(1-isopropyl-1H-pyrazol-4-yl)urea, 1-cyclohexyl-3-(2,3-difluoro-4-(2-(1-methyl-1H-pyrazol-4-yl)pyridin-4-yloxy)phenyl)urea, 1-cyclohexyl-3-(2-fluoro-3-methyl-4-(2-(1-methyl-1H-pyrazol-4-yl)pyridin-4-yloxy)phenyl)urea, 1-(1-cyclopentyl-5-methyl-1H-pyrazol-4-yl)-3-(2,3-difluoro-4-(2-(1n-methyl-1H-pyrazol-4-yl)pyridin-4-yloxy)phenyl)urea 1-(2-fluoro-4-(2-(1-methyl-1H-pyrazol-4-yl)pyridin-4-yloxy)phenyl)-3-(5-fluoropyridin-3-yl)urea, 1-cyanophenyl)-3-(2-fluoro-4-(2-(1-methyl-1H-pyrazol-4-yl)pyridin-4-yloxy)phenyl)urea, 1-(3-tert-butylisoxazol-5-yl)-3-(2-fluoro-3-methyl-4-(2-(1-methyl-1H-pyrazol-4-yl)pyridin-4-yloxy)phenyl)urea, 1-(3-tert-butylisoxazol-5-yl)-3-(3-fluoro-4-(2-(1-methyl-1H-pyrazol-4-yl)pyridin-4-yloxy)phenyl)urea, 1-(3-tert-butyl-1-methyl-1H-pyrazol-5-yl)-3-(2,3-difluoro-4-(2-(1-methyl-1H-pyrazol-4-yl)pyridin-4-yloxy)phenyl)urea 1-(3-tert-butyl-1-methyl-1H-pyrazol-5-yl)-3-(2-fluoro-3-methyl-4-(2-(1-methyl-1H-pyrazol-4-yl)pyridin-4-yloxy)phenyl)urea, 1-(1-cyclopentyl-1H-pyrazol-4-yl)-3-(2,3-difluoro-4-(2-(1-methyl-1H-pyrazol-4-yl)pyridin-4-yloxy)phenyl)urea, 1-(2,3-difluoro-4-(2-(1-methyl-1H-pyrazol-4-yl)pyridin-4-yloxy)phenyl)-3-(3-isopropylisoxazol-5-yl)urea, 1-(2-fluoro-3-methyl-4-(2-(1-methyl-1H-pyrazol-4-yl)pyridin-4-yloxy)phenyl)-3-(3-isopropylisoxazol-5-yl)urea, 1-(2-fluoro-3-methyl-4-(2-(1-methyl-1H-pyrazol-4-yl)pyridin-4-yloxy)phenyl)-3-6-fluorobenzo[d]thiazol-2-yl)urea, 1-(2-fluoro-3-methyl-4-(2-(1-methyl-1H-pyrazol-4-yl)pyridin-4-yloxy)phenyl)-3-(5-isopropylpyridin-3-yl)urea, 1-(2,3-difluoro-4-(2-(1-methyl-1H-pyrazol-4-yl)pyridin-4-yloxy) phenyl)-3-(5-isopropylpyridin-3-yl)urea, 1-(2-fluoro-4-(2-(1-methyl-1H-pyrazol-4-yl)pyridin-4-yloxy)phenyl)-3-(5-methylpyridin-3-yl)urea, 1-(2-fluoro-3-methyl-4-(2-(1-methyl-1H-pyrazol-4-yl)pyridin-4-yloxy)phenyl)-3-(5-(trifluoromethyl)pyridin-3-yl)urea, 1-(2,3-difluoro-4-(2-(1-methyl-1H-pyrazol-4-yl)pyridin-4-yloxy)phenyl)-3-(5-(trifluoromethyl)pyridin-3-yl)urea, 1-(5-chloropyridin-3-yl)-3-(2-fluoro-4-(2-(1-methyl-1H-pyrazol-4-yl)pyridin-4-yloxy)phenyl)urea, and 1-(2-fluoro-4-(2-(1-methyl-1H-pyrazol-4-yl)pyridin-4-yloxy)phenyl)-3-(3-isopropyl-1-methyl-1H-pyrazol-5-yl)urea, Using the synthetic procedures and methods described herein and methods known to those skilled in the art, the following compounds are made: 1-(3-tert-butylisoxazol-5-yl)-3-(2-fluoro-4-(2-(1-methyl-1H-pyrazol-3-yl)pyridin-4-yloxy) phenyl)urea, 1-(3-tert-butylisoxazol-5-yl)-3-(2-fluoro-4-(2-(1-methyl-1H-pyrazol-5-yl)pyridin-4-yloxy)phenyl)urea, 1-(3-tert-butyl-1-methyl-1H-pyrazol-5-yl)-3-(2-fluoro-4-(2-(1-methyl-1H-pyrazol-3-yl)pyridin-4-yloxy)phenyl)urea, 1-(3-tert-butyl-1-methyl-1H-pyrazol-5-yl)-3-(2-fluoro-4-(2-(1-methyl-1H-pyrazol-5-yl)pyridin-4-yloxy)phenyl)urea, 1-(3-tert-butyl-1-methyl-1H-pyrazol-5-yl)-3-(2-fluoro-4-(2-(3-methyl-1H-pyrazol-1-yl)pyridin-4-yloxy)phenyl)urea, 1-(2-fluoro-4-(2-(1-methyl-1H-pyrazol-4-yl)pyridin-4-yloxy)phenyl)-3-(3-(1-hydroxy-2-methylpropan-2-yl)-1-methyl-1H-pyrazol-5-yl)urea, 1-(2-fluoro-4-(2-(1-methyl-1H-pyrazol-4-yl)pyridin-4-yloxy)phenyl)-3-(3-(1-hydroxy-2-2-methylpropan-2-yl)isoxazol-5-yl)urea 1-(2-fluoro-4-(2-(1-methyl-1H-pyrazol-4-yl)pyridin-4-yloxy)phenyl)-3-(5-(2-hydroxypropan-2-yl)pyridin-3-yl)urea, 1-(3-tert-butyl-1-methyl-1H-pyrazol-5-yl)-3-(2-fluoro-4-(2-(1-(2-hydroxyethyl)-1H-pyrazol-4-yl)pyridin-4-yloxy)phenyl) urea, 1-(3-tert-butyl-1-methyl-1H-pyrazol-5-yl)-3-(4-(2-(1-(2-(dimethylamino)ethyl)-1H-pyrazol-4-yl)pyridin-4-yloxy)-2-fluorophenyl)urea, 1(3-tert-butyl-1-methyl-1H-pyrazol-5-yl)-3-(4-(2-(1-(cyanomethyl)-1H-pyrazol-4-yl) pyridin-4-yloxy)-2-fluorophenyl)urea, 1-(4-(2-(1-(2-amino-2-oxoethyl)-1H-pyrazol-4-yl)pyridin-4-yloxy)-2,3-difluorophenyl)-3-(5-isopropylpyridin-3-yl)urea, 1-(4-(2-(1-(cyanomethyl)-1H-pyrazol-4-yl)pyridin-4-yloxy)-2,3- difluorophenyl)-3-(5-isopropylpyridin-3-yl)urea, 1-(2,3-difluoro-4-(2-(1-(2-morpholinoethyl)-1H-pyrazol-4-yl)pyridin-4-yloxy)phenyl)-3-(5-isopropylpyridin-3-yl)urea, 1-(2-fluoro-4-(2-(1-(2-morpholinoethyl)-1H-pyrazol-4-yl)pyridin-4-yloxy)phenyl)-3-(5-isopropylpyridin-3-yl)urea, 1-(2-fluoro-4-(2-(1-propyl-1H-pyrazol-4-yl)pyridin-4-yloxy)phenyl)-3-(5-isopropylpyridin-3-yl)urea, 1-(2,3-difluoro-4-(2-(1-(2-methoxyethyl)-1H-pyrazol-4-yl)pyridin-4-yloxy)phenyl)-3-(5-isopropylpyridin-3-yl)urea 1-(2,3-difluoro-4-(2-(1-(2-hydroxyethyl)-1H-pyrazol-4-yl)pyridin-4-yloxy)phenyl)-3-(5-isopropylpyridin-1-yl)urea, 1-(4-(2-(1-(2-(dimethylamino)ethyl)-1H-pyrazol-4-yl)pyridin-4-yloxy)-2,3-difluorophenyl)-3-(5-isopropylpyridin-3-yl)urea, 1-(4-(2-(1-(3-(dimethylamino)propyl)-1H-pyrazol-4-yl)pyridin-4-yloxy)-2,3-difluorophenyl)-3-(5-isopropylpyridin-3-yl)urea, 1-(2,3-difluoro-4-(2-(1-(3-hydroxypropyl)-1H-pyrazol-4-yl)pyridin-4-yloxy)phenyl)-3-(5-isopropylpyridin-3-yl)urea, 1-(4-(2-(1-(2-(dimethylamino)ethyl)-1H-pyrazol-4-yl)pyridin-4-yloxy)-2-fluorophenyl)-3-(5-isopropylpyridin-3-yl)urea, 1-(2-fluoro-4-(2-(1-methyl-1H-pyrazol-4-yl)pyridin-4-yloxy)phenyl)-3-(4-(trifluoromethyl)pyridin-2-yl)urea, 1-(3-fluoro-4-(2-(1-(2-(4-methylpiperazin-1-yl)ethyl)-1H-pyrazol-4-yl)pyridin-4-yloxy)phenyl)-3-(5-isopropylpyridin-3-yl)urea, 1-(2-fluoro-4-(2-(1-(3-hydroxypropyl)-1H-pyrazol-4-yl)pyridin-4-yloxy)phenyl)-3-(5-isopropylpyridin-3-yl)urea, 1-(2-fluoro-4-(2-(1-methyl-1H-pyrazol-4-yl)pyridin-4-yloxy phenyl)-3-(4-(trifluoromethyl(pyridin-2-yl)urea, 1-(3-tert-butyl-1-methyl-1H-pyrazol-5-yl)-3-(4-(2-(1-(2-(dimethylamino)ethyl)-1H-pyrazol-4-yl)pyridin-4-yloxy)-2,3-difluorophenyl)urea, 1-(3-tert-butyl-1-methyl-1H-pyrazol-5-yl)-3-(2,3-difluoro-4-(2-(1-(2-methoxyethyl)-1H-pyrazol-4-yl)pyridin-4-yloxy)phenyl)urea 1-(3-tert-butyl-1-methyl-1H-pyrazol-5-yl)-3-(2,3-difluoro-4-(2-(1-(2-hydroxyethyl)-1H-pyrazol-4-yl)pyridin-4-yloxy)phenyl)urea, 1-(3-tert-butyl-1-methyl-1H-pyrazol-5-yl)-3-(3-fluoro-4-(2-(1-(2-(4-methylpiperazin-1-yl)ethyl)-1H-pyrazol-4-yl)pyridin-4-yloxy)phenyl)urea, 1-(3-tert-butyl-1-methyl-1H-pyrazol-5-yl)-3-(4-(2-(1-(3-(dimethylamino)propyl)-1H-pyrazol-4-yl)pyridin-4-yloxy)-2,3-difluorophenyl)urea, 1-(3'-tert-butyl-1-methyl-1H-pyrazol-5-yl)-3-(2,3-difluoro-4-(2-(1-(3-hydroxypropyl)-1H-pyrazol-4-yl)pyridin-4-yloxy)phenyl)urea, 1-(5-tert-butylpyridin-3-yl)-3-(2-fluoro-4-(2-(1-(3-hydroxypropyl)-1H-pyrazol-4-yl)pyridin-4-yloxy)phenyl)urea, 1-(5-tert-butylpyridin-3-yl)-3-(2-fluoro-4-(2-(1-methyl-1H-pyrazol-4-yl)pyridin-4-yloxy)phenyl)urea, 1-(3,4-tert-butyl-1-methyl-1H-pyrazol-5-yl)-3-(2-fluoro-4-(2-(1-methyl-1H-pyrazol-3-yl)pyridin-4-yloxy)phenyl)urea, 1-(3-tert-butyl-1-methyl-1H-pyrazol-5-yl)-3-(2-fluoro-4-(2-(1-methyl-1H-pyrazol-5-yl)pyridin-4-yloxy)phenyl)urea, 1-(3-tert-butylisoxazol-5-yl)-3-(2-fluoro-4-(2-(1-methyl-1H-pyrazol-3-yl)pyridin-4-yloxy)phenyl)urea, 1-(3-tert-butylisoxazol-5-yl)-3-(2-fluoro-4-(2-(1-methyl-1H-pyrazol-5-yl)pyridin-4-yloxy)phenyl)urea, 1-(3-tert-butyl-1-methyl-1H-pyrazol-5-yl)-3-(2-fluoro-4-(2-(3-methyl-1H-pyrazol-1-yl)pyridin-4-yloxy)phenyl)urea, 1-(2,3-difluoro-4-(2-(1-methyl-1H-pyrazol-4-yl)pyridin-4-yloxy)phenyl)-3-(3-(1-hydroxy-2-methylpropan-2-yl)-1-methyl-1H-pyrazol-5-yl)urea, 1-(2-fluoro-3-methyl-4-(2-(1-methyl-1H-pyrazol-4-yl)pyridin-4-yloxy)phenyl)-3-(3-(1-hydroxy-2-methylpropan-2-yl)-1-methyl-1H-pyrazol-5-yl)urea, 1-(2-fluoro-3-methyl-4-(2-(1-methyl-1H-pyrazol-4-yl)pyridin-4-yloxy)phenyl)-3-(3-(1-hydroxy-2-methylpropan-2-yl)isoxazol-5-yl)urea, 1-(2,3-difluoro-4-(2-(1-methyl-1H-pyrazol-4-yl)pyridin-4-yloxy)phenyl)-3-(3-(1-hydroxy-2-methylpropan-2-yl)isoxazol-5-yl)urea, 1-(2-fluoro-4-(2-(1-methyl-1H-pyrazol-4-yl)pyridin-4-yloxy)phenyl)-3-(5-(1-hydroxy-2-methylpropan-2-yl)pyridin-3-yl)urea, 1-(2-fluoro-3-methyl-4-(2-(1-methyl-1H-pyrazol-4-yl)pyridin-4-yloxy)phenyl)-3-(5-(1-hydroxy-2-methylpropan-2-yl)pyridin-3-yl)urea, 1-(2,3-difluoro-4-(2-(1-methyl-1H-pyrazol-4-yl)pyridin-4-yloxy)phenyl)-3-(5-(1-hydroxy-2-methylpropan-2-yl)pyridin-3-yl)urea, 1-(2-fluoro-4-(2-(1-methyl-1H-pyrazol-4-yl)pyridin-4-yloxy)phenyl)-3-(5-(1-hydroxypropan-2-yl)pyridin-3-yl)urea, 1-(2-fluoro-3-methyl-4-(2-(1-methyl-1H-pyrazol-4-yl)pyridin-4-yloxy-phenyl)-3-(5-(1-hydroxypropan-2-yl)pyridin-3-yl)urea, 1-(2,3-difluoro-4-(2-(1-methyl-1H-pyrazol-4-yl)pyridin-4-yloxy)phenyl)-3-(5-(1-hydroxypropan-2-yl)pyridin-3-yl)urea, 1-(2,3-difluoro-4-(2-(1-methyl-1H-pyrazol-4-yl)pyridin-4-yloxy)phenyl)-3-(5-ethylpyridin-3-yl)urea, 1-(5-ethylpyridin-3-yl)-3-(2-fluoro-3-methyl-4-(2-(1-methyl-1H-pyrazol-4-yl)pyridin-4-yloxy)phenyl)urea, 1-(1-tert-butyl-1H-pyrazol-3-yl)-3-(2-fluoro-4-(2-(1-methyl-1H-pyrazol-4-yl)pyridin-4-yloxy)phenyl)urea, 1-(3-tert-butyl-1-methyl-1H-pyrazol-5-yl)-3-(4-(2-(1-ethyl-1H-pyrazol-4-yl)pyridin-4-yloxy)-2-fluorophenyl)urea, 1-(4-(2-(1-(2-amino-2-oxoethyl)-1H-pyrazol-4-yl)pyridin-4-yloxy)-2-fluorophenyl)-3-(3-tert-butyl-1-methyl-1H-pyrazol-5-yl)urea 1-(3-tert-butyl-1-methyl-1H-pyrazol-5-yl)-3-(2-fluoro-4-(2-(1-(2-morpholinoethyl)-1H-pyrazol-4-yl)pyridin-4-yloxy)phenyl)urea, 1-(3-tert-butylisoxazol-5-yl)-3-(4-(2-(1-ethyl-1H-pyrazol-4-yl)pyridin-4-yloxy)-2-fluorophenyl)urea, 1-(3-tert-butylisoxazol-5-yl)-3-(4-(2-(1-(cyanomethyl)-1H-pyrazol-4-yl)pyridin-4-yloxy)-2-fluorophenyl)urea, 1-(4-(2-(1-(2-amino-2-oxoethyl)-1H-pyrazol-4-yl)pyridin-4-yloxy)-2-fluorophenyl)-3-(3-tert-butylisoxazol-5-yl urea, 1-(3-tert-butylisoxazol-5-yl)-3-(2-fluoro-4-(2-(1-(2-morpholinoethyl)-1H-pyrazol-4-yl)pyridin-4-yloxy)phenyl)urea, 1-(3-tert-butylisoxazol-5-yl)-3-(2-fluoro-4-(2-(1-(2-hydroxyethyl)-1H-pyrazol-4-yl)pyridin-4-yloxy)phenyl)urea, 1-(3-tert-butylisoxazol-5-yl)-3-(4-(2-(1-(2-(dimethylamino)ethyl)-1H-pyrazol-4-yl)pyridin-4-yloxy)-2-fluorophenyl)urea, 1-(1-tert-butyl-1H-pyrazol-4-yl)-3-(4-(2-(1-ethyl-1H-pyrazol-4-yl)pyridin-4-yloxy)-2-fluorophenyl)urea, 1-(1-tert-butyl-1H-pyrazol-4-yl)-3-(4-(2-(1-(cyanomethyl)-1H-pyrazol-4-yl)pyridin-4-yloxy)-2-fluorophenyl)urea, 1-(4-(2-(1-(2-amino-2-oxoethyl)-1H-pyrazol-4-yl)pyridin-4-yloxy)-2-fluorophenyl)-3-(1-tert-butyl-1H-pyrazol-4-yl)urea, 1-(1-tert-butyl-1H-pyrazol-4-yl)-3-(4-(2-(1-(2-(dimethylamino)ethyl)-1H-pyrazol-4-yl)pyridin-4-yloxy)-2-fluorophenyl)urea, 1-(1-tert-butyl-1H-pyrazol-4-yl)-3-(2-fluoro-4-(2-(1-(2-hydroxyethyl)-1H-pyrazol-4-yl)pyridin-4-yloxy)phenyl)urea, 1-(1-tert-butyl-1H-pyrazol-4-yl)-3-(2-fluoro-4-(2-(1-(2-morpholinoethyl)-1H-pyrazol-4-yl)pyridin-4-yloxy)phenyl)urea, 1-(1-tert-butyl-1H-pyrazol-3-yl)-3-(4-(2-(1-ethyl-1H-pyrazol-4-yl)pyridin-4-yloxy)-2-fluorophenyl)urea, 1-(1-tert-butyl-1H-pyrazol-3-yl)-3-(4-(2-(1-(cyanomethyl)-1H-pyrazol-4-yl)pyridin-4-yloxy)-2-fluorophenyl)urea, 1-(4-(2-(1-(2-amino-2-oxoethyl)-1H-pyrazol-4-yl)pyridin-4-yloxy)-2-fluorophenyl)-3-(1-tert-butyl-1H-pyrazol-3-yl)urea, 1-(1-tert-butyl-1H-pyrazol-3-yl)-3-(4-(2-(1-(2-(dimethylamino)ethyl)-1H-pyrazol-4-yl)pyridin-4-yloxy)-2-fluorophenyl)urea, 1-(1-tert-butyl-1H-pyrazol-3-yl)-3-(2-fluoro-4-(2-(1-(2-hydroxyethyl)-1H-pyrazol-4-yl)pyridin-4-yloxy)phenyl)urea, 1-(1-tert-butyl-1H-pyrazol-3-yl)-3-(2-fluoro-4-(2-(1-(2-morpholinoethyl)-1H-pyrazol-4-yl)pyridin-4-yloxy)phenyl)urea, 1-(4-(2-(1-ethyl-1H-pyrazol-4-yl)pyridin-4-yloxy)-2-fluorophenyl)-3-(5-isopropylpyridin-3-yl)urea, 1-(4-(2-(1-(cyanomethyl)-1H-pyrazol-4-yl)pyridin-4-yloxy)-2-fluorophenyl)-3-(5-isopropylpyridin-3-yl)urea, 1-(4-(2-(1-(2-amino-2-oxoethyl)-1H-pyrazol-4-yl)pyridin-4-yloxy)-2-fluorophenyl)-3-(5-isopropylpyridin-3-yl)urea, 1-(4-(2-(1-(2-(dimethylamino)ethyl)-1H-pyrazol-4-yl)pyridin-4-yloxy)-2-fluorophenyl)-1-(5-isopropylpyridin-1-yl)urea, 1-(2-fluoro-4-(2-(1-(2-hydroxyethyl)-1H-pyrazol-4-yl)pyridin-4-yloxy)phenyl)-3-(5-isopropylpyridin-3-yl)urea 1-(2-fluoro-4-(2-(1-(2-morpholinoethyl)-1H-pyrazol-4-yl)pyridin-4-yloxy)phenyl)-3-(5-isopropylpyridin-3-yl)urea, 1-(5-tert-butylpyridin-3-yl)-3-(4-(2-(1-ethyl-1H-pyrazol-4-yl)pyridin-4-yloxy)-2-fluorophenyl)urea, 1-(5-tert-butylpyridin-3-yl)-3-(4-(2-(1-(cyanomethyl)-1H-pyrazol-4-yl)pyridin-4-yloxy)-2-fluorophenyl)urea, 1-(4-(2-(1-(2-amino-2-oxoethyl)-1H-pyrazol-4-yl)pyridin-4-yloxy)-2-fluorophenyl)-3-(5-tert-butylpyridin-3-yl)urea, 1-(5-tert-butylpyridin-3-yl)-3-(4-(2-(1-(2-(dimethylamino)ethyl)-1H-pyrazol-4-yl)pyridin-4-yloxy)-2-fluorophenyl)urea, 1-(5-tert-butylpyridin-3-yl)-3-(2-fluoro-4-(2-(1-(2-hydroxyethyl)-1H-pyrazol-4-yl)pyridin-4-yloxy)phenyl)urea, 1-(5-tert-butylpyridin-3-yl)-3-(2-fluoro-4-(2-(1-(2-morpholinoethyl)-1H-pyrazol-4-yl)pyridin-4-yloxy)phenyl)urea, 1-(4-(2-(1-ethyl-1H-pyrazol-4-yl)pyridin-4-yloxy)-2-fluorophenyl)-3-(5-(trifluoromethyl)pyridin-3-yl)urea, 1-(4-(2-(1-(cyanomethyl)-1H-pyrazol-4-yl)pyridin-4-yloxy)-2-fluorophenyl)-3-(5-(trifluoromethyl)pyridin-3-yl)urea, 1-(4-(2-(1-(2-amino-2-oxoethyl)-1H-pyrazol-4-yl)pyridin-4-yloxy)-2-fluorophenyl)-3-(5-(trifluoromethyl)pyridin-3-yl)urea, 1-(4-(2-(1-(2-(dimethylamino)ethyl))-1H-pyrazol-4-yl)pyridin-4-yloxy)-2-fluorophenyl)-3-(5-(trifluoromethylpyridin-3-yl)urea, 1-(2-fluoro-4-(2-(1-(2-hydroxyethyl)-1H-pyrazol-4-yl)pyridin-4-yloxy)phenyl)-3-(5-(trifluoromethyl)pyridin-3-yl)urea 1-(2-fluoro-4-(2-(1-(2-morpholinoethyl)-1H-pyrazol-4-yl)pyridin-4-yloxy)phenyl)-3-(5-(trifluoromethyl)pyridin-3-yl)urea, 1-(2-fluoro-5-(2-(1-methyl-1H-pyrazol-4-yl)pyridin-4-yloxy)phenyl)-3-(5-(trifluoromethyl)pyridin-3-yl)urea, 1-(2-fluoro-5-(2-(1-methyl-1H-pyrazol-4-yl pyridin-4-yloxy phenyl)-3-(5-isopropylpyridin-3-yl)urea, 1-(1-tert-butyl-1H-pyrazol-4-yl)-3-(2-fluoro-5-(2-(1-methyl-1H-pyrazol-4-yl)pyridin-4-yloxy)phenyl urea, 1-(1-tert-butyl-1H-pyrazol-3-yl)-3-(2-fluoro-5-(2-(1-methyl-1H-pyrazol-4-yl)pyridin-4-yloxy)phenyl)urea, 1-(A-tert-butylisoxazol-5-yl)-3-(2-fluoro-5-(2-(1-methyl-1H-pyrazol-4-yl)pyridin-4-yloxy)phenyl)urea, 1-(3-tert-butyl-1-methyl-1H-pyrazol-5-yl)-3-(2-fluoro-5-(2-(1-methyl-1H-pyrazol-4-yl)pyridin-4-yloxy)phenyl)urea, 1-(5-(6-(1H-pyrazol-4-yl)pyridin-2-yloxy)-2-fluorophenyl)-3-(3-(3-(dimethylamino)pyrrolidin-1-yl)phenyl)urea, 1-(5-(6-(1H-pyrazol-4-yl)pyridin-2-yloxy)-2-fluorophenyl)-3-(3-chloro-5-(3-(dimethylamino)pyrrolidin-1-yl)phenyl)urea, 1-(5-(6-(1H-pyrazol-4-yl)pyridin-2-yloxy)-2-fluorophenyl)-3-(3-(3-(dimethylamino)pyrrolidin-1-yl)-5-methyl)phenyl)urea, 1-(5-(6-(1H-pyrazol-4-yl)pyridin-2-yloxy)-2-fluorophenyl)-3-(3-(3-oxopyrrolidin-1-yl)phenyl)urea, 1-(5-(6-(1H-pyrazol-4-yl)pyridin-2-yloxy)-2-fluorophenyl)-3-(3-methyl-5-(3-oxopyrrolidin-1-yl)phenyl-urea, 1-(5-(6-(1H-pyrazol-4-yl)pyridin-2-yloxy)-2-fluorophenyl)-3-(3-chloro-5-(3-oxopyrrolidin-1-yl)phenyl)urea, 1-(5-(6-(1H-pyrazol-4-yl)pyridin-2-yloxy)-2-fluorophenyl)-3-(3-(3-oxopyrrolidin-1-yl)-5-(trifluoromethyl)phenyl)urea, 1-(3-(3-(dimethylamino)pyrrolidin-1-yl)phenyl)-3-(2-fluoro-5-(6-(1-methyl-1H-pyrazol-4-yl)pyridin-2-yloxy)phenyl)urea, 1-(3-chloro-5-(3-(dimethylamino)pyrrolidin-1-yl)phenyl)-3-(2-fluoro-5-(6-(1-methyl-1H-pyrazol-4-yl)pyridin-2-yloxy)phenyl)urea, 1-(3-(3-(dimethylamino)pyrrolidin-1-yl)-5-methyl)phenyl)-3-(2-fluoro-5-(6-(1-methyl-1H-pyrazol-4-yl)pyridin-2-yloxy)phenyl)urea, 1-(2-fluoro-5-(6-(1-methyl-1H-pyrazol-4-yl)pyridin-2-yloxy)phenyl)-3-(3-(3-oxopyrrolidin-1-yl)phenyl)urea, 1-(2-fluoro-5-(6-(1-methyl-1H-pyrazol-4-yl)pyridin-2-yloxy)phenyl)-3-(3-methyl-5-(3-oxopyrrolidin-1-yl)phenyl)urea, 1-(3-chloro-5-(3-oxopyrrolidin-1-yl)phenyl)-3-(2-fluoro-5-(6-(1-methyl-1H-pyrazol-4-yl)pyridin-2-yloxy)phenyl)urea, 1-(2-fluoro-5-(6-(1-methyl-1H-pyrazol-4-yl)pyridin-2-yloxy)phenyl)-3-(3-(3-oxopyrrolidin-1-yl)-5-(trifluoromethyl)phenyl)urea, 1-(5-(2-(1H-pyrazol-4-yl)pyridin-4-yloxy)-2-fluorophenyl)-3-(3-(3-(dimethylamino)pyrrolidin-1-yl)phenyl)urea, 1-(5-(2-(1H-pyrazol-4-yl)pyridin-4-yloxy)-2-fluorophenyl)-3-(3-chloro-5-(3-(dimethylamino)pyrrolidin-1-yl)phenyl)urea, 1-(5-(2-(1H-pyrazol-4-yl)pyridin-4-yloxy)-2-fluorophenyl)-3-(3-(3-(dimethylamino)pyrrolidin-1-yl)-5-methyl)phenyl)urea, 1-(5-(2-(1H-pyrazol-4-yl)pyridin-4-yloxy)-2-fluorophenyl)-3-(3-(3-oxopyrrolidin-1-yl)phenyl)urea, 1-(5-(2-(1H-pyrazol-4-yl)pyridin-4-yloxy)-2-fluorophenyl)-3-(3-methyl-5-(3-oxopyrrolidin-1-yl)phenyl)urea, 1-(5-(2-(1H-pyrazol-4-yl)pyridin-4-yloxy)-2-fluorophenyl)-3-(3-chloro-5-(3-oxopyrrolidin-1-yl)phenyl)urea, 1-(5-(2-(1H-pyrazol-4-yl)pyridin-4-yloxy)-2-fluorophenyl)-3-(3-(3-oxopyrrolidin-1-yl)-5-(trifluoromethyl)phenyl)urea, 1-(3-(3-(dimethylamino)pyrrolidin-1-yl)phenyl)-3-(2-fluoro-5-(2-(1-methyl-1H-pyrazol-4-yl)pyridin-4-yloxy)phenyl)urea 1-(3-chloro-5-(3-(dimethylamino)pyrrolidin-1-yl)phenyl)-3-(2-fluoro-5-(2-(1-methyl-1H-pyrazol-4-yl)pyridin-4-yloxy)phenyl)urea, 1-(3-(3-(dimethylamino)pyrrolidin-1-yl)-5-methyl)phenyl)-3-(2-fluoro-5-(2-(1-methyl-1H-pyrazol-4-yl)pyridin-4-yloxy)phenyl)urea, 1-(2-fluoro-5-(2-(1-methyl-1H-pyrazol-4-yl)pyridin-4-yloxy)phenyl)-3-(3-(3-oxopyrrolidin-1-yl)phenyl)urea, 1-(2-fluoro-5-(2-(1-methyl-1H-pyrazol-4-yl)pyridin-4-yloxy)phenyl)-3-(3-methyl-5-(3-oxopyrrolidin-1-yl)phenyl)urea, 1-(3-chloro-5-(3-oxopyrrolidin-1-yl)phenyl)-3-(2-fluoro-5-(2-(1-methyl-1H-pyrazol-4-yl)pyridin-4-yloxy)phenyl)urea, 1-(2-fluoro-5-(2-(1-methyl-1H-pyrazol-4-yl)pyridin-4-yloxy)phenyl)-3-(3-(3-oxopyrrolidin-1-yl)-5-(trifluoromethyl)phenyl)urea, 1-(4-(2-(1H-pyrazol-4-yl)pyridin-4-yloxy)-2-fluorophenyl)-3-(3-(3-(dimethylamino)pyrrolidin-1-yl)phenyl)urea, 1-(4-(2-(1H-pyrazol-4-yl)pyridin-4-yloxy)-2-fluorophenyl)-3-(3-chloro-5-(3-(dimethylamino)pyrrolidin-1-yl)phenyl)urea, 1-(4-(2-(1H-pyrazol-4-yl)pyridin-4-yloxy)-2-fluorophenyl)-3-(3-(3-(dimethylamino)pyrrolidin-1-yl)-5-methylphenyl)urea, 1-(4-(2-(1H-pyrazol-4-yl)pyridin-4-yloxy)-2-fluorophenyl)-3-(3-(3-(dimethylamino)pyrrolidin-1-yl)-5-(trifluoromethyl)phenyl)urea, 1-(4-(2-(1H-pyrazol-4-yl)pyridin-4-yloxy)-2-fluorophenyl)-1-(3-(3-oxopyrrolidin-1-yl)phenyl)urea, 1-(4-(2-(1H-pyrazol-4-yl)pyridin-4-yloxy)-2-fluorophenyl)-3-(3-chloro-5-(3-oxopyrrolidin-1-yl)phenyl)urea, 1-(4-(2-(1H-pyrazol-4-yl)pyridin-4-yloxy)-2-fluorophenyl)-3-(3-methyl-5-(3-oxopyrrolidin-1-yl)phenyl)urea, 1-(4-(2-(1H-pyrazol-4-yl)pyridin-4-yloxy)-2-fluorophenyl)-3-(3-(3-oxopyrrolidin-1-yl)-5-(trifluoromethyl)phenyl)urea, 1-(3-(dimethylamino)pyrrolidin-1-yl)phenyl)-3-(2-fluoro-4-(2-(1-methyl-1H-pyrazol-4-yl)pyridin-4-yloxy)phenyl)urea, 1-(3-chloro-5-(3-(dimethylamino)pyrrolidin-1-yl)phenyl)-3-(2-fluoro-4-(2-(1-methyl-1H-pyrazol-4-yl)pyridin-4-yloxy)phenyl)urea, 1-(3-(3-(dimethylamino)pyrrolidin-1-yl)-5-methylphenyl)-3-(2-fluoro-4-(2-(1-methyl-1H-pyrazol-4-yl)pyridin-4-yloxy)phenyl)urea, 1-(3-(3-(dimethylamino)pyrrolidin-1-yl-)-5-(trifluoromethyl)phenyl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(3-((3-oxopyrrolidin-1-yl)phenyl)urea, 1-(3-chloro-5-(3-oxopyrrolidin-1-yl)phenyl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(3-methyl-5-(3-oxopyrrolidin-1-yl)phenyl)urea, 1-(2-fluoro-4-(2-(1-methyl-1H-pyrazol-4-yl)pyridin-4-yloxy)phenyl)-3-

(3-(3-oxopyrrolidin-1-yl)-5-(trifluoromethyl)phenyl)urea, 1-(4-(2-(1H-pyrazol-4-yl)pyridin-4-yloxy)-3-fluorophenyl)-3-(3-(3-(dimethylamino)pyrrolidin-1-yl)phenyl)urea, 1-(4-(2-(1H-pyrazol-4-yl)pyridin-4-yloxy)-3-fluorophenyl)-3-(3-chloro-5-(3-(dimethylamino)pyrrolidin-1-yl)phenyl)urea, 1-(4-(2-(1H-pyrazol-4-yl)pyridin-4-yloxy)-3-fluorophenyl)-3-(3-(3-(dimethylamino)pyrrolidin-1-yl)-5-methyl)phenyl)urea, 1-(4-(2-(1H-pyrazol-4-yl)pyridin-4-yloxy)-3-fluorophenyl)-3-(3-(3-(dimethylamino)pyrrolidin-1-yl)-5-(trifluoromethyl)phenyl)urea, 1-(4-(2-(1H-pyrazol-4-yl)pyridin-4-yloxy)-3-fluorophenyl)-3-(3-(3-oxopyrrolidin-1-yl)phenyl)urea, 1-(4-(2-(1H-pyrazol-4-yl)pyridin-4-yloxy)-3-fluorophenyl)-3-(3-chloro-5-(3-oxopyrrolidin-1-yl)phenyl)urea, 1-(4-(2-(1H-pyrazol-4-yl)pyridin-4-yloxy)-3-fluorophenyl)-3-(3-methyl-5-(3-oxopyrrolidin-1-yl)phenyl)urea, 1-(4-(2-(1H-pyrazol-4-yl)pyridin-4-yloxy)-3-fluorophenyl)-3-(3-(3-oxopyrrolidin-1-yl)-5-(trifluoromethyl)phenyl)urea, 1-(3-(3-(dimethylamino)pyrrolidin-1-yl)phenyl)-3-(3-fluoro-4-(2-(1-methyl-1H-pyrazol-4-yl)pyridin-4-yloxy)phenyl)urea, 1-(3-chloro-5-(3-(dimethylamino)pyrrolidin-1-yl)phenyl)-3-(3-fluoro-4-(2-(1-methyl-1H-pyrazol-4-yl)pyridin-4-yloxy)phenyl)urea, 1-(3-(3-(dimethylamino)pyrrolidin-1-yl)-5-methyl)phenyl)-3-(3-fluoro-4-(2-(1-methyl-1H-pyrazol-4-yl)pyridin-4-yloxy)phenyl)urea, 1-(3-(3-(dimethylamino)pyrrolidin-1-yl)-5-(trifluoromethyl)phenyl)-3-(3-fluoro-4-(2-(1-methyl-1H-pyrazol-4-yl)pyridin-4-yloxy)phenyl)urea, 1-(3-fluoro-4-(2-(1-methyl-1H-pyrazol-4-yl)pyridin-4-yloxy)phenyl)-3-(3-(3-oxopyrrolidin-1-yl)phenyl)urea, 1-(3-chloro-5-(3-oxopyrrolidin-1-yl)phenyl)-3-(3-fluoro-4-(2-(1-methyl-1H-pyrazol-4-yl)pyridin-4-yloxy)phenyl)urea, 1-(3-fluoro-4-(2-(1-methyl-1H-pyrazol-4-yl)pyridin-4-yloxy)phenyl)-3-(3-methyl-5-(3-oxopyrrolidin-1-yl)phenyl)urea, 1-(3-fluoro-4-(2-(1-methyl-1H-pyrazol-4-yl)pyridin-4-yloxy)phenyl)-3-(3-(3-oxopyrrolidin-1-yl)-5-(trifluoromethyl)phenyl)urea, 1-(5-(6-(1H-pyrazol-4-yl)pyridin-2-yloxy)-2-fluorophenyl)-3-(3-(pyrrolidin-1-yl)phenyl)urea, 1-(5-(6-(1H-pyrazol-4-yl)pyridin-2-yloxy)-2-fluorophenyl)-3-(3-chloro-5-(pyrrolidin-1-yl)phenyl)urea, 1-(5-(6-(1H-pyrazol-4-yl)pyridin-2-yloxy)-2-fluorophenyl)-3-(3-methyl-5-(pyrrolidin-1-yl)phenyl)urea, 1-(5-(6-(1H-pyrazol-4-yl)pyridin-2-yloxy)-2-fluorophenyl)-3-(3-pyrrolidin-1-yl)-5-(trifluoromethyl)phenyl)urea, 1-(5-(6-(1H-pyrazol-4-yl)pyridin-2-yloxy)-2-fluorophenyl)-3-(3-(4-methyl-1H-imidazol-1-yl)phenyl)urea, 1-(5-(6-(1H-pyrazol-4-yl)pyridin-2-yloxy)-2-fluorophenyl)-3-(3-chloro-5-(4-methyl-1H-imidazol-1-yl)phenyl)urea, 1-(5-(6-(1H-pyrazol-4-yl)pyridin-2-yloxy)-2-fluorophenyl)-3-(3-methyl-5-(4-methyl-1H-imidazol-1-yl)phenyl)urea, 1-(5-(6-(1H-pyrazol-4-yl)pyridin-2-yloxy)-2-fluorophenyl)-3-(3-(4-methyl-1H-imidazol-1-yl)-5-(trifluoromethyl)phenyl)urea, 1-(2-fluoro-5-(6-(1-methyl-1H-pyrazol-4-yl)pyridin-2-yl oxy)phenyl)-3-(3-(pyrrolidin-1-yl)phenyl)urea, 1-(3-chloro-5-(pyrrolidin-1-yl)phenyl)-3-(2-fluoro-5-(6-(1-methyl-1H-pyrazol-4-yl)pyridin-2-yloxy)phenyl)urea, 1-(2-fluoro-5-(6-(1-methyl-1H-pyrazol-4-yl)pyridin-2-yloxy)phenyl)-3-(3-methyl-5-(pyrrolidin-1-yl)phenyl)urea, 1-(2-fluoro-5-(6-(1-methyl-1H-pyrazol-4-yl)pyridin-2-yloxy)phenyl)-1-3-(pyrrolidin-1-yl)-5-(trifluoromethyl)phenyl)urea, 1-(2-fluoro-5-(6-(1-methyl-1H-pyrazol-4-yl)pyridin-2-yloxy)phenyl)-3-(3-(4-methyl-1H-imidazol-1-yl)phenyl)urea, 1-(3-chloro-5-(4-methyl-1H-imidazol-1-yl)phenyl)-3-(2-fluoro-5-(6-(1-methyl-1H-pyrazol-4-yl)pyridin-2-yloxy)phenyl)urea, 1-(2-fluoro-5-(6-(1-methyl-1H-pyrazol-4-yl)pyridin-2-yloxy)phenyl)-3-(3-methyl-5-(4-methyl-1H-imidazol-1-yl)phenyl)urea, 1-(2-fluoro-5-(6-(1-methyl-1H-pyrazol-4-yl)pyridin-2-yloxy) phenyl)-3-(3-(4-methyl-1H-imidazol-1-yl)-5-(trifluoromethyl)phenyl)urea, 1-(5-(2-(1H-pyrazol-4-yl)pyridin-4-yloxy)-2-fluorophenyl)-3-(3-(pyrrolidin-1-yl)phenyl)urea, 1-(5-(2-(1H-pyrazol-4-yl)pyridin-4-yloxy)-2-fluorophenyl)-3-(3-chloro-5-(pyrrolidin-1-yl)phenyl)urea, 1-(5-(2-(1H-pyrazol-4-yl)pyridin-4-yloxy)-2-fluorophenyl)-3-(3-methyl-5-(pyrrolidin-1-yl)phenyl)urea, 1-(5-(2-(1H-pyrazol-4-yl)pyridin-4-yloxy)-2-fluorophenyl)-3-(3-(pyrrolidin-1-yl)-5-(trifluoromethyl)phenyl)urea, 1-(5-(2-(1H-pyrazol-4-yl)pyridin-4-yloxy)-2-fluorophenyl)-3-(3-(4-methyl-1H-imidazol-1-yl)phenyl)urea, 1-(5-(2-(1H-pyrazol-4-yl)pyridin-4-yloxy)-2-fluorophenyl)-3-(3-chloro-5-(4-methyl-1H-imidazol-1-yl)phenyl)urea, 1-(5-(2-(1H-pyrazol-4-yl)pyridin-4-yloxy)-2-fluorophenyl)-3-(3-methyl-5-(4-methyl-1H-imidazol-1-yl)phenyl)urea, 1-(5-(2-(1H-pyrazol-4-yl)pyridin-4-yloxy)-2-fluorophenyl)-3-(3-(4-methyl-1H-imidazol-1-yl)-5-(trifluoromethyl)phenyl)urea, 1-(2-fluoro-5-(2-(1-methyl-1H-pyrazol-4-yl)pyridin-4-yloxy)phenyl)-3-(3-(pyrrolidin-1-yl)phenyl)urea, 1-(3-chloro-5-(pyrrolidin-1-yl)phenyl)-3-(2-fluoro-5-(2-(1-methyl-1H-pyrazol-4-yl)pyridin-4-yloxy)phenyl)urea, 1-(2-fluoro-5-(2-(1-methyl-1H-pyrazol-4-yl)pyridin-4-yloxy)phenyl)-3-(3-methyl-5-(pyrrolidin-1-yl)phenyl)urea, 1-(2-fluoro-5-(2-(1-methyl-1H-pyrazol-4-yl)pyridin-4-yloxy)phenyl)-3-(3-(pyrrolidin-1-yl)-5-(trifluoromethyl)phenyl)urea 1-(2-fluoro-5-(2-(1-methyl-1H-pyrazol-4-yl)pyridin-4-yloxy)phenyl)-3-(3-(4-methyl-1H-imidazol-1-yl)phenyl)urea, 1-(3-chloro-5-(4-methyl-1H-imidazol-1-yl)phenyl)-3-(2-fluoro-5-(2-(1-methyl-1H-pyrazol-4-yl)pyridin-4-yloxy)phenyl)urea, 1-(2-fluoro-5-(2-(1-methyl-1H-pyrazol-4-yl)pyridin-4-yloxy) phenyl)-3-(3-methyl-5-(4-methyl-1H-imidazol-1-yl)phenyl)urea, 1-(2-fluoro-5-(2-(1-methyl-1H-pyrazol-4-yl)pyridin-4-yloxy)phenyl)-3-(3-(4-methyl-1H-imidazol-1-yl)-5-(trifluoromethyl)phenyl)urea, 1-(4-(2-(1H-pyrazol-4-yl)pyridin-4-yloxy)-2-fluorophenyl)-1-(4-(pyrrolidin-1-yl)phenyl)urea, 1-(4-(2-(1H-pyrazol-4-yl)pyridin-4-yloxy)-2-fluorophenyl)-3-(3-chloro-5-(pyrrolidin-1-yl)phenyl)urea, 1-(4-(2-(1H-pyrazol-4-yl)pyridin-4-yloxy)-2-fluorophenyl)-3-(3-methyl-5-(pyrrolidin-1-yl)phenyl)urea, 1-(4-(2-(1H-pyrazol-4-yl)pyridin-4-yloxy)-2-fluorophenyl)-3-(3-(pyrrolidin-1-yl)-5-(trifluoromethyl)phenyl)urea, 1-(4-(2-(1H-pyrazol-4-yl)pyridin-4-yloxy)-2-fluorophenyl)-3-(3-(4-methyl-1H-imidazol-1-yl)phenyl)urea, 1-(4-(2-(1H-pyrazol-4-yl)pyridin-4-yloxy)-2-fluorophenyl)-3-(3-chloro-5-(4-methyl-1H-imidazol-1-yl)phenyl)urea, 1-(4-(2-(1H-pyrazol-4-yl)pyridin-4-yloxy)-2-fluorophenyl)-3-(3-methyl-5-(4-methyl-1H-imidazol-1-yl)phenyl)urea, 1-(4-(2-(1H-pyrazol-4-yl)pyridin-4-yloxy)-2-fluorophenyl)-3-(3-(4-methyl-1H-imidazol-1-yl)-5-(trifluoromethyl)phenyl)urea 1-(2-fluoro-4-(2-(1-methyl-1H-pyrazol-4-yl)pyridin-4-yloxy)phenyl)-3-(3-(pyrrolidin-1-yl)phenyl)urea, 1-(3-chloro-5-(pyrrolidin-1-yl)phenyl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(3-methyl-5-(pyrrolidin-1-yl)phenyl)urea, 1-(2-fluoro-4-(2-(1-methyl-1H-pyrazol-4-yl)pyridin-4-yloxy)phenyl)-3-(3-(pyrrolidin-1-yl)-5-(trifluoromethyl)phenyl)urea, 1-(2-fluoro-4-(2-(1-methyl-1H-pyrazol-4-yl)pyridin-4-yloxy)phenyl)-3-(3-(4-methyl-1H-imidazol-1-yl)phenyl)urea, 1-(3-chloro-5-(4-methyl-1H-imidazol-1-yl)phenyl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(3-methyl-5-(4-methyl-1H-imidazol-1-yl)phenyl)urea, 1-(2-fluoro-4-(2-(1-methyl-1H-pyrazol-4-yl)pyridin-4-yloxy)phenyl)-3-(3-(4-methyl-1H-imidazol-1-yl)-5-(trifluoromethyl)phenyl)urea, 1-(4-(2-(1H-pyrazol-4-yl)pyridin-4-yloxy)-3-fluorophenyl)-3-(3-(pyrrolidin-1-yl)phenyl)urea, 1-(4-(2-(1H-pyrazol-4-yl)pyridin-4-yloxy)-3- fluorophenyl)-3-(3-chloro-5-(pyrrolidin-1-yl)phenyl)urea, 1-(4-(2-(1H-pyrazol-4-yl)pyridin-4-yloxy)-3-fluorophenyl)-3-(3-methyl-5-(pyrrolidin-1-yl)phenyl)urea, 1-(4-(2-(1H-pyrazol-4-yl)pyridin-4-yloxy)-3-fluorophenyl)-3-(3-(pyrrolidin-1-yl)-5-(trifluoromethyl)phenyl)urea, 1-(4-(2-(1H-pyrazol-4-yl)pyridin-4-yloxy)-3-fluorophenyl)-3-(3-(4-methyl-1H-imidazol-1-yl)phenyl)urea, 1-(4-(2-(1H-pyrazol-4-yl)pyridin-4-yloxy)-3-fluorophenyl)-3-(3-chloro-5-(4-methyl-1H-imidazol-1-yl)phenyl)urea, 1-(4-(2-(1H-pyrazol-4-yl)pyridin-4-yloxy)-3-fluorophenyl)-3-(3-methyl-5-(4-methyl-1H-imidazol-1-yl)phenyl)urea, 1-(4-(2-(1H-pyrazol-4-yl)pyridin-4-yloxy)-3-fluorophenyl)-3-(3-(4-methyl-1H-imidazol-1-yl)-5-(trifluoromethyl)phenyl)urea, 1-(3-fluoro-4-(2-(1-methyl-1H-pyrazol-4-yl)pyridin-4-yloxy)phenyl)-3-(3-(pyrrolidin-1-yl)phenyl)urea, 1-(3-chloro-5-(pyrrolidin-1-yl)phenyl)-3-(3-fluoro-4-(2-(1-methyl-1H-pyrazol-4-yl)pyridin-4-yloxy)phenyl)urea, 1-(3-fluoro-4-(2-(1-methyl-1H-pyrazol-4-yl)pyridin-4-yloxy)phenyl)-3-(3-methyl-5-pyrrolidin-1-yl)phenyl)urea, 1-(3-fluoro-4-(2-(1-methyl-1H-pyrazol-4-yl)pyridin-4-yloxy)phenyl)-3-(3-(pyrrolidin-1-yl)-5-(trifluoromethyl)phenyl)urea, 1-(3-fluoro-4-(2-(1-methyl-1H-pyrazol-4-yl)pyridin-4-yloxy)phenyl)-3-(3-(4-methyl-1H-imidazol-1-yl)phenyl)urea, 1-(3-chloro-5-(4-methyl-1H-imidazol-1-yl)phenyl)-3-(3-fluoro-4-(2-(1-methyl-1H-pyrazol-4-yl)pyridin-4-yloxy)phenyl)urea, 1-(3-fluoro-4-(2-(1-methyl-1H-pyrazol-4-yl)pyridin-4-yloxy)phenyl)-3-(3-methyl-5-(4-methyl-1H-imidazol-1-yl)phenyl)urea, 1-(3-fluoro-4-(2-(1-methyl-1H-pyrazol-4-yl)pyridin-4-yloxy)phenyl)-3-(3-(4-methyl-1H-imidazol-1-yl)-5-(trifluoromethyl)phenyl)urea, 1-(5-(2-(1H-pyrazol-4-yl)pyridin-4-yloxy)-2-fluorophenyl)-3-(3-(piperidin-1-yl)phenyl)urea, 1-(5-(2-(1H-pyrazol-4-yl)pyridin-4-yloxy)-2-fluorophenyl)-3-(3-methyl-5-(piperidin-1-yl)phenyl)urea, 1-(5-(2-(1H-pyrazol-4-yl)pyridin-4-yloxy)-2-fluorophenyl)-3-(3-chloro-5-(piperidin-1-yl)phenyl)urea, 1-(5-(2-(1H-pyrazol-4-yl)pyridin-4-yloxy)-2-fluorophenyl)-3-(3-(piperidin-1-yl)-5-(trifluoromethyl)phenyl)urea, 1-(5-(2-(1H-pyrazol-4-yl)pyridin-4-yloxy)-2-fluorophenyl)-3-(3-(4-methylpiperazin-1-yl)phenyl)urea, 1-(5-(2-(1H-pyrazol-4-yl)pyridin-4-yloxy)-2-fluorophenyl)-3-(3-methyl-5-(4-methylpiperazin-1-yl)phenyl)urea, 1-(5-(2-(1H-pyrazol-4-yl)pyridin-4-yloxy)-2-fluorophenyl)-3-(3-chloro-5-(4-methylpiperazin-1-yl)phenyl)urea, 1-(5-(2-(1H-pyrazol-4-yl pyridin-4-yloxy)-2-fluorophenyl)-3-(3-(4-methylpiperazin-1-yl)-5-(trifluoromethyl)phenyl)urea, 1-(2-fluoro-5-(2-(1-methyl-1H-pyrazol-4-yl)pyridin-4-yloxy)phenyl)-3-(3-(piperidin-1-yl)phenyl)urea, 1-(2-fluoro-5-(2-(1-methyl-1H-pyrazol-4-yl)pyridin-4-yloxy)phenyl)-3-(3-methyl-5-piperidin-1-yl)phenyl)urea, 1-(3-chloro-5-(piperidin-1-yl)phenyl)-3-(2-fluoro-5-(2-(1-methyl-1H-pyrazol-4-yl)pyridin-4-yloxy)phenyl)urea, 1-(2-fluoro-5-(2-(1-methyl-1H-pyrazol-4-yl)pyridin-4-yloxy)phenyl)-3-(3-(piperidin-1-yl)-5-(trifluoromethyl)phenyl)urea, 1-(5-(2-(H-pyrazol-4-yl)pyridin-4-yloxy)-2-fluorophenyl)-3-(3-(4-methylpiperazin-1-yl)phenyl)urea, 1-(2-fluoro-5-(2-(1-methyl-1H-pyrazol-4-yl)pyridin-4-yloxy)phenyl)-3-(3-methyl-5-(4-methylpiperazin-1-yl)phenyl)urea, 1-(3-chloro-5-(4-methylpiperazin-1-yl)phenyl)-3-(2-fluoro-5-(2-(1-methyl-1H-pyrazol-4-yl)pyridin-4-yloxy)phenyl)urea, 1-(2-fluoro-5-(2-(1 methyl-1H-pyrazol-4-yl)pyridin-4-yloxy)phenyl)-3-(3-(4-methylpiperazin-1-yl)-5-(trifluoromethyl)phenyl)urea, 1-(5-(6-(1H-pyrazol-4-yl)pyridin-2-yloxy)-2-fluorophenyl)-3-(3-(piperidin-1-yl)phenyl)urea, 1-(5-(6-(1H-pyrazol-4-yl)pyridin-2-yloxy)-2-fluorophenyl)-3-(3-methyl-5-(piperidin-1-yl)phenyl)urea, 1-(5-(6-(1H-pyrazol-4-yl)pyridin-2-yloxy)-2-fluorophenyl)-3-(3-chloro-5-(piperidin-1-yl)phenyl)urea, 1-(5-(6-(1H-pyrazol-4-yl)pyridin-2-yloxy)-2-fluorophenyl)-3-(3-(piperidin-1-yl)-5-(trifluoromethyl)phenyl)urea, 1-(5-(6-(1H-pyrazol-4-yl)pyridin-2-yloxy)-2-fluorophenyl)-3-(3-(4-methylpiperazin-1-yl)phenyl)urea, 1-(5-(6-(1H-pyrazol-4-yl)pyridin-2-yloxy)-2-fluorophenyl)-3-(3-methyl-5-(4-methylpiperazin-1-yl)phenylurea, 1-(5-(6-(1H-pyrazol-4-yl)pyridin-2-yloxy)-2-fluorophenyl)-3-(3-chloro-5-(4-methylpiperazin-1-yl)phenyl)urea, 1-(5-(6-(1H-pyrazol-4-yl)pyridin-2-yloxy)-2-fluorophenyl)-3-(3-(4-methylpiperazin-1-yl)-5-(trifluoromethyl)phenyl)urea, 1-(2-fluoro-5-(6-(1-methyl-1H-pyrazol-4-yl)pyridin-2-yloxy)phenyl)-3-(3-(piperidin-1-yl)phenyl)urea, 1-(2-fluoro-5-(6-(1-methyl-1H-pyrazol-4-yl)pyridin-2-yloxy)phenyl)-3-(3-methyl-5-(piperidin-1-yl)phenyl)urea, 1-(3-chloro-5-(piperidin-1-yl)phenyl)-3-(2-fluoro-5-(6-(1-methyl-1H-pyrazol-4-yl)pyridin-2-yloxy)phenyl)urea, 1-(2-fluoro-5-(6-(1-methyl-1H-pyrazol-4-yl)pyridin-2-yloxy)phenyl)-3-(3-(piperidin-1-yl)-5-(trifluoromethyl)phenyl)urea 1-(5-(6-(1H-pyrazol-4-yl)pyridin-2-yloxy)-2-fluorophenyl)-3-(3-(4-methylpiperazin-1-yl)phenyl)urea, 1-(2-fluoro-5-(6-(1-methyl-1H-pyrazol-4-yl)pyridin-2-yloxy)phenyl)-3-(3-methyl-5-(4-methylpiperazin-1-yl)phenyl)urea, 1-(3-chloro-5-(4-methylpiperazin-1-yl)phenyl)-3-(2-fluoro-5-(6-(1-methyl-1H-pyrazol-4-yl)pyridin-2-yloxy)phenyl)urea, 1-(2-fluoro-5-(6-(1-methyl-1H-pyrazol-4-yl)pyridin-2-yloxy)phenyl)-3-(3-(4-methylpiperazin-1-yl)-5-(trifluoromethyl)phenyl)urea, 1-(4-(2-(1H-pyrazol-4-yl)pyridin-4-yloxy)-2-fluorophenyl)-3-(3-(piperidin-1-yl)phenyl)urea, 1-(4-(2-(1H-pyrazol-4-yl)pyridin-4-yloxy)-2-fluorophenyl)-3-(3-chloro-5-(piperidin-1-yl)phenyl)urea, 1-(4-(2-(1H-pyrazol-4-yl)pyridin-4-yloxy)-2-fluorophenyl)-3-(3-methyl-5-(piperidin-1-yl)phenyl)urea, 1-(4-(2-(1H-pyrazol-4-yl)pyridin-4-yloxy)-2-fluorophenyl)-3-(3-(piperidin-1-yl)-5-(trifluoromethyl)phenyl)urea, 1-(4-(2-(1H-pyrazol-4-yl)pyridin-4-yloxy)-2-fluorophenyl)-3-(3-(4-methylpiperazin-1-yl)phenyl)urea, 1-(4-(2-(1H-pyrazol-4-yl)pyridin-4-yloxy)-2-fluorophenyl)-3-(3-chloro-5-(4-methylpiperazin-1-yl)phenyl)urea, 1-(4-(2-(1H-pyrazol-4-yl)pyridin-4-yloxy)-2-fluorophenyl)-3-(3-methyl-5-(4-methylpiperazin-1-yl)phenyl)urea, 1-(4-(2-(1H-pyrazol-4-yl)pyridin-4-yloxy)-2-fluorophenyl)-3-(3-(4-methylpiperazin-1-yl)-5-(trifluoromethyl)phenyl)urea, 1-(2-fluoro-4-(2-(1-methyl-1H-pyrazol-4-yl)pyridin-4-yloxy)phenyl)-3-(3-(piperidin-1-yl)phenyl)urea, 1-(3-chloro-5-(piperidin-1-yl)phenyl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(3-methyl-5-(piperidin-1-yl)phenyl)urea, 1-(2-fluoro-4-(2-(1-methyl-1H-pyrazol-4-yl)pyridin-4-yloxy)phenyl)-3-(3-(piperidin-1-yl)-5-(trifluoromethyl)phenyl)urea, 1-(2-fluoro-4-(2-(1-methyl-1H-pyrazol-4-yl)pyridin-4-yloxy)phenyl)-3-(3-(4-methylpiperazin-1-yl)phenyl)urea, 1-(3-chloro-5-(4-methylpiperazin-1-yl)phenyl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(3-methyl-5-(4-methylpiperazin-1-yl)phenyl)urea, 1-(2-fluoro-4-(2-(1-methyl-1H-pyrazol-4-yl)pyridin-4-yloxy)phenyl)-3-(3-(4-methylpiperazin-1-yl)-5-(trifluoromethyl)phenyl)urea, 1-(4-(2-(1H-pyrazol-4-yl)pyridin-4-yloxy)-3-fluorophenyl)-3-(3-(piperidin-1-yl)phenyl)urea, 1-(4-(2-(1H-pyrazol-4-yl)pyridin-4-yloxy)-3-fluorophenyl)-3-(3-chloro-5-(piperidin-1-yl)phenyl)urea, 1-(4-(2-(1H-pyrazol-4-yl)pyridin-4-yloxy)-3-fluorophenyl)-3-(3-methyl-5-(piperidin-1-yl)phenyl)urea, 1-(4-(2-(1H-pyrazol-4-yl)pyridin-4-yloxy)-3-fluorophenyl)-3-(3-(piperidin-1-yl)-5-((trifluoromethyl)phenyl)urea, 1-(4-(2-(1H-pyrazol-4-yl)pyridin-4-yloxy)-3-fluorophenyl)-3-(3-(4-methylpiperazin-1-yl)phenyl)urea, 1-(4-(2-(1H-pyrazol-4-yl)pyridin-4- yloxy)-3-fluorophenyl)-3-(3-chloro-5-(4-methylpiperazin-1-yl)phenyl)urea, 1-(4-(2-(1H-pyrazol-4-yl)pyridin-4-yloxy)-3-fluorophenyl)-3-(3-methyl-5-(4-methylpiperazin-1-yl)phenyl)urea, 1-(4-(2-(1H-pyrazol-4-yl)pyridin-4-yloxy)-3-fluorophenyl)-3-(3-(4-methylpiperazin-1-yl)-5-(trifluoromethyl)phenyl)urea, 1-(3-fluoro-4-(2-(1-methyl-1H-pyrazol-4-yl)pyridin-4-yloxy)phenyl)-3-(3-(piperidin-1-yl)phenyl)urea, 1-(3-chloro-5-(piperidin-1-yl)phenyl)-3-(3-fluoro-4-(2-(1-methyl-1H-pyrazol-4-yl)pyridin-4-yloxy)phenyl)urea, 1-(3-fluoro-4-(2-(1-methyl-1H-pyrazol-4-yl)pyridin-4-yloxy)phenyl)-3-(3-methyl-5-(piperidin-1-yl)phenyl)urea, 1-(3-fluoro-4-(2-(1-methyl-1H-pyrazol-4-yl)pyridin-4-yloxy)phenyl)-3-(3-(piperidin-1-yl)-5-(trifluoromethyl)phenyl)urea, 1-(3-fluoro-4-(2-(1-methyl-1H-pyrazol-4-yl)pyridin-4-yloxy)phenyl)-3-(3-(4-methylpiperazin-1-yl)phenyl)urea, 1-(3-chloro-5-(4-methylpiperazin-1-yl)phenyl)-3-(3-fluoro-4-(2-(1-methyl-1H-pyrazol-4-yl)pyridin-4-yloxy)phenyl)urea, 1-(3-fluoro-4-(2-(1-methyl-1H-pyrazol-4-yl)pyridin-4-yloxy)phenyl)-3-(3-methyl-5-(4-methylpiperazin-1-yl)phenyl)urea, 1-(3-fluoro-4-(2-(1-methyl-1H-pyrazol-4-yl)pyridin-4-yloxy)phenyl)-3-(3-(4-methylpiperazin-1-yl)-5-(trifluoromethyl)phenyl)urea, 1-(5-(6-(1H-pyrazol-4-yl)pyridin-2-yloxy)-2-fluorophenyl)-3-(3-morpholinophenyl)urea, 1-(5-(6-(1H-pyrazol-4-yl)pyridin-2-yloxy)-2-fluorophenyl)-3-(3-methyl-5-(piperidin-1-yl)phenyl)urea, 1-(5-(6-(1H-pyrazol-4-yl)pyridin-2-yloxy)-2-fluorophenyl)-3-(3-chloro-5-morpholinophenyl)urea, 1-(5-(6-(1H-pyrazol-4-yl)pyridin-2-yloxy)-2-fluorophenyl)-3-(3-morpholino-5-(trifluoromethyl)phenyl)urea, 1-(2-fluoro-5-(6-(1-methyl-1H-pyrazol-4-yl)pyridin-2-yloxy)phenyl)-3-(3-morpholinophenyl)urea, 1-(2-fluoro-5-(6-(1-methyl-1H-pyrazol-4-yl)pyridin-2-yloxy)phenyl)-3-(3-methyl-5-morpholinophenyl)urea, 1-(3-chloro-5-morpholinophenyl)-3-(2-fluoro-5-(6-(1-methyl-1H-pyrazol-4-yl)pyridin-2-yloxy)phenyl)urea, 1-(2-fluoro-5-(6-(1-methyl-1H-pyrazol-4-yl)pyridin-2-yloxy)phenyl)-3-(3-morpholino-5-(trifluoromethyl)phenyl)urea, 1-(5-(2-(1H-pyrazol-4-yl)pyridin-4-yloxy)-1-fluorophenyl)-3-(3-morpholinophenyl)urea, 1-(5-(2-(1H-pyrazol-4-yl)pyridin-4-yloxy)-2-fluorophenyl)-1-(1-methyl-5-(piperidin-1-yl)phenyl)urea, 1-(5-(2-(1H-pyrazol-4-yl)pyridin-4-yloxy)-2-fluorophenyl)-3-(3-chloro-5-morpholinophenyl)urea, 1-(5-(2-(1H-pyrazol-4-yl)pyridin-4-yloxy)-2-fluorophenyl)-3-(3-morpholino-5-(trifluoromethyl)phenyl)urea, 1-(2-fluoro-5-(2-(1-methyl-1H-pyrazol-4-yl)pyridin-4-yloxy)phenyl)-3-(3-morpholinophenyl)urea, 1-(2-fluoro-5-(2-(1-methyl-1H-pyrazol-4-yl)pyridin-4-yloxy)phenyl)-3-(3-methyl-5-morpholinophenyl)urea, 1-(3-chloro-5-morpholinophenyl)-3-(2-fluoro-5-(2-(1-methyl-1H-pyrazol-4-yl)pyridin-4-yloxy)phenyl)urea, 1-(2-fluoro-5-(2-(1-methyl-1H-pyrazol-4-yl)pyridin-4-yloxy phenyl)-3-(3-morpholino-5-(trifluoromethyl)phenyl)urea, 1-(4-(2-(1H-pyrazol-4-yl)pyridin-4-yloxy)-2-fluorophenyl)-3-(3-morpholinophenyl)urea, 1-(4-(2-(1H-pyrazol-4-yl)pyridin-4-yloxy)-2-fluorophenyl)-3-(3-chloro-5-morpholinophenyl)urea, 1-(4-(2-(1H-pyrazol-4-yl)pyridin-4-yloxy)-2-fluorophenyl)-3-(3-methyl-5-morpholinophenyl)urea, 1-(4-(2-(1H-pyrazol-4-yl)pyridin-4-yloxy)-2-fluorophenyl)-3-(3-morpholino-5-(trifluoromethyl)phenyl)urea, 1-(2-fluoro-4-(2-(1-methyl-1H-pyrazol-4-yl)pyridin-4-yloxy(phenyl)-3-(3-morpholinophenyl)urea, 1-(3-chloro-5-morpholinophenyl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(3-methyl-5-morpholinophenyl)urea, 1-(2-fluoro-4-(2-(1-methyl-1H-pyrazol-4-yl)pyridin-4-yloxy)phenyl)-3-(3-morpholino-5-(trifluoromethyl)phenyl)urea, 1-(4-(2-(1H-pyrazol-4-yl)pyridin-4-yloxy)-3-fluorophenyl)-3-(3-morpholinophenyl)urea, 1-(4-(2-(1H-pyrazol-4-yl)pyridin-4-yloxy)-3-fluorophenyl)-3-(3-chloro-5-morpholinophenyl)urea, 1-(4-(2-(1H-pyrazol-4-yl)pyridin-4-yloxy)-3-fluorophenyl)-3-(3-methyl-5-morpholinophenyl)urea, 1-(4-(2-(1H-pyrazol-4-yl)pyridin-4-yloxy)-3-fluorophenyl)-3-(3-morpholino-5-(trifluoromethyl)phenyl)urea, 1H-fluoro-4-(2-(1-methyl-1H-pyrazol-4-yl)pyridin-4-yloxy)phenyl)-3-(3-morpholinophenyl)urea, 1-(1-chloro-5-morpholinophenyl)-3-(3-fluoro-4-(2-(1-methyl-1H-pyrazol-4-yl)pyridin-4-yloxy)phenyl)urea, 1-(3-fluoro-4-(2-(1-methyl-1H-pyrazol-4-yl)pyridin-4-yloxy)phenyl)-3-(3-methyl-5-morpholinophenyl)urea, 1-(3-fluoro-4-(2-(1-methyl-1H-pyrazol-4-yl)pyridin-4-yloxy)phenyl)-3-(3-morpholino-5-(trifluoromethylphenyl)urea, 1-(2-fluoro-4-(2-(1-methyl-1H-pyrazol-4-yl)pyridin-4-yloxy)phenyl)-3-(6-(pyrrolidin-1-yl)benzo[d]thiazol-2-yl)urea, 1-(2-fluoro-4-(2-(1-methyl-1H-pyrazol-4-yl)pyridin-4-yloxy)phenyl)-3-(6-(4-methyl-1H-imidazol-1-yl)benzo[d]thiazol-2-yl)urea, 1-(2-fluoro-4-(2-(1-methyl-1H-pyrazol-4-yl)pyridin-4-yloxy)phenyl)-3-(6-piperidin-1-yl)benzo[d]thiazol-2-yl)urea, 1-(2-fluoro-4-(2-(1-methyl-1H-pyrazol-4-yl)pyridin-4-yloxy)phenyl)-3-(6-morpholinobenzo[d]thiazol-2-yl)urea 1-(2-fluoro-4-(2-(1-methyl-1H-pyrazol-4-yl)pyridin-4-yloxy)phenyl)-3-(6-(4-methylpiperazin-1-yl)benzo[d]thiazol-2-yl)urea 1-(3-fluoro-4-(2-(1-methyl-1H-pyrazol-4-yl)pyridin-4-yloxy)phenyl)-3-(6-(pyrrolidin-1-yl)benzo[d]thiazol-2-yl)urea, 1-(3-fluoro-4-(2-(1-methyl-1H-pyrazol-4-yl)pyridin-4-yloxy)phenyl)-3-(6-(4-methyl-1H-imidazol-1-yl)benzo[d]triazol-2-yl)urea, 1-(3-fluoro-4-(2-(1-methyl-1H-pyrazol-4-yl)pyridin-4-yloxy)phenyl)-3-(6-(piperidin-1-yl)benzo[d]thiazol-2-yl)urea, 1-(3-fluoro-4-(2-(1-methyl-1H-pyrazol-4-yl)pyridin-4-yloxy)phenyl)-3-(6-morpholinobenzo[d]thiazol-2-yl)urea, 1-(3-fluoro-4-(2-(1-methyl-1H-pyrazol-4-yl)pyridin-4-yloxy)phenyl)-3-(6-(4-methylpiperazin-1-yl)benzo[d]thiazol-2-yl)urea, 1-(2-fluoro-4-(2-(1-methyl-1H-pyrazol-4-yl)pyridin-4-yloxy)phenyl)-3-(2-oxo-6-(pyrrolidin-1-yl)indolin-3-yl)urea, 1-(2-fluoro-4-(2-(1-methyl-1H-pyrazol-4-yl)pyridin-4-yloxy)phenyl)-3-(6-(4-methyl-1H-imidazol-1-yl)-2-oxoindolin-3-yl)urea, 1-(2-fluoro-4-(2-(1-methyl-1H-pyrazol-4-yl)pyridin-4-yloxy)phenyl)-3-(2-oxo-6-(piperidin-1-yl)indolin-3-yl)urea, 1-(2-fluoro-4-(2-(1-methyl-1H-pyrazol-4-yl)pyridin-4-yloxy)phenyl)-3-(6-morpholino-2-oxoindolin-3-yl)urea, 1-(2-fluoro-4-(2-(1-methyl-1H-pyrazol-4-yl)pyridin-4-yloxy)phenyl)-3-(6-(4-methylpiperazin-1-yl)-2-oxoindolin-3-yl)urea, 1-(3-fluoro-4-(2-(1-methyl-1H-pyrazol-4-yl)pyridin-4-yloxy)phenyl)-3-(2-oxo-6-(pyrrolidin-1-yl)indolin-3-yl)urea, 1-(3-fluoro-4-(2-(1-methyl-1H-pyrazol-4-yl)pyridin-4-yloxy)phenyl)-3-(6-(4-methyl-1H-imidazol-1-yl)-2-oxoindolin-3-yl)urea, 1-(3-fluoro-4-(2-(1-methyl-1-pyrazol-4-yl)pyridin-4-yloxy)phenyl)-3-(2-oxo-6-(piperidin-1-yl)indolin-3-yl)urea, 1-(3-fluoro-4-(2-(1-methyl-1H-pyrazol-4-yl)pyridin-4-yloxy)phenyl)-3-(6-morpholino-2-oxoindolin-3-yl)urea, 1-(3-fluoro-4-(2-(1-methyl-1H-pyrazol-4-yl)pyridin-4-yloxy)phenyl)-3-(6-(4-methylpiperazin-1-yl)-2-oxoindolin-3-yl)urea, 1-(2-fluoro-4-(2-(1-methyl-1H-pyrazol-4-yl)pyridin-4-yloxy)phenyl)-3-(2-(pyrrolidin-1-yl)quinolin-6-yl)urea, 1-(2-fluoro-4-(2-(1-methyl-1H-pyrazol-4-yl)pyridin-4-yloxy)phenyl)-3-(2-(4-methyl-1H-imidazol-1-yl)quinolin-6-yl)urea, 1-(2-fluoro-4-(2-(1-methyl-1H-pyrazol-4-yl)pyridin-4-yloxy)phenyl)-3-(2-(piperidin-1-yl)quinolin-6-yl)urea, 1-(2-fluoro-4-(2-(1-methyl-1H-pyrazol-4-yl)pyridin-4-yloxy)phenyl)-3-(2-morpholinoquinolin-6-yl)urea, 1-(2-fluoro-4-(2-(1-methyl-1H-pyrazol-4-yl)pyridin-4-yloxy)phenyl)-3-(2-(4-methylpiperazin-1-yl)

quinolin-6-yl)urea, 1-(3-fluoro-4-(2-((1-methyl-1H-pyrazol-4-yl)pyridin-4-yloxy)phenyl)-3-(2-pyrrolidin-1-yl)quinolin-6-yl)urea, 1-(3-fluoro-4-(2-(1-methyl-1H-pyrazol-4-yl)pyridin-4-yloxy)phenyl)-3-(2-(4-methyl-1H-imidazol-1-yl)quinolin-6-yl)urea, 1-(3-fluoro-4-(2-(1-methyl-1H-pyrazol-4-yl)pyridin-4-yloxy)phenyl)-3-(2-(piperidin-1-yl)quinolin-6-yl)urea, 1-(3-fluoro-4-(2-(1-methyl-1H-pyrazol-4-yl)pyridin-4-yloxy)phenyl)-3-(2-morpholinoquinolin-6-yl)urea, 1-(3-fluoro-4-(2-(1-methyl-1H-pyrazol-4-yl)pyridin-4-yloxy)phenyl)-3-(2-(4-methylpiperazin-1-yl)quinolin-6-yl)urea, 1-(2-fluoro-4-(2-(1-methyl-1H-pyrazol-4-yl)pyridin-4-yloxy)phenyl)-3-(3-(1-hydroxy-2-methylpropan-2-yl)-1-methyl-1H-pyrazol-5-yl)urea, 1-(2-fluoro-4-(2-(1-methyl-1H-pyrazol-4-yl)pyridin-4-yloxy)phenyl)-3-(3-(1-hydroxy-2-methylpropan-2-yl)isoxazol-5-yl)urea, 1-(2-fluoro-4-(2-(1-methyl-1H-pyrazol-4-yl)pyridin-4-yloxy)phenyl)-3-(5-(2-hydroxypropan-2-yl)pyridin-3-yl)urea, 1-(3-tert-butyl-1-methyl-1H-pyrazol-5-yl)-3-(2-fluoro-4-(2-(1-(2-hydroxyethyl)-1H-pyrazol-4-yl)pyridin-4-yloxy)phenyl)urea, 1-(3-tert-butyl-1-methyl-1H-pyrazol-5-yl)-3-(4-(2-(1-(2-(dimethylamino)ethyl)-1H-pyrazol-4-yl)pyridin-4-yloxy)-2-fluorophenyl)urea, 1-(3-tert-butyl-1-methyl-1H-pyrazol-5-yl)-3-(4-(2-(1-(cyanomethyl)-1H-pyrazol-4-yl)pyridin-4-yloxy)-2-fluorophenyl)urea, 1-(4-(2-(1-(2-amino-2-oxoethyl)-1H-pyrazol-4-yl)pyridin-4-yloxy)-2,3-difluorophenyl)-3-(5-isopropylpyridin-3-yl)urea, -(4-(2-(1-(cyanomethyl)-1H-pyrazol-4-yl)pyridin-4-yloxy)-2,3-difluorophenyl)-3-(5-isopropylpyridin-3-yl)urea, 1-(2,3-difluoro-4-(2-(1-(2-morpholinoethyl)-1H-pyrazol-4-yl)pyridin-4-yloxy)phenyl)-3-(5-isopropylpyridin-3-yl)urea, 1-(2-fluoro-4-(2-(1-(2-morpholinoethyl)-1H-pyrazol-4-yl)pyridin-4-yloxy)phenyl)-3-(5-isopropylpyridin-3-yl)urea, 1-(2-fluoro-4-(2-(1-propyl-1H-pyrazol-4-yl)pyridin-4-yloxy)phenyl)-3-(5-isopropylpyridin-3-yl)urea, 1-(2,3-difluoro-4-(2-(1-(2-methoxyethyl)-1H-pyrazol-4-yl)pyridin-4-yloxy)phenyl)-3-(5-isopropylpyridin-3-yl)urea, 1-(2,3-difluoro-4-(2-(1-(2-hydroxyethyl)-1H-pyrazol-4-yl)pyridin-4-yloxy)phenyl)-3-(5-isopropylpyridin-3-yl)urea, 1-(4-(2-(1-(2-(dimethylamino)ethyl)-1H-pyrazol-4-yl)pyridin-4-yloxy)-2,3-difluorophenyl)-3-(5-isopropylpyridin-3-yl)urea, 1-(4-(2-(1-(3-(dimethylamino)propyl)-1H-pyrazol-4-yl)pyridin-4-yloxy)-2,3-difluorophenyl)-3-(5-isopropylpyridin-3-yl)urea, 1-(2,3-difluoro-4-(2-(1-(3-hydroxypropyl)-1H-pyrazol-4-yl)pyridin-4-yloxy)phenyl)-3-(5-isopropylpyridin-3-yl)urea, 1-(4-(2-(1-(2-(dimethylamino)ethyl)-1H-pyrazol-4-yl)pyridin-4-yloxy)-2-fluorophenyl)-3-(5-isopropylpyridin-3-yl)urea, 1-(2-fluoro-4-(2-(1-methyl-1H-pyrazol-4-yl)pyridin-4-yloxy)phenyl)-3-(4-(trifluoromethylpyridin-2-yl)urea, 1-(3-fluoro-4-(2-(1-(2-(4-methylpiperazin-1-yl)ethyl)-1H-pyrazol-4-yl)pyridin-4-yloxy)phenyl)-3-(5-isopropylpyridin-3-yl)urea, 1-(2-fluoro-4-(2-(1-(3-hydroxypropyl)-1H-pyrazol-4-yl)pyridin-4-yloxy)phenyl)-3-(5-isopropylpyridin-3-yl)urea, 1-(2-fluoro-4-(2-(1-methyl-1H-pyrazol-4-yl)pyridin-4-yloxy)phenyl)-3-(4-(trifluoromethyl)pyridin-2-yl)urea, 1-(3-tert-butyl-1-methyl-1H-pyrazol-5-yl)-3-(4-(2-(1-(2-(dimethylamino)ethyl)-1H-pyrazol-4-yl)pyridin-4-yloxy)-2,3-difluorophenyl)urea, 1-(3-tert-butyl-1-methyl-1H-pyrazol-5-yl)-3-(2,3-difluoro-4-(2-(1-(2-methoxyethyl)-1H-pyrazol-4-yl)pyridin-4-yloxy)phenyl)urea, 1-(3-tert-butyl-1-methyl-1H-pyrazol-5-yl)-3-(2,3-difluoro-4-(2-(1-(2-hydroxyethyl)-1H-pyrazol-4-yl)pyridin-4-yloxy)phenyl)urea, 1-(3-tert-butyl-1-methyl-1H-pyrazol-5-yl)-3-(3-fluoro-4-(2-(1-(2-(4-methylpiperazin-1-yl)ethyl)-1H-pyrazol-4-yl)pyridin-4-yloxy)phenyl)urea, 1-(3-tert-butyl-1-methyl-1H-pyrazol-5-yl)-3-(4-(2-(1-(3-(dimethylamino)propyl)-1H-pyrazol-4-yl)pyridin-4-yloxy)-2,3-difluorophenyl)urea, 1-(3-tert-butyl-1-methyl-1H-pyrazol-5-yl)-3-(2,3-difluoro-4-(2-(1-(3-hydroxypropyl)-1H-pyrazol-4-yl)pyridin-4-yloxy)phenyl)urea, 1-(5-tert-butylpyridin-3-yl)-3-(2-fluoro-4-(2-(1-(3-hydroxypropyl)-1H-pyrazol-4-yl)pyridin-4-yloxy)phenyl)urea, and 1-(5-tert-butylpyridin-3-yl)-3-(2-fluoro-4-(2-(1-methyl-1H-pyrazol-4-yl)pyridin-4-yloxy)phenyl)urea,

SECTION 4. BIOLOGICAL DATA

Abl Kinase (SEQ ID NO:1) Assay

Activity of Abl kinase (SEQ ID NO: 1) was determined by following the production of ADP from the kinase reaction through coupling with the pyruvate kinase/lactate dehydrogenase system (e.g., Schindler, et al. Science (2000) 289, 1938-1942). In this assay, the oxidation of NADH (thus the decrease at $A_{340\,nm}$) was continuously monitored spectrophometrically. The reaction mixture (100 μl) contained Abl kinase (1 nM. Abl from deCode Genetics), peptide substrate (EAIYAAPFAKKK, 0.2 mM), $MgCl_2$ (10 mM), pyruvate kinase (4 units), lactate dehydrogenase (0.7 units), phosphoenol pyruvate (1 mM), and NADH (0.28 mM) in 90 mM Tris buffer containing 0.2% octyl-glucoside and 3.5% DMSO, pH 7.5. Test compounds were incubated with Abl (SEQ ID NO:1) and other reaction reagents at 30° C. for 2 h before ATP (500 μM) was added to start the reaction. The absorption at 340 nm was monitored continuously for 2 hours at 30° C. on Polarstar Optima plate reader (BMG). The reaction rate was calculated using the 1.0 to 2.0 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package.

```
Abl kinase
                                            (SEQ ID NO: 1)
GTSMDPSSPNYDKWEMERTDITMKHKLGGGQYGEVYEGVWKKYSLTVAVK

TLKEDTMEVEEFLKEAAVMKEIKHPNLVQLLGVCTREPPFYIITEFMTYG

NLLDYLRECNRQEVNAVVLLYMATQISSAMEYLEKKNFIHRDLAARNCLV

GENHLVKVADFGLSRLMTGDTYTAHAGAKFPIKWTAPESLAYNKFSIKSD

VWAFGVLLWEIATYGMSPYPGIDLSQVYELLEKDYRMERPEGCPEKVYEL

MRACWQWNPSDRPSFAEIHQAFETMFQE
```

Abl Kinase (SEQ ID NO:2) Assay

Activity of T315I Abl kinase (SEQ ID NO:2) was determined by following the production of ADP from the kinase reaction through coupling with the pyruvate kinase/lactate dehydrogenase system (e.g., Schindler, et al. *Science* (2000) 289, 1938-1942). In this assay, the oxidation of NADH (thus the decrease at $A_{340\,nm}$) was continuously monitored spectrophometrically. The reaction mixture (100 μl) contained Abl kinase (4.4 nM, M315I Abl from deCode Genetics), peptide substrate (EAIYAAPFAKKK, 0.2 mM), $MgCl_2$ (10 mM), pyruvate kinase (4 units), lactate dehydrogenase (0.7 units), phosphoenol pyruvate (1 mM), and NADH (0.28 mM) in 90 mM Tris buffer containing 0.2% octyl-glucoside and 1% DMSO, pH 7.5. Test compounds were incubated with T315I Abl (SEQ ID NO:2) and other reaction reagents at 30° C. for 1 h before ATP (500 μM) was added to start the reaction. The absorption at 340 nm was monitored continuously for 2 hours at 30° C. on Polarstar Optima plate reader (BMG). The reaction rate was calculated using the 1.0 to 2.0 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package.

Abl T315I kinase (SEQ ID NO: 2)

GTSMDPSSPNYDKWEMERTDITMKHKLGGGQYGEVYEGVWKKYSLTVAVKTLKEDTMEVE
EFLKEAAVMKEIKHPNLVQLLGVCTREPPFYIIIEFMTYGNLLDYLRECNRQEVNAVVLL
YMATQISSAMEYLEKKNFIHRDLAARNCLVGENHLVKVADFGLSRLMTGDTYTAHAGAKF
PIKWTAPESLAYNKFSIKSDVWAFGVLLWEIATYGMSPYPGIDLSQVYELLEKDYRMERP
EGCPEKVYELMRACWQWNPSDRPSFAEIHQAFETMFQE

BCR-Abl p210-e14a2

(SEQ ID NO: 3)

MVDPVGFAEAWKAQFPDSEPPRMELRSVGDIEQELERCKASIRRLEQEVNQERFRMIYLQ
TLLAKEKKSYDRQRWGFRRAAQAPDGASEPRASASRPQPAPADGADPPPAEEPEARPDGE
GSPGKARPGTARRPGAAASGERDDRGPPASVAALRSNFERIRKGHGQPGADAEKPFYVNV
EFHHERGLVKVNDKEVSDRISSLGSQAMQMERKKSQHGAGSSVGDASRPPYRGRSSESSC
GVDGDYEDAELNPRFLKDNLIDANGGSRPPWPPLEYQPYQSIYVGGIMEGEGKGPLLRSQ
STSEQEKRLTWPRRSYSPRSFEDCGGGYTPDCSSNENLTSSEEDFSSGQSSRVSPSPTTY
RMFRDKSRSPSQNSQQSFDSSSPPTPQCHKRHRHCPVVVSEATIVGVRKTGQIWPNDDEG
AFHGDADGSFGTPPGYGCAADRAEEQRRHQDGLPYIDDSPSSSPHLSSKGRGSRDALVSG
ALKSTKASELDLEKGLEMRKWVLSGILASEETYLSHLEALLLPMKPLKAAATTSQPVLTS
QQIETIFFKVPELYEIHKESYDGLFPRVQQWSHQQRVGDLFQKLASQLGVYRAFVDNYGV
AMEMAEKCCQANAQFAEISENLRARSNKDAKDPTTKNSLETLLYKPVDRVTRSTLVLHDL
LKHTPASHPDHPLLQDALRISQNFLSSINEEITPRRQSMTVKKGEHRQLLKDSFMVELVE
GARKLRHVFLFTDLLLCTKLKKQSGGKTQQYDCKWYIPLTDLSFQMVDELEAVPNIPLVP
DEELDALKIKISQIKSDIQREKRANKGSKATERLKKKLSEQESLLLLMSPSMAFRVHSRN
GKSYTFLISSDYERAEWRENIREQQKKCFRSFSLTSVELQMLTNSCVKLQTVHSIPLTIN
KEDDESPGLYGFLNVIVHSATGFKQSSKALQRPVASDFEPQGLSEAARWNSKENLLAGPS
ENDPNLFVALYDFVASGDNTLSITKGEKLRVLGYNHNGEWCEAQTKNGQGWVPSNYITPV
NSLEKHSWYHGPVSRNAAEYPLSSGINGSFLVRESESSPSQRSISLRYEGRVYHYRINTA
SDGKLYVSSESRFNTLAELVHHHSTVADGLITTLHYPAPKRNKPTVYGVSPNYDKWEMER
TDITMKHKLGGGQYGEVYEGVWKKYSLTVAVKTLKEDTMEVEEFLKEAAVMKEIKHPNLV
QLLGVCTREPPFYIITEFMTYGNLLDYLRECNRQEVNAVVLLYMATQISSAMEYLEKKNF
IHRDLAARNCLVGENHLVKVADFGLSRLMTGDTYTAHAGAKFPIKWTAPESLAYNKFSIK
SDVWAFGVLLWEIATYGMSPYPGIDRSQVYELLEKDYRMKRPEGCPEKVYELMRACWQWN
PSDRPSFAEIHQAFETMFQESSISDEVEKELGKQGVRGAVTTLLQAPELPTKTRTSRRAA
EHRDTTDVPEMPHSKGQGESDPLDHEPAVSPLLPRKERGPPEGGLNEDERLLPKDKKTNL
FSALIKKKKKTAPTPPKRSSSFREMDGQPERRGAGEEEGRDISNGALAFTPLDTADPAKS
PKPSNGAGVPNGALRESGGSGFRSPHLWKKSSTLTSSRLATGEEEGGGSSSKRFLRSCSV
SCVPHGAKDTEWRSVTLPRDLQSTGRQFDSSTFGGHKSEKPALPRKRAGENRSDQVTRGT
VTPPPRLVKKNEEAADEVFKDIMESSPGSSPPNLTPKPLRRQVTVAPASGLPHKEEAWKG
SALGTPAAAEPVTPTSKAGSGAPRGTSKGPAEESRVRRHKHSSESPGRDKGKLSKLKPAP
PPPPAASAGKAGGKPSQRPGQEAAGEAVLGAKTKATSLVDAVNSDAAKPSQPAEGLKKPV
LPATPKPHPAKPSGTPISPAPVPLSTLPSASSALAGDQPSSTAFIPLISTRVSLRKTRQP

```
PERASGAITKGVVLDSTEALCLAISGNSEQMASHSAVLEAGKNLYTFCVSYVDSIQQMRN

KFAFREAINKLENNLRELQICPASAGSGPAATQDFSKLLSSVKEISDIVQR
```

BCR-Abl p210-e13a2

(SEQ ID NO: 4)

```
MVDPVGFAEAWKAQFPDSEPPRMELRSVGDIEQELERCKASIRRLEQEVNQERFRMIYLQ

TLLAKEKKSYDRQRWGFRRAAQAPDGASEPRASASRPQPAPADGADPPPAEEPEARPDGE

GSPGKARPGTARRPGAAASGERDDRGPPASVAALRSNFERIRKGHGQPGADAEKPFYVNV

EFHHERGLVKVNDKEVSDRISSLGSQAMQMERKKSQHGAGSSVGDASRPPYRGRSSESSC

GVDGDYEDAELNPRFLKDNLIDANGGSRPPWPPLEYQPYQSIYVGGIMEGEGKGPLLRSQ

STSEQEKRLTWPRRSYSPRSFEDCGGGYTPDCSSNENLTSSEEDFSSGQSSRVSPSPTTY

RMFRDKSRSPSQNSQQSFDSSSPPTPQCHKRHRHCPVVVSEATIVGVRKTGQIWPNDDEG

AFHGDADGSFGTPPGYGCAADRAEEQRRHQDGLPYIDDSPSSSPHLSSKGRGSRDALVSG

ALKSTKASELDLEKGLEMRKWVLSGILASEETYLSHLEALLLPMKPLKAAATTSQPVLTS

QQIETIFFKVPELYEIHKESYDGLFPRVQQWSHQQRVGDLFQKLASQLGVYRAFVDNYGV

AMEMAEKCCQANAQFAEISENLRARSNKDAKDPTTKNSLETLLYKPVDRVTRSTLVLHDL

LKHTPASHPDHPLLQDALRISQNFLSSINEEITPRRQSMTVKKGEHRQLLKDSFMVELVE

GARKLRHVFLFTDLLLCTKLKKQSGGKTQQYDCKWYIPLTDLSFQMVDELEAVPNIPLVP

DEELDALKIKISQIKSDIQREKRANKGSKATERLKKKLSEQESLLLLMSPSMAFRVRSRN

GKSYTFLISSDYERAEWRENIREQQKKCFRSFSLTSVELQMLTNSCVKLQTVHSIPLTIN

KEEALQRPVASDFEPQGLSEAARWNSKENLLAGPSENDPNLFVALYDFVASGDNTLSITK

GEKLRVLGYNHNGEWCEAQTKNGQGWVPSNYITPVNSLEKHSWYHGPVSRNAAEYPLSSG

INGSFLVRESESSPSQRSISLRYEGRVYHYRINTASDGKLYVSSESRFNTLAELVHHHST

VADGLITTLHYPAPKRNKPTVYGVSPNYDKWEMERTDITMKHKLGGGQYGEVYEGVWKKY

SLTVAVKTLKEDTMEVEEFLKEAAVMKEIKHPNLVQLLGVCTREPPFYIITEFMTYGNLL

DYLRECNRQEVNAVVLLYMATQISSAMEYLEKKNFIHRDLAARNCLVGENHLVKVADFGL

SRLMTGDTYTAHAGAKFPIKWTAPESLAYNKFSIKSDVWAFGVLLWEIATYGMSPYPGID

RSQVYELLEKDYRMKRPEGCPEKVYELMRACWQWNPSDRPSFAEIHQAFETMFQESSISD

EVEKELGKQGVRGAVTTLLQAPELPTKTRTSRRAAEHRDTTDVPEMPHSKGQGESDPLDH

EPAVSPLLPRKERGPPEGGLNEDERLLPKDKKTNLFSALIKKKKKTAPTPPKRSSSFREM

DGQPERRGAGEEEGRDISNGALAFTPLDTADPAKSPKPSNGAGVPNGALRESGGSGFRSP

HLWKKSSTLTSSRLATGEEEGGGSSSKRFLRSCSVSCVPHGAKDTEWRSVTLPRDLQSTG

RQFDSSTFGGHKSEKPALPRKRAGENRSDQVTRGTVTPPPRLVKKNEEAADEVFKDIMES

SPGSSPPNLTPKPLRRQVTVAPASGLPHKEEAWKGSALGTPAAAEPVTPTSKAGSGAPRG

TSKGPAEESRVRRHKHSSESPGRDKGKLSKLKPAPPPPPAASAGKAGGKPSQRPGQEAAG

EAVLGAKTKATSLVDAVNSDAAKPSQPAEGLKKPVLPATPKPHPAKPSGTPISPAPVPLS

TLPSASSALAGDQPSSTAFIPLISTRVSLRKTRQPPERASGAITKGVVLDSTEALCLAIS

GNSEQMASHSAVLEAGKNLYTFCVSYVDSIQQMRNKFAFREAINKLENNLRELQICPASA

GSGPAATQDFSKLLSSVKEISDIVQR
```

BCR-Abl p190-e1a2

(SEQ ID NO: 5)

```
MVDPVGFAEAWKAQFPDSEPPRMELRSVGDIEQELERCKASIRRLEQEVNQERFRMIYLQ

TLLAKEKKSYDRQRWGFRRAAQAPDGASEPRASASRPQPAPADGADPPPAEEPEARPDGE
```

-continued

GSPGKARPGTARRPGAAASGERDDRGPPASVAALRSNFERIRKGHGQPGADAEKPFYVNV

EFHHERGLVKVNDKEVSDRISSLGSQAMQMERKKSQHGAGSSVGDASRPPYRGRSSESSC

GVDGDYEDAELNPRFLKDNLIDANGGSRPPWPPLEYQPYQSIYVGGIMEGEGKGPLLRSQ

STSEQEKRLTWPRRSYSPRSFEDCGGGYTPDCSSNENLTSSEEDFSSGQSSRVSPSPTTY

RMFRDKSRSPSQNSQQSFDSSSPPTPQCHKRHRHCPVVVSEATIVGVRKTGQIWPNDDEG

AFHGDAEALQRPVASDFEPQGLSEAARWNSKENLLAGPSENDPNLFVALYDFVASGDNTL

SITKGEKLRVLGYNHNGEWCEAQTKNGQGWVPSNYITPVNSLEKHSWYHGPVSRNAAEYP

LSSGINGSFLVRESESSPSQRSISLRYEGRVYHYRINTASDGKLYVSSESRFNTLAELVH

HHSTVALGLITTLHYPAPKRNKPTVYGVSPNYDKWEMERTDITMKHKLGGGQYGEVYEGV

WKKYSLTVAVKTLKEDTMEVEEFLKEAAVMKEIKHPNLVQLLGVCTREPPFYIITEFMTY

GNLLDYLRECNRQEVNAVVLLYMATQISSAMEYLEKKNFIHRDLAARNCLVGENHLVKVA

DFGLSRLMTGDTYTAHAGAKFPIKWTAPESLAYNKFSIKSDVWAFGVLLWEIATYGMSPY

PGIDRSQVYELLEKDYRMKRPEGCPEKVYELMRACWQWNPSDRPSFAEIHQAFETMFQES

SISDEVEKELGKQGVRGAVTTLLQAPELPTKTRTSRRAAEHRDTTDVPEMPHSKGQGESD

PLDHEPAVSPLLPRKERGPPEGGLNEDERLLPKDKKTNLFSALIKKKKKTAPTPPKRSSS

FREMDGQPERRGAGEEEGRDISNGALAFTPLDTADPAKSPKPSNGAGVPNGALRESGGSG

FRSPHLWKKSSTLTSSRLATGEEEGGGSSSKRFLRSCSVSCVPHGAKDTEWRSVTLPRDL

QSTGRQFDSSTFGGHKSEKPALPRKRAGENRSDQVTRGTVTPPPRLVKKNEEAADEVFKD

IMESSPGSSPPNLTPKPLRRQVTVAPASGLPHKEEAWKGSALGTPAAAEPVTPTSKAGSG

APRGTSKGPAEESRVRRHKHSSESPGRDKGKLSKLKPAPPPPPAASAGKAGGKPSQRPGQ

EAAGEAVLGAKTKATSLVDAVNSDAAKPSQPAEGLKKPVLPATPKPHPAKPSGTPISPAP

VPLSTLPSASSALAGDQPSSTAFIPLISTRVSLRKTRQPPERASGAITKGVVLDSTEALC

LAISGNSEQMASHSAVLEAGKNLYTFCVSYVDSIQQMRNKFAFREAINKLENNLRELQIC

PASAGSGPAATQDFSKLLSSVKEISDIVQR

BCR-Abl p210-e14a2 T315I (SEQ ID NO: 6)

MVDPVGFAEAWKAQFPDSEPPRMELRSVGDIEQELERCKASIRRLEQEVNQERFRMIYLQ

TLLAKEKKSYDRQRWGFRRAAQAPDGASEPRASASRPQPAPADGADPPPAEEPEARPDGE

GSPGKARPGTARRPGAAASGERDDRGPPASVAALRSNFERIRKGHGQPGADAEKPFYVNV

EFHHERGLVKVNDKEVSDRISSLGSQAMQMERKKSQHGAGSSVGDASRPPYRGRSSESSC

GVDGDYEDAELNPRFLKDNLIDANGGSRPPWPPLEYQPYQSIYVGGIMEGEGKGPLLRSQ

STSEQEKRLTWPRRSYSPRSFEDCGGGYTPDCSSNENLTSSEEDFSSGQSSRVSPSPTTY

RMFRDKSRSPSQNSQQSFDSSSPPTPQCHKRHRHCPVVVSEATIVGVRKTGQIWPNDDEG

AFHGDADGSFGTPPGYGCAADRAEEQRRHQDGLPYIDDSPSSSPHLSSKGRGSRDALVSG

ALKSTKASELDLEKGLEMRKWVLSGILASEETYLSHLEALLLPMKPLKAAATTSQPVLTS

QQIETIFFKVPELYEIHKESYDGLFPRVQQWSHQQRVGDLFQKLASQLGVYRAFVDNYGV

AMEMAEKCCQANAQFAEISENLRARSNKDAKDPTTKNSLETLLYKPVDRVTRSTLVLHDL

LKHTPASHPDHPLLQDALRISQNFLSSINEEITPRRQSMTVKKGEHRQLLKDSFMVELVE

GARKLRHVFLFTDLLLCTKLKKQSGGKTQQYDCKWYIPLTDLSFQMVDELEAVPNIPLVP

DEELDALKIKISQIKSDIQREKRANKGSKATERLKKKLSEQESLLLLMSPSMAFRVHSRN

GKSYTFLISSDYERAEWRENIREQQKKCFRSFSLTSVELQMLTNSCVKLQTVHSIPLTIN

KEDDESPGLYGFLNVIVHSATGFKQSSKALQRPVASDFEPQGLSEAARWNSKENLLAGPS

-continued

ENDPNLFVALYDFVASGDNTLSITKGEKLRVLGYNHNGEWCEAQTKNGQGWVPSNYITPV

NSLEKHSWYHGPVSRNAAEYPLSSGINGSFLVRESESSPSQRSISLRYEGRVYHYRINTA

SDGKLYVSSESRFNTLAELVHHHSTVADGLITTLHYPAPKRNKPTVYGVSPNYDKWEMER

TDITMKHKLGGGQYGEVYEGVWKKYSLTVAVKTLKEDTMEVEEFLKEAAVMKEIKHPNLV

QLLGVCTREPPFYII<u>I</u>EFMTYGNLLDYLRECNRQEVNAVVLLYMATQISSAMEYLEKKNF

IHRDLAARNCLVGENHLVKVADFGLSRLMTGDTYTAHAGAKFPIKWTAPESLAYNKFSIK

SDVWAFGVLLWEIATYGMSPYPGIDRSQVYELLEKDYRMKRPEGCPEKVYELMRACWQWN

PSDRPSFAEIHQAFETMFQESSISDEVEKELGKQGVRGAVTTLLQAPELPTKTRTSRRAA

EHRDTTDVPEMPHSKGQGESDPLDHEPAVSPLLPRKERGPPEGGLNEDERLLPKDKKTNL

FSALIKKKKTAPTPPKRSSSFREMDGQPERRGAGEEEGRDISNGALAFTPLDTADPAKS

PKPSNGAGVPNGALRESGGSGFRSPHLWKKSSTLTSSRLATGEEEGGGSSSKRFLRSCSV

SCVPHGAKDTEWRSVTLPRDLQSTGRQFDSSTFGGHKSEKPALPRKNAGENRSDQVTRGT

VTPPPRLVKKNEEAADEVFKDIMESSPGSSPPNLTPKPLRRQVTVAPASGLPHKEEAWKG

SALGTPAAAEPVTPTSKAGSGAPRGTSKGPAEESRVRRHKHSSESPGRDKGKLSKLKPAP

PPPPAASAGKAGGKPSQRPGQEAAGEAVLGAKTKATSLVDAVNSDAAKPSQPAEGLKKPV

LPATPKPHPAKPSGTPISPAPVPLSTLPSASSALAGDQPSSTAFIPLISTRVSLRKTRQP

PERASGAITKGVVLDSTEALCLAISGNSEQMASHSAVLEAGKNLYTFCVSYVDSIQQMRN

KFAFREAINKLENNLRELQICPASAGSGPAATQDFSKLLSSVKEISDIVQR

BCR-Abl p210-e13a2 T315I
(SEQ ID NO: 7)
MVDPVGFAEAWKAQFPDSEPPRMELRSVGDIEQELERCKASIRRLEQEVNQERFRMIYLQ

TLLAKEKKSYDRQRWGFRRAAQAPDGASEPRASASRPQPAPADGADPPPAEEPEARPDGE

GSPGKARPGTARRPGAAASGERDDRGPPASVAALRSNFERIRKGHGQPGADAEKPFYVNV

EFHHERGLVKVNDKEVSDRISSLGSQAMQMERKKSQHGAGSSVGDASRPPYRGRSSESSC

GVDGDYEDAELNPRFLKDNLIDANGGSRPPWPPLEYQPYQSIYVGGIMEGEGKGPLLRSQ

STSEQEKRLTWPRRSYSPRSFEDCGGGYTPDCSSNENLTSSEEDFSSGQSSRVSPSPTTY

RMFRDKSRSPSQNSQQSFDSSSPPTPQCHKRHRHCPVVVSEATIVGVRKTGQIWPNDDEG

AFHGDADGSFGTPPGYGCAADRAEEQRRHQDGLPYIDDSPSSSPHLSSKGRGSPDALVSG

ALKSTKASELDLEKGLEMRKWVLSGILASEETYLSHLEALLLPMKPLKAAATTSQPVLTS

QQIETIFFKVPELYEIHKESYDGLFPRVQQWSHQQRVGDLFQKLASQLGVYRAFVDNYGV

AMEMAEKCCQANAQFAEISENLRARSNKDAKDPTTKNSLETLLYKPVDRVTRSTLVLHDL

LKHTPASHPDHPLLQDALRISQNFLSSINEEITPRRQSMTVKKGEHRQLLKDSFMVELVE

GARKLRHVFLFTDLLLCTKLKKQSGGKTQQYDCKWYIPLTDLSFQMVDELEAVPNIPLVP

DEELDALKIKISQIKSDIQREKRANKGSKATERLKKKLSEQESLLLLMSPSMAFRVHSRN

GKSYTFLISSDYERAEWRENIREQQKKCFRSFSLTSVELQMLTNSCVKLQTVHSIPLTIN

KEEALQRPVASDFEPQGLSEAARWKSENLLAGPSENDPNLFVALYDFVASGDNTLSITK

GEKLRVLGYNHNGEWCEAQTKNGQGWVPSNYITPVNSLEKHSWYHGPVSRNAAEYPLSSG

INGSFLVRESESSPSQRSISLRYEGRVYHYRINTASDGKLYVSSESRFNTLAELVHHHST

VADGLITTLHYPAPKRNKPTVYGVSPNYDKWEMERTDITMKHKLGGGQYGEVYEGVWKKY

SLTVAVKTLKEDTMEVEEFLKEAAVMKEIKHPNLVQLLGVCTREPPFYII<u>I</u>EFMTYGNLL

DYLRECNRQEVNAVVLLYMATQISSAMEYLEKKNFIHRDLAARNCLVGENHLVKVADFGL

-continued

```
SRLMTGDTYTAHAGAKFPIKWTAPESLAYNKFSIKSDVWAFGVLLWEIATYGMSPYPGID

RSQVYELLEKDYRMKRPEGCPEKVYELMRACWQWNPSDRPSFAEIHQAFETMFQESSISD

EVEKELGKQGVRGAVTTLLQAPELPTKTRTSRRAAEHRDTTDVPEMPHSKGQGESDPLDH

EPAVSPLLPRKERGPPEGGLNEDERLLPKDKKTNLFSALIKKKKKTAPTPPKRSSSFREM

DGQPERRGAGEEEGRDISNGALAFTPLDTADPAKSPKPSNGAGVPNGALRESGGSGFRSP

HLWKKSSTLTSSRLATGEEEGGGSSSKRFLRSCSVSCVPHGAKDTEWRSVTLPRDLQSTG

RQFDSSTFGGHKSEKPALPRKRAGENRSDQVTRGTVTPPPRLVKKNEEAADEVFKDIMES

SPGSSPPNLTPKPLRRQVTVAPASGLPHKEEAWKGSALGTPAAAEPVTPTSKAGSGAPRG

TSKGPAEESRVRRHKHSSESPGRDKGKLSKLKPAPPPPPAASAGKAGGKPSQRPGQEAAG

EAVLGAKTKATSLVDAVNSDAAKPSQPAEGLKKPVLPATPKPHPAKPSGTPISPAPVPLS

TLPSASSALAGDQPSSTAFIPLISTRVSLRKTRQPPERASGAITKGVVLDSTEALCLAIS

GNSEQMASHSAVLEAGKNLYTFCVSYVDSIQQMRNKFAFREAINKLENNLRELQICPASA

GSGPAATQDFSKLLSSVKEISDIVQR
```

BCR-Abl p190-e1a2
(SEQ ID NO: 8)

```
MVDPVGFAEAWKAQFPDSEPPRMELRSVGDIEQELERCKASIRRLEQEVNQERFRMIYLQ

TLLAKEKKSYDRQRWGFRRAAQAPDGASEPRASASRPQPAPADGADPPPAEEPEARPDGE

GSPGKARPGTARRPGAAASGERDDRGPPASVAALRSNFERIRKGHGQPGADAEKPFYVNV

EFHHERGLVKVNDKEVSDRISSLGSQAMQMERKKSQHGAGSSVGDASRPPYRGRSSESSC

GVDGDYEDAELNPRFLKDNLIDANGGSRPPWPPLEYQPYQSIYVGGIMEGEGKGPLLRSQ

STSEQEKRLTWPRRSYSPRSFEDCGGGYTPDCSSNENLTSSEEDFSSGQSSRVSPSPTTY

RMFRDKSRSPSQNSQQSFDSSSPPTPQCHKRHRHCPVVVSEATIVGVRKTGQIWPNDDEG

AFHGDAEALQRPVASDFEPQGLSEAARWNSKENLLAGPSENDPNLFVALYDFVASGDNTL

SITKGEKLRVLGYNHNGEWCEAQTKNGQGWVPSNYITPVNSLEKHSWYHGPVSRNAAEYP

LSSGINGSFLVRESESSPSQRSISLRYEGRVYHYRINTASDGKLYVSSESRFNTLAELVH

HHSTVADGLITTLHYPAPKRNKPTVYGVSPNYDKWEMERTDITMKHKLGGGQYGEVYEGV

WKKYSLTVAVKTLKEDTMEVEEFLKEAAVMKEIKHPNLVQLLGVCTREPPFYIIIEFMTY

GNLLDYLRECNRQEVNAVVLLYMATQISSAMEYLEKKNFIHRDLAARNCLVGENHLVKVA

DFGLSRLMTGDTYTAHAGAKFPIKWTAPESLAYNKFSIKSDVWAFGVLLWEIATYGMSPY

PGIDRSQVYELLEKDYRMKRPEGCPEKVYELMRACWQWNPSDRPSFAEIHQAFETMFQES

SISDEVEKELGKQGVRGAVTTLLQAPELPTKTRTSRRAAEHRDTTDVPEMPHSKGQGESD

PLDHEPAVSPLLPRKERGPPEGGLNEDERLLPKDKKTNLFSALIKKKKKTAPTPPKRSSS

FREMDGQPERRGAGEEEGRDISNGALAFTPLDTADPAKSPKPSNGAGVPNGALRESGGSG

FRSPHLWKKSSTLTSSRLATGEEEGGGSSSKRFLRSCSVSCVPHGAKDTEWRSVTLPRDL

QSTGRQFDSSTFGGHKSEKPALPRKRAGENRSDQVTRGTVTPPPRLVKKNEEAADEVFKD

IMESSPGSSPPNLTPKPLRRQVTVAPASGLPHKEEAWKGSALGTPAAAEPVTPTSKAGSG

APRGTSKGPAEESRVRRHKHSSESPGRDKGKLSKLKPAPPPPPAASAGKAGGKPSQRPGQ

EAAGEAVLGAKTKATSLVDAVNSDAAKPSQPAEGLKKPVLPATPKPHPAKPSGTPISPAP

VPLSTLPSASSALAGDQPSSTAFIPLISTRVSLRKTRQPPERASGAITKGVVLDSTEALC

LAISGNSEQMASHSAVLEAGKNLYTFCVSYVDSIQQMRNKFAFREAINKLENNLRELQIC

PASAGSGPAATQDFSKLLSSVKEISDIVQR
```

C-Kit Kinase (SEQ ID NO:9) Assay

Activity of c-Kit kinase (SEQ ID NO:9) was determined by following the production of ADP from the kinase reaction through coupling with the pyruvate kinase/lactate dehydrogenase system (e.g., Schindler, et al. Science (2000) 289, 1938-1942). In this assay, the oxidation of NADH (thus the decrease at A340 nm) was continuously monitored spectrophometrically. The reaction mixture (100 µl) contained c-Kit (cKIT residues T544-V976, from ProQinase, 5.4 nM), polyE4Y (1 mg/ml), MgCl2 (10 mM), pyruvate kinase (4 units), lactate dehydrogenase (0.7 units), phosphoenol pyruvate (1 mM), and NADH (0.28 mM) in 90 mM Tris buffer containing 0.2% octyl-glucoside and 1% DMSO, pH 7.5. Test compounds were incubated with C-Met (SEQ ID NO:9) and other reaction reagents at 22° C. for <2 min before ATP (200 µM) was added to start the reaction. The absorption at 340 nm was monitored continuously for 0.5 hours at 30° C. on Polarstar Optima plate reader (BMG). The reaction rate was calculated using the 0 to 0.5 h time frame. Percent inhibition was obtained by comparison of reaction rate with that of a control (i.e. with no test compound). IC50 values were calculated from a series of percent inhibition values determined at a range of inhibitor concentrations using software routines as implemented in the GraphPad Prism software package.

c-Kit with N-terminal GST fusion
(SEQ ID NO: 9)
LGYWKIKGLVQPTRLLLEYLEEKYEEHLYERDEGDKWRNKKFELGLEFPN

LPYYIDGDVKLTQSMAIIRYIADKHNMLGGCPKERAEISMLEGAVDIRYG

VSRIAYSKDFETLKVDFLSKLPEMLKMFEDRLCHKTYLNGDHVTHPDFML

YDALDVVLYMDPMCLDAFPKLVCFKKRIEAIPQIDKYLKSSKYIWPLQGW

QATFGGGDHPPKSDLVPRHNQTSLYKKAGSAAAVLEENLYFQGTYKYLQK

PMYEVQWKVVEEINGNNYVYIDPTQLPYDHKWEFPRNRLSFGKTLGAGAF

GKVVEATAYGLIKSDAAMTVAVKMLKPSAHLTEREALMSELKVLSYLGNH

MNIVNLLGACTIGGPTLVITEYCCYGDLLNFLRRKRDSFICSKQEDHAEA

ALYKNLLHSKESSCSDSTNEYMDMKPGVSYVVPTKADKRRSVRIGSYIER

DVTPAIMEDDELALDLEDLLSFSYQVAKGMAFLASKNCIHRDLAARNILL

THGRITKICDFGLARDIKNDSNYVVKGNARLPVKWMAPESIFNCVYTFES

DVWSYGIFLWELFSLGSSPYPGMPVDSKFYKMIKEGFRMLSPEHAPAEMY

DIMKTCWDADPLKRPTFKQIVQLIEKQISESTNHIYSNLANCSPNRQKPV

VDHSVRINSVGSTASSSQPLLVHDDV

C-Met Kinase (SEQ ID NO:10) Assay

Activity of C-Met kinase (SEQ ID NO:10) was determined by following the production of ADP from the kinase reaction through coupling with the pyruvate kinase/lactate dehydrogenase system (e.g., Schindler, et al. Science (2000) 289, 1938-1942). In this assay, the oxidation of NADH (thus the decrease at A340 nm) was continuously monitored spectrophometrically. The reaction mixture (100 µl) contained C-Met (c-Met residues; 956-1390, from Invitrogen, catalogue #PV3143, 6 mM), polyE4Y (1 mg/ml), MgCl2 (10 mM), pyruvate kinase (4 units), lactate dehydrogenase (0.7 units), phosphoenol pyruvate (1 mM), and NADH (0.28 mM) in 90 mM Tris buffer containing 0.25 mM DTT, 0.2% octyl-glucoside and 1% DMSO, pH 7.5. Test compounds were incubated with C-Met (SEQ ID NO:10) and other reaction reagents at 22° C. for 0.5 h before ATP (100 µM) was added to start the reaction. The absorption at 340 nm was monitored continuously for 2 hours at 30° C. on Polarstar Optima plate reader (BMG). The reaction rate was calculated using the 1.0 to 2.0 h time frame. Percent inhibition was obtained by comparison of reaction rate with that of a control (i.e. with no test compound). IC50 values were calculated from a series of percent inhibition values determined at a range of inhibitor concentrations using software routines as implemented in the GraphPad Prism software package.

cMet Kinase
(SEQ ID NO: 10)
MSYYHHHHHHDYDIPTTENLYFQGAMLVPRGSPWIPFTMKKRKQIKDLGS

ELVRYDARVHTPHLDRLVSARSVSPTTEMVSNESVDYRATFPEDQFPNSS

QNGSCRQVQYPLTDMSPILTSGDSDISSPLLQNTVHIDLSALNPELVQAV

QHVVIGPSSLIVHFNEVIGRGHFGCVYHGTLLDNDGKKIHCAVKSLNRIT

DIGEVSQFLTEGIIMKDFSHPNVLSLLGICLRSEGSPLVVLPYMKHGDLR

NFIRNETHNPTVKDLIGFGLQVAKGMKYLASKKFVHRDLAARNCMLDEKF

TVKVADFGLARDMYDKEYYSVHNKTGAKLPVKWMALESLQTQKFTTKSDV

WSFGVLLWELMTRGAPPYPDVNTFDITVYLLQGRRLLQPEYCPDPLYEVM

LKCWHPKAEMRPSFSELVSRISAIFSTFIGEHYVHVNATYVNVKCVAPYP

SLLSSEDNADDEVDTRPASFWETS

TABLE 1

Biological Data Summary.
Biochemical IC$_{50}$ values of compounds of Formula I.

| Example | Abl Enzyme Assay | Abl T315I Enzyme Assay | c-Kit Enzyme Assay | c-Met Enzyme Assay |
|---|---|---|---|---|
| 1 | +++ | +++ | +++ | ++ |
| 2 | +++ | +++ | +++ | ++ |
| 3 | +++ | +++ | +++ | ++ |
| 4 | +++ | +++ | n/a | ++ |
| 5 | +++ | +++ | +++ | + |
| 6 | +++ | +++ | +++ | + |
| 7 | +++ | +++ | n/a | + |
| 8 | +++ | +++ | +++ | ++ |
| 9 | +++ | ‡ | +++ | + |
| 10 | +++ | + | +++ | + |
| 11 | +++ | +++ | +++ | + |
| 12 | +++ | +++ | +++ | + |
| 13 | +++ | + | n/a | ++ |
| 14 | +++ | +++ | +++ | ++ |
| 15 | +++ | +++ | +++ | + |
| 16 | +++ | ++ | n/a | + |
| 17 | +++ | +++ | n/a | ++ |
| 18 | +++ | n/a | n/a | + |
| 19 | ++ | ++ | n/a | + |
| 20 | +++ | +++ | n/a | + |
| 21 | +++ | +++ | +++ | ++ |
| 22 | +++ | +++ | +++ | ++ |
| 23 | +++ | n/a | n/a | n/a |
| 24 | +++ | n/a | +++ | + |
| 25 | +++ | +++ | +++ | +++ |
| 26 | +++ | n/a | n/a | n/a |
| 27 | +++ | +++ | +++ | ++ |
| 28 | +++ | +++ | +++ | + |
| 29 | +++ | n/a | n/a | n/a |
| 30 | +++ | +++ | n/a | + |
| 31 | +++ | +++ | n/a | n/a |
| 32 | +++ | +++ | n/a | n/a |
| 33 | ++ | ++ | n/a | n/a |
| 34 | +++ | +++ | n/a | n/a |
| 35 | ++ | + | n/a | n/a |
| 36 | ++ | + | n/a | n/a |
| 37 | +++ | +++ | n/a | n/a |

TABLE 1-continued

Biological Data Summary.
Biochemical $IC_{50}$ values of compounds of Formula I.

| Example | Abl Enzyme Assay | Abl T315I Enzyme Assay | c-Kit Enzyme Assay | c-Met Enzyme Assay |
|---|---|---|---|---|
| 38 | +++ | ++ | n/a | n/a |
| 39 | +++ | +++ | n/a | n/a |
| 40 | +++ | ++ | n/a | ‡ |
| 41 | ++ | ‡ | ‡ | ‡ |
| 42 | +++ | +++ | +++ | ++ |

+++ = <0.1 μM; ++ = <1.0 μM; + = <10 μM; ‡ <100 μM; n/a = not available

The biochemical $IC_{50}$ values of other compounds disclosed herein are at least 10 μM against Abl enzyme.

Cell Culture

BaF3 cells (parental or transfected with the following: wild type p210 BCR-Abl and T315I p210 BCR-Abl was obtained from Professor Richard Van Etten (New England Medical Center, Boston, Mass.). Briefly, cells were grown in RPMI 1640 supplemented with 10% characterized fetal bovine serum (HyClone, Logan, Utah) at 37 degrees Celsius, 5% $CO_2$, 95% humidity. Cells were allowed to expand until reaching 80% saturation at which point they were subcultured or harvested for assay use.

Cell Proliferation Assay

A serial dilution of test compound was dispensed into a 96 well black clear bottom plate (Corning, Corning, N.Y.). For each cell line, three thousand cells were added per well in complete growth medium. Plates were incubated for 72 hours at 37 degrees Celsius, 5% $CO_2$, 95% humidity. At the end of the incubation period Cell Titer Blue (Promega, Madison, Wis.) was added to each well and an additional 4.5 hour incubation at 37 degrees Celsius, 5% $CO_2$, 95% humidity was performed. Plates were then read on a BMG Fluostar Optima (BMG, Durham, N.C.) using an excitation of 544 nM and an emission of 612 nM. Data was analyzed using Prism software (Graphpad, San Diego, Calif.) to calculate IC50's.

TABLE 2

Biological Data Summary.
Whole Cell Antiproliferation $IC_{50}$ values of compounds of Formula I.

| Example | Ba/F3 p210 whole cell proliferation assay | Ba/F3 p210 T315I whole cell proliferation assay |
|---|---|---|
| 1 | +++ | +++ |
| 2 | +++ | +++ |
| 3 | +++ | +++ |
| 4 | +++ | +++ |
| 5 | +++ | +++ |
| 6 | +++ | +++ |
| 7 | +++ | ++ |
| 8 | +++ | +++ |
| 9 | +++ | ++ |
| 10 | +++ | ++ |
| 11 | +++ | +++ |
| 12 | +++ | +++ |
| 13 | +++ | +++ |
| 14 | +++ | +++ |
| 15 | +++ | +++ |
| 16 | +++ | ++ |
| 17 | +++ | +++ |
| 18 | +++ | +++ |
| 19 | +++ | + |
| 20 | +++ | ++ |
| 21 | +++ | +++ |
| 22 | +++ | +++ |
| 23 | +++ | ++ |
| 24 | +++ | ‡ |
| 25 | +++ | +++ |
| 26 | n/a | n/a |
| 27 | +++ | +++ |
| 28 | +++ | ++ |
| 29 | ++ | ‡ |
| 30 | +++ | ++ |
| 31 | +++ | +++ |
| 32 | +++ | +++ |
| 33 | ++ | ++ |
| 34 | +++ | ++ |
| 35 | ++ | ‡ |
| 36 | + | ‡ |
| 37 | +++ | +++ |
| 38 | ++ | ‡ |
| 39 | ++ | + |
| 40 | ++ | ++ |
| 41 | ++ | ++ |
| 42 | +++ | +++ |

+++ = <0.1 μM; ++ = <1.0 μM; + = <10 μM; ‡ <100 μM; n/a = not available

The invention claimed is:
1. A compound of the formula Ia

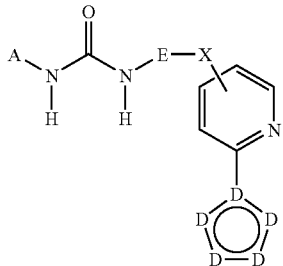

Ia wherein the pyridine ring may be optionally substituted with one or more R20 moieties;
each D is individually taken from the group consisting of C, CH, C—R20, N—Z3, and N, such that the resultant ring is a pyrazole;
wherein E is phenyl;
E may be optionally substituted with one or two R16 moieties;
wherein A is a ring system selected from the group consisting of G1, phenyl, naphthyl, and G2;
G1 is a heteroaryl taken from the group consisting of pyrrolyl, furyl, thienyl, oxazolyl, thiazolyl, isoxazol-4-yl, isoxazol-5-yl, isothiazolyl, imidazolyl, pyrazolyl, oxadiazolyl, thiadiazolyl, triazolyl, tetrazolyl, pyrazinyl, pyridazinyl, triazinyl, pyridinyl, and pyrimidinyl;
G2 is a fused bicyclic heteroaryl taken from the group consisting of indolyl, indolinyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, pyrazolopyridinyl, imidazolonopyridinyl, thiazolopyridinyl, thiazolonopyridinyl, oxazolopyridinyl, oxazolonopyridinyl, isoxazolopyridinyl, isothiazolopyridinyl, triazolopyridinyl, imidazopyrimidinyl, pyrazolopyrimidinyl, imidazolonopyrimidinyl, thiazolopyridiminyl, thiazolonopyrimidinyl, oxazolopyrimidinyl, oxazolonopyrimidinyl, isoxazolopyrimidinyl, isothiazolopyrimidinyl, triazolopyrimidinyl, dihydropurinonyl, pyrrolopyrimidinyl, purinyl, pyrazolopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, benzisothiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, and benzoxazepinyl;
G3 is a heterocyclyl taken from the group consisting of oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, pyrrolidinonyl and homotropanyl;
the A ring may be optionally substituted with one or two R2 moieties;
X is selected from the group consisting of —O—, —S(CH$_2$)$_n$—, —N(R3)(CH$_2$)$_n$—, and —(CH$_2$)$_p$—, and wherein the carbon atoms of —(CH$_2$)$_n$—, and —(CH$_2$)$_p$— of X may be further substituted by oxo or one or more C1-C6alkyl moieties;
when A, G1, G2 or G3 has one or more substitutable sp2-hybridized carbon atoms, each respective sp2 hybridized carbon atom may be optionally substituted with a Z1 substituent;
when A, G1, G2 or G3 has one or more substitutable sp3-hybridized carbon atoms, each respective sp3 hybridized carbon atom may be optionally substituted with a Z2 substituent;
when A, G1, G2 or G3 has one or more substitutable nitrogen atoms, each respective nitrogen atom may be optionally substituted with a Z4 substituent;
each Z1 is independently and individually selected from the group consisting of C1-6alkyl, branched C3-C7alkyl, C3-C8cycloalkyl, halogen, fluoroC1-C6alkyl wherein the alkyl moiety can be partially or fully fluorinated, cyano, C1-C6alkoxy, fluoroC1-C6alkoxy wherein the alkyl moiety can be partially or fully fluorinated, —(CH$_2$)$_n$OH, oxo, C1-C6alkoxyC1-C6alkyl, (R4)$_2$N(CH$_2$)$_n$—, (R3)$_2$N(CH$_2$)$_n$—, (R4)$_2$N(CH$_2$)$_q$N(R4)(CH$_2$)$_n$—, (R4)$_2$N(CH$_2$)$_q$O(CH$_2$)$_n$—, (R3)$_2$NC(O)—, (R4)$_2$NC(O)—, (R4)$_2$NC(O)C1-C6alkyl-, —(R4)NC(O)R8, C1-C6alkoxycarbonyl-, -carboxyC1-C6alkyl, C1-C6alkoxycarbonylC1-C6alkyl-, (R3)$_2$NSO$_2$—, —SOR3, (R4)$_2$NSO$_2$—, —N(R4)SO$_2$R8, —O(CH$_2$)$_q$OC1-C6alkyl, —SO$_2$R3, —SOR4, —C(O)R8, —C(O)R6, —C(=NOH)R6, —C(=NOR3)R6, —(CH$_2$)$_n$N(R4)C(O)R8, —N(R3)(CH$_2$)$_q$O-alkyl, —N(R3)(CH$_2$)$_q$N(R4)$_2$, nitro, —CH(OH)CH(OH)R4, —C(=NH)N(R4)$_2$, —C(=NOR3)N(R4)$_2$, —NHC(=NH)R8, R17 substituted G3, R17 substituted pyrazolyl and R17 substituted imidazolyl;
in the event that Z1 contains an alkyl or alkylene moiety, such moieties may be further substituted with one or more C1-C6alkyls;
each Z2 is independently and individually selected from the group consisting of aryl, C1-C6alkyl, C3-C8cycloalkyl, branched C3-C7alkyl, hydroxyl, hydroxyC1-C6alkyl-, cyano, (R3)$_2$N—, (R4)$_2$N—, (R4)$_2$NC1-C6alkyl-, (R4)$_2$NC2-C6alkylN(R4)(CH$_2$)$_n$—, (R4)$_2$NC2-C6alkylO(CH$_2$)$_n$—, (R3)$_2$NC(O)—, (R4)$_2$NC(O)—, (R4)$_2$NC(O)—C1-C6alkyl-, carboxyl, -carboxyC1-C6alkyl, C1-C6alkoxycarbonyl-, C1-C6alkoxycarbonylC1-C6alkyl-, (R3)$_2$NSO$_2$—, (R4)$_2$NSO$_2$—, —SO$_2$R8, —(CH$_2$)$_n$N(R4)C(O)R8, —C(O)R8, =O, =NOH, and =N(OR6);
in the event that Z2 contains an alkyl or alkylene moiety, such moieties may be further substituted with one or more C1-C6alkyls;
each Z3 is independently and individually selected from the group consisting of H, C1-C6alkyl, branched C3-C7alkyl, C3-C8cycloalkyl, fluoroC1-C6alkyl wherein the alkyl moiety can be partially or fully fluorinated, hydroxyC2-C6alkyl-, C1-C6alkoxycarbonyl-, —C(O)R8, R5C(O)(CH$_2$)$_n$—, (R4)$_2$NC(O)—, (R4)$_2$NC(O)C1-C6alkyl-, R8C(O)N(R4)(CH$_2$)$_q$—, (R3)$_2$NSO$_2$—, (R4)$_2$NSO$_2$—, —(CH$_2$)$_q$N(R3)$_2$, and —(CH$_2$)$_q$N(R4)$_2$;
each Z4 is independently and individually selected from the group consisting of C1-C6alkyl, branched C3-7alkyl, hydroxyC2-C6alkyl-, C1-C6alkoxyC2-C6alkyl-, (R4)$_2$N—C2-C6alkyl-, (R4)$_2$N—C2-C6alkylN(R4)-C2-C6alkyl-, (R4)$_2$N—C2-C6alkyl-O—C2-C6alkyl-, (R4)$_2$NC(O)C1-C6alkyl-, carboxyC1-C6alkyl, C1-C6alkoxycarbonylC1-

C6alkyl-, —C2-C6alkylN(R4)C(O)R8, R8-C(=NR3)-, —SO₂R8, and —COR8;
in the event that Z4 contains an alkyl or alkylene moiety, such moieties may be further substituted with one or more C1-C6alkyls;
each R2 is selected from the group consisting of H, C1-C6alkyl, branched C3-C8alkyl, R19 substituted C3-C8cycloalkyl-, fluoroC1-C6alkyl- wherein the alkyl is fully or partially fluorinated, halogen, cyano, C1-C6alkoxy-, fluoroC1-C6alkoxy- wherein the alkyl group is fully or partially fluorinated, hydroxyl substituted C1-C6alkyl-, hydroxyl substituted branched C3-C8alkyl-, cyano substituted C1-C6alkyl-, cyano substituted branched C3-C8alkyl-, (R3)₂NC(O)C1-C6alkyl-, and (R3)₂NC(O)C3-C8 branched alkyl-;
wherein each R3 is independently and individually selected from the group consisting of H, C1-C6alkyl, branched C3-C7alkyl, and C3-C8cycloalkyl;
each R4 is independently and individually selected from the group consisting of H, C1-C6alkyl, hydroxyC1-C6alkyl-, dihydroxyC1-C6alkyl-, C1-C6alkoxyC1-C6alkyl-, branched C3-C7 alkyl, branched hydroxyC1-C6alkyl-, branched C1-C6alkoxyC1-C6alkyl-, branched dihydroxyC1-C6alkyl-, —(CH₂)ₚN(R7)₂, —(CH₂)ₚC(O)N(R7)₂, —(CH₂)ₙC(O)OR3, and R19 substituted C3-C8cycloalkyl-;
each R5 is independently and individually selected from the group consisting of

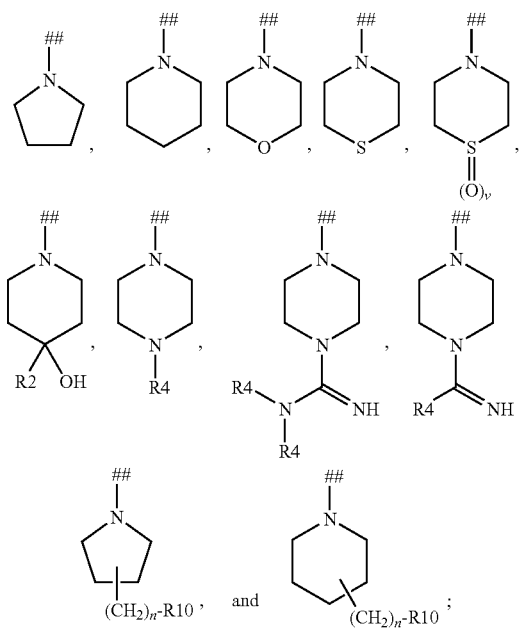

and wherein the symbol (##) is the point of attachment to Z3;
each R6 is independently and individually selected from the group consisting of C1-C6alkyl, branched C3-C7alkyl, and R19 substituted C3-C8cycloalkyl-;
each R7 is independently and individually selected from the group consisting of H, C1-C6alkyl, hydroxyC2-C6alkyl-, dihydroxyC2-C6alkyl-, C1-C6alkoxyC2-C6alkyl-, branched C3-C7alkyl, branched hydroxyC2-C6alkyl-, branched C1-C6alkoxyC2-C6alkyl-, branched dihydroxyC2-C6alkyl-, —(CH₂)ₙC(O)OR3, R19 substituted C3-C8cycloalkyl- and —(CH₂)ₙR17;

each R8 is independently and individually selected from the group consisting of C1-C6alkyl, branched C3-C7alkyl, fluoroC1-C6alkyl- wherein the alkyl moiety is partially or fully fluorinated, R19 substituted C3-C8cycloalkyl-, —OH, C1-C6alkoxy, —N(R3)₂, and —N(R4)₂;

each R10 is independently and individually selected from the group consisting of —CO₂H, —CO₂C1-C6alkyl, —C(O)N(R4)₂, OH, C1-C6alkoxy, and —N(R4)₂;

each R16 is independently and individually selected from the group consisting of H, C1-C6alkyl, branched C3-C7alkyl, R19 substituted C3-C8cycloalkyl-, halogen, fluoroC1-C6alkyl- wherein the alkyl moiety can be partially or fully fluorinated, cyano, hydroxyl, C1-C6alkoxy, fluoroC1-C6alkoxy- wherein the alkyl moiety can be partially or fully fluorinated, —N(R3)₂, —N(R4)₂, R3 substituted C2C3alkynyl- and nitro;

each R17 is independently and individually selected from the group consisting of H, C1-C6alkyl, branched C3-C7alkyl, R19 substituted C3-C8cycloalkyl-, halogen, fluoroC1-C6alkyl- wherein the alkyl moiety can be partially or fully fluorinated, cyano, hydroxyl, C1-C6alkoxy, fluoroC1-C6alkoxy- wherein the alkyl moiety can be partially or fully fluorinated, —N(R3)₂, —N(R4)₂, and nitro;

each R19 is independently and individually selected from the group consisting of H, OH and C1-C6alkyl;

each R20 is independently and individually selected from the group consisting of C1-C6alkyl, branched C3-C7alkyl, R19 substituted C3-C8cycloalkyl-, halogen, fluoroC1-C6alkyl- wherein the alkyl moiety can be partially or fully fluorinated, cyano, hydroxyl, C1-C6alkoxy, fluoroC1-C 6alkoxy- wherein the alkyl moiety can be partially or fully fluorinated, —N(R3)₂, —N(R4)₂, —N(R3)C(O)R3, —C(O)N(R3)₂ and nitro and wherein two R4 moieties independently and individually taken from the group consisting of C1-C6alkyl, branched C3-C6alkyl, hydroxyalkyl-, and alkoxyalkyl and attached to the same nitrogen heteroatom may cyclize to form a C3-C7 heterocyclyl ring;

n is 0-6; p is 1-4; q is 2-6; v is 1 or 2;

or a pharmaceutically acceptable salt, a stereoisomer, a regioisomer or a tautomer of such compounds.

2. The compound of claim 1 having formula Ib

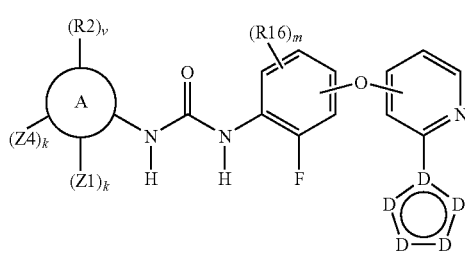

wherein A is any possible isomer of pyrazole;
k is 0 or 1; and m is 0-2.

3. The compound of claim 2 having formula Ic

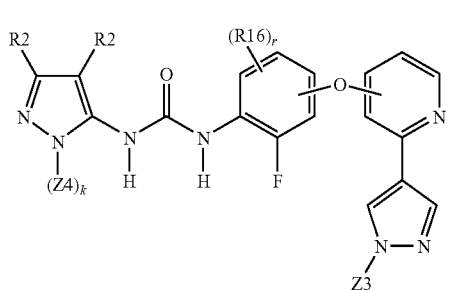

wherein r is 0 or 1.

4. The compound of claim 2 having formula Id

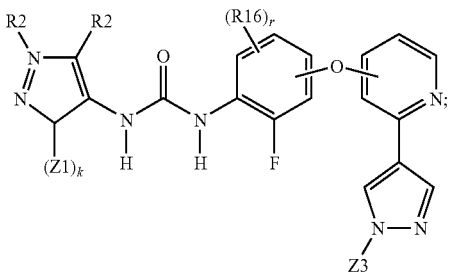

wherein r is 0 or 1.

5. The compound of claim 2 having formula Ie

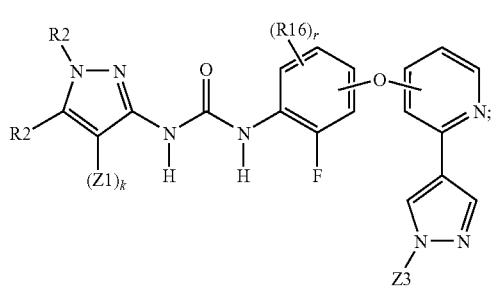

wherein r is 0 or 1.

6. The compounds of claim 1, wherein each D is individually selected from the group consisting of C, CH, N-Z3, and N, such that the resultant ring is a pyrazole.

7. The compound of claim 6 having formula Ig

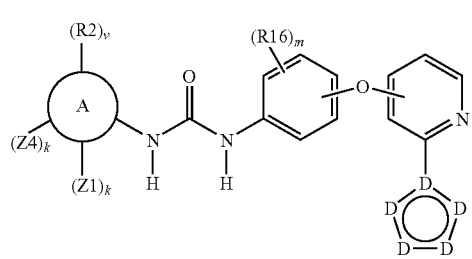

wherein A is selected from the group consisting of any possible isomer of phenyl and pyridine;
k is 0 or 1; and m is 0-2.

8. The compound of claim 7 having the formula Ih

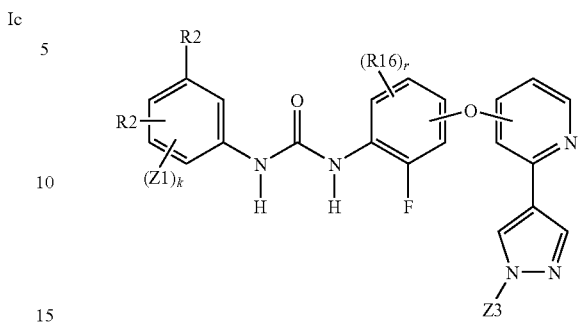

wherein r is 0 or 1.

9. The compound of claim 7 having the formula Ii

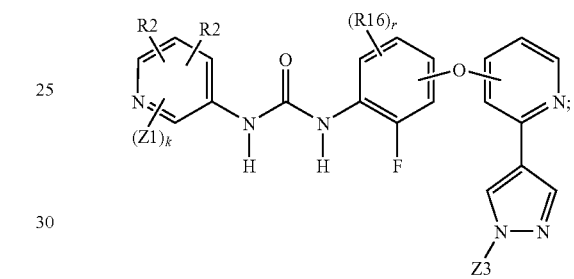

wherein r is 0 or 1.

10. The compound of claim 6 having formula Il

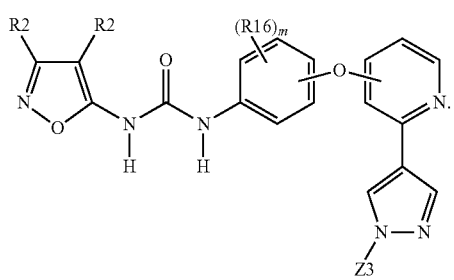

11. The compound of claim 10 having formula If

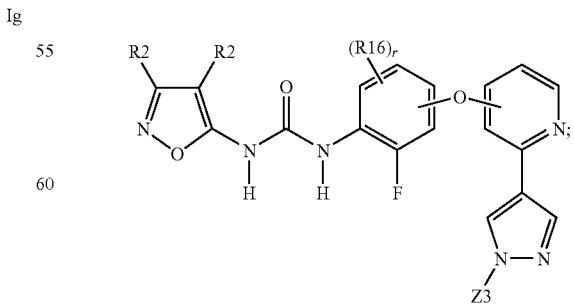

wherein r is 0 or 1.

12. A pharmaceutical composition comprising a compound of claim 1, together with a pharmaceutically acceptable carrier, optionally containing an additive selected from the group including adjuvants, excipients, diluents, and stabilizers.

13. A compound selected from the group consisting of 1-(3-tert-butylisoxazol-5-yl)-3-(2-fluoro-4-(2-(1-methyl-1H-pyrazol-4-yl) pyridin-4-yloxy)phenyl)urea, 1-(3-tert-butyl-1-methyl-1H-pyrazol-5-yl)-3-(2-fluoro-4-(2-(1-methyl-1H-pyrazol-4-yl) pyridin-4-yloxy)phenyl)urea, 1-(2-fluoro-4-(2-(1-methyl-1H-pyrazol-4-yl)pyridin-4-yloxy) phenyl)-3-(3-(trifluoromethyl)phenyl)urea, 1-(5-tert-butylisoxazol-3-yl)-3-(2-fluoro-4-(2-(1-methyl-1H-pyrazol-4-yl) pyridin-4-yloxy)phenyl)urea, 1-(1-tert-butyl-1H-pyrazol-4-yl)-3-(2-fluoro-4-(2-(1-methyl-1H-pyrazol-4-yl) pyridin-4-yloxy)phenyl)urea, 1-(4-(2-(1-methyl-1H-pyrazol-4-yl)pyridin-4-yloxy)phenyl)-3-(5-(trifluoromethyl) pyridin-3-yl)urea, 1-(2-fluoro-4-(2-(1-methyl-1H-pyrazol-4-yl)pyridin-4-yloxy) phenyl)-3-(3-(trifluoromethyl)isoxazol-5-yl) urea, 1-(1-tert-butyl-1H-pyrazol-4-yl)-3-(2,3-difluoro-4-(2-(1-methyl-1H-pyrazol-4-yl) pyridin-4-yloxy)phenyl)urea, 1-(1-tert-butyl-5-(trifluoromethyl)-1H-pyrazol-4-yl)-3-(2-fluoro-4-(2-(1-methyl-1H-pyrazol-4-yl)pyridin-4-yloxy)phenyl)urea, 1-(1-tert-butyl-5-methyl-1H-pyrazol-4-yl)-3-(2-fluoro-4-(2-(1-methyl-1H-pyrazol-4-yl) pyridin-4-yloxy)phenyl)urea, 1-(5-tert-butyl-1,3,4-thiadiazol-2-yl)-3-(2-fluoro-4-(2-(1-methyl-1H-pyrazol-4-yl) pyridin-4-yloxy)phenyl)urea, 1-(3-tert-butyl-1-(2-(dimethylamino)ethyl)-1H-pyrazol-5-yl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy)phenyl)-3-(3-(1-methylcyclopentyl) isoxazol-5-yl)urea, 1-(3-cyclopentylisoxazol-5-yl)-3-(2-fluoro-4-(2-(1-methyl-1H-pyrazol-4-yl) pyridin-4-yloxy)phenyl)urea, 1-(1-cyclopentyl-1H-pyrazol-4-yl)-3-(2-fluoro-4-(2-(1-methyl-1H-pyrazol-4-yl) pyridin-4-yloxy)phenyl)urea, 1-(2-fluoro-4-(2-(1-methyl-1H-pyrazol-4-yl)pyridin-4-yloxy) phenyl)-3-(1-methyl-3-(trifluoromethyl)-1H-pyrazol-5-yl)urea, 1-(1-tert-butyl-1H-pyrazol-4-yl)-3-(2-fluoro-3-methyl-4-(2-(1-methyl-1H-pyrazol-4-yl) pyridin-4-yloxy)phenyl)urea, 1-(2-fluoro-4-(2-(1-methyl-1H-pyrazol-4-yl)pyridin-4-yloxy) phenyl)-3-(1-isopropyl-3-(trifluoromethyl)-1H-pyrazol-4-yl)urea, 1-(2-fluoro-4-(2-(1-methyl-1H-pyrazol-4-yl) pyridin-4-yloxy)phenyl)-3-(1-isopropyl-5-methyl-1H-pyrazol-4-yl)urea, 1-(2-fluoro-4-(2-(1-methyl-1H-pyrazol-4-yl)pyridin-4-yloxy) phenyl)-3-(1-isopropyl-3-methyl-1H-pyrazol-4-yl)urea, 1-(2-fluoro-4-(2-(1-methyl-1H-pyrazol-4-yl)pyridin-4-yloxy) phenyl)-3-(5-(trifluoromethyl)pyridin-3-yl)urea, 1-(2-fluoro-4-(2-(1-methyl-1H-pyrazol-4-yl)pyridin-4-yloxy)phenyl)-3-(5-isopropylpyridin-3-yl)urea, 1-(1-cyclopentyl-5-methyl-1H-pyrazol-4-yl)-3-(2-fluoro-4-(2-(1-methyl-1H-pyrazol-4-yl) pyridin-4-yloxy)phenyl)urea, 1-(benzo[d]isoxazol-3-yl)-3-(2-fluoro-4-(2-(1-methyl-1H-pyrazol-4-yl) pyridin-4-yloxy)phenyl)urea, 1-(3-tert-butylisoxazol-5-yl)-3-(2,3-difluoro-4-(2-(1-methyl-1H-pyrazol-4-yl) pyridin-4-yloxy)phenyl)urea, 1-(2-tert-butyloxazol-5-yl)-3-(2-fluoro-4-(2-(1-methyl-1H-pyrazol-4-yl) pyridin-4-yloxy)phenyl)urea, 1-(2-fluoro-4-(2-(1-methyl-1H-pyrazol-4-yl)pyridin-4-yloxy) phenyl)-3-(2-oxo-5-(trifluoromethyl)-1,2-dihydropyridin-3-yl)urea, 1-(5-tert-butyl-2-methylfuran-3-yl)-3-(2-fluoro-4-(2-(1-methyl-1H-pyrazol-4-yl) pyridin-4-yloxy)phenyl)urea, 1-(2-fluoro-4-(2-(1-methyl-1H-pyrazol-4-yl)pyridin-4-yloxy)phenyl)-3-(6-fluorobenzo[d]thiazol-2-yl)urea, 1-(1-tert-butyl-1H-pyrrol-3-yl)-3-(2-fluoro-4-(2-methyl-1H-pyrazol-4-yl) pyridin-4-yloxy)phenyl)urea, 1-(3-tert-butyl-4-methylisoxazol-5-yl)-3-(2-fluoro-4-(2-(1-methyl-1H-pyrazol-4-yl)pyridin-4-yloxy)phenyl) urea, 1-(5-ethylpyridin-3-yl)-3-(2-fluoro-4-(2-(1-methyl-1H-pyrazol-4-yl)pyridin-4-yloxy)phenyl)urea, 1-(3-cyclopropyl-1-methyl-1H-pyrazol-5-yl)-3-(2-fluoro-4-(2-(1-methyl-1H-pyrazol-4-yl)pyridin-4-yloxy)phenyl)urea, 1-(2-fluoro-4-(2-(1-methyl-1H-pyrazol-4-yl)pyridin-4-yloxy) phenyl)-3-(1-isopropyl-1H-imidazol-4-yl)urea, 1-(2-fluoro-4-(2-(1-methyl-1H-pyrazol-4-yl)pyridin-4-yloxy) phenyl)-3-(2-methyl-5-(trifluoromethyl)pyridin-3-yl)urea, 1-(1-tert-butyl-5-methyl-1H-pyrazol-3-yl)-3-(2-fluoro-4-(2-(1-methyl-1H-pyrazol-4-yl) pyridin-4-yloxy)phenyl)urea, 1-(2-tert-butyl-4-(piperazin-1-yl)pyrimidin-5-yl)-3-(2-fluoro-4-(2-(1-methyl-1H-pyrazol-4-yl)pyridin-4-yloxy)phenyl)urea, 1-(2-tert-butyl-4-morpholinopyrimidin-5-yl)-3-(2-fluoro-4-(2-(1-methyl-1H-pyrazol-4-yl) pyridin-4-yloxy)phenyl)urea, 1-(2-fluoro-4-(2-(1-methyl-1H-pyrazol-4-yl)pyridin-4-yloxy) phenyl)-3-(2-(1-methyl-1H-pyrazol-4-yl)-5-(trifluoromethyl)pyridin-3-yl)urea and pharmaceutically acceptable salts and tautomers thereof.

14. A compound selected from the group consisting of 1-(2-fluoro-4-(2-(1-methyl-1H-pyrazol-4-yl)pyridin-4-yloxy)phenyl)-3-(1-isopropyl-1H-pyrazol-4-yl)urea, 1-(1-tert-butyl-1H-pyrazol-4-yl)-3-(3-fluoro-4-(2-(1-methyl-1H-pyrazol-4-yl) pyridin-4-yloxy)phenyl)urea, 1-(2-fluoro-4-(2-(1-methyl-1H-pyrazol-4-yl)pyridin-4-yloxy) phenyl)-3-(5-fluoropyridin-3-yl)urea, 1-(2-fluoro-3-methyl-4-(2-(1-methyl-1H-pyrazol-4-yl) pyridin-4-yloxy) phenyl)-3-(3-isopropylisoxazol-5-yl) urea, and 1-(2-fluoro-4-(2-(1-methyl-1H-pyrazol-4-yl)pyridin-4-yloxy) phenyl)-3-(5-methylpyridin-3-yl)urea.

15. The compound 1-(3-tert-butyl-1-methyl-1H-pyrazol-5-yl)-3-(2-fluoro-4-(2-(1-methyl-1H-pyrazol-4-yl) pyridin-4-yloxy)pheny)urea and pharmaceutically acceptable salts and tautomers thereof.

16. The compound 1-(1-tert-butyl-1H-pyrazol-4-yl)-3-(2-fluoro-4-(2-(1-methyl-1H-pyrazol-4-yl)pyridin-4-yloxy) phenyl)urea and pharmaceutically acceptable salts and tautomers thereof.

17. The compound 1-(2-fluoro-4-(2-(1-methyl-1H-pyrazol-4-yl)pyridin-4-yloxy) phenyl)-3-(1-isopropyl-1H-imidazol-4-yl)urea and pharmaceutically acceptable salts and tautomers thereof.

18. The compound 1-(3-tert-butylisoxazol-5-yl)-3-(2-fluoro-4-(2-(1-methyl-1H-pyrazol-4-yl)pyridin-4-yloxy)phenyl)urea and pharmaceutically acceptable salts and tautomers thereof.

19. The compound 1-(2-fluoro-4-(2-(1-methyl-1H-pyrazol-4-yl)pyridin-4-yloxy) phenyl)-3-(5-(trifluoromethyl)pyridin-3-yl)urea and pharmaceutically acceptable salts and tautomers thereof.

20. The compound 1-(2-fluoro-4-(2-(1-methyl-1H-pyrazol-4-yl)pyridin-4-yloxy) phenyl)-3-(1-isopropyl-1H-pyrazol-4-yl)urea and pharmaceutically acceptable salts and tautomers thereof.

21. The compound 1-(2-fluoro-4-(2-(1-methyl-1H-pyrazol-4-yl)pyridin-4-yloxy) phenyl)-3-(5-fluoropyridin-3-yl)urea and pharmaceutically acceptable salts and tautomers thereof.

22. The compound 1-(2-fluoro-4-(2-(1-methyl-1H-pyrazol-4-yl)pyridin-4-yloxy) phenyl)-3-(5-methylpyridin-3-yl)urea and pharmaceutically acceptable salts and tautomers thereof.

* * * * *

SEQUENCE LISTING

<160> NUMBER OF SEQ ID NOS: 10

<210> SEQ ID NO 1
<211> LENGTH: 278
<212> TYPE: PRT
<213> ORGANISM: Homo sapiens

<400> SEQUENCE: 1

Gly Thr Ser Met Asp Pro Ser Ser Pro Asn Tyr Asp Lys Trp Glu Met
1               5                   10                  15

Glu Arg Thr Asp Ile Thr Met Lys His Lys Leu Gly Gly Gly Gln Tyr
            20                  25                  30

Gly Glu Val Tyr Glu Gly Val Trp Lys Lys Tyr Ser Leu Thr Val Ala
        35                  40                  45

Val Lys Thr Leu Lys Glu Asp Thr Met Glu Val Glu Glu Phe Leu Lys
    50                  55                  60

-continued

Glu Ala Ala Val Met Lys Glu Ile Lys His Pro Asn Leu Val Gln Leu
65                  70                  75                  80

Leu Gly Val Cys Thr Arg Glu Pro Pro Phe Tyr Ile Ile Thr Glu Phe
                85                  90                  95

Met Thr Tyr Gly Asn Leu Leu Asp Tyr Leu Arg Glu Cys Asn Arg Gln
            100                 105                 110

Glu Val Asn Ala Val Val Leu Leu Tyr Met Ala Thr Gln Ile Ser Ser
        115                 120                 125

Ala Met Glu Tyr Leu Glu Lys Lys Asn Phe Ile His Arg Asp Leu Ala
    130                 135                 140

Ala Arg Asn Cys Leu Val Gly Glu Asn His Leu Val Lys Val Ala Asp
145                 150                 155                 160

Phe Gly Leu Ser Arg Leu Met Thr Gly Asp Thr Tyr Thr Ala His Ala
                165                 170                 175

Gly Ala Lys Phe Pro Ile Lys Trp Thr Ala Pro Glu Ser Leu Ala Tyr
            180                 185                 190

Asn Lys Phe Ser Ile Lys Ser Asp Val Trp Ala Phe Gly Val Leu Leu
        195                 200                 205

Trp Glu Ile Ala Thr Tyr Gly Met Ser Pro Tyr Pro Gly Ile Asp Leu
210                 215                 220

Ser Gln Val Tyr Glu Leu Leu Glu Lys Asp Tyr Arg Met Glu Arg Pro
225                 230                 235                 240

Glu Gly Cys Pro Glu Lys Val Tyr Glu Leu Met Arg Ala Cys Trp Gln
                245                 250                 255

Trp Asn Pro Ser Asp Arg Pro Ser Phe Ala Glu Ile His Gln Ala Phe
            260                 265                 270

Glu Thr Met Phe Gln Glu
            275

<210> SEQ ID NO 2
<211> LENGTH: 278
<212> TYPE: PRT
<213> ORGANISM: Homo sapiens

<400> SEQUENCE: 2

Gly Thr Ser Met Asp Pro Ser Ser Pro Asn Tyr Asp Lys Trp Glu Met
1               5                   10                  15

Glu Arg Thr Asp Ile Thr Met Lys His Lys Leu Gly Gly Gly Gln Tyr
            20                  25                  30

Gly Glu Val Tyr Glu Gly Val Trp Lys Lys Tyr Ser Leu Thr Val Ala
        35                  40                  45

Val Lys Thr Leu Lys Glu Asp Thr Met Glu Val Glu Glu Phe Leu Lys
    50                  55                  60

Glu Ala Ala Val Met Lys Glu Ile Lys His Pro Asn Leu Val Gln Leu
65                  70                  75                  80

Leu Gly Val Cys Thr Arg Glu Pro Pro Phe Tyr Ile Ile Ile Glu Phe
                85                  90                  95

Met Thr Tyr Gly Asn Leu Leu Asp Tyr Leu Arg Glu Cys Asn Arg Gln
            100                 105                 110

Glu Val Asn Ala Val Val Leu Leu Tyr Met Ala Thr Gln Ile Ser Ser
        115                 120                 125

Ala Met Glu Tyr Leu Glu Lys Lys Asn Phe Ile His Arg Asp Leu Ala
    130                 135                 140

Ala Arg Asn Cys Leu Val Gly Glu Asn His Leu Val Lys Val Ala Asp
145                 150                 155                 160

-continued

```
Phe Gly Leu Ser Arg Leu Met Thr Gly Asp Thr Tyr Thr Ala His Ala
            165                 170                 175

Gly Ala Lys Phe Pro Ile Lys Trp Thr Ala Pro Glu Ser Leu Ala Tyr
        180                 185                 190

Asn Lys Phe Ser Ile Lys Ser Asp Val Trp Ala Phe Gly Val Leu Leu
        195                 200                 205

Trp Glu Ile Ala Thr Tyr Gly Met Ser Pro Tyr Pro Gly Ile Asp Leu
        210                 215                 220

Ser Gln Val Tyr Glu Leu Leu Glu Lys Asp Tyr Arg Met Glu Arg Pro
225                 230                 235                 240

Glu Gly Cys Pro Glu Lys Val Tyr Glu Leu Met Arg Ala Cys Trp Gln
                245                 250                 255

Trp Asn Pro Ser Asp Arg Pro Ser Phe Ala Glu Ile His Gln Ala Phe
        260                 265                 270

Glu Thr Met Phe Gln Glu
        275

<210> SEQ ID NO 3
<211> LENGTH: 2031
<212> TYPE: PRT
<213> ORGANISM: Homo sapiens

<400> SEQUENCE: 3

Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
        115                 120                 125

Gly Thr Ala Arg Arg Pro Gly Ala Ala Ser Gly Glu Arg Asp Asp
    130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
        195                 200                 205

Gln Met Glu Arg Lys Lys Ser Gln His Gly Ala Gly Ser Ser Val Gly
    210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255
```

-continued

```
Lys Asp Asn Leu Ile Asp Ala Asn Gly Gly Ser Arg Pro Pro Trp Pro
            260                 265                 270

Pro Leu Glu Tyr Gln Pro Tyr Gln Ser Ile Tyr Val Gly Gly Ile Met
        275                 280                 285

Glu Gly Glu Gly Lys Gly Pro Leu Leu Arg Ser Gln Ser Thr Ser Glu
    290                 295                 300

Gln Glu Lys Arg Leu Thr Trp Pro Arg Arg Ser Tyr Ser Pro Arg Ser
305                 310                 315                 320

Phe Glu Asp Cys Gly Gly Tyr Thr Pro Asp Cys Ser Ser Asn Glu
                325                 330                 335

Asn Leu Thr Ser Ser Glu Glu Asp Phe Ser Ser Gly Gln Ser Ser Arg
            340                 345                 350

Val Ser Pro Ser Pro Thr Thr Tyr Arg Met Phe Arg Asp Lys Ser Arg
        355                 360                 365

Ser Pro Ser Gln Asn Ser Gln Gln Ser Phe Asp Ser Ser Ser Pro Pro
    370                 375                 380

Thr Pro Gln Cys His Lys Arg His Arg His Cys Pro Val Val Val Ser
385                 390                 395                 400

Glu Ala Thr Ile Val Gly Val Arg Lys Thr Gly Gln Ile Trp Pro Asn
                405                 410                 415

Asp Asp Glu Gly Ala Phe His Gly Asp Ala Asp Gly Ser Phe Gly Thr
            420                 425                 430

Pro Pro Gly Tyr Gly Cys Ala Ala Asp Arg Ala Glu Glu Arg Arg
        435                 440                 445

His Gln Asp Gly Leu Pro Tyr Ile Asp Asp Ser Pro Ser Ser Ser Pro
    450                 455                 460

His Leu Ser Ser Lys Gly Arg Gly Ser Arg Asp Ala Leu Val Ser Gly
465                 470                 475                 480

Ala Leu Lys Ser Thr Lys Ala Ser Glu Leu Asp Leu Glu Lys Gly Leu
                485                 490                 495

Glu Met Arg Lys Trp Val Leu Ser Gly Ile Leu Ala Ser Glu Glu Thr
            500                 505                 510

Tyr Leu Ser His Leu Glu Ala Leu Leu Leu Pro Met Lys Pro Leu Lys
        515                 520                 525

Ala Ala Ala Thr Thr Ser Gln Pro Val Leu Thr Ser Gln Gln Ile Glu
    530                 535                 540

Thr Ile Phe Phe Lys Val Pro Glu Leu Tyr Glu Ile His Lys Glu Ser
545                 550                 555                 560

Tyr Asp Gly Leu Phe Pro Arg Val Gln Gln Trp Ser His Gln Gln Arg
                565                 570                 575

Val Gly Asp Leu Phe Gln Lys Leu Ala Ser Gln Leu Gly Val Tyr Arg
            580                 585                 590

Ala Phe Val Asp Asn Tyr Gly Val Ala Met Glu Met Ala Glu Lys Cys
        595                 600                 605

Cys Gln Ala Asn Ala Gln Phe Ala Glu Ile Ser Glu Asn Leu Arg Ala
    610                 615                 620

Arg Ser Asn Lys Asp Ala Lys Asp Pro Thr Thr Lys Asn Ser Leu Glu
625                 630                 635                 640

Thr Leu Leu Tyr Lys Pro Val Asp Arg Val Thr Arg Ser Thr Leu Val
                645                 650                 655

Leu His Asp Leu Leu Lys His Thr Pro Ala Ser His Pro Asp His Pro
            660                 665                 670

Leu Leu Gln Asp Ala Leu Arg Ile Ser Gln Asn Phe Leu Ser Ser Ile
        675                 680                 685
```

```
Asn Glu Glu Ile Thr Pro Arg Arg Gln Ser Met Thr Val Lys Lys Gly
    690                 695                 700

Glu His Arg Gln Leu Leu Lys Asp Ser Phe Met Val Glu Leu Val Glu
705                 710                 715                 720

Gly Ala Arg Lys Leu Arg His Val Phe Leu Phe Thr Asp Leu Leu Leu
                725                 730                 735

Cys Thr Lys Leu Lys Lys Gln Ser Gly Gly Lys Thr Gln Gln Tyr Asp
            740                 745                 750

Cys Lys Trp Tyr Ile Pro Leu Thr Asp Leu Ser Phe Gln Met Val Asp
        755                 760                 765

Glu Leu Glu Ala Val Pro Asn Ile Pro Leu Val Pro Asp Glu Glu Leu
    770                 775                 780

Asp Ala Leu Lys Ile Lys Ile Ser Gln Ile Lys Ser Asp Ile Gln Arg
785                 790                 795                 800

Glu Lys Arg Ala Asn Lys Gly Ser Lys Ala Thr Glu Arg Leu Lys Lys
                805                 810                 815

Lys Leu Ser Glu Gln Glu Ser Leu Leu Leu Met Ser Pro Ser Met
            820                 825                 830

Ala Phe Arg Val His Ser Arg Asn Gly Lys Ser Tyr Thr Phe Leu Ile
        835                 840                 845

Ser Ser Asp Tyr Glu Arg Ala Glu Trp Arg Glu Asn Ile Arg Glu Gln
    850                 855                 860

Gln Lys Lys Cys Phe Arg Ser Phe Ser Leu Thr Ser Val Glu Leu Gln
865                 870                 875                 880

Met Leu Thr Asn Ser Cys Val Lys Leu Gln Thr Val His Ser Ile Pro
                885                 890                 895

Leu Thr Ile Asn Lys Glu Asp Asp Glu Ser Pro Gly Leu Tyr Gly Phe
            900                 905                 910

Leu Asn Val Ile Val His Ser Ala Thr Gly Phe Lys Gln Ser Ser Lys
        915                 920                 925

Ala Leu Gln Arg Pro Val Ala Ser Asp Phe Glu Pro Gln Gly Leu Ser
    930                 935                 940

Glu Ala Ala Arg Trp Asn Ser Lys Glu Asn Leu Leu Ala Gly Pro Ser
945                 950                 955                 960

Glu Asn Asp Pro Asn Leu Phe Val Ala Leu Tyr Asp Phe Val Ala Ser
                965                 970                 975

Gly Asp Asn Thr Leu Ser Ile Thr Lys Gly Glu Lys Leu Arg Val Leu
            980                 985                 990

Gly Tyr Asn His Asn Gly Glu Trp Cys Glu Ala Gln Thr Lys Asn Gly
        995                 1000                1005

Gln Gly Trp Val Pro Ser Asn Tyr Ile Thr Pro Val Asn Ser Leu
    1010                1015                1020

Glu Lys His Ser Trp Tyr His Gly Pro Val Ser Arg Asn Ala Ala
    1025                1030                1035

Glu Tyr Pro Leu Ser Ser Gly Ile Asn Gly Ser Phe Leu Val Arg
    1040                1045                1050

Glu Ser Glu Ser Ser Pro Ser Gln Arg Ser Ile Ser Leu Arg Tyr
    1055                1060                1065

Glu Gly Arg Val Tyr His Tyr Arg Ile Asn Thr Ala Ser Asp Gly
    1070                1075                1080

Lys Leu Tyr Val Ser Ser Glu Ser Arg Phe Asn Thr Leu Ala Glu
    1085                1090                1095

Leu Val His His His Ser Thr Val Ala Asp Gly Leu Ile Thr Thr
```

-continued

```
              1100           1105           1110
Leu His Tyr Pro Ala Pro Lys Arg Asn Lys Pro Thr Val Tyr Gly
        1115           1120           1125

Val Ser Pro Asn Tyr Asp Lys Trp Glu Met Glu Arg Thr Asp Ile
        1130           1135           1140

Thr Met Lys His Lys Leu Gly Gly Gln Tyr Gly Glu Val Tyr
        1145           1150           1155

Glu Gly Val Trp Lys Lys Tyr Ser Leu Thr Val Ala Val Lys Thr
        1160           1165           1170

Leu Lys Glu Asp Thr Met Glu Val Glu Glu Phe Leu Lys Glu Ala
        1175           1180           1185

Ala Val Met Lys Glu Ile Lys His Pro Asn Leu Val Gln Leu Leu
        1190           1195           1200

Gly Val Cys Thr Arg Glu Pro Pro Phe Tyr Ile Ile Thr Glu Phe
        1205           1210           1215

Met Thr Tyr Gly Asn Leu Leu Asp Tyr Leu Arg Glu Cys Asn Arg
        1220           1225           1230

Gln Glu Val Asn Ala Val Val Leu Leu Tyr Met Ala Thr Gln Ile
        1235           1240           1245

Ser Ser Ala Met Glu Tyr Leu Glu Lys Lys Asn Phe Ile His Arg
        1250           1255           1260

Asp Leu Ala Ala Arg Asn Cys Leu Val Gly Glu Asn His Leu Val
        1265           1270           1275

Lys Val Ala Asp Phe Gly Leu Ser Arg Leu Met Thr Gly Asp Thr
        1280           1285           1290

Tyr Thr Ala His Ala Gly Ala Lys Phe Pro Ile Lys Trp Thr Ala
        1295           1300           1305

Pro Glu Ser Leu Ala Tyr Asn Lys Phe Ser Ile Lys Ser Asp Val
        1310           1315           1320

Trp Ala Phe Gly Val Leu Leu Trp Glu Ile Ala Thr Tyr Gly Met
        1325           1330           1335

Ser Pro Tyr Pro Gly Ile Asp Arg Ser Gln Val Tyr Glu Leu Leu
        1340           1345           1350

Glu Lys Asp Tyr Arg Met Lys Arg Pro Glu Gly Cys Pro Glu Lys
        1355           1360           1365

Val Tyr Glu Leu Met Arg Ala Cys Trp Gln Trp Asn Pro Ser Asp
        1370           1375           1380

Arg Pro Ser Phe Ala Glu Ile His Gln Ala Phe Glu Thr Met Phe
        1385           1390           1395

Gln Glu Ser Ser Ile Ser Asp Glu Val Glu Lys Glu Leu Gly Lys
        1400           1405           1410

Gln Gly Val Arg Gly Ala Val Thr Thr Leu Leu Gln Ala Pro Glu
        1415           1420           1425

Leu Pro Thr Lys Thr Arg Thr Ser Arg Arg Ala Ala Glu His Arg
        1430           1435           1440

Asp Thr Thr Asp Val Pro Glu Met Pro His Ser Lys Gly Gln Gly
        1445           1450           1455

Glu Ser Asp Pro Leu Asp His Glu Pro Ala Val Ser Pro Leu Leu
        1460           1465           1470

Pro Arg Lys Glu Arg Gly Pro Pro Glu Gly Gly Leu Asn Glu Asp
        1475           1480           1485

Glu Arg Leu Leu Pro Lys Asp Lys Lys Thr Asn Leu Phe Ser Ala
        1490           1495           1500
```

-continued

```
Leu Ile Lys Lys Lys Lys Lys Thr Ala Pro Thr Pro Pro Lys Arg
1505            1510                1515

Ser Ser Ser Phe Arg Glu Met Asp Gly Gln Pro Glu Arg Arg Gly
1520            1525                1530

Ala Gly Glu Glu Glu Gly Arg Asp Ile Ser Asn Gly Ala Leu Ala
1535            1540                1545

Phe Thr Pro Leu Asp Thr Ala Asp Pro Ala Lys Ser Pro Lys Pro
1550            1555                1560

Ser Asn Gly Ala Gly Val Pro Asn Gly Ala Leu Arg Glu Ser Gly
1565            1570                1575

Gly Ser Gly Phe Arg Ser Pro His Leu Trp Lys Lys Ser Ser Thr
1580            1585                1590

Leu Thr Ser Ser Arg Leu Ala Thr Gly Glu Glu Glu Gly Gly Gly
1595            1600                1605

Ser Ser Ser Lys Arg Phe Leu Arg Ser Cys Ser Val Ser Cys Val
1610            1615                1620

Pro His Gly Ala Lys Asp Thr Glu Trp Arg Ser Val Thr Leu Pro
1625            1630                1635

Arg Asp Leu Gln Ser Thr Gly Arg Gln Phe Asp Ser Ser Thr Phe
1640            1645                1650

Gly Gly His Lys Ser Glu Lys Pro Ala Leu Pro Arg Lys Arg Ala
1655            1660                1665

Gly Glu Asn Arg Ser Asp Gln Val Thr Arg Gly Thr Val Thr Pro
1670            1675                1680

Pro Pro Arg Leu Val Lys Lys Asn Glu Glu Ala Ala Asp Glu Val
1685            1690                1695

Phe Lys Asp Ile Met Glu Ser Ser Pro Gly Ser Ser Pro Pro Asn
1700            1705                1710

Leu Thr Pro Lys Pro Leu Arg Arg Gln Val Thr Val Ala Pro Ala
1715            1720                1725

Ser Gly Leu Pro His Lys Glu Glu Ala Trp Lys Gly Ser Ala Leu
1730            1735                1740

Gly Thr Pro Ala Ala Ala Glu Pro Val Thr Pro Thr Ser Lys Ala
1745            1750                1755

Gly Ser Gly Ala Pro Arg Gly Thr Ser Lys Gly Pro Ala Glu Glu
1760            1765                1770

Ser Arg Val Arg Arg His Lys His Ser Ser Glu Ser Pro Gly Arg
1775            1780                1785

Asp Lys Gly Lys Leu Ser Lys Leu Lys Pro Ala Pro Pro Pro Pro
1790            1795                1800

Pro Ala Ala Ser Ala Gly Lys Ala Gly Gly Lys Pro Ser Gln Arg
1805            1810                1815

Pro Gly Gln Glu Ala Ala Gly Glu Ala Val Leu Gly Ala Lys Thr
1820            1825                1830

Lys Ala Thr Ser Leu Val Asp Ala Val Asn Ser Asp Ala Ala Lys
1835            1840                1845

Pro Ser Gln Pro Ala Glu Gly Leu Lys Lys Pro Val Leu Pro Ala
1850            1855                1860

Thr Pro Lys Pro His Pro Ala Lys Pro Ser Gly Thr Pro Ile Ser
1865            1870                1875

Pro Ala Pro Val Pro Leu Ser Thr Leu Pro Ser Ala Ser Ser Ala
1880            1885                1890

Leu Ala Gly Asp Gln Pro Ser Ser Thr Ala Phe Ile Pro Leu Ile
1895            1900                1905
```

```
Ser Thr Arg Val Ser Leu Arg Lys Thr Arg Gln Pro Pro Glu Arg
    1910                1915                1920

Ala Ser Gly Ala Ile Thr Lys Gly Val Val Leu Asp Ser Thr Glu
    1925                1930                1935

Ala Leu Cys Leu Ala Ile Ser Gly Asn Ser Glu Gln Met Ala Ser
    1940                1945                1950

His Ser Ala Val Leu Glu Ala Gly Lys Asn Leu Tyr Thr Phe Cys
    1955                1960                1965

Val Ser Tyr Val Asp Ser Ile Gln Gln Met Arg Asn Lys Phe Ala
    1970                1975                1980

Phe Arg Glu Ala Ile Asn Lys Leu Glu Asn Asn Leu Arg Glu Leu
    1985                1990                1995

Gln Ile Cys Pro Ala Ser Ala Gly Ser Gly Pro Ala Ala Thr Gln
    2000                2005                2010

Asp Phe Ser Lys Leu Leu Ser Ser Val Lys Glu Ile Ser Asp Ile
    2015                2020                2025

Val Gln Arg
    2030

<210> SEQ ID NO 4
<211> LENGTH: 2006
<212> TYPE: PRT
<213> ORGANISM: Homo sapiens

<400> SEQUENCE: 4

Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
        115                 120                 125

Gly Thr Ala Arg Arg Pro Gly Ala Ala Ala Ser Gly Glu Arg Asp Asp
    130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
        195                 200                 205

Gln Met Glu Arg Lys Lys Ser Gln His Gly Ala Gly Ser Ser Val Gly
    210                 215                 220

Asp Ala Ser Arg Pro Pro Tyr Arg Gly Arg Ser Ser Glu Ser Ser Cys
225                 230                 235                 240
```

Gly Val Asp Gly Asp Tyr Glu Asp Ala Glu Leu Asn Pro Arg Phe Leu
            245                 250                 255

Lys Asp Asn Leu Ile Asp Ala Asn Gly Gly Ser Arg Pro Pro Trp Pro
                260                 265                 270

Pro Leu Glu Tyr Gln Pro Tyr Gln Ser Ile Tyr Val Gly Gly Ile Met
            275                 280                 285

Glu Gly Glu Gly Lys Gly Pro Leu Leu Arg Ser Gln Ser Thr Ser Glu
        290                 295                 300

Gln Glu Lys Arg Leu Thr Trp Pro Arg Arg Ser Tyr Ser Pro Arg Ser
305                 310                 315                 320

Phe Glu Asp Cys Gly Gly Tyr Thr Pro Asp Cys Ser Ser Asn Glu
                325                 330                 335

Asn Leu Thr Ser Ser Glu Glu Asp Phe Ser Ser Gly Gln Ser Ser Arg
                340                 345                 350

Val Ser Pro Ser Pro Thr Thr Tyr Arg Met Phe Arg Asp Lys Ser Arg
            355                 360                 365

Ser Pro Ser Gln Asn Ser Gln Gln Ser Phe Asp Ser Ser Pro Pro
            370                 375                 380

Thr Pro Gln Cys His Lys Arg His Arg His Cys Pro Val Val Val Ser
385                 390                 395                 400

Glu Ala Thr Ile Val Gly Val Arg Lys Thr Gly Gln Ile Trp Pro Asn
                405                 410                 415

Asp Asp Glu Gly Ala Phe His Gly Asp Ala Asp Gly Ser Phe Gly Thr
            420                 425                 430

Pro Pro Gly Tyr Gly Cys Ala Ala Asp Arg Ala Glu Gln Arg Arg
            435                 440                 445

His Gln Asp Gly Leu Pro Tyr Ile Asp Asp Ser Pro Ser Ser Ser Pro
    450                 455                 460

His Leu Ser Ser Lys Gly Arg Gly Ser Arg Asp Ala Leu Val Ser Gly
465                 470                 475                 480

Ala Leu Lys Ser Thr Lys Ala Ser Glu Leu Asp Leu Glu Lys Gly Leu
                485                 490                 495

Glu Met Arg Lys Trp Val Leu Ser Gly Ile Leu Ala Ser Glu Glu Thr
            500                 505                 510

Tyr Leu Ser His Leu Glu Ala Leu Leu Leu Pro Met Lys Pro Leu Lys
        515                 520                 525

Ala Ala Ala Thr Thr Ser Gln Pro Val Leu Thr Ser Gln Gln Ile Glu
    530                 535                 540

Thr Ile Phe Phe Lys Val Pro Glu Leu Tyr Glu Ile His Lys Glu Ser
545                 550                 555                 560

Tyr Asp Gly Leu Phe Pro Arg Val Gln Gln Trp Ser His Gln Gln Arg
                565                 570                 575

Val Gly Asp Leu Phe Gln Lys Leu Ala Ser Gln Leu Gly Val Tyr Arg
            580                 585                 590

Ala Phe Val Asp Asn Tyr Gly Val Ala Met Glu Met Ala Glu Lys Cys
            595                 600                 605

Cys Gln Ala Asn Ala Gln Phe Ala Glu Ile Ser Glu Asn Leu Arg Ala
    610                 615                 620

Arg Ser Asn Lys Asp Ala Lys Asp Pro Thr Thr Lys Asn Ser Leu Glu
625                 630                 635                 640

Thr Leu Leu Tyr Lys Pro Val Asp Arg Val Thr Arg Ser Thr Leu Val
                645                 650                 655

Leu His Asp Leu Leu Lys His Thr Pro Ala Ser His Pro Asp His Pro

```
                660             665             670
Leu Leu Gln Asp Ala Leu Arg Ile Ser Gln Asn Phe Leu Ser Ser Ile
            675             680             685
Asn Glu Glu Ile Thr Pro Arg Arg Gln Ser Met Thr Val Lys Lys Gly
        690             695             700
Glu His Arg Gln Leu Leu Lys Asp Ser Phe Met Val Glu Leu Val Glu
705             710             715             720
Gly Ala Arg Lys Leu Arg His Val Phe Leu Phe Thr Asp Leu Leu Leu
                725             730             735
Cys Thr Lys Leu Lys Lys Gln Ser Gly Gly Lys Thr Gln Gln Tyr Asp
            740             745             750
Cys Lys Trp Tyr Ile Pro Leu Thr Asp Leu Ser Phe Gln Met Val Asp
            755             760             765
Glu Leu Glu Ala Val Pro Asn Ile Pro Leu Val Pro Asp Glu Glu Leu
        770             775             780
Asp Ala Leu Lys Ile Lys Ile Ser Gln Ile Lys Ser Asp Ile Gln Arg
785             790             795             800
Glu Lys Arg Ala Asn Lys Gly Ser Lys Ala Thr Glu Arg Leu Lys Lys
            805             810             815
Lys Leu Ser Glu Gln Glu Ser Leu Leu Leu Met Ser Pro Ser Met
            820             825             830
Ala Phe Arg Val His Ser Arg Asn Gly Lys Ser Tyr Thr Phe Leu Ile
            835             840             845
Ser Ser Asp Tyr Glu Arg Ala Glu Trp Arg Glu Asn Ile Arg Glu Gln
        850             855             860
Gln Lys Lys Cys Phe Arg Ser Phe Ser Leu Thr Ser Val Glu Leu Gln
865             870             875             880
Met Leu Thr Asn Ser Cys Val Lys Leu Gln Thr Val His Ser Ile Pro
                885             890             895
Leu Thr Ile Asn Lys Glu Glu Ala Leu Gln Arg Pro Val Ala Ser Asp
                900             905             910
Phe Glu Pro Gln Gly Leu Ser Glu Ala Ala Arg Trp Asn Ser Lys Glu
            915             920             925
Asn Leu Leu Ala Gly Pro Ser Glu Asn Asp Pro Asn Leu Phe Val Ala
        930             935             940
Leu Tyr Asp Phe Val Ala Ser Gly Asp Asn Thr Leu Ser Ile Thr Lys
945             950             955             960
Gly Glu Lys Leu Arg Val Leu Gly Tyr Asn His Asn Gly Glu Trp Cys
                965             970             975
Glu Ala Gln Thr Lys Asn Gly Gln Gly Trp Val Pro Ser Asn Tyr Ile
            980             985             990
Thr Pro Val Asn Ser Leu Glu Lys  His Ser Trp Tyr His  Gly Pro Val
        995             1000            1005
Ser Arg  Asn Ala Ala Glu Tyr  Pro Leu Ser Ser Gly  Ile Asn Gly
            1010            1015            1020
Ser Phe Leu Val Arg Glu Ser  Glu Ser Ser Pro Ser  Gln Arg Ser
        1025            1030            1035
Ile Ser Leu Arg Tyr Glu Gly  Arg Val Tyr His Tyr  Arg Ile Asn
        1040            1045            1050
Thr Ala  Ser Asp Gly Lys Leu  Tyr Val Ser Ser Glu  Ser Arg Phe
            1055            1060            1065
Asn Thr  Leu Ala Glu Leu Val  His His Ser Thr  Val Ala Asp
        1070            1075            1080
```

-continued

```
Gly Leu Ile Thr Thr Leu His Tyr Pro Ala Pro Lys Arg Asn Lys
1085                1090                1095

Pro Thr Val Tyr Gly Val Ser Pro Asn Tyr Asp Lys Trp Glu Met
1100                1105                1110

Glu Arg Thr Asp Ile Thr Met Lys His Lys Leu Gly Gly Gly Gln
1115                1120                1125

Tyr Gly Glu Val Tyr Glu Gly Val Trp Lys Lys Tyr Ser Leu Thr
1130                1135                1140

Val Ala Val Lys Thr Leu Lys Glu Asp Thr Met Glu Val Glu Glu
1145                1150                1155

Phe Leu Lys Glu Ala Ala Val Met Lys Glu Ile Lys His Pro Asn
1160                1165                1170

Leu Val Gln Leu Leu Gly Val Cys Thr Arg Glu Pro Pro Phe Tyr
1175                1180                1185

Ile Ile Thr Glu Phe Met Thr Tyr Gly Asn Leu Leu Asp Tyr Leu
1190                1195                1200

Arg Glu Cys Asn Arg Gln Glu Val Asn Ala Val Val Leu Leu Tyr
1205                1210                1215

Met Ala Thr Gln Ile Ser Ser Ala Met Glu Tyr Leu Glu Lys Lys
1220                1225                1230

Asn Phe Ile His Arg Asp Leu Ala Ala Arg Asn Cys Leu Val Gly
1235                1240                1245

Glu Asn His Leu Val Lys Val Ala Asp Phe Gly Leu Ser Arg Leu
1250                1255                1260

Met Thr Gly Asp Thr Tyr Thr Ala His Ala Gly Ala Lys Phe Pro
1265                1270                1275

Ile Lys Trp Thr Ala Pro Glu Ser Leu Ala Tyr Asn Lys Phe Ser
1280                1285                1290

Ile Lys Ser Asp Val Trp Ala Phe Gly Val Leu Leu Trp Glu Ile
1295                1300                1305

Ala Thr Tyr Gly Met Ser Pro Tyr Pro Gly Ile Asp Arg Ser Gln
1310                1315                1320

Val Tyr Glu Leu Leu Glu Lys Asp Tyr Arg Met Lys Arg Pro Glu
1325                1330                1335

Gly Cys Pro Glu Lys Val Tyr Glu Leu Met Arg Ala Cys Trp Gln
1340                1345                1350

Trp Asn Pro Ser Asp Arg Pro Ser Phe Ala Glu Ile His Gln Ala
1355                1360                1365

Phe Glu Thr Met Phe Gln Glu Ser Ser Ile Ser Asp Glu Val Glu
1370                1375                1380

Lys Glu Leu Gly Lys Gln Gly Val Arg Gly Ala Val Thr Thr Leu
1385                1390                1395

Leu Gln Ala Pro Glu Leu Pro Thr Lys Thr Arg Thr Ser Arg Arg
1400                1405                1410

Ala Ala Glu His Arg Asp Thr Thr Asp Val Pro Glu Met Pro His
1415                1420                1425

Ser Lys Gly Gln Gly Glu Ser Asp Pro Leu Asp His Glu Pro Ala
1430                1435                1440

Val Ser Pro Leu Leu Pro Arg Lys Glu Arg Gly Pro Pro Glu Gly
1445                1450                1455

Gly Leu Asn Glu Asp Glu Arg Leu Leu Pro Lys Asp Lys Lys Thr
1460                1465                1470

Asn Leu Phe Ser Ala Leu Ile Lys Lys Lys Lys Lys Thr Ala Pro
1475                1480                1485
```

-continued

```
Thr Pro Pro Lys Arg Ser Ser Ser Phe Arg Glu Met Asp Gly Gln
    1490            1495            1500

Pro Glu Arg Arg Gly Ala Gly Glu Glu Gly Arg Asp Ile Ser
    1505            1510            1515

Asn Gly Ala Leu Ala Phe Thr Pro Leu Asp Thr Ala Asp Pro Ala
    1520            1525            1530

Lys Ser Pro Lys Pro Ser Asn Gly Ala Gly Val Pro Asn Gly Ala
    1535            1540            1545

Leu Arg Glu Ser Gly Gly Ser Gly Phe Arg Ser Pro His Leu Trp
    1550            1555            1560

Lys Lys Ser Ser Thr Leu Thr Ser Ser Arg Leu Ala Thr Gly Glu
    1565            1570            1575

Glu Glu Gly Gly Gly Ser Ser Ser Lys Arg Phe Leu Arg Ser Cys
    1580            1585            1590

Ser Val Ser Cys Val Pro His Gly Ala Lys Asp Thr Glu Trp Arg
    1595            1600            1605

Ser Val Thr Leu Pro Arg Asp Leu Gln Ser Thr Gly Arg Gln Phe
    1610            1615            1620

Asp Ser Ser Thr Phe Gly Gly His Lys Ser Glu Lys Pro Ala Leu
    1625            1630            1635

Pro Arg Lys Arg Ala Gly Glu Asn Arg Ser Asp Gln Val Thr Arg
    1640            1645            1650

Gly Thr Val Thr Pro Pro Arg Leu Val Lys Lys Asn Glu Glu
    1655            1660            1665

Ala Ala Asp Glu Val Phe Lys Asp Ile Met Glu Ser Ser Pro Gly
    1670            1675            1680

Ser Ser Pro Pro Asn Leu Thr Pro Lys Pro Leu Arg Arg Gln Val
    1685            1690            1695

Thr Val Ala Pro Ala Ser Gly Leu Pro His Lys Glu Glu Ala Trp
    1700            1705            1710

Lys Gly Ser Ala Leu Gly Thr Pro Ala Ala Ala Glu Pro Val Thr
    1715            1720            1725

Pro Thr Ser Lys Ala Gly Ser Gly Ala Pro Arg Gly Thr Ser Lys
    1730            1735            1740

Gly Pro Ala Glu Glu Ser Arg Val Arg Arg His Lys His Ser Ser
    1745            1750            1755

Glu Ser Pro Gly Arg Asp Lys Gly Lys Leu Ser Lys Leu Lys Pro
    1760            1765            1770

Ala Pro Pro Pro Pro Ala Ala Ser Ala Gly Lys Ala Gly Gly
    1775            1780            1785

Lys Pro Ser Gln Arg Pro Gly Gln Glu Ala Ala Gly Glu Ala Val
    1790            1795            1800

Leu Gly Ala Lys Thr Lys Ala Thr Ser Leu Val Asp Ala Val Asn
    1805            1810            1815

Ser Asp Ala Ala Lys Pro Ser Gln Pro Ala Glu Gly Leu Lys Lys
    1820            1825            1830

Pro Val Leu Pro Ala Thr Pro Lys Pro His Pro Ala Lys Pro Ser
    1835            1840            1845

Gly Thr Pro Ile Ser Pro Ala Pro Val Pro Leu Ser Thr Leu Pro
    1850            1855            1860

Ser Ala Ser Ser Ala Leu Ala Gly Asp Gln Pro Ser Ser Thr Ala
    1865            1870            1875

Phe Ile Pro Leu Ile Ser Thr Arg Val Ser Leu Arg Lys Thr Arg
```

```
                1880            1885            1890

Gln Pro  Pro Glu Arg Ala Ser  Gly Ala Ile Thr Lys  Gly Val Val
    1895             1900                  1905

Leu Asp Ser Thr Glu Ala Leu  Cys Leu Ala Ile Ser  Gly Asn Ser
    1910            1915                  1920

Glu Gln Met Ala Ser His Ser  Ala Val Leu Glu Ala  Gly Lys Asn
    1925            1930                  1935

Leu Tyr  Thr Phe Cys Val Ser  Tyr Val Asp Ser Ile  Gln Gln Met
    1940            1945                  1950

Arg Asn  Lys Phe Ala Phe Arg  Glu Ala Ile Asn Lys  Leu Glu Asn
    1955            1960                  1965

Asn Leu  Arg Glu Leu Gln Ile  Cys Pro Ala Ser Ala  Gly Ser Gly
    1970            1975                  1980

Pro Ala  Ala Thr Gln Asp Phe  Ser Lys Leu Leu Ser  Ser Val Lys
    1985            1990                  1995

Glu Ile  Ser Asp Ile Val Gln  Arg
    2000            2005

<210> SEQ ID NO 5
<211> LENGTH: 1530
<212> TYPE: PRT
<213> ORGANISM: Homo sapiens

<400> SEQUENCE: 5

Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
        115                 120                 125

Gly Thr Ala Arg Arg Pro Gly Ala Ala Ala Ser Gly Glu Arg Asp Asp
    130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
        195                 200                 205

Gln Met Glu Arg Lys Lys Ser Gln His Gly Ala Gly Ser Ser Val Gly
    210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
```

```
                245                 250                 255
Lys Asp Asn Leu Ile Asp Ala Asn Gly Gly Ser Arg Pro Pro Trp Pro
            260                 265                 270

Pro Leu Glu Tyr Gln Pro Tyr Gln Ser Ile Tyr Val Gly Gly Ile Met
        275                 280                 285

Glu Gly Glu Gly Lys Gly Pro Leu Leu Arg Ser Gln Ser Thr Ser Glu
    290                 295                 300

Gln Glu Lys Arg Leu Thr Trp Pro Arg Arg Ser Tyr Ser Pro Arg Ser
305                 310                 315                 320

Phe Glu Asp Cys Gly Gly Tyr Thr Pro Asp Cys Ser Ser Asn Glu
                325                 330                 335

Asn Leu Thr Ser Ser Glu Glu Asp Phe Ser Ser Gly Gln Ser Ser Arg
            340                 345                 350

Val Ser Pro Ser Pro Thr Thr Tyr Arg Met Phe Arg Asp Lys Ser Arg
        355                 360                 365

Ser Pro Ser Gln Asn Ser Gln Gln Ser Phe Asp Ser Ser Ser Pro Pro
    370                 375                 380

Thr Pro Gln Cys His Lys Arg His Arg His Cys Pro Val Val Val Ser
385                 390                 395                 400

Glu Ala Thr Ile Val Gly Val Arg Lys Thr Gly Gln Ile Trp Pro Asn
                405                 410                 415

Asp Asp Glu Gly Ala Phe His Gly Asp Ala Glu Ala Leu Gln Arg Pro
            420                 425                 430

Val Ala Ser Asp Phe Glu Pro Gln Gly Leu Ser Glu Ala Ala Arg Trp
        435                 440                 445

Asn Ser Lys Glu Asn Leu Leu Ala Gly Pro Ser Glu Asn Asp Pro Asn
    450                 455                 460

Leu Phe Val Ala Leu Tyr Asp Phe Val Ala Ser Gly Asp Asn Thr Leu
465                 470                 475                 480

Ser Ile Thr Lys Gly Glu Lys Leu Arg Val Leu Gly Tyr Asn His Asn
                485                 490                 495

Gly Glu Trp Cys Glu Ala Gln Thr Lys Asn Gly Gln Gly Trp Val Pro
            500                 505                 510

Ser Asn Tyr Ile Thr Pro Val Asn Ser Leu Glu Lys His Ser Trp Tyr
        515                 520                 525

His Gly Pro Val Ser Arg Asn Ala Ala Glu Tyr Pro Leu Ser Ser Gly
    530                 535                 540

Ile Asn Gly Ser Phe Leu Val Arg Glu Ser Glu Ser Ser Pro Ser Gln
545                 550                 555                 560

Arg Ser Ile Ser Leu Arg Tyr Glu Gly Arg Val Tyr His Tyr Arg Ile
                565                 570                 575

Asn Thr Ala Ser Asp Gly Lys Leu Tyr Val Ser Ser Glu Ser Arg Phe
            580                 585                 590

Asn Thr Leu Ala Glu Leu Val His His Ser Thr Val Ala Asp Gly
        595                 600                 605

Leu Ile Thr Thr Leu His Tyr Pro Ala Pro Lys Arg Asn Lys Pro Thr
    610                 615                 620

Val Tyr Gly Val Ser Pro Asn Tyr Asp Lys Trp Glu Met Glu Arg Thr
625                 630                 635                 640

Asp Ile Thr Met Lys His Lys Leu Gly Gly Gly Gln Tyr Gly Glu Val
                645                 650                 655

Tyr Glu Gly Val Trp Lys Lys Tyr Ser Leu Thr Val Ala Val Lys Thr
            660                 665                 670
```

-continued

Leu Lys Glu Asp Thr Met Glu Val Glu Glu Phe Leu Lys Glu Ala Ala
            675                 680                 685

Val Met Lys Glu Ile Lys His Pro Asn Leu Val Gln Leu Leu Gly Val
    690                 695                 700

Cys Thr Arg Glu Pro Pro Phe Tyr Ile Ile Thr Glu Phe Met Thr Tyr
705                 710                 715                 720

Gly Asn Leu Leu Asp Tyr Leu Arg Glu Cys Asn Arg Gln Glu Val Asn
                725                 730                 735

Ala Val Val Leu Leu Tyr Met Ala Thr Gln Ile Ser Ser Ala Met Glu
            740                 745                 750

Tyr Leu Glu Lys Lys Asn Phe Ile His Arg Asp Leu Ala Ala Arg Asn
            755                 760                 765

Cys Leu Val Gly Glu Asn His Leu Val Lys Val Ala Asp Phe Gly Leu
770                 775                 780

Ser Arg Leu Met Thr Gly Asp Thr Tyr Thr Ala His Ala Gly Ala Lys
785                 790                 795                 800

Phe Pro Ile Lys Trp Thr Ala Pro Glu Ser Leu Ala Tyr Asn Lys Phe
                805                 810                 815

Ser Ile Lys Ser Asp Val Trp Ala Phe Gly Val Leu Leu Trp Glu Ile
            820                 825                 830

Ala Thr Tyr Gly Met Ser Pro Tyr Pro Gly Ile Asp Arg Ser Gln Val
            835                 840                 845

Tyr Glu Leu Leu Glu Lys Asp Tyr Arg Met Lys Arg Pro Glu Gly Cys
850                 855                 860

Pro Glu Lys Val Tyr Glu Leu Met Arg Ala Cys Trp Gln Trp Asn Pro
865                 870                 875                 880

Ser Asp Arg Pro Ser Phe Ala Glu Ile His Gln Ala Phe Glu Thr Met
                885                 890                 895

Phe Gln Glu Ser Ser Ile Ser Asp Glu Val Glu Lys Glu Leu Gly Lys
            900                 905                 910

Gln Gly Val Arg Gly Ala Val Thr Thr Leu Leu Gln Ala Pro Glu Leu
            915                 920                 925

Pro Thr Lys Thr Arg Thr Ser Arg Arg Ala Ala Glu His Arg Asp Thr
    930                 935                 940

Thr Asp Val Pro Glu Met Pro His Ser Lys Gly Gln Gly Glu Ser Asp
945                 950                 955                 960

Pro Leu Asp His Glu Pro Ala Val Ser Pro Leu Leu Pro Arg Lys Glu
                965                 970                 975

Arg Gly Pro Pro Glu Gly Gly Leu Asn Glu Asp Glu Arg Leu Leu Pro
            980                 985                 990

Lys Asp Lys Lys Thr Asn Leu Phe Ser Ala Leu Ile Lys Lys Lys Lys
            995                 1000                1005

Lys Thr Ala Pro Thr Pro Pro Lys Arg Ser Ser Ser Phe Arg Glu
    1010                1015                1020

Met Asp Gly Gln Pro Glu Arg Arg Gly Ala Gly Glu Glu Glu Gly
    1025                1030                1035

Arg Asp Ile Ser Asn Gly Ala Leu Ala Phe Thr Pro Leu Asp Thr
    1040                1045                1050

Ala Asp Pro Ala Lys Ser Pro Lys Pro Ser Asn Gly Ala Gly Val
    1055                1060                1065

Pro Asn Gly Ala Leu Arg Glu Ser Gly Gly Ser Gly Phe Arg Ser
    1070                1075                1080

Pro His Leu Trp Lys Lys Ser Ser Thr Leu Thr Ser Ser Arg Leu
    1085                1090                1095

```
Ala Thr Gly Glu Glu Gly Gly Gly Ser Ser Lys Arg Phe
    1100            1105            1110

Leu Arg Ser Cys Ser Val Ser Cys Val Pro His Gly Ala Lys Asp
    1115            1120            1125

Thr Glu Trp Arg Ser Val Thr Leu Pro Arg Asp Leu Gln Ser Thr
    1130            1135            1140

Gly Arg Gln Phe Asp Ser Ser Thr Phe Gly Gly His Lys Ser Glu
    1145            1150            1155

Lys Pro Ala Leu Pro Arg Lys Arg Ala Gly Glu Asn Arg Ser Asp
    1160            1165            1170

Gln Val Thr Arg Gly Thr Val Thr Pro Pro Arg Leu Val Lys
    1175            1180            1185

Lys Asn Glu Glu Ala Ala Asp Glu Val Phe Lys Asp Ile Met Glu
    1190            1195            1200

Ser Ser Pro Gly Ser Ser Pro Pro Asn Leu Thr Pro Lys Pro Leu
    1205            1210            1215

Arg Arg Gln Val Thr Val Ala Pro Ala Ser Gly Leu Pro His Lys
    1220            1225            1230

Glu Glu Ala Trp Lys Gly Ser Ala Leu Gly Thr Pro Ala Ala Ala
    1235            1240            1245

Glu Pro Val Thr Pro Thr Ser Lys Ala Gly Ser Gly Ala Pro Arg
    1250            1255            1260

Gly Thr Ser Lys Gly Pro Ala Glu Glu Ser Arg Val Arg Arg His
    1265            1270            1275

Lys His Ser Ser Glu Ser Pro Gly Arg Asp Lys Gly Lys Leu Ser
    1280            1285            1290

Lys Leu Lys Pro Ala Pro Pro Pro Pro Pro Ala Ala Ser Ala Gly
    1295            1300            1305

Lys Ala Gly Gly Lys Pro Ser Gln Arg Pro Gly Gln Glu Ala Ala
    1310            1315            1320

Gly Glu Ala Val Leu Gly Ala Lys Thr Lys Ala Thr Ser Leu Val
    1325            1330            1335

Asp Ala Val Asn Ser Asp Ala Ala Lys Pro Ser Gln Pro Ala Glu
    1340            1345            1350

Gly Leu Lys Lys Pro Val Leu Pro Ala Thr Pro Lys Pro His Pro
    1355            1360            1365

Ala Lys Pro Ser Gly Thr Pro Ile Ser Pro Ala Pro Val Pro Leu
    1370            1375            1380

Ser Thr Leu Pro Ser Ala Ser Ser Ala Leu Ala Gly Asp Gln Pro
    1385            1390            1395

Ser Ser Thr Ala Phe Ile Pro Leu Ile Ser Thr Arg Val Ser Leu
    1400            1405            1410

Arg Lys Thr Arg Gln Pro Pro Glu Arg Ala Ser Gly Ala Ile Thr
    1415            1420            1425

Lys Gly Val Val Leu Asp Ser Thr Glu Ala Leu Cys Leu Ala Ile
    1430            1435            1440

Ser Gly Asn Ser Glu Gln Met Ala Ser His Ser Ala Val Leu Glu
    1445            1450            1455

Ala Gly Lys Asn Leu Tyr Thr Phe Cys Val Ser Tyr Val Asp Ser
    1460            1465            1470

Ile Gln Gln Met Arg Asn Lys Phe Ala Phe Arg Glu Ala Ile Asn
    1475            1480            1485

Lys Leu Glu Asn Asn Leu Arg Glu Leu Gln Ile Cys Pro Ala Ser
```

-continued

```
                1490                1495                1500
Ala Gly Ser Gly Pro Ala Ala Thr Gln Asp Phe Ser Lys Leu Leu
    1505                1510                1515

Ser Ser Val Lys Glu Ile Ser Asp Ile Val Gln Arg
    1520                1525                1530

<210> SEQ ID NO 6
<211> LENGTH: 2031
<212> TYPE: PRT
<213> ORGANISM: Homo sapiens

<400> SEQUENCE: 6

Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
        115                 120                 125

Gly Thr Ala Arg Arg Pro Gly Ala Ala Ala Ser Gly Glu Arg Asp Asp
    130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
        195                 200                 205

Gln Met Glu Arg Lys Lys Ser Gln His Gly Ala Gly Ser Ser Val Gly
    210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
            260                 265                 270

Pro Leu Glu Tyr Gln Pro Tyr Gln Ser Ile Tyr Val Gly Gly Ile Met
        275                 280                 285

Glu Gly Glu Gly Lys Gly Pro Leu Leu Arg Ser Gln Ser Thr Ser Glu
    290                 295                 300

Gln Glu Lys Arg Leu Thr Trp Pro Arg Arg Ser Tyr Ser Pro Arg Ser
305                 310                 315                 320

Phe Glu Asp Cys Gly Gly Gly Tyr Thr Pro Asp Cys Ser Ser Asn Glu
                325                 330                 335

Asn Leu Thr Ser Ser Glu Glu Asp Phe Ser Ser Gly Gln Ser Ser Arg
```

```
                340                 345                 350
Val Ser Pro Ser Pro Thr Thr Tyr Arg Met Phe Arg Asp Lys Ser Arg
            355                 360                 365

Ser Pro Ser Gln Asn Ser Gln Gln Ser Phe Asp Ser Ser Pro Pro
    370                 375                 380

Thr Pro Gln Cys His Lys Arg His Arg His Cys Pro Val Val Val Ser
385                 390                 395                 400

Glu Ala Thr Ile Val Gly Val Arg Lys Thr Gly Gln Ile Trp Pro Asn
                405                 410                 415

Asp Asp Glu Gly Ala Phe His Gly Asp Ala Asp Gly Ser Phe Gly Thr
            420                 425                 430

Pro Pro Gly Tyr Gly Cys Ala Ala Asp Arg Ala Glu Glu Gln Arg Arg
            435                 440                 445

His Gln Asp Gly Leu Pro Tyr Ile Asp Asp Ser Pro Ser Ser Ser Pro
        450                 455                 460

His Leu Ser Ser Lys Gly Arg Gly Ser Arg Asp Ala Leu Val Ser Gly
465                 470                 475                 480

Ala Leu Lys Ser Thr Lys Ala Ser Glu Leu Asp Leu Glu Lys Gly Leu
                485                 490                 495

Glu Met Arg Lys Trp Val Leu Ser Gly Ile Leu Ala Ser Glu Glu Thr
            500                 505                 510

Tyr Leu Ser His Leu Glu Ala Leu Leu Leu Pro Met Lys Pro Leu Lys
            515                 520                 525

Ala Ala Ala Thr Thr Ser Gln Pro Val Leu Thr Ser Gln Gln Ile Glu
            530                 535                 540

Thr Ile Phe Phe Lys Val Pro Glu Leu Tyr Glu Ile His Lys Glu Ser
545                 550                 555                 560

Tyr Asp Gly Leu Phe Pro Arg Val Gln Gln Trp Ser His Gln Gln Arg
                565                 570                 575

Val Gly Asp Leu Phe Gln Lys Leu Ala Ser Gln Leu Gly Val Tyr Arg
            580                 585                 590

Ala Phe Val Asp Asn Tyr Gly Val Ala Met Glu Met Ala Glu Lys Cys
            595                 600                 605

Cys Gln Ala Asn Ala Gln Phe Ala Glu Ile Ser Glu Asn Leu Arg Ala
    610                 615                 620

Arg Ser Asn Lys Asp Ala Lys Asp Pro Thr Thr Lys Asn Ser Leu Glu
625                 630                 635                 640

Thr Leu Leu Tyr Lys Pro Val Asp Arg Val Thr Arg Ser Thr Leu Val
                645                 650                 655

Leu His Asp Leu Leu Lys His Thr Pro Ala Ser His Pro Asp His Pro
            660                 665                 670

Leu Leu Gln Asp Ala Leu Arg Ile Ser Gln Asn Phe Leu Ser Ser Ile
        675                 680                 685

Asn Glu Glu Ile Thr Pro Arg Arg Gln Ser Met Thr Val Lys Lys Gly
            690                 695                 700

Glu His Arg Gln Leu Leu Lys Asp Ser Phe Met Val Glu Leu Val Glu
705                 710                 715                 720

Gly Ala Arg Lys Leu Arg His Val Phe Leu Phe Thr Asp Leu Leu Leu
                725                 730                 735

Cys Thr Lys Leu Lys Lys Gln Ser Gly Gly Lys Thr Gln Gln Tyr Asp
            740                 745                 750

Cys Lys Trp Tyr Ile Pro Leu Thr Asp Leu Ser Phe Gln Met Val Asp
            755                 760                 765
```

-continued

```
Glu Leu Glu Ala Val Pro Asn Ile Pro Leu Val Pro Asp Glu Glu Leu
770                 775                 780

Asp Ala Leu Lys Ile Lys Ile Ser Gln Ile Lys Ser Asp Ile Gln Arg
785                 790                 795                 800

Glu Lys Arg Ala Asn Lys Gly Ser Lys Ala Thr Glu Arg Leu Lys Lys
                805                 810                 815

Lys Leu Ser Glu Gln Glu Ser Leu Leu Leu Met Ser Pro Ser Met
            820                 825                 830

Ala Phe Arg Val His Ser Arg Asn Gly Lys Ser Tyr Thr Phe Leu Ile
                835                 840                 845

Ser Ser Asp Tyr Glu Arg Ala Glu Trp Arg Glu Asn Ile Arg Glu Gln
850                 855                 860

Gln Lys Lys Cys Phe Arg Ser Phe Ser Leu Thr Ser Val Glu Leu Gln
865                 870                 875                 880

Met Leu Thr Asn Ser Cys Val Lys Leu Gln Thr Val His Ser Ile Pro
                885                 890                 895

Leu Thr Ile Asn Lys Glu Asp Asp Glu Ser Pro Gly Leu Tyr Gly Phe
            900                 905                 910

Leu Asn Val Ile Val His Ser Ala Thr Gly Phe Lys Gln Ser Ser Lys
            915                 920                 925

Ala Leu Gln Arg Pro Val Ala Ser Asp Phe Glu Pro Gln Gly Leu Ser
930                 935                 940

Glu Ala Ala Arg Trp Asn Ser Lys Glu Asn Leu Leu Ala Gly Pro Ser
945                 950                 955                 960

Glu Asn Asp Pro Asn Leu Phe Val Ala Leu Tyr Asp Phe Val Ala Ser
                965                 970                 975

Gly Asp Asn Thr Leu Ser Ile Thr Lys Gly Glu Lys Leu Arg Val Leu
            980                 985                 990

Gly Tyr Asn His Asn Gly Glu Trp Cys Glu Ala Gln Thr Lys Asn Gly
            995                 1000                1005

Gln Gly Trp Val Pro Ser Asn Tyr Ile Thr Pro Val Asn Ser Leu
    1010                1015                1020

Glu Lys His Ser Trp Tyr His Gly Pro Val Ser Arg Asn Ala Ala
    1025                1030                1035

Glu Tyr Pro Leu Ser Ser Gly Ile Asn Gly Ser Phe Leu Val Arg
    1040                1045                1050

Glu Ser Glu Ser Ser Pro Ser Gln Arg Ser Ile Ser Leu Arg Tyr
    1055                1060                1065

Glu Gly Arg Val Tyr His Tyr Arg Ile Asn Thr Ala Ser Asp Gly
    1070                1075                1080

Lys Leu Tyr Val Ser Ser Glu Ser Arg Phe Asn Thr Leu Ala Glu
    1085                1090                1095

Leu Val His His His Ser Thr Val Ala Asp Gly Leu Ile Thr Thr
    1100                1105                1110

Leu His Tyr Pro Ala Pro Lys Arg Asn Lys Pro Thr Val Tyr Gly
    1115                1120                1125

Val Ser Pro Asn Tyr Asp Lys Trp Glu Met Glu Arg Thr Asp Ile
    1130                1135                1140

Thr Met Lys His Lys Leu Gly Gly Gly Gln Tyr Gly Glu Val Tyr
    1145                1150                1155

Glu Gly Val Trp Lys Lys Tyr Ser Leu Thr Val Ala Val Lys Thr
    1160                1165                1170

Leu Lys Glu Asp Thr Met Glu Val Glu Glu Phe Leu Lys Glu Ala
    1175                1180                1185
```

```
Ala Val Met Lys Glu Ile Lys His Pro Asn Leu Val Gln Leu Leu
        1190            1195                1200
Gly Val Cys Thr Arg Glu Pro Pro Phe Tyr Ile Ile Ile Glu Phe
        1205            1210                1215
Met Thr Tyr Gly Asn Leu Leu Asp Tyr Leu Arg Glu Cys Asn Arg
        1220            1225                1230
Gln Glu Val Asn Ala Val Val Leu Leu Tyr Met Ala Thr Gln Ile
        1235            1240                1245
Ser Ser Ala Met Glu Tyr Leu Glu Lys Lys Asn Phe Ile His Arg
        1250            1255                1260
Asp Leu Ala Ala Arg Asn Cys Leu Val Gly Glu Asn His Leu Val
        1265            1270                1275
Lys Val Ala Asp Phe Gly Leu Ser Arg Leu Met Thr Gly Asp Thr
        1280            1285                1290
Tyr Thr Ala His Ala Gly Ala Lys Phe Pro Ile Lys Trp Thr Ala
        1295            1300                1305
Pro Glu Ser Leu Ala Tyr Asn Lys Phe Ser Ile Lys Ser Asp Val
        1310            1315                1320
Trp Ala Phe Gly Val Leu Leu Trp Glu Ile Ala Thr Tyr Gly Met
        1325            1330                1335
Ser Pro Tyr Pro Gly Ile Asp Arg Ser Gln Val Tyr Glu Leu Leu
        1340            1345                1350
Glu Lys Asp Tyr Arg Met Lys Arg Pro Glu Gly Cys Pro Glu Lys
        1355            1360                1365
Val Tyr Glu Leu Met Arg Ala Cys Trp Gln Trp Asn Pro Ser Asp
        1370            1375                1380
Arg Pro Ser Phe Ala Glu Ile His Gln Ala Phe Glu Thr Met Phe
        1385            1390                1395
Gln Glu Ser Ser Ile Ser Asp Glu Val Glu Lys Glu Leu Gly Lys
        1400            1405                1410
Gln Gly Val Arg Gly Ala Val Thr Thr Leu Leu Gln Ala Pro Glu
        1415            1420                1425
Leu Pro Thr Lys Thr Arg Thr Ser Arg Arg Ala Ala Glu His Arg
        1430            1435                1440
Asp Thr Thr Asp Val Pro Glu Met Pro His Ser Lys Gly Gln Gly
        1445            1450                1455
Glu Ser Asp Pro Leu Asp His Glu Pro Ala Val Ser Pro Leu Leu
        1460            1465                1470
Pro Arg Lys Glu Arg Gly Pro Pro Glu Gly Gly Leu Asn Glu Asp
        1475            1480                1485
Glu Arg Leu Leu Pro Lys Asp Lys Lys Thr Asn Leu Phe Ser Ala
        1490            1495                1500
Leu Ile Lys Lys Lys Lys Lys Thr Ala Pro Thr Pro Pro Lys Arg
        1505            1510                1515
Ser Ser Ser Phe Arg Glu Met Asp Gly Gln Pro Glu Arg Arg Gly
        1520            1525                1530
Ala Gly Glu Glu Glu Gly Arg Asp Ile Ser Asn Gly Ala Leu Ala
        1535            1540                1545
Phe Thr Pro Leu Asp Thr Ala Asp Pro Ala Lys Ser Pro Lys Pro
        1550            1555                1560
Ser Asn Gly Ala Gly Val Pro Asn Gly Ala Leu Arg Glu Ser Gly
        1565            1570                1575
Gly Ser Gly Phe Arg Ser Pro His Leu Trp Lys Lys Ser Ser Thr
```

-continued

```
                1580                1585                1590

Leu Thr Ser Ser Arg Leu Ala Thr Gly Glu Glu Glu Gly Gly Gly
    1595                1600                1605

Ser Ser Ser Lys Arg Phe Leu Arg Ser Cys Ser Val Ser Cys Val
    1610                1615                1620

Pro His Gly Ala Lys Asp Thr Glu Trp Arg Ser Val Thr Leu Pro
    1625                1630                1635

Arg Asp Leu Gln Ser Thr Gly Arg Gln Phe Asp Ser Ser Thr Phe
    1640                1645                1650

Gly Gly His Lys Ser Glu Lys Pro Ala Leu Pro Arg Lys Arg Ala
    1655                1660                1665

Gly Glu Asn Arg Ser Asp Gln Val Thr Arg Gly Thr Val Thr Pro
    1670                1675                1680

Pro Pro Arg Leu Val Lys Lys Asn Glu Glu Ala Ala Asp Glu Val
    1685                1690                1695

Phe Lys Asp Ile Met Glu Ser Ser Pro Gly Ser Ser Pro Pro Asn
    1700                1705                1710

Leu Thr Pro Lys Pro Leu Arg Arg Gln Val Thr Val Ala Pro Ala
    1715                1720                1725

Ser Gly Leu Pro His Lys Glu Glu Ala Trp Lys Gly Ser Ala Leu
    1730                1735                1740

Gly Thr Pro Ala Ala Ala Glu Pro Val Thr Pro Thr Ser Lys Ala
    1745                1750                1755

Gly Ser Gly Ala Pro Arg Gly Thr Ser Lys Gly Pro Ala Glu Glu
    1760                1765                1770

Ser Arg Val Arg Arg His Lys His Ser Ser Glu Ser Pro Gly Arg
    1775                1780                1785

Asp Lys Gly Lys Leu Ser Lys Leu Lys Pro Ala Pro Pro Pro Pro
    1790                1795                1800

Pro Ala Ala Ser Ala Gly Lys Ala Gly Gly Lys Pro Ser Gln Arg
    1805                1810                1815

Pro Gly Gln Glu Ala Ala Gly Glu Ala Val Leu Gly Ala Lys Thr
    1820                1825                1830

Lys Ala Thr Ser Leu Val Asp Ala Val Asn Ser Asp Ala Ala Lys
    1835                1840                1845

Pro Ser Gln Pro Ala Glu Gly Leu Lys Lys Pro Val Leu Pro Ala
    1850                1855                1860

Thr Pro Lys Pro His Pro Ala Lys Pro Ser Gly Thr Pro Ile Ser
    1865                1870                1875

Pro Ala Pro Val Pro Leu Ser Thr Leu Pro Ser Ala Ser Ser Ala
    1880                1885                1890

Leu Ala Gly Asp Gln Pro Ser Ser Thr Ala Phe Ile Pro Leu Ile
    1895                1900                1905

Ser Thr Arg Val Ser Leu Arg Lys Thr Arg Gln Pro Pro Glu Arg
    1910                1915                1920

Ala Ser Gly Ala Ile Thr Lys Gly Val Val Leu Asp Ser Thr Glu
    1925                1930                1935

Ala Leu Cys Leu Ala Ile Ser Gly Asn Ser Glu Gln Met Ala Ser
    1940                1945                1950

His Ser Ala Val Leu Glu Ala Gly Lys Asn Leu Tyr Thr Phe Cys
    1955                1960                1965

Val Ser Tyr Val Asp Ser Ile Gln Gln Met Arg Asn Lys Phe Ala
    1970                1975                1980
```

```
Phe Arg Glu Ala Ile Asn Lys Leu Glu Asn Asn Leu Arg Glu Leu
    1985                1990                1995

Gln Ile Cys Pro Ala Ser Ala Gly Ser Gly Pro Ala Ala Thr Gln
    2000                2005                2010

Asp Phe Ser Lys Leu Leu Ser Ser Val Lys Glu Ile Ser Asp Ile
    2015                2020                2025

Val Gln Arg
    2030

<210> SEQ ID NO 7
<211> LENGTH: 2006
<212> TYPE: PRT
<213> ORGANISM: Homo sapiens

<400> SEQUENCE: 7

Met Val Asp Pro Val Gly Phe Ala Glu Ala Trp Lys Ala Gln Phe Pro
  1               5                  10                  15

Asp Ser Glu Pro Pro Arg Met Glu Leu Arg Ser Val Gly Asp Ile Glu
             20                  25                  30

Gln Glu Leu Glu Arg Cys Lys Ala Ser Ile Arg Arg Leu Glu Gln Glu
         35                  40                  45

Val Asn Gln Glu Arg Phe Arg Met Ile Tyr Leu Gln Thr Leu Leu Ala
     50                  55                  60

Lys Glu Lys Lys Ser Tyr Asp Arg Gln Arg Trp Gly Phe Arg Arg Ala
 65                  70                  75                  80

Ala Gln Ala Pro Asp Gly Ala Ser Glu Pro Arg Ala Ser Ala Ser Arg
                 85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
            115                 120                 125

Gly Thr Ala Arg Arg Pro Gly Ala Ala Ala Ser Gly Glu Arg Asp Asp
130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
            195                 200                 205

Gln Met Glu Arg Lys Lys Ser Gln His Gly Ala Gly Ser Ser Val Gly
        210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
            260                 265                 270

Pro Leu Glu Tyr Gln Pro Tyr Gln Ser Ile Tyr Val Gly Gly Ile Met
            275                 280                 285

Glu Gly Glu Gly Lys Gly Pro Leu Leu Arg Ser Gln Ser Thr Ser Glu
        290                 295                 300

Gln Glu Lys Arg Leu Thr Trp Pro Arg Arg Ser Tyr Ser Pro Arg Ser
305                 310                 315                 320
```

```
Phe Glu Asp Cys Gly Gly Tyr Thr Pro Asp Cys Ser Ser Asn Glu
                325                 330                 335

Asn Leu Thr Ser Ser Glu Glu Asp Phe Ser Ser Gly Gln Ser Arg
            340                 345                 350

Val Ser Pro Ser Pro Thr Thr Tyr Arg Met Phe Arg Asp Lys Ser Arg
        355                 360                 365

Ser Pro Ser Gln Asn Ser Gln Gln Ser Phe Asp Ser Ser Ser Pro Pro
    370                 375                 380

Thr Pro Gln Cys His Lys Arg His Arg His Cys Pro Val Val Val Ser
385                 390                 395                 400

Glu Ala Thr Ile Val Gly Val Arg Lys Thr Gly Gln Ile Trp Pro Asn
                405                 410                 415

Asp Asp Glu Gly Ala Phe His Gly Asp Ala Asp Gly Ser Phe Gly Thr
            420                 425                 430

Pro Pro Gly Tyr Gly Cys Ala Ala Asp Arg Ala Glu Glu Gln Arg Arg
        435                 440                 445

His Gln Asp Gly Leu Pro Tyr Ile Asp Asp Ser Pro Ser Ser Ser Pro
    450                 455                 460

His Leu Ser Ser Lys Gly Arg Gly Ser Arg Asp Ala Leu Val Ser Gly
465                 470                 475                 480

Ala Leu Lys Ser Thr Lys Ala Ser Glu Leu Asp Leu Glu Lys Gly Leu
                485                 490                 495

Glu Met Arg Lys Trp Val Leu Ser Gly Ile Leu Ala Ser Glu Glu Thr
            500                 505                 510

Tyr Leu Ser His Leu Glu Ala Leu Leu Leu Pro Met Lys Pro Leu Lys
        515                 520                 525

Ala Ala Ala Thr Thr Ser Gln Pro Val Leu Thr Ser Gln Gln Ile Glu
    530                 535                 540

Thr Ile Phe Phe Lys Val Pro Glu Leu Tyr Glu Ile His Lys Glu Ser
545                 550                 555                 560

Tyr Asp Gly Leu Phe Pro Arg Val Gln Gln Trp Ser His Gln Gln Arg
                565                 570                 575

Val Gly Asp Leu Phe Gln Lys Leu Ala Ser Gln Leu Gly Val Tyr Arg
            580                 585                 590

Ala Phe Val Asp Asn Tyr Gly Val Ala Met Glu Met Ala Glu Lys Cys
        595                 600                 605

Cys Gln Ala Asn Ala Gln Phe Ala Glu Ile Ser Glu Asn Leu Arg Ala
    610                 615                 620

Arg Ser Asn Lys Asp Ala Lys Asp Pro Thr Thr Lys Asn Ser Leu Glu
625                 630                 635                 640

Thr Leu Leu Tyr Lys Pro Val Asp Arg Val Thr Arg Ser Thr Leu Val
                645                 650                 655

Leu His Asp Leu Leu Lys His Thr Pro Ala Ser His Pro Asp His Pro
            660                 665                 670

Leu Leu Gln Asp Ala Leu Arg Ile Ser Gln Asn Phe Leu Ser Ser Ile
        675                 680                 685

Asn Glu Glu Ile Thr Pro Arg Arg Gln Ser Met Thr Val Lys Lys Gly
    690                 695                 700

Glu His Arg Gln Leu Leu Lys Asp Ser Phe Met Val Glu Leu Val Glu
705                 710                 715                 720

Gly Ala Arg Lys Leu Arg His Val Phe Leu Phe Thr Asp Leu Leu Leu
                725                 730                 735

Cys Thr Lys Leu Lys Lys Gln Ser Gly Gly Lys Thr Gln Gln Tyr Asp
            740                 745                 750
```

-continued

Cys Lys Trp Tyr Ile Pro Leu Thr Asp Leu Ser Phe Gln Met Val Asp
         755                 760                 765

Glu Leu Glu Ala Val Pro Asn Ile Pro Leu Val Pro Asp Glu Glu Leu
770                 775                 780

Asp Ala Leu Lys Ile Lys Ile Ser Gln Ile Lys Ser Asp Ile Gln Arg
785                 790                 795                 800

Glu Lys Arg Ala Asn Lys Gly Ser Lys Ala Thr Glu Arg Leu Lys Lys
                805                 810                 815

Lys Leu Ser Glu Gln Glu Ser Leu Leu Leu Met Ser Pro Ser Met
            820                 825                 830

Ala Phe Arg Val His Ser Arg Asn Gly Lys Ser Tyr Thr Phe Leu Ile
            835                 840                 845

Ser Ser Asp Tyr Glu Arg Ala Glu Trp Arg Glu Asn Ile Arg Glu Gln
    850                 855                 860

Gln Lys Lys Cys Phe Arg Ser Phe Ser Leu Thr Ser Val Glu Leu Gln
865             870                 875                 880

Met Leu Thr Asn Ser Cys Val Lys Leu Gln Thr Val His Ser Ile Pro
                885                 890                 895

Leu Thr Ile Asn Lys Glu Ala Leu Gln Arg Pro Val Ala Ser Asp
                900                 905                 910

Phe Glu Pro Gln Gly Leu Ser Glu Ala Ala Arg Trp Asn Ser Lys Glu
            915                 920                 925

Asn Leu Leu Ala Gly Pro Ser Glu Asn Asp Pro Asn Leu Phe Val Ala
    930                 935                 940

Leu Tyr Asp Phe Val Ala Ser Gly Asp Asn Thr Leu Ser Ile Thr Lys
945                 950                 955                 960

Gly Glu Lys Leu Arg Val Leu Gly Tyr Asn His Asn Gly Glu Trp Cys
                965                 970                 975

Glu Ala Gln Thr Lys Asn Gly Gln Gly Trp Val Pro Ser Asn Tyr Ile
                980                 985                 990

Thr Pro Val Asn Ser Leu Glu Lys His Ser Trp Tyr His Gly Pro Val
        995                 1000                1005

Ser Arg Asn Ala Ala Glu Tyr Pro Leu Ser Ser Gly Ile Asn Gly
    1010                1015                1020

Ser Phe Leu Val Arg Glu Ser Glu Ser Ser Pro Ser Gln Arg Ser
    1025                1030                1035

Ile Ser Leu Arg Tyr Glu Gly Arg Val Tyr His Tyr Arg Ile Asn
    1040                1045                1050

Thr Ala Ser Asp Gly Lys Leu Tyr Val Ser Ser Glu Ser Arg Phe
    1055                1060                1065

Asn Thr Leu Ala Glu Leu Val His His His Ser Thr Val Ala Asp
    1070                1075                1080

Gly Leu Ile Thr Thr Leu His Tyr Pro Ala Pro Lys Arg Asn Lys
    1085                1090                1095

Pro Thr Val Tyr Gly Val Ser Pro Asn Tyr Asp Lys Trp Glu Met
    1100                1105                1110

Glu Arg Thr Asp Ile Thr Met Lys His Lys Leu Gly Gly Gly Gln
    1115                1120                1125

Tyr Gly Glu Val Tyr Glu Gly Val Trp Lys Lys Tyr Ser Leu Thr
    1130                1135                1140

Val Ala Val Lys Thr Leu Lys Glu Asp Thr Met Glu Val Glu Glu
    1145                1150                1155

Phe Leu Lys Glu Ala Ala Val Met Lys Glu Ile Lys His Pro Asn

```
              1160              1165              1170

Leu Val Gln Leu Leu Gly Val Cys Thr Arg Glu Pro Pro Phe Tyr
    1175              1180              1185

Ile Ile Ile Glu Phe Met Thr Tyr Gly Asn Leu Leu Asp Tyr Leu
    1190              1195              1200

Arg Glu Cys Asn Arg Gln Glu Val Asn Ala Val Val Leu Leu Tyr
    1205              1210              1215

Met Ala Thr Gln Ile Ser Ser Ala Met Glu Tyr Leu Glu Lys Lys
    1220              1225              1230

Asn Phe Ile His Arg Asp Leu Ala Ala Arg Asn Cys Leu Val Gly
    1235              1240              1245

Glu Asn His Leu Val Lys Val Ala Asp Phe Gly Leu Ser Arg Leu
    1250              1255              1260

Met Thr Gly Asp Thr Tyr Thr Ala His Ala Gly Ala Lys Phe Pro
    1265              1270              1275

Ile Lys Trp Thr Ala Pro Glu Ser Leu Ala Tyr Asn Lys Phe Ser
    1280              1285              1290

Ile Lys Ser Asp Val Trp Ala Phe Gly Val Leu Leu Trp Glu Ile
    1295              1300              1305

Ala Thr Tyr Gly Met Ser Pro Tyr Pro Gly Ile Asp Arg Ser Gln
    1310              1315              1320

Val Tyr Glu Leu Leu Glu Lys Asp Tyr Arg Met Lys Arg Pro Glu
    1325              1330              1335

Gly Cys Pro Glu Lys Val Tyr Glu Leu Met Arg Ala Cys Trp Gln
    1340              1345              1350

Trp Asn Pro Ser Asp Arg Pro Ser Phe Ala Glu Ile His Gln Ala
    1355              1360              1365

Phe Glu Thr Met Phe Gln Glu Ser Ser Ile Ser Asp Glu Val Glu
    1370              1375              1380

Lys Glu Leu Gly Lys Gln Gly Val Arg Gly Ala Val Thr Thr Leu
    1385              1390              1395

Leu Gln Ala Pro Glu Leu Pro Thr Lys Thr Arg Thr Ser Arg Arg
    1400              1405              1410

Ala Ala Glu His Arg Asp Thr Thr Asp Val Pro Glu Met Pro His
    1415              1420              1425

Ser Lys Gly Gln Gly Glu Ser Asp Pro Leu Asp His Glu Pro Ala
    1430              1435              1440

Val Ser Pro Leu Leu Pro Arg Lys Glu Arg Gly Pro Pro Glu Gly
    1445              1450              1455

Gly Leu Asn Glu Asp Glu Arg Leu Leu Pro Lys Asp Lys Lys Thr
    1460              1465              1470

Asn Leu Phe Ser Ala Leu Ile Lys Lys Lys Lys Thr Ala Pro
    1475              1480              1485

Thr Pro Pro Lys Arg Ser Ser Ser Phe Arg Glu Met Asp Gly Gln
    1490              1495              1500

Pro Glu Arg Arg Gly Ala Gly Glu Glu Glu Gly Arg Asp Ile Ser
    1505              1510              1515

Asn Gly Ala Leu Ala Phe Thr Pro Leu Asp Thr Ala Asp Pro Ala
    1520              1525              1530

Lys Ser Pro Lys Pro Ser Asn Gly Ala Gly Val Pro Asn Gly Ala
    1535              1540              1545

Leu Arg Glu Ser Gly Gly Ser Gly Phe Arg Ser Pro His Leu Trp
    1550              1555              1560
```

-continued

```
Lys Lys Ser Ser Thr Leu Thr Ser Ser Arg Leu Ala Thr Gly Glu
1565            1570                1575

Glu Glu Gly Gly Gly Ser Ser Ser Lys Arg Phe Leu Arg Ser Cys
1580            1585                1590

Ser Val Ser Cys Val Pro His Gly Ala Lys Asp Thr Glu Trp Arg
1595            1600                1605

Ser Val Thr Leu Pro Arg Asp Leu Gln Ser Thr Gly Arg Gln Phe
1610            1615                1620

Asp Ser Ser Thr Phe Gly Gly His Lys Ser Glu Lys Pro Ala Leu
1625            1630                1635

Pro Arg Lys Arg Ala Gly Glu Asn Arg Ser Asp Gln Val Thr Arg
1640            1645                1650

Gly Thr Val Thr Pro Pro Arg Leu Val Lys Lys Asn Glu Glu
1655            1660                1665

Ala Ala Asp Glu Val Phe Lys Asp Ile Met Glu Ser Ser Pro Gly
1670            1675                1680

Ser Ser Pro Pro Asn Leu Thr Pro Lys Pro Leu Arg Arg Gln Val
1685            1690                1695

Thr Val Ala Pro Ala Ser Gly Leu Pro His Lys Glu Glu Ala Trp
1700            1705                1710

Lys Gly Ser Ala Leu Gly Thr Pro Ala Ala Glu Pro Val Thr
1715            1720                1725

Pro Thr Ser Lys Ala Gly Ser Gly Ala Pro Arg Gly Thr Ser Lys
1730            1735                1740

Gly Pro Ala Glu Glu Ser Arg Val Arg Arg His Lys His Ser Ser
1745            1750                1755

Glu Ser Pro Gly Arg Asp Lys Gly Lys Leu Ser Lys Leu Lys Pro
1760            1765                1770

Ala Pro Pro Pro Pro Ala Ala Ser Ala Gly Lys Ala Gly Gly
1775            1780                1785

Lys Pro Ser Gln Arg Pro Gly Gln Glu Ala Ala Gly Glu Ala Val
1790            1795                1800

Leu Gly Ala Lys Thr Lys Ala Thr Ser Leu Val Asp Ala Val Asn
1805            1810                1815

Ser Asp Ala Ala Lys Pro Ser Gln Pro Ala Glu Gly Leu Lys Lys
1820            1825                1830

Pro Val Leu Pro Ala Thr Pro Lys Pro His Pro Ala Lys Pro Ser
1835            1840                1845

Gly Thr Pro Ile Ser Pro Ala Pro Val Pro Leu Ser Thr Leu Pro
1850            1855                1860

Ser Ala Ser Ser Ala Leu Ala Gly Asp Gln Pro Ser Ser Thr Ala
1865            1870                1875

Phe Ile Pro Leu Ile Ser Thr Arg Val Ser Leu Arg Lys Thr Arg
1880            1885                1890

Gln Pro Pro Glu Arg Ala Ser Gly Ala Ile Thr Lys Gly Val Val
1895            1900                1905

Leu Asp Ser Thr Glu Ala Leu Cys Leu Ala Ile Ser Gly Asn Ser
1910            1915                1920

Glu Gln Met Ala Ser His Ser Ala Val Leu Glu Ala Gly Lys Asn
1925            1930                1935

Leu Tyr Thr Phe Cys Val Ser Tyr Val Asp Ser Ile Gln Gln Met
1940            1945                1950

Arg Asn Lys Phe Ala Phe Arg Glu Ala Ile Asn Lys Leu Glu Asn
1955            1960                1965
```

```
Asn Leu Arg Glu Leu Gln Ile Cys Pro Ala Ser Ala Gly Ser Gly
    1970                1975                1980

Pro Ala Ala Thr Gln Asp Phe Ser Lys Leu Leu Ser Ser Val Lys
    1985                1990                1995

Glu Ile Ser Asp Ile Val Gln Arg
    2000                2005

<210> SEQ ID NO 8
<211> LENGTH: 1530
<212> TYPE: PRT
<213> ORGANISM: Homo sapiens

<400> SEQUENCE: 8

Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
                20                  25                  30

Gln Glu Leu Glu Arg Cys Lys Ala Ser Ile Arg Arg Leu Glu Gln Glu
            35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
                100                 105                 110

Pro Glu Ala Arg Pro Asp Gly Glu Gly Ser Pro Gly Lys Ala Arg Pro
            115                 120                 125

Gly Thr Ala Arg Arg Pro Gly Ala Ala Ser Gly Glu Arg Asp Asp
            130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
                180                 185                 190

Asp Lys Glu Val Ser Asp Arg Ile Ser Ser Leu Gly Ser Gln Ala Met
            195                 200                 205

Gln Met Glu Arg Lys Lys Ser Gln His Gly Ala Gly Ser Ser Val Gly
        210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
                260                 265                 270

Pro Leu Glu Tyr Gln Pro Tyr Gln Ser Ile Tyr Val Gly Gly Ile Met
            275                 280                 285

Glu Gly Glu Gly Lys Gly Pro Leu Leu Arg Ser Gln Ser Thr Ser Glu
        290                 295                 300

Gln Glu Lys Arg Leu Thr Trp Pro Arg Arg Ser Tyr Ser Pro Arg Ser
305                 310                 315                 320

Phe Glu Asp Cys Gly Gly Gly Tyr Thr Pro Asp Cys Ser Ser Asn Glu
                325                 330                 335
```

```
Asn Leu Thr Ser Ser Glu Glu Asp Phe Ser Ser Gly Gln Ser Ser Arg
            340                 345                 350

Val Ser Pro Ser Pro Thr Thr Tyr Arg Met Phe Arg Asp Lys Ser Arg
            355                 360                 365

Ser Pro Ser Gln Asn Ser Gln Gln Ser Phe Asp Ser Ser Pro Pro
370                 375                 380

Thr Pro Gln Cys His Lys Arg His Arg His Cys Pro Val Val Val Ser
385                 390                 395                 400

Glu Ala Thr Ile Val Gly Val Arg Lys Thr Gly Gln Ile Trp Pro Asn
                405                 410                 415

Asp Asp Glu Gly Ala Phe His Gly Asp Ala Glu Ala Leu Gln Arg Pro
                420                 425                 430

Val Ala Ser Asp Phe Glu Pro Gln Gly Leu Ser Glu Ala Ala Arg Trp
            435                 440                 445

Asn Ser Lys Glu Asn Leu Leu Ala Gly Pro Ser Glu Asn Asp Pro Asn
450                 455                 460

Leu Phe Val Ala Leu Tyr Asp Phe Val Ala Ser Gly Asp Asn Thr Leu
465                 470                 475                 480

Ser Ile Thr Lys Gly Glu Lys Leu Arg Val Leu Gly Tyr Asn His Asn
                485                 490                 495

Gly Glu Trp Cys Glu Ala Gln Thr Lys Asn Gly Gln Gly Trp Val Pro
                500                 505                 510

Ser Asn Tyr Ile Thr Pro Val Asn Ser Leu Glu Lys His Ser Trp Tyr
            515                 520                 525

His Gly Pro Val Ser Arg Asn Ala Ala Glu Tyr Pro Leu Ser Ser Gly
            530                 535                 540

Ile Asn Gly Ser Phe Leu Val Arg Glu Ser Ser Ser Pro Ser Gln
545                 550                 555                 560

Arg Ser Ile Ser Leu Arg Tyr Glu Gly Arg Val Tyr His Tyr Arg Ile
                565                 570                 575

Asn Thr Ala Ser Asp Gly Lys Leu Tyr Val Ser Ser Glu Ser Arg Phe
            580                 585                 590

Asn Thr Leu Ala Glu Leu Val His His His Ser Thr Val Ala Asp Gly
            595                 600                 605

Leu Ile Thr Thr Leu His Tyr Pro Ala Pro Lys Arg Asn Lys Pro Thr
610                 615                 620

Val Tyr Gly Val Ser Pro Asn Tyr Asp Lys Trp Glu Met Glu Arg Thr
625                 630                 635                 640

Asp Ile Thr Met Lys His Lys Leu Gly Gly Gly Gln Tyr Gly Glu Val
                645                 650                 655

Tyr Glu Gly Val Trp Lys Lys Tyr Ser Leu Thr Val Ala Val Lys Thr
                660                 665                 670

Leu Lys Glu Asp Thr Met Glu Val Glu Glu Phe Leu Lys Glu Ala Ala
            675                 680                 685

Val Met Lys Glu Ile Lys His Pro Asn Leu Val Gln Leu Leu Gly Val
            690                 695                 700

Cys Thr Arg Glu Pro Pro Phe Tyr Ile Ile Ile Glu Phe Met Thr Tyr
705                 710                 715                 720

Gly Asn Leu Leu Asp Tyr Leu Arg Glu Cys Asn Arg Gln Glu Val Asn
                725                 730                 735

Ala Val Val Leu Leu Tyr Met Ala Thr Gln Ile Ser Ser Ala Met Glu
                740                 745                 750

Tyr Leu Glu Lys Lys Asn Phe Ile His Arg Asp Leu Ala Ala Arg Asn
```

```
                    755                 760                 765
Cys Leu Val Gly Glu Asn His Leu Val Lys Val Ala Asp Phe Gly Leu
770                 775                 780

Ser Arg Leu Met Thr Gly Asp Thr Tyr Thr Ala His Ala Gly Ala Lys
785                 790                 795                 800

Phe Pro Ile Lys Trp Thr Ala Pro Glu Ser Leu Ala Tyr Asn Lys Phe
                    805                 810                 815

Ser Ile Lys Ser Asp Val Trp Ala Phe Gly Val Leu Leu Trp Glu Ile
                820                 825                 830

Ala Thr Tyr Gly Met Ser Pro Tyr Pro Gly Ile Asp Arg Ser Gln Val
                835                 840                 845

Tyr Glu Leu Leu Glu Lys Asp Tyr Arg Met Lys Arg Pro Glu Gly Cys
                850                 855                 860

Pro Glu Lys Val Tyr Glu Leu Met Arg Ala Cys Trp Gln Trp Asn Pro
865                 870                 875                 880

Ser Asp Arg Pro Ser Phe Ala Glu Ile His Gln Ala Phe Glu Thr Met
                    885                 890                 895

Phe Gln Glu Ser Ser Ile Ser Asp Glu Val Glu Lys Glu Leu Gly Lys
                900                 905                 910

Gln Gly Val Arg Gly Ala Val Thr Thr Leu Leu Gln Ala Pro Glu Leu
                915                 920                 925

Pro Thr Lys Thr Arg Thr Ser Arg Arg Ala Ala Glu His Arg Asp Thr
930                 935                 940

Thr Asp Val Pro Glu Met Pro His Ser Lys Gly Gln Gly Glu Ser Asp
945                 950                 955                 960

Pro Leu Asp His Glu Pro Ala Val Ser Pro Leu Leu Pro Arg Lys Glu
                    965                 970                 975

Arg Gly Pro Pro Glu Gly Gly Leu Asn Glu Asp Glu Arg Leu Leu Pro
                980                 985                 990

Lys Asp Lys Lys Thr Asn Leu Phe Ser Ala Leu Ile Lys Lys Lys Lys
                995                 1000                1005

Lys Thr Ala Pro Thr Pro Pro Lys Arg Ser Ser Ser Phe Arg Glu
    1010                1015                1020

Met Asp Gly Gln Pro Glu Arg Arg Gly Ala Gly Glu Glu Glu Gly
    1025                1030                1035

Arg Asp Ile Ser Asn Gly Ala Leu Ala Phe Thr Pro Leu Asp Thr
    1040                1045                1050

Ala Asp Pro Ala Lys Ser Pro Lys Pro Ser Asn Gly Ala Gly Val
    1055                1060                1065

Pro Asn Gly Ala Leu Arg Glu Ser Gly Gly Ser Gly Phe Arg Ser
    1070                1075                1080

Pro His Leu Trp Lys Lys Ser Ser Thr Leu Thr Ser Ser Arg Leu
    1085                1090                1095

Ala Thr Gly Glu Glu Glu Gly Gly Gly Ser Ser Ser Lys Arg Phe
    1100                1105                1110

Leu Arg Ser Cys Ser Val Ser Cys Val Pro His Gly Ala Lys Asp
    1115                1120                1125

Thr Glu Trp Arg Ser Val Thr Leu Pro Arg Asp Leu Gln Ser Thr
    1130                1135                1140

Gly Arg Gln Phe Asp Ser Ser Thr Phe Gly Gly His Lys Ser Glu
    1145                1150                1155

Lys Pro Ala Leu Pro Arg Lys Arg Ala Gly Glu Asn Arg Ser Asp
    1160                1165                1170
```

| | | | | | | | | | | |
|---|---|---|---|---|---|---|---|---|---|---|
| Gln | Val | Thr | Arg | Gly | Thr | Val | Thr | Pro | Pro | Arg | Leu | Val | Lys |
| | 1175 | | | | 1180 | | | | | 1185 | | | |
| Lys | Asn | Glu | Glu | Ala | Ala | Asp | Glu | Val | Phe | Lys | Asp | Ile | Met | Glu |
| | 1190 | | | | | 1195 | | | | | 1200 | | | |
| Ser | Ser | Pro | Gly | Ser | Ser | Pro | Pro | Asn | Leu | Thr | Pro | Lys | Pro | Leu |
| | 1205 | | | | | 1210 | | | | | 1215 | | | |
| Arg | Arg | Gln | Val | Thr | Val | Ala | Pro | Ala | Ser | Gly | Leu | Pro | His | Lys |
| | 1220 | | | | | 1225 | | | | | 1230 | | | |
| Glu | Glu | Ala | Trp | Lys | Gly | Ser | Ala | Leu | Gly | Thr | Pro | Ala | Ala | Ala |
| | 1235 | | | | | 1240 | | | | | 1245 | | | |
| Glu | Pro | Val | Thr | Pro | Thr | Ser | Lys | Ala | Gly | Ser | Gly | Ala | Pro | Arg |
| | 1250 | | | | | 1255 | | | | | 1260 | | | |
| Gly | Thr | Ser | Lys | Gly | Pro | Ala | Glu | Glu | Ser | Arg | Val | Arg | Arg | His |
| | 1265 | | | | | 1270 | | | | | 1275 | | | |
| Lys | His | Ser | Ser | Glu | Ser | Pro | Gly | Arg | Asp | Lys | Gly | Lys | Leu | Ser |
| | 1280 | | | | | 1285 | | | | | 1290 | | | |
| Lys | Leu | Lys | Pro | Ala | Pro | Pro | Pro | Pro | Ala | Ala | Ser | Ala | Gly |
| | 1295 | | | | | 1300 | | | | | 1305 | | | |
| Lys | Ala | Gly | Gly | Lys | Pro | Ser | Gln | Arg | Pro | Gly | Gln | Glu | Ala | Ala |
| | 1310 | | | | | 1315 | | | | | 1320 | | | |
| Gly | Glu | Ala | Val | Leu | Gly | Ala | Lys | Thr | Lys | Ala | Thr | Ser | Leu | Val |
| | 1325 | | | | | 1330 | | | | | 1335 | | | |
| Asp | Ala | Val | Asn | Ser | Asp | Ala | Ala | Lys | Pro | Ser | Gln | Pro | Ala | Glu |
| | 1340 | | | | | 1345 | | | | | 1350 | | | |
| Gly | Leu | Lys | Lys | Pro | Val | Leu | Pro | Ala | Thr | Pro | Lys | Pro | His | Pro |
| | 1355 | | | | | 1360 | | | | | 1365 | | | |
| Ala | Lys | Pro | Ser | Gly | Thr | Pro | Ile | Ser | Pro | Ala | Pro | Val | Pro | Leu |
| | 1370 | | | | | 1375 | | | | | 1380 | | | |
| Ser | Thr | Leu | Pro | Ser | Ala | Ser | Ser | Ala | Leu | Ala | Gly | Asp | Gln | Pro |
| | 1385 | | | | | 1390 | | | | | 1395 | | | |
| Ser | Ser | Thr | Ala | Phe | Ile | Pro | Leu | Ile | Ser | Thr | Arg | Val | Ser | Leu |
| | 1400 | | | | | 1405 | | | | | 1410 | | | |
| Arg | Lys | Thr | Arg | Gln | Pro | Pro | Glu | Arg | Ala | Ser | Gly | Ala | Ile | Thr |
| | 1415 | | | | | 1420 | | | | | 1425 | | | |
| Lys | Gly | Val | Val | Leu | Asp | Ser | Thr | Glu | Ala | Leu | Cys | Leu | Ala | Ile |
| | 1430 | | | | | 1435 | | | | | 1440 | | | |
| Ser | Gly | Asn | Ser | Glu | Gln | Met | Ala | Ser | His | Ser | Ala | Val | Leu | Glu |
| | 1445 | | | | | 1450 | | | | | 1455 | | | |
| Ala | Gly | Lys | Asn | Leu | Tyr | Thr | Phe | Cys | Val | Ser | Tyr | Val | Asp | Ser |
| | 1460 | | | | | 1465 | | | | | 1470 | | | |
| Ile | Gln | Gln | Met | Arg | Asn | Lys | Phe | Ala | Phe | Arg | Glu | Ala | Ile | Asn |
| | 1475 | | | | | 1480 | | | | | 1485 | | | |
| Lys | Leu | Glu | Asn | Asn | Leu | Arg | Glu | Leu | Gln | Ile | Cys | Pro | Ala | Ser |
| | 1490 | | | | | 1495 | | | | | 1500 | | | |
| Ala | Gly | Ser | Gly | Pro | Ala | Ala | Thr | Gln | Asp | Phe | Ser | Lys | Leu | Leu |
| | 1505 | | | | | 1510 | | | | | 1515 | | | |
| Ser | Ser | Val | Lys | Glu | Ile | Ser | Asp | Ile | Val | Gln | Arg |
| | 1520 | | | | | 1525 | | | | | 1530 |

<210> SEQ ID NO 9
<211> LENGTH: 676
<212> TYPE: PRT
<213> ORGANISM: Homo sapiens

<400> SEQUENCE: 9

-continued

```
Leu Gly Tyr Trp Lys Ile Lys Gly Leu Val Gln Pro Thr Arg Leu Leu
1               5                   10                  15
Leu Glu Tyr Leu Glu Lys Tyr Glu His Leu Tyr Glu Arg Asp
            20                  25                  30
Glu Gly Asp Lys Trp Arg Asn Lys Phe Glu Leu Gly Leu Glu Phe
            35                  40                  45
Pro Asn Leu Pro Tyr Tyr Ile Asp Gly Asp Val Lys Leu Thr Gln Ser
50                          55                  60
Met Ala Ile Ile Arg Tyr Ile Ala Asp Lys His Asn Met Leu Gly Gly
65                  70                  75                  80
Cys Pro Lys Glu Arg Ala Glu Ile Ser Met Leu Glu Gly Ala Val Asp
                85                  90                  95
Ile Arg Tyr Gly Val Ser Arg Ile Ala Tyr Ser Lys Asp Phe Glu Thr
                100                 105                 110
Leu Lys Val Asp Phe Leu Ser Lys Leu Pro Glu Met Leu Lys Met Phe
            115                 120                 125
Glu Asp Arg Leu Cys His Lys Thr Tyr Leu Asn Gly Asp His Val Thr
            130                 135                 140
His Pro Asp Phe Met Leu Tyr Asp Ala Leu Asp Val Val Leu Tyr Met
145                 150                 155                 160
Asp Pro Met Cys Leu Asp Ala Phe Pro Lys Leu Val Cys Phe Lys Lys
                165                 170                 175
Arg Ile Glu Ala Ile Pro Gln Ile Asp Lys Tyr Leu Lys Ser Ser Lys
                180                 185                 190
Tyr Ile Trp Pro Leu Gln Gly Trp Gln Ala Thr Phe Gly Gly Gly Asp
            195                 200                 205
His Pro Pro Lys Ser Asp Leu Val Pro Arg His Asn Gln Thr Ser Leu
210                 215                 220
Tyr Lys Lys Ala Gly Ser Ala Ala Val Leu Glu Glu Asn Leu Tyr
225                 230                 235                 240
Phe Gln Gly Thr Tyr Lys Tyr Leu Gln Lys Pro Met Tyr Glu Val Gln
                245                 250                 255
Trp Lys Val Val Glu Glu Ile Asn Gly Asn Asn Tyr Val Tyr Ile Asp
                260                 265                 270
Pro Thr Gln Leu Pro Tyr Asp His Lys Trp Glu Phe Pro Arg Asn Arg
            275                 280                 285
Leu Ser Phe Gly Lys Thr Leu Gly Ala Gly Ala Phe Gly Lys Val Val
            290                 295                 300
Glu Ala Thr Ala Tyr Gly Leu Ile Lys Ser Asp Ala Ala Met Thr Val
305                 310                 315                 320
Ala Val Lys Met Leu Lys Pro Ser Ala His Leu Thr Glu Arg Glu Ala
                325                 330                 335
Leu Met Ser Glu Leu Lys Val Leu Ser Tyr Leu Gly Asn His Met Asn
                340                 345                 350
Ile Val Asn Leu Leu Gly Ala Cys Thr Ile Gly Gly Pro Thr Leu Val
            355                 360                 365
Ile Thr Glu Tyr Cys Cys Tyr Gly Asp Leu Leu Asn Phe Leu Arg Arg
            370                 375                 380
Lys Arg Asp Ser Phe Ile Cys Ser Lys Gln Glu Asp His Ala Glu Ala
385                 390                 395                 400
Ala Leu Tyr Lys Asn Leu Leu His Ser Lys Glu Ser Ser Cys Ser Asp
                405                 410                 415
Ser Thr Asn Glu Tyr Met Asp Met Lys Pro Gly Val Ser Tyr Val Val
                420                 425                 430
```

```
Pro Thr Lys Ala Asp Lys Arg Arg Ser Val Arg Ile Gly Ser Tyr Ile
        435                 440                 445

Glu Arg Asp Val Thr Pro Ala Ile Met Glu Asp Glu Leu Ala Leu
    450                 455                 460

Asp Leu Glu Asp Leu Leu Ser Phe Ser Tyr Gln Val Ala Lys Gly Met
465                 470                 475                 480

Ala Phe Leu Ala Ser Lys Asn Cys Ile His Arg Asp Leu Ala Ala Arg
                485                 490                 495

Asn Ile Leu Leu Thr His Gly Arg Ile Thr Lys Ile Cys Asp Phe Gly
            500                 505                 510

Leu Ala Arg Asp Ile Lys Asn Asp Ser Asn Tyr Val Val Lys Gly Asn
        515                 520                 525

Ala Arg Leu Pro Val Lys Trp Met Ala Pro Glu Ser Ile Phe Asn Cys
    530                 535                 540

Val Tyr Thr Phe Glu Ser Asp Val Trp Ser Tyr Gly Ile Phe Leu Trp
545                 550                 555                 560

Glu Leu Phe Ser Leu Gly Ser Ser Pro Tyr Pro Gly Met Pro Val Asp
                565                 570                 575

Ser Lys Phe Tyr Lys Met Ile Lys Glu Gly Phe Arg Met Leu Ser Pro
            580                 585                 590

Glu His Ala Pro Ala Glu Met Tyr Asp Ile Met Lys Thr Cys Trp Asp
        595                 600                 605

Ala Asp Pro Leu Lys Arg Pro Thr Phe Lys Gln Ile Val Gln Leu Ile
    610                 615                 620

Glu Lys Gln Ile Ser Glu Ser Thr Asn His Ile Tyr Ser Asn Leu Ala
625                 630                 635                 640

Asn Cys Ser Pro Asn Arg Gln Lys Pro Val Val Asp His Ser Val Arg
                645                 650                 655

Ile Asn Ser Val Gly Ser Thr Ala Ser Ser Ser Gln Pro Leu Leu Val
            660                 665                 670

His Asp Asp Val
        675

<210> SEQ ID NO 10
<211> LENGTH: 474
<212> TYPE: PRT
<213> ORGANISM: Homo sapiens

<400> SEQUENCE: 10

Met Ser Tyr Tyr His His His His His His Asp Tyr Asp Ile Pro Thr
1               5                   10                  15

Thr Glu Asn Leu Tyr Phe Gln Gly Ala Met Leu Val Pro Arg Gly Ser
            20                  25                  30

Pro Trp Ile Pro Phe Thr Met Lys Lys Arg Lys Gln Ile Lys Asp Leu
        35                  40                  45

Gly Ser Glu Leu Val Arg Tyr Asp Ala Arg Val His Thr Pro His Leu
    50                  55                  60
```

-continued

```
Asp Arg Leu Val Ser Ala Arg Ser Val Ser Pro Thr Thr Glu Met Val
 65                  70                  75                  80

Ser Asn Glu Ser Val Asp Tyr Arg Ala Thr Phe Pro Glu Asp Gln Phe
             85                  90                  95

Pro Asn Ser Ser Gln Asn Gly Ser Cys Arg Gln Val Gln Tyr Pro Leu
        100                 105                 110

Thr Asp Met Ser Pro Ile Leu Thr Ser Gly Asp Ser Asp Ile Ser Ser
    115                 120                 125

Pro Leu Leu Gln Asn Thr Val His Ile Asp Leu Ser Ala Leu Asn Pro
130                 135                 140

Glu Leu Val Gln Ala Val Gln His Val Val Ile Gly Pro Ser Ser Leu
145                 150                 155                 160

Ile Val His Phe Asn Glu Val Ile Gly Arg Gly His Phe Gly Cys Val
                165                 170                 175

Tyr His Gly Thr Leu Leu Asp Asn Asp Gly Lys Lys Ile His Cys Ala
            180                 185                 190

Val Lys Ser Leu Asn Arg Ile Thr Asp Ile Gly Glu Val Ser Gln Phe
        195                 200                 205

Leu Thr Glu Gly Ile Ile Met Lys Asp Phe Ser His Pro Asn Val Leu
    210                 215                 220

Ser Leu Leu Gly Ile Cys Leu Arg Ser Glu Gly Ser Pro Leu Val Val
225                 230                 235                 240

Leu Pro Tyr Met Lys His Gly Asp Leu Arg Asn Phe Ile Arg Asn Glu
                245                 250                 255

Thr His Asn Pro Thr Val Lys Asp Leu Ile Gly Phe Gly Leu Gln Val
            260                 265                 270

Ala Lys Gly Met Lys Tyr Leu Ala Ser Lys Lys Phe Val His Arg Asp
        275                 280                 285

Leu Ala Ala Arg Asn Cys Met Leu Asp Glu Lys Phe Thr Val Lys Val
    290                 295                 300

Ala Asp Phe Gly Leu Ala Arg Asp Met Tyr Asp Lys Glu Tyr Tyr Ser
305                 310                 315                 320

Val His Asn Lys Thr Gly Ala Lys Leu Pro Val Lys Trp Met Ala Leu
                325                 330                 335

Glu Ser Leu Gln Thr Gln Lys Phe Thr Thr Lys Ser Asp Val Trp Ser
            340                 345                 350

Phe Gly Val Leu Leu Trp Glu Leu Met Thr Arg Gly Ala Pro Pro Tyr
        355                 360                 365

Pro Asp Val Asn Thr Phe Asp Ile Thr Val Tyr Leu Leu Gln Gly Arg
    370                 375                 380

Arg Leu Leu Gln Pro Glu Tyr Cys Pro Asp Pro Leu Tyr Glu Val Met
385                 390                 395                 400

Leu Lys Cys Trp His Pro Lys Ala Glu Met Arg Pro Ser Phe Ser Glu
                405                 410                 415

Leu Val Ser Arg Ile Ser Ala Ile Phe Ser Thr Phe Ile Gly Glu His
            420                 425                 430

Tyr Val His Val Asn Ala Thr Tyr Val Asn Val Lys Cys Val Ala Pro
        435                 440                 445

Tyr Pro Ser Leu Leu Ser Ser Glu Asp Asn Ala Asp Asp Glu Val Asp
    450                 455                 460

Thr Arg Pro Ala Ser Phe Trp Glu Thr Ser
465                 470
```